US009504737B2

(12) United States Patent
Ishibashi et al.

(10) Patent No.: US 9,504,737 B2
(45) Date of Patent: Nov. 29, 2016

(54) IMMUNE RESPONSE INDUCER

(75) Inventors: Masaki Ishibashi, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 578 days.

(21) Appl. No.: 12/739,723

(22) PCT Filed: Oct. 23, 2008

(86) PCT No.: PCT/JP2008/069267
§ 371 (c)(1),
(2), (4) Date: Apr. 23, 2010

(87) PCT Pub. No.: WO2009/054471
PCT Pub. Date: Apr. 30, 2009

(65) Prior Publication Data
US 2010/0297071 A1 Nov. 25, 2010

(30) Foreign Application Priority Data

Oct. 25, 2007 (JP) ................ 2007-277240
Oct. 25, 2007 (JP) ................ 2007-277578
Oct. 25, 2007 (JP) ................ 2007-277611
Oct. 26, 2007 (JP) ................ 2007-279113

(51) Int. Cl.
*A61K 39/00* (2006.01)
*A61K 38/20* (2006.01)
*A61K 38/21* (2006.01)

(52) U.S. Cl.
CPC ......... *A61K 39/0011* (2013.01); *A61K 38/208* (2013.01); *A61K 38/212* (2013.01); *A61K 38/215* (2013.01); *A61K 2039/53* (2013.01)

(58) Field of Classification Search
None
See application file for complete search history.

(56) References Cited

U.S. PATENT DOCUMENTS 5,698,396 A 12/1997 Pfreundschuh
7,745,391 B2 * 6/2010 Mintz et al. ............. 514/19.3

FOREIGN PATENT DOCUMENTS

| WO | WO 02/083876 A2 | 10/2002 |
| WO | WO 03/009814 A2 | 2/2003 |
| WO | WO 2004/024887 A2 | 3/2004 |
| WO | WO 2004/080148 A2 | 9/2004 |
| WO | WO 2005/040414 A1 | 5/2005 |

OTHER PUBLICATIONS

Akiyoshi, "Cancer Vaccine Therapy Using Peptide Derived from Tumor-Rejection Antigens", Jpn. J. Cancer and Chemotherapy., vol. 24, No. 5, pp. 511-519, Mar. 1997.
Brass et al., "Translation initiation factor eIF-4gamma is encoded by an amplified gene and induces an immune response in squamous cell lung carcinoma", Human Molecular Genetics, vol. 6, No. 1, pp. 33-39, 1997.
Gromley et al., "A novel human protein of the maternal centriole is required for the final stages of cytokinesis and entry into S phase", The Journal of Cell Biology, vol. 161, No. 3, pp. 535-545, May 12, 2003.
Guasch et al., "FGFR1 is fused to the centrosome-associated protein CEP110 in the 8p12 stem cell myeloproliferative disorder with t(8;9)(p12;q33)", Blood, vol. 95, No. 5, pp. 1788-1796, Mar. 1, 2000.
Gure et al., "Human Lung Cancer Antigens Recognized by Autologous Antibodies: Definition of a Novel cDNA Derived from the Tumor Suppressor Gene Locus on Chromosome 3p21.3", Cancer Research, vol. 58, pp. 1034-1041, Mar. 1, 1998.
Gure et al., "SSX: A Multigene Family with Several Members Transcribed in Normal Testis and Human Cancer", International Journal of Cancer, vol. 72, pp. 965-971, May 1, 1997.
Infante et al., "GMAP-210, A Cis-Golgi Network-associated Protein, Is a Minus End Microtubule-binding Protein", The Journal of Cell Biology, vol. 145, No. 1, pp. 83-98, Apr. 5, 1999.
Inoue et al., "How far was fertilization elucidated?", Protein, Nucleic Acid and Enzyme, Institute for Microbial Disease, vol. 50, No. 11, pp. 1405-1412, 2005 (Abstract only provided).
International Search Report dated Jan. 6, 2009 for International Application No. PCT/JP2008/069267.
Itoh et al., "Autoantigen frequently eliciting humoral immune response in patients with adult T cell leukemia", Int. J. Oncol., vol. 14, No. 4, pp. 703-708, Apr. 1999 (Abstract only provided).
Lee et al., "Two classes of proteins dependent on either the presence or absence of thyroid hormone for interaction with the thyroid hormone receptor", Mol Endocrinol, vol. 9, No. 2, pp. 243-254, Feb. 9, 1995 (Abstract only provided).
Ou et al., "CEP110 and ninein are located in a specific domain of the centrosome associated with centrosome maturation", Journal of Cell Science, vol. 115, pp. 1825-1835, Feb. 16, 2002.
Scanlan et al., "Characterization of Human Colon Cancer Antigens Recognized by Autologous Antibodies", International Journal of Cancer, vol. 76, pp. 652-658, Jan. 5, 1998.
Tanaka et al., "Cloning and Characterization of the human Calmegin gene encoding putative testis-specific chaperone", Gene, vol. 204, pp. 159-163, 1997.
Tureci et al., "The SSX-2 Gene, Which is Involved in the t(X;18) Translocation of Synovial Sarcomas, Codes for the Human Tumor Antigen HOM-MEL-40", Cancer Research, vol. 56, pp. 4766-4772, Oct. 15, 1996.
Extended European Search Report issued in European Application No. 08840900.8 mailed Dec. 13, 2010.

* cited by examiner

*Primary Examiner* — Yunsoo Kim
(74) *Attorney, Agent, or Firm* — Birch, Stewart, Kolasch & Birch, LLP

(57) ABSTRACT

An immunity-inducing agent comprising as an effective ingredient a specific polypeptide is disclosed. These polypeptides were isolated, by the SEREX method using a cDNA library derived from canine testis and serum from a cancer-bearing dog, as a polypeptide which binds to an antibody existing specifically in serum derived from a cancer-bearing living body. The polypeptides can induce immunity in a living body and cause regression of a tumor in a cancer-bearing living body. Therefore, these polypeptides are especially effective as a therapeutic and/or prophylactic agent for a cancer(s).

11 Claims, 5 Drawing Sheets

IMMUNE RESPONSE INDUCER

TECHNICAL FIELD

The present invention relates to a novel immunity-inducing agent useful as a therapeutic and/or prophylactic agent for a cancer(s).

BACKGROUND ART

Cancers are the commonest cause for death among all of the causes for death, and the therapies therefor are mainly surgical treatment in combination with radiotherapy and chemotherapy. In spite of the developments of new surgical methods and discovery of new anti-cancer agents in recent years, treatment results of cancers are not improved very much at present except for some cancers. In recent years, by virtue of the development in molecular biology and cancer immunology, cancer antigens recognized by cytotoxic T cells reactive with cancers, as well as the genes encoding the cancer antigens, were identified, and expectations for antigen-specific immunotherapies have been raised (see Non-patent Literature 1). In immunotherapy, to reduce side effects, it is necessary that the peptide or protein recognized as the antigen exist hardly in normal cells and exist specifically in cancer cells. In 1991, Boon et al. of Ludwig Institute in Belgium isolated human melanoma antigen MAGE 1 recognized by CD8-positive T cells by a cDN-expression cloning method using an autologous cancer cell line and cancer-reactive T cells (see Non-patent Literature 2). Thereafter, the SEREX (serological identifications of antigens by recombinant expression cloning) method, wherein tumor antigens recognized by antibodies produced in the living body of a cancer patient in response to the cancer of the patient himself are identified by application of a gene expression cloning method, was reported (Non-patent Literature 3; Patent Literature 1), and various cancer antigens have been isolated (see Non-patent Literatures 4 to 9). Using a part thereof as targets, clinical tests for cancer immunotherapy have started.

On the other hand, as in human, a number of tumors such as mammary gland tumor and squamous cell carcinoma are known in dogs and cats, and they rank high also in the statistics of diseases in dogs and cats. However, at present, no therapeutic, prophylactic or diagnostic agents exist which are effective for cancers in dogs and cats. Most of tumors in dogs and cats are realized by owners only after they advance to grow bigger, and in many cases, it is already too late to visit a hospital to receive surgical excision of the tumor or administration of a human drug (an anticancer preparation or the like), so that those dogs and cats die shortly after the treatment. Under such circumstances, if therapeutic agents, prophylactic agents and diagnostic agents for cancers effective for dogs and cats become available, their uses for canine cancers are expected to be developed.

Patent Literature 1: U.S. Pat. No. 5,698,396 B
Non-patent Literature 1: Tsuyoshi Akiyoshi, Cancer and Chemotherapy, 24, 551-519 (1997)
Non-patent Literature 2: Bruggen P. et al., Science, 254: 1643-1647 (1991)
Non-patent Literature 3: Proc. Natl. Acad. Sci. USA, 92:11810-11813 (1995)
Non-patent Literature 4: Int. J. Cancer, 72:965-971 (1997)
Non-patent Literature 5: Cancer Res., 58:1034-1041 (1998)
Non-patent Literature 6: Int. J. Cancer, 29:652-658 (1998)
Non-patent Literature 7: Int. J. Oncol., 14:703-708 (1999)
Non-patent Literature 8: Cancer Res., 56:4766-4772 (1996)
Non-patent Literature 9: Hum. Mol. Genet 6:33-39, 1997
Non-patent Literature 10: Naokazu Inoue, Ryo Yamaguchi and Masahito Ikawa, Protein, Nucleic Acid and Enzyme, Vol. 50, No. 11, 1405-1412
Non-patent Literature 11: J Cell Sci. 115:1825-35
Non-patent Literature 12: Blood. 95:1788-96
Non-patent Literature 13: Mol Endocrinol. 9:243-54 (1995)
Non-patent Literature 14: J Cell Biol. 145: 83-98 (1999)

DISCLOSURE OF THE INVENTION

Problems to be Solved by the Invention

An object of the present invention is to provide a novel immunity-inducing agent which is useful as a therapeutic and/or prophylactic agent for a cancer(s)

Means for Solving the Problems

The present inventors intensively studied to obtain a cDNA encoding a protein which binds to an antibody existing in serum derived from a cancer-bearing living body by the SEREX method using a cDNA library derived from canine testis and serum of a cancer-bearing dog, which cDNA was used to prepare a polypeptide having the amino acid sequence shown in SEQ ID NO:2, a canine calmegin protein having the amino acid sequence shown in SEQ ID NO:16, a canine centrosomal protein (which may be hereinafter abbreviated as CEP) having the amino acid sequence shown in SEQ ID NO:26, and the canine thyroid hormone receptor interactor 11 (which may be hereinafter described as "TRIP11") having the amino acid sequence shown in SEQ ID NO:39. Further, based on a registered canine gene having a high homology to the canine CEP of the above-described SEQ ID NO:26, a canine CEP having the amino acid sequence shown in SEQ ID NO:28 was prepared. Further, based on a human gene homologous to the obtained gene, a polypeptide having the amino acid sequence shown in SEQ ID NO:4, a human calmegin protein having the amino acid sequence shown in SEQ ID NO:18, a human CEP having the amino acid sequence shown in SEQ ID NO:30, and a human TRIP11 having the amino acid sequence shown in SEQ ID NO:41 were prepared. The inventors then discovered that these polypeptides can induce immunocytes in a living body and cause regression of an already occurred tumor when administered to the living body, thereby completing the present invention.

That is, the present invention provides an immunity-inducing agent comprising as an effective ingredient any one of the polypeptides (a) to (c) below, the polypeptide having an immunity-inducing activity, or as an effective ingredient a recombinant vector which comprises a polynucleotide encoding the polypeptide and is capable of expressing the polypeptide in vivo: (a) a polypeptide consisting of not less than 7 consecutive amino acids of the amino acid sequence shown in SEQ ID NO:2, 4, 16, 18, 26, 28, 30, 39 or 41 in SEQUENCE LISTING; (b) a polypeptide having a homology of not less than 80% to the polypeptide (a) and consisting of not less than 7 amino acids; and (c) a polypeptide comprising the polypeptide (a) or (b) as a partial sequence thereof. The present invention also provides a method for inducing immunity, the method comprising administering to an individual an effective amount of any one of the above-described polypeptides (a) to (c), the polypeptide having an immunity-inducing activity, or an effective amount of a recombinant vector which comprises a polynucleotide encoding the polypeptide and is capable of expressing the polypeptide in vivo. The present invention further provides a method for treating antigen-presenting cells, the method comprising bringing any one of the above-described polypeptides (a) to (c), the polypeptide having an immunity-inducing activity, into contact with antigen-presenting cells. The present invention further provides use of any one of the above-described polypeptides (a) to (c), the polypeptide having an immunity-inducing activity, or a recombinant vector which comprises a polynucleotide encoding the polypeptide and is capable of expressing the polypeptide in vivo, for production of an immunity-inducing agent.

Effect of the Invention

By the present invention, a novel immunity-inducing agent useful as a therapeutic and/or prophylactic agent for a cancer(s) was provided. As indicated in the Examples below, the polypeptide used in the present invention can induce immunocytes in a cancer-bearing dog and also can cause reduction or regression of an already occurred tumor when administered to a cancer-bearing dog. Therefore, the polypeptide is useful for therapy and prophylaxis of a cancer(s).

BEST MODE FOR CARRYING OUT THE INVENTION

Figure 1:
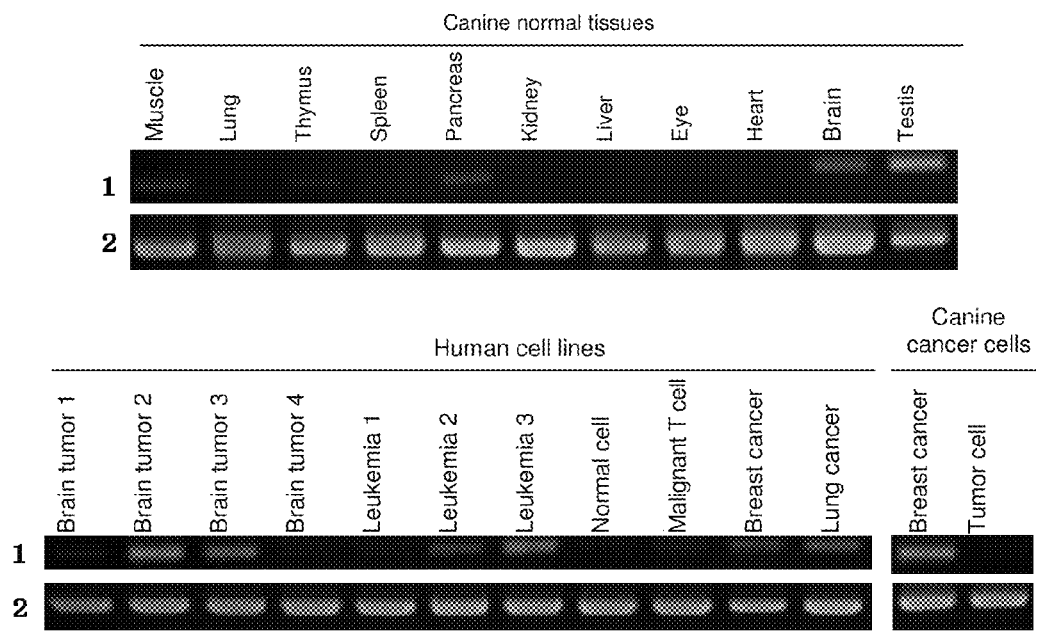
FIG. 1 shows the expression pattern of the gene identified in Example A-1 in normal tissues and tumor cell lines. Reference numeral 1: the expression pattern of the identified gene; Reference numeral 2: the expression pattern of the GAPDH gene.

The polypeptides contained in the immunity-inducing agents of the present invention as effective ingredients are as follows. It should be noted that the term "polypeptide" in the present invention means a molecule formed by peptide bonding of a plurality of amino acids, and includes not only polypeptide molecules having large numbers of amino acids constituting them, but also low molecular weight molecules having small numbers of amino acids (oligopeptides) and full-length proteins. Thus, in the present invention, proteins consisting of the full length of SEQ ID NO:2, 4, 16, 18, 26, 28, 30, 39 or 41 are also included in "polypeptide".

(a) A polypeptide which consists of not less than 7 consecutive amino acids of a polypeptide having the amino acid sequence shown in SEQ ID NO:2, 4, 16, 18, 26, 28, 30, 39 or 41 in SEQUENCE LISTING and has an immunity-inducing activity.

(b) A polypeptide which has a homology of not less than 80% to the polypeptide (a), consists of not less than 7 amino acids, and has an immunity-inducing activity.

(c) A polypeptide which comprises the polypeptide (a) or (b) as a partial sequence thereof and has an immunity-inducing activity.

It should be noted that the term "having the amino acid sequence" in the present invention means that amino acid residues are aligned in that order. Accordingly, for example, "a polypeptide having the amino acid sequence shown in SEQ ID NO:2" means a polypeptide having a size of 306 amino acid residues, whose amino acid sequence is Met Ala Ala Leu . . . (snip) . . . Ile Thr Ser Pro as shown in SEQ ID NO:2. Further, "a polypeptide having the amino acid sequence shown in SEQ ID NO:2" may be abbreviated as "a polypeptide of SEQ ID NO:2". This also applies to the term "having the base sequence".

As used herein, the term "immunity-inducing activity" means an ability to induce immunocytes which secrete cytokines such as interferon in a living body. Whether or not a polypeptide has an immunity-inducing activity can be confirmed using, for example, the known ELISPOT assay. More particularly, for example, as described in the Examples below, cells such as peripheral blood mononuclear cells are obtained from a living body to which a polypeptide whose immunity-inducing activity is to be evaluated was administered, which cells are then cocultivated with the polypeptide, followed by measuring the amount of a cytokine produced by the cells using a specific antibody, thereby measuring the number of immunocytes in the cells, which enables evaluation of the immunity-inducing activity. Further, as described in the Examples below, a recombinant polypeptide prepared based on the amino acid sequence of SEQ ID NO:2, 4, 16, 18, 26, 28, 30, 39 or 41 can cause regression of a tumor by its immunity-inducing activity when administered to a cancer-bearing living body. Therefore, the above-described immunity-inducing activity can be evaluated also as the ability to inhibit the growth of cancer cells expressing the polypeptide of SEQ ID NO:2, 4, 16, 18, 26, 28, 30, 39 or 41 or to cause reduction or disappearance of a cancer tissue (tumor) (hereinafter referred to as "anti-tumor activity"). The anti-tumor activity of a polypeptide can be confirmed by, for example, observation of whether or not the tumor is reduced when the polypeptide was administered to a cancer-bearing living body, as more particularly described in the Examples below. Further, the anti-tumor activity of a polypeptide can be evaluated also by observation of whether or not T cells stimulated with the polypeptide (that is, T cells brought into contact with antigen-presenting cells which present the polypeptide) show a cytotoxic activity against tumor cells in vitro. The contact between T cells and antigen-presenting cells can be carried out by cocultivation of the both in a liquid medium, as mentioned below. Measurement of the cytotoxic activity can be carried out by, for example, a known method called $^{51}$Cr release assay described in Int. J. Cancer, 58:p 317, 1994. In cases where a polypeptide is used for therapy and/or prophylaxis of a cancer(s), the evaluation of the immunity-inducing activity is preferably carried out using the anti-tumor activity as an index, although the index is not restricted.

The amino acid sequence shown in SEQ ID NO:2 in SEQUENCE LISTING is the amino acid sequence of the polypeptide with unknown function isolated as a polypeptide which binds to an antibody existing specifically in serum derived from a cancer-bearing dog, which isolation was carried out by the SEREX method using a canine testis-derived cDNA library and serum of a cancer-bearing dog (see Example A-1). It is registered in the NCBI database under Accession No. XP_535343 (protein) and Accession No. XM_535343 (coding gene), but its function has not been reported. Further, the amino acid sequence shown in SEQ ID NO:4 is an amino acid sequence of a human homologous factor of the polypeptide of SEQ ID NO:2 isolated as described above. This human homologous factor is also a protein whose function is unknown, which is registered in the NCBI database under Accession No. NP_689873 (protein) and Accession No. NM_152660 (coding gene). The homology between them is 93% in terms of base sequence and 99% in terms of amino acid sequence.

The respective amino acid sequences shown in SEQ ID NOs:16 and 18 are those of the calmegin protein isolated as a polypeptide and a human homologous factor thereof, which polypeptide binds to an antibody existing specifically in serum derived from a cancer-bearing dog, which isolation was carried out by the SEREX method using a canine testis-derived cDNA library and serum of a cancer-bearing dog (see Example B-1). Calmegin was identified as a protein which is expressed specifically at the time of differentiation of a spermatid, and it has a chaperone activity in vitro. Since it is expressed only in testis and disappears in a mature sperm, calmegin is considered to have a function to fold proteins involved in differentiation of spermatid (Non-patent Literature 10, Naokazu Inoue, Ryo Yamaguchi and Masahito Ikawa, Protein, Nucleic Acid and Enzyme, Vol. 50, No. 11, 1405-1412). However, there has been no report showing that the protein is expressed in a cancer and useful for therapy or prophylaxis thereof. The homology between the canine calmegin gene and the human calmegin gene is 90% in terms of base sequence and 89% in terms of amino acid sequence.

The respective amino acid sequences shown in SEQ ID NOs:26, 28 and 30 are those of the CEP isolated as a polypeptide, a canine factor having a high homology to the polypeptide and a human homologous factor of the polypeptide, which polypeptide binds to an antibody existing specifically in serum derived from a cancer-bearing dog, which isolation was carried out by the SEREX method using a canine testis-derived cDNA library and serum of a cancer-bearing dog (see Example C-1). CEP is a protein which is required by the centrosome to control microtubules and also involved in maturation of the centrosome. It is known that chromosomal translocation frequently occurs in some of myeloproliferative disorders, and since the CEP gene exists at the point where the translocation occurs, CEP is considered to have a certain relationship with the disorders. However, there has been no report showing that the protein is expressed in a cancer and useful for therapy or prophylaxis thereof (Non-patent Literature 11: J Cell Sci. 115:1825-35; Non-patent Literature 12: Blood. 95:1788-96). The homology between the canine CEP gene encoding the CEP of SEQ ID NO:26 and the human CEP gene is 87% in terms of base sequence and 84% in terms of amino acid sequence.

The respective amino acid sequences shown in SEQ ID NOs:39 and 41 are those of the TRIP11 protein isolated as a polypeptide and a human homologous factor thereof, which polypeptide binds to an antibody existing specifically in serum derived from a cancer-bearing dog, which isolation was carried out by the SEREX method using a canine testis-derived cDNA library and serum of a cancer-bearing dog (see Example D-1). TRIP11 (thyroid hormone receptor interactor 11) was first identified as a factor which interacts with the thyroid hormone receptor β, and its binding to Golgi bodies and microtubules also became evident, so that TRIP11 is considered to play a role in maintaining the shapes of these organelles. However, there has been no report showing that the protein is expressed in a cancer and useful for therapy or prophylaxis thereof (Non-patent Literature 13, Mol Endocrinol. 9:243-54 (1995); Non-patent Literature 14, J Cell Biol. 145: 83-98 (1999)). The homology between the canine TRIP11 gene and the human TRIP11 gene is 88% in terms of base sequence and 86% in terms of amino acid sequence.

The polypeptide (a) consists of not less than 7 consecutive, preferably not less than 9 consecutive amino acids of a polypeptide having the amino acid sequence shown in SEQ ID NO:2, 4, 16, 18, 26, 28, 30, 39 or 41, and has an immunity-inducing activity. The polypeptide especially preferably has the amino acid sequence shown in SEQ ID NO:2, 4, 16, 18, 26, 28, 30, 39 or 41. As known in the art, a polypeptide consists of not less than about 7 amino acid residues can exert its antigenicity. Thus, a polypeptide consists of not less than 7 consecutive amino acid residues of the amino acid sequence shown in SEQ ID NO:2, 4, 16, 18, 26, 28, 30, 39 or 41 can have an immunity-inducing activity, so that it can be used for preparation of the immunity-inducing agent of the present invention. However, in view of the fact that antibodies produced against antigenic substances in a living body are polyclonal antibodies, it is thought that an antigenic substance composed of larger number of amino acid residues can induce more types of antibodies which can recognize various sites on the antigenic substance, thereby attaining higher immunity-inducing activity. Therefore, in order to increase the immunity-inducing activity, in the case of SEQ ID NO:2 or 4, the number of the amino acid residues may be preferably not less than 30, more preferably not less than 100, still more preferably not less than 200, still more preferably not less than 250. In the case of SEQ ID NO:16 or 18, the number of the amino acid residues may be preferably not less than 30, more preferably not less than 100, still more preferably not less than 200, still more preferably not less than 400, still more preferably not less than 550. In the case of SEQ ID NO:26, 28 or 30, the number of the amino acid residues may be preferably not less than 30, more preferably not less than 100, still more preferably not less than 300, still more preferably not less than 600, still more preferably not less than 1000, still more preferably not less than 1500, still more preferably not less than 2000. In the case of SEQ ID NO:39 or 41, the number of the amino acid residues may be preferably not less than 30, more preferably not less than 100, still more preferably not less than 300, still more preferably not less than 600, still more preferably not less than 1000, still more preferably not less than 1500.

As a principle of immune induction by administration of a cancer antigenic polypeptide, the following process is known: the polypeptide is incorporated into an antigen-presenting cell and then degraded into smaller fragments by peptidases in the cell, followed by presentation of the fragments on the surface of the cell. The fragments are then recognized by a cytotoxic T cell or the like, which selectively kills cells presenting the antigen.

The size of the polypeptide presented on the surface of the antigen-presenting cell is relatively small and about 7 to 30 amino acids. Therefore, from the view point of presenting thereof on the surface of the antigen-presenting cell, a polypeptide consisting of about 7 to 30, preferably about 9 to 30 consecutive amino acids of the amino acid sequence shown in SEQ ID NO:2, 4, 16, 18, 26, 28, 30, 39 or 41 is sufficient as the above-described polypeptide (a). In some cases, these relatively small polypeptides are presented directly on the surface of the antigen-presenting cells without incorporation thereof into the antigen-presenting cells.

However, as described above, since a polypeptide incorporated into an antigen-presenting cell is cleaved at random sites by peptidases in the cell to yield various polypeptide fragments, which are then presented on the surface of the antigen-presenting cell, administration of a large polypeptide such as the entire region of SEQ ID NO:2, 4, 16, 18, 26, 28, 30, 39 or 41 inevitably causes production of polypeptide fragments by degradation thereof in the antigen-presenting cell, which fragments are effective for immune induction via the antigen-presenting cell. Therefore, for immune induction via antigen-presenting cells, a large polypeptide can also be preferably used. In the case of SEQ ID NO:2 or 4, the number of the amino acids may be preferably not less than 30, more preferably not less than 100, still more preferably not less than 200, still more preferably not less than 250. In the case of SEQ ID NO:16 or 18, the number of the amino acids may be preferably not less than 30, more preferably not less than 100, still more preferably not less than 200, still more preferably not less than 400, still more preferably not less than 550. In the case of SEQ ID NO:26, 28 or 30, the number of the amino acids may be preferably not less than 30, more preferably not less than 100, still more preferably not less than 300, still more preferably not less than 600, still more preferably not less than 1000, still more preferably not less than 1500, still more preferably not less than 2000. In the case of SEQ ID NO:39 or 41, the number of the amino acids may be preferably not less than 30, more preferably not less than 100, still more preferably not less than 300, still more preferably not less than 600, still more preferably not less than 1000, still more preferably not less than 1500.

The above-described polypeptide (b) is the same polypeptide as the above-described polypeptide (a) except that a small number of amino acid residues are substituted, deleted and/or inserted, which has a homology of not less than 80%, preferably not less than 90%, more preferably not less than 95%, still more preferably not less than 98% to the original sequence, and has an immunity-inducing activity. It is well known in the art that, in general, there are cases where a protein antigen retains substantially the same antigenicity as the original even if the amino acid sequence of the protein is modified such that a small number of amino acids are substituted, deleted and/or inserted. Therefore, since the above-described polypeptide (b) may also exert an immunity-inducing activity, it can be used for preparation of the immunity-inducing agent of the present invention. Further, the above-described polypeptide (b) is also preferably the same polypeptide as one having the amino acid sequence shown in SEQ ID NO:2, 4, 16, 18, 26, 28, 30, 39 or 41 except that one or several amino acid residues are substituted, deleted and/or inserted.

As used herein, the term "homology" of amino acid sequences means a value expressed in percentage which is calculated by aligning two amino acid sequences to be compared such that the number of matched amino acid residues is the maximum, and dividing the number of the matched amino acid residues by the number of the total amino acid residues. When the above-described alignment is carried out, a gap(s) is/are inserted into one or both of the two sequences to be compared as required. Such alignment of sequences can be carried out using a well-known program such as BLAST, FASTA or CLUSTAL W. When a gap(s) is/are inserted, the above-described number of the total amino acid residues is calculated by counting one gap as one amino acid residue. When the thus counted numbers of the total amino acid residues are different between the two sequences to be compared, the homology (%) is calculated by dividing the number of matched amino acid residues by the number of the total amino acid residues in the longer sequence.

The 20 types of amino acids constituting the naturally occurring proteins may be classified into groups each of which has similar properties, for example, into neutral amino acids with side chains having low polarity (Gly, Ile, Val, Leu, Ala, Met, Pro), neutral amino acids having hydrophilic side chains (Asn, Gln, Thr, Ser, Tyr, Cys), acidic amino acids (Asp, Glu), basic amino acids (Arg, Lys, His) and aromatic amino acids (Phe, Tyr, Trp). It is known that, in most cases, substitutions of amino acids within the same group do not change the properties of the polypeptide. Therefore, in cases where amino acid residue(s) in the above described polypeptide (a) in the present invention is/are substituted, the probability that the immunity-inducing activity can be maintained may be made high by conducting the substitution(s) within the same group.

The above-described polypeptide (c) comprises the above-described polypeptide (a) or (b) as a partial sequence and has an immunity-inducing activity. That is, the polypeptide (c) has another/other amino acid(s) or polypeptide(s) added at one or both ends of the polypeptide (a) or (b), and has an immunity-inducing activity. Such a polypeptide can also be used for preparation of the immunity-inducing agent of the present invention.

For example, the above-described polypeptides can be synthesized by a chemical synthesis method such as the Fmoc method (fluorenylmethylcarbonyl method) or the tBoc method (t-butyloxycarbonyl method). Further, they can be synthesized by conventional methods using various commercially available peptide synthesizers. Further, the polypeptide of interest can be obtained by a known genetic engineering method wherein a polynucleotide encoding the above-described polypeptide is prepared and incorporated into an expression vector, which is then introduced into a host cell, in which the polypeptide is produced.

The polynucleotide encoding the above-described polypeptide can be easily prepared by a known genetic engineering method or a conventional method using a commercially available nucleic acid synthesizer. For example, DNA having the base sequence of SEQ ID NO:1, 15, 25, 27 or 38 can be prepared by carrying out PCR using the chromosomal DNA or a cDNA library of a dog as a template and using a pair of primers designed such that the primers can amplify the base sequence described in SEQ ID NO:1, 15, 25, 27 or 38, respectively. DNA having the base sequence of SEQ ID NO:3, 17, 29 or 40 can be prepared similarly by using as the above-described template the human chromosomal DNA or a cDNA library. Conditions for the PCR reaction can be selected as appropriate, and examples of the conditions include, but are not limited to, those wherein a cycle comprising the reaction steps of 94° C. for 30 seconds (denaturing), 55° C. for 30 seconds to 1 minute (annealing), and 72° C. for 2 minutes (extension) is repeated, for example, 30 times, followed by allowing the reaction to proceed at 72° C. for 7 minutes. Further, a desired DNA can be isolated by preparing an appropriate probe or primer based on the information of the base sequence and the amino acid sequence shown in SEQ ID NOs:1 to 4, 15 to 18, 25 to 30, 38 to 41 in SEQUENCE LISTING of the present specification and then using the probe or primer for screening of a cDNA library from a dog or a human. The cDNA library is preferably prepared from cells, an organ or a tissue expressing the protein of SEQ ID NO:2, 4, 16, 18, 26, 28, 30, 39 or 41. Operations such as the above-described preparation of a probe or a primer, construction of a cDNA library, screening of a cDNA library and cloning of a gene of interest are known to those skilled in the art, and can be carried out according to, for example, Molecular Cloning, 2nd Ed. or Current Protocols in Molecular Biology. From the thus obtained DNA, DNA encoding the above-described polypeptide (a) can be obtained. Further, since codons encoding each amino acid are known, the base sequence of a polynucleotide encoding a specific amino acid sequence can be easily specified. Therefore, the base sequences of polynucleotides encoding the above-described polypeptide (b) and polypeptide (c) can also be easily specified, so that such polynucleotides can also be easily synthesized using a commercially available nucleic acid synthesizer according to a conventional method.

The above-described host cells are not restricted as long as they can express the above-described polypeptide, and examples thereof include, but are not limited to, prokaryotic cells such as *E. coli*; and eukaryotic cells such as mammalian cultured cells including monkey kidney cells COS 1 and Chinese hamster ovary cells CHO, budding yeast, fission yeast, silkworm cells, and *Xenopus laevis* egg cells.

In cases where prokaryotic cells are used as the host cells, an expression vector having the origin that enables its replication in a prokaryotic cell, a promoter, a ribosome binding site, a DNA cloning site, a terminator and the like is used as the expression vector. Examples of the expression vector for *E. coli* include the pUC system, pBluescript II, pET expression system and pGEX expression system. By incorporating DNA encoding the above-described polypeptide into such an expression vector and transforming prokaryotic host cells with the vector, followed by culturing the obtained transformant, the polypeptide encoded by the above-described DNA can be expressed in the prokaryotic host cells. In this case, the polypeptide can also be expressed as a fusion protein with another protein.

In cases where eukaryotic cells are used as the host cells, an expression vector for eukaryotic cells having a promoter, splicing site, poly(A) addition site and the like is used as the expression vector. Examples of such an expression vector include pKA1, pCDM8, pSVK3, pMSG, pSVL, pBK-CMV, pBK-RSV, the EBV vector, pRS, pcDNA3, pMSG and pYES2. In the same manner as described above, by incorporating DNA encoding the above-described polypeptide into such an expression vector and transforming eukaryotic host cells with the vector, followed by culturing the obtained transformant, the polypeptide encoded by the above-described DNA can be expressed in the eukaryotic host cells. In cases where pIND/V5-His, pFLAG-CMV-2, pEGFP-N1 or pEGFP-C1 was used as the expression vector, the above-described polypeptide can be expressed as a fusion protein having various added tags such as His tag, FLAG tag, myc tag, HA tag or GFP.

Introduction of the expression vector to the host cells can be carried out using a well-known method such as electroporation, the calcium phosphate method, the liposome method or the DEAE dextran method.

Isolation and purification of a polypeptide of interest from the host cells can be carried out by a combination of known separation operations. Examples of the operations include, but are not limited to, treatment by a denaturant such as urea or by a surfactant; ultrasonication treatment; enzyme digestion; salting-out and solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method include, as mentioned above, those in the form of a fusion protein with another arbitrary protein. Examples thereof include fusion proteins with glutathion S-transferase (GST) and with a His tag. Such a polypeptide in the form of a fusion protein is also included within the scope of the present invention as the above-described polypeptide (c). Further, in some cases, a polypeptide expressed in a transformed cell is modified in various ways in the cell after translation thereof. Such a polypeptide having a post-translational modification is also included within the scope of the present invention as long as it has an immunity-inducing activity. Examples of such a post-translational modification include elimination of N-terminus methionine, N-terminus acetylation, glycosylation, limited degradation by an intracellular protease, myristoylation, isoprenylation and phosphorylation.

As described concretely in the following Examples, the above-described polypeptide having an immunity-inducing activity can cause regression of an already occurred tumor when administered to a cancer-bearing living body. Therefore, the immunity-inducing agent of the present invention can be used as a therapeutic and/or prophylactic agent for a cancer(s). In this case, cancers to be treated are those expressing the gene encoding the polypeptide of SEQ ID NO:2 or 4, and examples thereof include, but are not limited to, brain tumor; squamous cell carcinomas of head, neck, lung, uterus and esophagus; melanoma; adenocarcinomas of lung, breast and uterus; renal cancer; malignant mixed tumor; hepatocellular carcinoma; basal cell carcinoma; acanthomatous epulis; intraoral tumor; perianal adenocarcinoma; anal sac tumor; anal sac apocrine carcinoma; Sertoli cell tumor; vulva cancer; sebaceous adenocarcinoma; sebaceous epithelioma; sebaceous adenoma; sweat gland carcinoma; intranasal adenocarcinoma; nasal adenocarcinoma; thyroid cancer; colon cancer; bronchial adenocarcinoma; adenocarcinoma; ductal carcinoma; mammary adenocarcinoma; combined mammary adenocarcinoma; mammary gland malignant mixed tumor; intraductal papillary adenocarcinoma; fibrosarcoma; hemangiopericytoma; osteosarcoma; chondrosarcoma; soft tissue sarcoma; histiocytic sarcoma; myxosarcoma; undifferentiated sarcoma; lung cancer; mastocytoma; cutaneous leiomyoma; intra-abdominal leiomyoma; leiomyoma; chronic lymphocytic leukemia; lymphoma; gastrointestinal lymphoma; digestive organ lymphoma; small cell or medium cell lymphoma; adrenomedullary tumor; granulosa cell tumor; pheochromocytoma; bladder cancer (transitional cell carcinoma); suppurative inflammation; intra-abdominal liver tumor; liver cancer; plasmacytoma; malignant hemangiopericytoma; angiosarcoma; anal sac adenocarcinoma; oral cancer; metastatic malignant melanoma; amelanotic malignant melanoma; cutaneous malignant melanoma; malignant myoepithelioma; malignant seminoma; seminoma; adenocarcinoma of the large intestine; gastric adenocarcinoma; low-grade sebaceous carcinoma; ceruminous adenocarcinoma; apocrine carcinoma; poorly differentiated apocrine sweat gland carcinoma; malignant fibrous histiocytoma; multiple myeloma; mesenchymal malignant tumor; liposarcoma; osteosarcoma; sarcoma of unknown origin; soft part sarcoma (spindle cell tumor); poorly differentiated sarcoma; synovial sarcoma; angiosarcoma; metastatic malignant epithelioma; tubular mammary adenocarcinoma; mammary ductal carcinoma; inflammatory breast cancer; germinoma; leukemia; invasive trichoepithelioma; medium cell lymphoma; multicentric lymphoma; osteosarcoma (mammary gland); mastocytoma (Patnaik II type); mastocytoma (Grade II); and leiomyosarcoma. The animals to be treated are mammals, especially preferably humans, dogs and cats.

The administration route of the immunity-inducing agent of the present invention to a living body may be either oral administration or parenteral administration, and is preferably parenteral administration such as intramuscular administration, subcutaneous administration, intravenous administration or intraarterial administration. In cases where the immunity-inducing agent is used for therapy of a cancer, it may be administered to a regional lymph node in the vicinity of the tumor to be treated, as described in the Examples below, in order to enhance its anticancer activity. The dose may be any dose as long as the dose is effective for immune induction, and in cases where the agent is used for therapy and/or prophylaxis of a cancer, the dose may be one effective for therapy and/or prophylaxis of the cancer. The dose effective for therapy and/or prophylaxis of a cancer is appropriately selected depending on the size of the tumor, the symptom and the like, and usually, 0.000 µg to 1000 µg, preferably 0.00 µg to 1000 µg of the agent in terms of the effective ingredient may be administered once or in several times per day per animal to be treated. The agent is preferably administered in several times, every several days to several months. As concretely shown in the Examples below, the immunity-inducing agent of the present invention can cause regression of an already occurred tumor. Therefore, since the agent can exert its anticancer activity also against a small number of cancer cells in the early stage, development or recurrence of the cancer can be prevented by using the agent before development of a cancer or after therapy for a cancer. That is, the immunity-inducing agent of the present invention is effective for both therapy and prophylaxis of a cancer.

The immunity-inducing agent of the present invention may contain only a polypeptide or may be formulated by mixing as appropriate with an additive such as a pharmaceutically acceptable carrier, diluent or vehicle suitable for each administration mode. Formulation methods and additives which may be used are well-known in the field of formulation of pharmaceuticals, and any of the methods and additives may be used. Specific examples of the additive include, but are not limited to, diluents such as physiological buffer solutions; vehicles such as sucrose, lactose, corn starch, calcium phosphate, sorbitol and glycine; binders such as syrup, gelatin, gum arabic, sorbitol, polyvinyl chloride and tragacanth; and lubricants such as magnesium stearate, polyethylene glycol, talc and silica. Examples of the formulation include oral preparations such as tablets, capsules, granules, powders and syrups; and parenteral preparations such as inhalants, injection solutions, suppositories and solutions. These formulations may be prepared by commonly known production methods.

The immunity-inducing agent of the present invention may be used in combination with an immunoenhancer capable of enhancing the immune response in a living body. The immunoenhancer may be contained in the immunity-inducing agent of the present invention or administered as a separate composition to a patient in combination with the immunity-inducing agent of the present invention.

Examples of the above-described immunoenhancer include adjuvants. Adjuvants can enhance the immune response by providing a reservoir of antigen (extracellularly or within macrophages), activating macrophages and stimulating specific sets of lymphocytes, thereby enhancing the anticancer activity. Therefore, especially in cases where the immunity-inducing agent of the present invention is used for therapy and/or prophylaxis of a cancer, the immunity-inducing agent preferably comprises an adjuvant, in addition to the above-described polypeptide as an effective ingredient. Many types of adjuvants are well-known in the art, and any of these adjuvants may be used. Specific examples of the adjuvants include MPL (SmithKline Beecham) and homologues of *Salmonella minnesota* Re 595 lipopolysaccharide obtained after purification and acid hydrolysis of the lipopolysaccharide; QS21 (SmithKline Beecham), pure Q-21 saponin purified from extract of *Quillja saponaria*; DQS21 described in WO96/33739 (SmithKline Beecham); QS-7, QS-17, QS-18 and QS-L1 (So and 10 others, "Molecules and cells", 1997, Vol. 7, p. 178-186); Freund's incomplete adjuvant; Freund's complete adjuvant; vitamin E; Montanide; alum; CpG oligonucleotides (see, for example, Kreig and 7 others, "Nature", Vol. 374, p. 546-549); poly-I:C and derivatives thereof (e.g., poly ICLC); and various water in oil emulsions prepared from biodegradable oils such as squalene and/or tocopherol. Among these, Freund's incomplete adjuvant; Montanide; poly-I:C and derivatives thereof, and CpG oligonucleotides are preferred. The mixing ratio between the above-described adjuvant and polypeptide is typically about 1:10 to 10:1, preferably about 1:5 to 5:1, more preferably about 1:1. However, the adjuvant is not limited to the above-described examples, and adjuvants known in the art other than the above-described ones (for example, see Goding, "Monoclonal Antibodies: Principles and Practice", 2nd edition, 1986) may be used when the immunity-inducing agent of the present invention is administered. Preparation methods for mixtures or emulsions of a polypeptide and an adjuvant are well-known to those skilled in the art of vaccination.

Further, in addition to the above-described adjuvants, factors that stimulate the immune response of the subject may be used as the above-described immunoenhancer. For example, various cytokines having a property to stimulate lymphocytes and/or antigen-presenting cells may be used as the immunoenhancer in combination with the immunity-inducing agent of the present invention. A number of such cytokines capable of enhancing the immune response are known to those skilled in the art, and examples thereof include, but are not limited to, interleukin-12 (IL-12), GM-CSF, IL-18, interferon-α, interferon-β, interferon-ω, interferon-γ, and Flt3 ligand, which have been shown to promote the prophylactic action of vaccines. Such factors may also be used as the above-described immunoenhancer, and can be contained in the immunity-inducing agent of the present invention, or can be prepared as a separate composition to be administered to a patient in combination with the immunity-inducing agent of the present invention.

Further, by bringing the above-described polypeptide into contact with antigen-presenting cells in vitro, the antigen-presenting cells can be made to present the polypeptide. That is, the above-described polypeptides (a) to (c) can be used as agents for treating antigen-presenting cells. As the antigen-presenting cells, dendritic cells or B cells, which have MHC class I molecules, may preferably be employed. Various MHC class I molecules have been identified and well-known. MHC molecules in human are called HLA. Examples of HLA class I molecules include HL-A, HL-B and HL-C, more specifically, HL-A1, HL-A0201, HL-A0204, HL-A0205, HL-A0206, HL-A0207, HL-A11, HL-A24, HL-A31, HL-A6801, HL-B7, HL-B8, HL-B2705, HL-B37, HL-Cw0401 and HL-Cw0602.

The dendritic cells or B cells having MHC class I molecules can be prepared from peripheral blood by a well-known method. For example, tumor-specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-related peptide to the culture system. By administering an effective amount of such dendritic cells, a response desired for therapy of a cancer can be induced. As the cells to be used, bone marrow or umbilical cord blood donated by a healthy individual, or bone marrow, peripheral blood or the like from the patient himself may be used. When autologous cells of the patient are used, high safety can be attained and serious side effects are expected to be avoided. The peripheral blood or bone marrow may be a fresh sample, cold-stored sample or frozen sample. As for the peripheral blood, whole blood may be cultured or the leukocyte components alone may be separated and cultured, and the latter is efficient and thus preferred. Further, among the leukocyte components, mononuclear cells may be separated. In cases where the cells are originated from bone marrow or umbilical cord blood, the whole cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are originated, and also CD4-positive cells and the like. As for the cytokine to be used, the production method thereof is not restricted and naturally-occurring or recombinant cytokine or the like may be employed as long as its safety and physiological activity have been confirmed. Preferably, a preparation with assured quality for medical use is used in a minimum necessary amount. The concentration of the cytokine(s) to be added is not restricted as long as the dendritic cells are induced, and usually, the total concentration of the cytokine(s) is preferably about 10 to 1000 ng/mL, more preferably about 20 to 500 ng/mL. The culture may be carried out using a well-known medium usually used for the culture of leukocytes. The culturing temperature is not restricted as long as the proliferation of the leukocytes is attained, and about 37° C. which is the body temperature of human is most preferred. The atmospheric environment during the culturing is not restricted as long as the proliferation of the leukocytes is attained, and to flow 5% $CO_2$ is preferred. The culturing period is not restricted as long as the necessary number of the cells is induced, and is usually 3 days to 2 weeks. As for the apparatuses used for separation and culturing of the cells, appropriate apparatuses, preferably those whose safety when applied to medical uses have been confirmed, and whose operations are stable and simple, may be employed. Particularly, as for the cell-culturing apparatus, not only the general vessels such as a Petri dish, flask and bottle, but also a layer type vessel, multistage vessel, roller bottle, spinner type bottle, bag type culturing vessel, hollow fiber column and the like may be used.

Bringing the above-described peptide of the present invention into contact with the antigen presenting cells in vitro may be carried out by a well-known method. For example, it may be carried out by culturing the antigen-presenting cells in a culture medium containing the above-described polypeptide. The concentration of the peptide in the medium is not restricted, and usually about 1 μg/ml to 100 μg/ml, preferably about 5 μg/ml to 20 μg/ml. The cell density during the culturing is not restricted and is usually about $10^3$ cells/ml to $10^7$ cells/ml, preferably about $5 \times 10^4$ cells/ml to $5 \times 10^6$ cells/ml. The culturing may be carried out according to a conventional method, and is preferably carried out at 37° C. under atmosphere of 5% $CO_2$. The maximum length of the peptide which can be presented on the surface of the antigen-presenting cells is usually about 30 amino acid residues. Therefore, in cases where the antigen-presenting cells are brought into contact with the polypeptide in vitro, the polypeptide may be prepared such that its length is not more than about 30 amino acid residues.

By culturing the antigen-presenting cells in the coexistence of the above-described polypeptide, the polypeptide is incorporated into MHC molecules of the antigen-presenting cells and presented on the surface of the antigen-presenting cells. Therefore, using the above-described polypeptide, isolated antigen-presenting cells containing the complex between the polypeptide and the MHC molecule can be prepared. Such antigen-presenting cells can present the polypeptide against T cells in vivo or in vitro, and induce, and allow proliferation of, cytotoxic T cells specific to the polypeptide.

By bringing the antigen-presenting cells prepared as described above having the complex between the above-described polypeptide and the MHC molecule into contact with T cells in vitro, cytotoxic T cells specific to the polypeptide can be induced and allowed to proliferate. This may be carried out by cocultivating the above-described antigen-presenting cells and T cells in a liquid medium. For example, it may be attained by suspending the antigen-presenting cells in a liquid medium, placing the suspension in vessels such as wells of a microplate, adding thereto T cells and then culturing the cells. The mixing ratio of the antigen-presenting cells to the T cells in the cocultivation is not restricted, and is usually about 1:1 to 1:100, preferably about 1:5 to 1:20 in terms of the number of cells. The density of the antigen-presenting cells suspended in the liquid medium is not restricted, and is usually about 100 to 10,000,000 cells/ml, preferably about 10,000 to 1,000,000 cells/ml. The cocultivation is preferably carried out at 37° C. under atmosphere of 5% $CO_2$ in accordance with a conventional method. The culturing time is not restricted, and is usually 2 days to 3 weeks, preferably about 4 days to 2 weeks. The cocultivation is preferably carried out in the presence of one or more interleukins such as IL-2, IL-6, IL-7 and IL-12. In this case, the concentration of IL-2 and IL-7 is usually about 5 U/ml to 20 U/ml, the concentration of IL-6 is usually about 500 U/ml to 2000 U/ml, and the concentration of IL-12 is usually about 5 ng/ml to 20 ng/ml, but the concentrations of the interleukins are not restricted thereto. The above-described cocultivation may be repeated once to several times adding fresh antigen-presenting cells. For example, the operation of discarding the culture supernatant after the cocultivation and adding a fresh suspension of antigen-presenting cells to further conduct the cocultivation may be repeated once to several times. The conditions of the each cocultivation may be the same as described above.

By the above-described cocultivation, cytotoxic T cells specific to the polypeptide are induced and allowed to proliferate. Thus, using the above-described polypeptide, isolated T cells can be prepared which selectively bind the complex between the polypeptide and the MHC molecule.

As described in the Examples below, the genes encoding the polypeptides of SEQ ID NOs:2, 16, 26, 28 and 39 and SEQ ID NOs:4, 18, 30 and 41 are expressed specifically in cancer cells and testis of dogs and humans, respectively. Thus, in cancer cells, significantly higher numbers of the polypeptides of SEQ ID NOs:2, 16, 26, 28 and 39 or SEQ ID NOs:4, 18, 30 and 41 exist than in normal cells. When cytotoxic T cells prepared as described above are administered to a living body while a part of the polypeptides existing in cancer cells are presented by MHC molecules on the surfaces of the cancer cells, the cytotoxic T cells can damage the cancer cells using the presented polypeptides as markers. Since antigen-presenting cells presenting the above-described polypeptides can induce, and allow proliferation of, cytotoxic T cells specific to the polypeptides also in vivo, cancer cells can be damaged also by administering the antigen-presenting cells to a living body. That is, the above-described cytotoxic T cells and the above-described antigen-presenting cells prepared using the above-described polypeptide are also effective as therapeutic and/or prophylactic agents for a cancer(s).

In cases where the above-described isolated antigen-presenting cells or isolated T cells are administered to a living body, these are preferably prepared by treating antigen presenting cells or T cells collected from the patient to be treated with the polypeptide (a) to (c) as described above in order to avoid the immune response in the living body that attacks these cells as foreign bodies.

The therapeutic and/or prophylactic agent for a cancer(s) comprising as an effective ingredient the antigen-presenting cells or T cells is preferably administered via a parenteral administration route such as intravenous or intraarterial administration. The dose is appropriately selected depending on the symptom, the purpose of administration and the like, and is usually 1 cell to 10,000,000,000,000 cells, preferably 1,000,000 cells to 1,000,000,000 cells, which dose is preferably administered once per several days to once per several months. The formulation may be, for example, the cells suspended in physiological buffered saline, and the formulation may be used in combination with another/other anticancer preparation(s) and/or cytokine(s). Further, one or more additives well-known in the field of formulation of pharmaceuticals may also be added.

Also by expression of the polynucleotide encoding the above-described polypeptide (a) to (c) in the body of the animal to be treated, antibody production and cytotoxic T cells can be induced in the living body, and an effect comparable to the administration of a polypeptide can be obtained. That is, the immunity-inducing agent of the present invention may be one comprising as an effective ingredient a recombinant vector having a polynucleotide encoding the above-described polypeptide (a) to (c), which recombinant vector is capable of expressing the polypeptide in a living body. Such a recombinant vector capable of expressing an antigenic polypeptide is also called gene vaccine. The vector used for production of a gene vaccine is not restricted as long as it is a vector capable of expressing a polypeptide in cells of the animal to be treated (preferably in a mammalian cell), and may be either a plasmid vector or a virus vector, and any known vector in the field of gene vaccines may be used. The polynucleotide such as DNA or RNA encoding the above-described polypeptide can be easily prepared, as mentioned above, by a conventional method. Incorporation of the polynucleotide into a vector can be carried out using a method well-known to those skilled in the art.

The administration route of the gene vaccine is preferably a parenteral route such as intramuscular, subcutaneous, intravenous or intraarterial administration, and the dose may be appropriately selected depending on the type of the antigen and the like, and usually about 0.1 µg to 100 mg, preferably about 1 µg to 10 mg in terms of the weight of the gene vaccine per 1 kg of body weight.

Methods using a virus vector include those wherein a polynucleotide encoding the above-described polypeptide is incorporated into an RNA virus or DNA virus such as retrovirus, adenovirus, adeno-associated virus, herpes virus, vaccinia virus, pox virus, poliovirus or Sindbis virus, and then the animal to be treated is infected by the resulting virus. Among these methods, those using retrovirus, adenovirus, adeno-associated virus, vaccinia virus or the like are especially preferred.

Other methods include a method wherein an expression plasmid is directly intramuscularly administered (DNA vaccine method), the liposome method, lipofectin method, microinjection method, calcium phosphate method, electroporation method and the like, and the DNA vaccine method and liposome method are especially preferred.

Methods for actually making the gene encoding the above-described polypeptide of the present invention act as a pharmaceutical include the in vivo method wherein the gene is directly introduced into the body, and the ex vivo method wherein a kind of cells are collected from the animal to be treated, the gene is introduced into the cells ex vivo, and then the cells are returned to the body (Nikkei Science, 1994, April, p. 20-45; The Pharmaceutical Monthly, 1994, Vol. 36, No. 1, p. 23-48; Experimental Medicine, Extra Edition, 1994, Vol. 12, No. 15; and references cited in these papers and the like). The in vivo method is more preferred.

In cases where the gene is administered by the in vivo method, the gene may be administered through an appropriate administration route depending on the disease to be treated, symptom and so on. It may be administered, for example, by intravenous, intraarterial, subcutaneous, intramuscular administration or the like. In cases where the gene is administered by the in vivo method, the gene may be formulated into a preparation such as a solution, and in general, it is formulated into an injection solution or the like containing the DNA encoding the above-described peptide of the present invention as an effective ingredient. A commonly used carrier(s) may be added as required. In the case of a liposome or membrane fusion liposome (Sendai virus (HVJ)-liposome or the like) containing the DNA, the liposome may be formulated into a liposome preparation such as a suspension, frozen preparation or centrifugally concentrated frozen preparation.

In the present invention, "the base sequence shown in SEQ ID NO:1" includes not only the base sequence expressly written in SEQ ID NO:1, but also the sequence complementary thereto. Thus, "a polynucleotide having the base sequence shown in SEQ ID NO:1" includes a single-stranded polynucleotide having the base sequence expressly written in SEQ ID NO:1, a single-stranded polynucleotide having the base sequence complementary thereto, and a double-stranded polynucleotide composed of these single strand polynucleotides. When the polynucleotide encoding the polypeptide used in the present invention is prepared, any one of these base sequences should be appropriately selected, and those skilled in the art can easily carry out the selection.

EXAMPLES

The present invention will now be described more concretely by way of Examples.

Example A-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 µg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3 \times 10^6$ pfu/ml.

(2) Screening of cDNA Library with Serum

Using the dog testis-derived cDNA phage library prepared as described above, immunoscreening was carried out. More particularly, host E. coli cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking it at 4° C. overnight to suppress non-specific reactions. This filter was allowed to react with 500-fold diluted canine patient serum at room temperature for 2 to 3 hours.

As the above-described canine patient serum, serum collected from canine patients suffering from squamous cell carcinoma was used. The serum was stored at −80° C. and pretreated immediately before use. The method of the pretreatment of the serum was as follows. That is, host E. coli cells (XL1-Blue MRF') were infected with λZAP Express phage to which no foreign gene was inserted, and then cultured on NZY plate medium at 37° C. overnight. Subsequently, the buffer of 0.2 M NaHCO$_3$, pH 8.3 containing 0.5 M NaCl was added to the plate, and the plate was left to stand at 4° C. for 15 hours, followed by collecting the supernatant as an E. coli/phage extract. Thereafter, the collected E. coli/phage extract was allowed to flow through an NHS column (manufactured by GE Healthcare Bio-Science) to immobilize proteins derived from the E. coli/phage thereon. The serum from the canine patients was allowed to flow through and react with this protein-immobilized column to remove antibodies adsorbed on E. coli and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+l HRP conjugated: manufactured by BETHYL Laboratories) 5000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 µl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 µl of a solution prepared to contain a host E. coli (XL1-Blue MRF') such that the absorbance OD$_{600}$ should be 1.0 was mixed with 100 µl of a purified phage solution and further with 1 µl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 µl of a solution prepared to contain a phagemid host E. coli (SOLR) such that the absorbance OD$_{600}$ should be 1.0 was mixed with 10 µl of a purified phage solution, and the reaction was allowed to proceed at 37° C. for 15 minutes. Thereafter, 50 µl of the reaction mixture was plated on ampicillin (final concentration: 50 µg/ml)-containing LB agar medium, and cultured at 37° C. overnight. A single colony of transformed SOLR was recovered and cultured in ampicillin (final concentration: 50 µg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:1 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the gene (Accession No. XM_535343) encoding a protein (Accession No. XP_535343) whose function is unknown. The human homologous factor of this gene was the gene (Accession No. NM_152660) encoding a protein (Accession No. NP_689873) whose function is also unknown (homology: base sequence, 93%; amino acid sequence, 99%). The base sequence of the human homologous factor is shown in SEQ ID NO:3, and the amino acid sequence thereof is shown in SEQ ID NO:4.

(4) Analysis of Expression in Each Tissue

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to 10×10⁶ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:7 and 8) specific to the obtained canine gene and its human homologous gene. That is, respective reagents and the attached buffer were mixed such that the mixture should contain 0.25 µl of the sample prepared by the reverse transcription reaction, 2 µM each of the above primers, 0.2 mM each of dNTP and 0.65 U of ExTaq polymerase (manufactured by Takara Shuzo Co., Ltd.) in a total volume of 25 µl, and the reaction was carried out with 30 cycles of 94° C. for 30 seconds, 55° C. for 30 seconds and 72° C. for 1 minute using Thermal Cycler (manufactured by BIO RAD). The gene-specific primers having the base sequences shown in the above-described SEQ ID NOs:7 and 8 were those which amplify the regions of the 87th to 606th bases of the base sequence of SEQ ID NO:1 and the 173rd to 695th bases of the base sequence of SEQ ID NO:3, and can be used for investigation of the expression of both the canine gene and its human homologous gene. As a control for comparison, primers (described in SEQ ID NOs:9 and 10) specific to GAPDH were used simultaneously. As a result, as shown in FIG. 1, strong expression of the obtained canine gene was observed in testis among the normal dog tissues, and on the other hand, strong expression was observed in the canine breast cancer cell line. Expression of the human homologous gene was confirmed, as is the case with the canine gene, only in testis among the human normal tissues, but the expression was detected in brain tumor, leukemia, breast cancer and lung cancer cells among human cancer cell lines. Thus, the human homologous gene was also confirmed to be specifically expressed in testis and cancer cells.

In FIG. 1, reference numeral 1 in the ordinate indicates the expression pattern of the above identified gene, and reference numeral 2 indicates the expression pattern of the GAPDH gene as a control for comparison.

Example A-2

Preparation of Novel Cancer Antigen Proteins (1) Preparation of Recombinant Protein Based on the gene of SEQ ID NO:1 obtained in Example A-1, a recombinant protein was prepared by the following method. Respective reagents and the attached buffer were mixed such that the mixture should contain 1 µl of the vector which was prepared from the phagemid solution obtained in Example A-1 and was subjected to the sequence analysis, 0.4 µM each of two kinds of primers having NdeI and XhoI restriction sites (described in SEQ ID NOs:11 and 12), 0.2 mM dNTP and 1.25 U of PrimeSTAR HS polymerase (manufactured by Takara Shuzo Co., Ltd.) in a total volume of 50 µl and PCR was carried out with 30 cycles of 98° C. for 10 seconds, 55° C. for 15 seconds and 72° C. for 1 minute using Thermal Cycler (manufactured by BIO RAD). The above-described two kinds of primers were those which amplify the region encoding the entire amino acid sequence of SEQ ID NO:2. After the PCR, the amplified DNA was subjected to electrophoresis using 1% agarose gel, and a DNA fragment of about 930 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes NdeI and XhoI and purified using QIAquick Gel Extraction Kit, followed by inserting the gene sequence of interest into an expression vector for *E. coli*, pET16b (manufactured by Novagen) that had been treated with NdeI and XhoI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

On the other hand, based on the gene of SEQ ID NO:3, a recombinant protein of the human homologous gene was prepared by the following method. Respective reagents and the attached buffer were mixed such that the mixture should contain 1 µl of the cDNA prepared in Example A-1 whose expression could be confirmed by the RT-PCR method in various tissues/cells, 0.4 µM each of two kinds of primers having EcoRV and EcoRI restriction sites (described in SEQ ID NOs:13 and 14), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 15 seconds and 72° C. for 1 minute using Thermal Cycler (manufactured by BIO RAD). The above-described two kinds of primers were those which amplify the region encoding the entire amino acid sequence of SEQ ID NO:4. After the PCR, the amplified DNA was subjected to electrophoresis using 1% agarose gel, and a DNA fragment of about 930 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes EcoRV and EcoRI and purified using QIAquick Gel Extraction Kit, followed by inserting the gene sequence of interest into an expression vector for *E. coli*, pET30a (manufactured by Novagen) that had been treated with EcoRV and EcoRI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:1 and SEQ ID NO:3, respectively, were cultured in 100 µg/ml ampicillin-containing LB medium at 37° C. until the absorbance at 600 nm reached about 0.7, and then isopropyl-β-D-1-thiogalactopyranoside was added thereto such that its final concentration should be 1 mM, followed by culturing them at 37° C. for 4 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The cells were suspended in 50 mM Tris-HCl buffer (pH 8.0) and subjected to sonication on ice. The sonicated solution of *E. coli* was centrifuged at 6,000 rpm for 20 minutes to obtain the supernatant as the soluble fraction and the precipitate as the insoluble fraction.

The insoluble fraction was suspended in 50 mM Tris-HCl buffer (pH 8.0) and centrifuged at 6,000 rpm for 15 minutes. This operation was repeated twice and an operation of removal of proteases was carried out.

The residue was suspended in 6M guanidine hydrochloride, 0.15 M sodium chloride-containing 50 mM Tris-HCl buffer (pH 8.0), and the resulting suspension was left to stand at 4° C. for 20 hours to denature proteins. Thereafter, the suspension was centrifuged at 6,000 rpm for 30 minutes, and the obtained soluble fraction was placed in a nickel chelate column prepared by a conventional method (carrier: Chelating Sepharose (trademark) Fast Flow (GE Health Care); column volume: 5 mL; equilibration buffer: 6M guanidine hydrochloride, 0.15 M sodium chloride-containing 50 mM Tris-HCl buffer (pH 8.0)), followed by leaving it to stand at 4° C. overnight to allow adsorption to the nickel-chelated carrier. The supernatant was recovered by centrifugation of this column carrier at 1,500 rpm for 5 minutes, and the column carrier was suspended in phosphate-buffered saline, followed by refilling the column with the resulting suspension.

Figure 2:
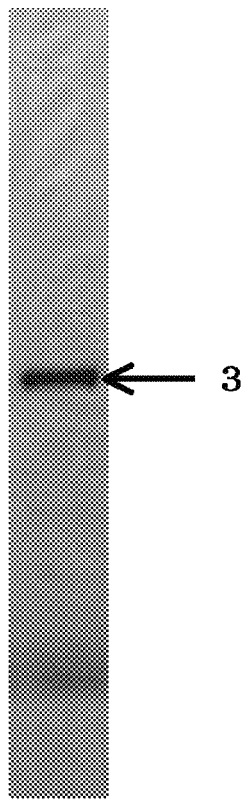
FIG. 2 shows the detection by Coomassie staining of the canine-derived protein produced in E. coli and purified in Example A, which protein was identified in the present invention. Reference numeral 3: the band for the canine-derived protein of the present invention.

The fraction that was not adsorbed to the column was washed away with 10 column volumes of 0.5 M sodium chloride-containing 0.1 M acetate buffer (pH 4.0), and elution was immediately carried out with 0.5 M sodium chloride-containing 0.1 M acetate buffer (pH 3.0) to obtain a purified fraction, which was used as the material for administration tests thereafter. The proteins of interest in respective eluted fractions were confirmed by Coomassie staining carried out according to a conventional method. Among these, the canine protein of interest is shown in FIG. 2.

The buffer contained in the purified preparation obtained by the above-described method was replaced with a reaction buffer (50 mM Tris-HCl, 100 mM NaCl, 5 mM $CaCl_2$; pH8.0), and cleavage of His tag by Factor Xa protease and purification of the protein of interest were carried out, using Factor Xa Cleavage Capture Kit (manufactured by Novagen), in accordance with the protocols attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 µm (manufactured by PALL) and used in the following experiments.

Example A-3

Test of Administration of Recombinant Protein to Cancer-Bearing Dogs (1) Antitumor Assay The anti-tumor effect of the two kinds of recombinant proteins which were purified as described above was assessed in two individuals of cancer-bearing dogs having epidermal tumor (2 individuals having mammary gland tumor).

An equal amount of Freund's incomplete adjuvant (manufactured by Wako Pure Chemicals) was mixed with 100 µg (0.5 ml) of the recombinant polypeptides (derived from dog and human), respectively, to prepare two kinds of therapeutic agents for a cancer(s). Each of these agents was administered to a regional lymph node in the vicinity of the tumor a total of 3 times, by carrying out the subsequent administrations 3 days and 7 days after the first administration. As a result, the tumors with a size of about 25 $mm^3$ and 50 $mm^3$ at the time of administration of the therapeutic agents for a cancer(s) (derived from dog and human), respectively, were reduced in size to 20 $mm^3$ and 42 $mm^3$, respectively, 10 days after the first administration; 13 $mm^3$ and 26 $mm^3$, respectively, 20 days after the first administration; and to 5 $mm^3$ and 10 $mm^3$, respectively, 30 days after the first administration.

Further, to a canine patient suffering from malignant melanoma, a mixture of 100 µg (0.5 ml) of the above-described polypeptide derived from dog and 0.5 ml of Freund's incomplete adjuvant was administered intracutaneously at the periphery of the tumor a total of 3 times at the same intervals as described above. Further, concurrently with the respective administrations, 10 MU of "Intercat" which is a recombinant feline interferon was administered subcutaneously. As a result, the tumor with a size of about 142 $mm^3$ at the time of administration of the therapeutic agent for a cancer(s) completely regressed 29 days after the first administration.

Further, to a canine patient suffering from nasal adenocarcinoma, a mixture of 100 µg (0.5 ml) of the above-described polypeptide derived from dog and 0.5 ml of Freund's incomplete adjuvant was administered in the same manner as described above a total of 3 times. Further, concurrently with the respective administrations, 100 µg of canine interleukin 12 was administered subcutaneously. As a result, the tumor with a size of about 57 $mm^3$ at the time of administration of the therapeutic agent for a cancer(s) completely regressed 14 days after the first administration.

(2) Immune Inducibility Assay

Blood from the canine patient in which the anti-tumor effect was obtained in the administration test in the above-described (1) was collected before administration of the therapeutic agent for a cancer(s), and 10 days and 30 days after the first administration. Peripheral blood mononuclear cells were isolated according to a conventional method, and by the ELISPOT assay for IFNγ using it, the immune inducibility of each administered recombinant protein was assayed.

In a 96-well plate manufactured by Millipore (Multi-Screen-IP, MAIPS 4510), 100 µL/well of 70% ethanol was placed and the plate was left to stand for 5 minutes, followed by removal of the ethanol by aspiration. The plate was washed with sterile water and 300 µl/well of 200 mM Sodium Bicarbonate (pH8.2) was placed therein. After leaving it to stand for 5 minutes, Sodium Bicarbonate was removed by aspiration, and then the plate was washed. Subsequently, 0.5 µl/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 µL/well of a blocking solution (1% BS-5% sucrose-200 mM Sodium Bicarbonate (pH8.2)) was added to the wells, and the plate was incubated at 4° C. overnight to block the plate. After removal of the blocking solution by aspiration, 300 µL/well of 10% fetal calf serum-containing RPMI medium (manufactured by Invitrogen) was placed in the wells, and the plate was left to stand for 5 minutes, followed by removal of the medium by aspiration. Subsequently, 5×10⁵ cells/well of the canine peripheral blood mononuclear cells suspended in 10% fetal calf serum-containing RPMI medium were placed in the plate, and 10 µL/well of the canine-derived polypeptide or human-derived polypeptide used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 µL of rabbit antidog polyclonal antibody 1000-fold diluted with the abovedescribed blocking solution was placed, and the plate was incubated at 4° C. overnight. After washing the wells 3 times with the above-described washing solution, 100 µL of HRP-labeled anti-rabbit antibody 1000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and the number of the appeared spots was counted using KS ELISPOT (manufactured by Carl Zeiss, Inc.).

As a result, in either canine patient to which the canine polypeptide or the human polypeptide was administered, peripheral blood mononuclear cells sampled before the administration of the polypeptide showed no spots. On the other hand, in the canine patient to which the canine polypeptide was administered, peripheral blood mononuclear cells sampled 10 days and 30 days after the administration showed 20 and 36 spots, respectively. In the canine patient to which the human polypeptide was administered, peripheral blood mononuclear cells sampled 10 days and 30 days after the administration showed 24 and 36 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in (1) was exerted by immunoreactions in which these immunocytes are mainly involved.

Example B-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 µg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was 1.3×10⁶ pfu/ml.

(2) Screening of cDNA Library with Serum

Using the dog testis-derived cDNA phage library prepared as described above, immunoscreening was carried out. More particularly, host *E. coli* cells (XL1-Blue MRF) were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking at 4° C. overnight to suppress non-specific reactions. This filter was allowed to react with 500-fold diluted canine patient serum at room temperature for 2 to 3 hours.

As the above-described canine patient serum, serum collected from canine patients suffering from tumor proximal to the anus was used. The serum was stored at −80° C. and pretreated immediately before use. The method of the pretreatment of the serum was as follows. That is, host *E. coli* cells (XL1-Blue MRF') were infected with λZAP Express phage to which no foreign gene was inserted, and then cultured on NZY plate medium at 37° C. overnight. Subsequently, the buffer of 0.2 M NaHCO₃, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+I HRP conjugated: manufactured by BETHYL Laboratories) 5000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 µl of SM buffer (100 mM NaCl, 10 mM MgClSO₄, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 µl of a solution prepared to contain a host *E. coli* (XL1-Blue MRF') such that the absorbance $OD_{600}$ should be 1.0 was mixed with 100 µl of a purified phage solution and further with 1 µl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 µl of a solution prepared to contain a phagemid host *E. coli* (SOLR) such that the absorbance $OD_{600}$ should be 1.0 was mixed with 10 µl of a purified phage solution, and the reaction was allowed to proceed at 37° C. for 15 minutes. Thereafter, 50 µl of the reaction mixture was plated on ampicillin (final concentration: 50 µg/ml)-containing LB agar medium, and cultured at 37° C. overnight. A single colony of transformed SOLR was recovered and cultured in ampicillin (final concentration: 50 µg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:15 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the calmegin gene. The human homologous factor of the canine calmegin gene was human calmegin (homology: base sequence, 90%; amino acid sequence, 89%). The base sequence of human calmegin is shown in SEQ ID NO:17, and the amino acid sequence thereof is shown in SEQ ID NO:18.

(4) Analysis of Expression in Each Tissue

Figure 3:
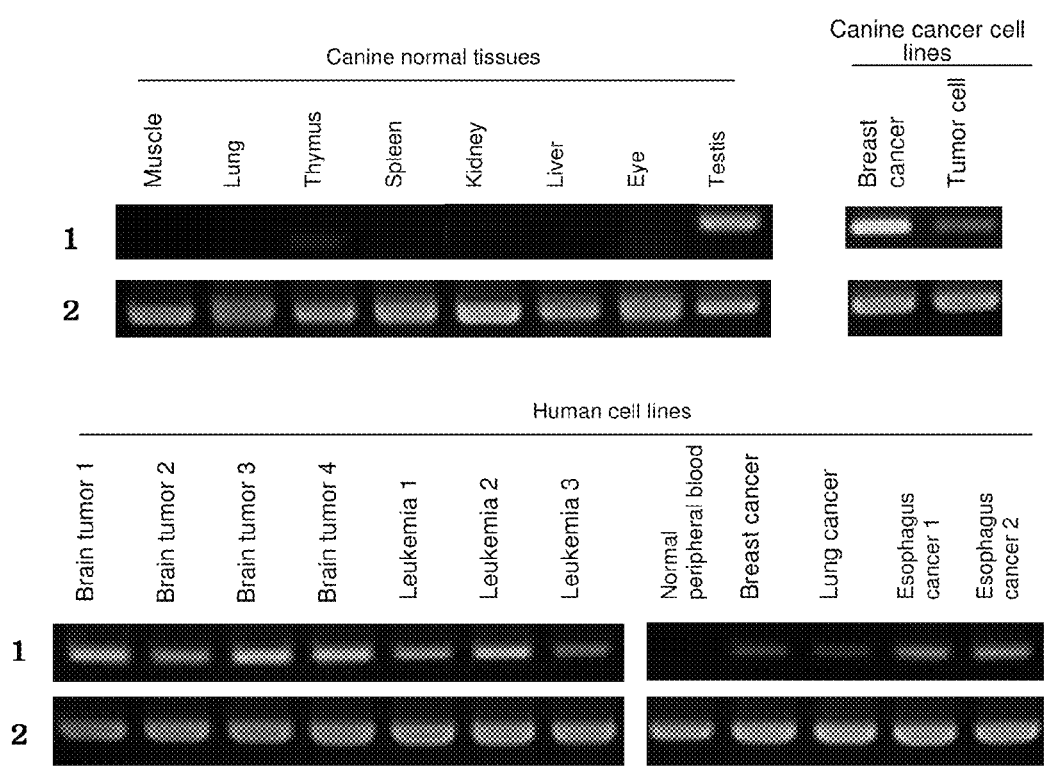
FIG. 3 shows the expression pattern of the calmegin gene identified in the present invention in normal tissues and tumor cell lines. Reference numeral 1: the expression pattern of the calmegin gene; Reference numeral 2: the expression pattern of the GAPDH gene.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to $10 \times 10^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:19 and 20) specific to the obtained gene. That is, respective reagents and the attached buffer were mixed such that the mixture should contain 0.25 µl of the sample prepared by the reverse transcription reaction, 2 µM each of the above primers, 0.2 mM each of dNTP and 0.65 U of ExTaq polymerase (manufactured by Takara Shuzo Co., Ltd.) in a total volume of 25 µl, and the reaction was carried out with 30 cycles of 94° C. for 30 seconds, 55° C. for 30 seconds and 72° C. for 1 minute using Thermal Cycler (manufactured by BIO RAD). The above-described gene-specific primers were those which amplify the regions of the 755th to 1318th bases of the base sequence of SEQ ID NO:15 (canine calmegin gene) and the 795th to 1358th bases of the base sequence of SEQ ID NO:17 (human calmegin gene), and can be used for investigation of the expression of both the canine calmegin gene and the human calmegin gene. As a control for comparison, primers (described in SEQ ID NOs:9 and 10) specific to GAPDH were used simultaneously. As a result, as shown in FIG. 3, strong expression of the canine calmegin gene was observed in testis among the normal dog tissues, and on the other hand, strong expression was observed in canine tumor cell lines. Expression of the human calmegin gene was confirmed, as is the case with the canine calmegin gene, only in testis among the human normal tissues, but the expression was detected in brain tumor, leukemia and esophagus cancer cells among human cancer cell lines. Thus, the human calmegin gene was also confirmed to be specifically expressed in testis and cancer cells.

In FIG. 3, reference numeral 1 in the ordinate indicates the expression pattern of the calmegin gene, and reference numeral 2 indicates the expression pattern of the GAPDH gene as a control for comparison.

Example B-2

Preparation of Canine and Human Calmegin Proteins (1) Preparation of Recombinant Protein Based on the gene of SEQ ID NO:15 obtained in Example B-1, a recombinant protein was prepared by the following method. Respective reagents and the attached buffer were mixed such that the mixture should contain 1 µl of the vector that was prepared from the phagemid solution obtained in Example B-1 and was subjected to the sequence analysis, 0.4 µM each of two kinds of primers having BamHI and EcoRI restriction sites (described in SEQ ID NOs:21 and 22), 0.2 mM dNTP and 1.25 U of PrimeSTAR HS polymerase (manufactured by Takara Shuzo Co., Ltd.) in a total volume of 50 µl and PCR was carried out with 30 cycles of 98° C. for 10 seconds, 55° C. for 15 seconds and 72° C. for 2 minutes using Thermal Cycler (manufactured by BIO RAD). The above-described two kinds of primers were those which amplify the region encoding the entire amino acid sequence of SEQ ID NO:16. After the PCR, the amplified DNA was subjected to electrophoresis using 1% agarose gel, and a DNA fragment of about 1.9 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and EcoRI and purified using QIAquick Gel Extraction Kit, followed by inserting the gene sequence of interest into an expression vector for *E. coli*, pET30a (manufactured by Novagen) that had been treated with BamHI and EcoRI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

On the other hand, based on the gene of SEQ ID NO:17, a recombinant protein of the human homologous gene was prepared by the following method. Respective reagents and the attached buffer were mixed such that the mixture should contain 1 µl of the cDNA prepared in Example B-1 whose expression could be confirmed by the RT-PCR method in various tissues/cells, 0.4 µM each of two kinds of primers having EcoRI and XhoI restriction sites (described in SEQ ID NOs:23 and 24), 0.2 mM dNTP and 1.25 U of Prime-STAR HS polymerase (manufactured by Takara Shuzo Co., Ltd.) in a total volume of 50 μl, and PCR was carried out with 30 cycles of 98° C. for 10 seconds, 55° C. for 15 seconds and 72° C. for 2 minutes using Thermal Cycler (manufactured by BIO RAD). The above-described two kinds of primers were those which amplify the region encoding the entire amino acid sequence of SEQ ID NO:18. After the PCR, the amplified DNA was subjected to electrophoresis using 1% agarose gel, and a DNA fragment of about 1.9 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes EcoRI and XhoI and purified using QIAquick Gel Extraction Kit, followed by inserting the gene sequence of interest into an expression vector for *E. coli*, pET30a (manufactured by Novagen) that had been treated with EcoRI and XhoI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:15 and SEQ ID NO:17, respectively, were cultured in 30 μg/ml kanamycin-containing LB medium at 37° C. until the absorbance at 600 nm reached about 0.7, and then isopropyl-β-D-1-thiogalactopyranoside was added thereto such that its final concentration should be 1 mM, followed by culturing them at 37° C. for 4 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The obtained pellet of *E. coli* cells was suspended in 20 mM phosphate buffer (pH 7.0) and subjected to sonication on ice. The sonicated solution of *E. coli* was centrifuged at 6,000 rpm for 20 minutes to obtain the supernatant as the soluble fraction and the precipitate as the insoluble fraction.

The soluble fraction was placed in an ion-exchange column (carrier: SP Sepharose (trademark) Fast Flow (GE Health Care); column volume: 5 mL; equilibration buffer: 20 mM phosphate buffer (pH 7.0)). The column was washed with 10 column volumes of 20 mM phosphate buffer (pH 7.0), and elution was carried out with density gradient of salt by 0.3 M-1.0 M sodium chloride-containing 20 mM phosphate buffer (pH 7.0). Six column volumes of the eluted fraction was collected in each elution step.

Among these eluted fractions, the 1st to 6th fractions eluted with 0.3 M sodium chloride-containing 20 mM phosphate buffer (pH 7.0) and the 1st fraction eluted with 1.0 M sodium chloride-containing 20 mM phosphate buffer (pH 7.0) were combined, and the resulting solution was subjected to additional purification by a secondary column.

Figure 4:
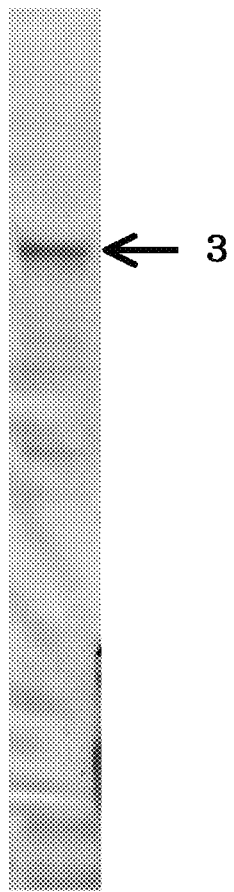
FIG. 4 shows the detection by Coomassie staining of the canine calmegin protein, which is an example of the polypeptide used in the present invention, produced in E. coli and purified in Example B. Reference numeral 3: the band for the canine calmegin protein.

For the secondary column, a column carrier Bio gel HT Type II (BioRad) was used. The column volume was 5 mL. The column was equilibrated with 10 column volumes of 0.3 M sodium chloride-containing 20 mM phosphate buffer (pH 7.0), and the above-described eluted fractions were placed in the column. The fractions that were not adsorbed to the column was washed away with 10 column volumes of 0.3 M sodium chloride-containing 20 mM phosphate buffer (pH 7.0) and 0.1 M phosphate buffer (pH 7.0), and elution was carried out with 0.2 M phosphate buffer (pH 7.0) to obtain a purified fraction, which was used as the material for administration tests thereafter. The proteins of interest in the eluted fractions were confirmed by Coomassie staining carried out according to a conventional method. Among these, the canine calmegin protein is shown in FIG. 4.

To 1 ml of a reaction buffer (20 mM Tris-HCl, 50 mM NaCl, 2 mM $CaCl_2$; pH 7.4), 200 μl of the purified preparation obtained by the above-described method was aliquoted, and 2 μl of enterokinase (manufactured by Novagen) was then added thereto, followed by leaving it to stand at room temperature overnight to cleave His tag. The resulting product was purified using Enterokinase Cleavage Capture Kit (manufactured by Novagen) in accordance with the protocol attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 μm (manufactured by PALL) and used in the following experiments.

Example B-3

Test of Administration of Recombinant Protein to Cancer-Bearing Dogs (1) Antitumor Assay The anti-tumor effect of the two kinds of recombinant proteins which were purified as described above was assessed in two individuals of cancer-bearing dogs having epidermal tumor (2 individuals having mammary gland tumor).

An equal amount of Freund's incomplete adjuvant (manufactured by Wako Pure Chemicals) was mixed with 100 μg (0.5 ml) of the recombinant canine calmegin and human calmegin proteins, respectively, to prepare therapeutic agents for a cancer(s). Each of these agents was administered to a regional lymph node in the vicinity of the tumor a total of 3 times, by carrying out the subsequent administrations 3 days and 7 days after the first administration. As a result, the tumors with a size of about 45 $mm^3$ and 78 $mm^3$, respectively, at the time of administration of the therapeutic agents were reduced to 27 $mm^3$ and 46 $mm^3$, respectively, 10 days after the first administration; 15 $mm^3$ and 26 $mm^3$, respectively, 20 days after the first administration; and to 7 $mm^3$ and 15 $mm^3$, respectively, 30 days after the first administration.

Further, to a canine patient suffering from malignant melanoma, a mixture of 100 μg (0.5 ml) of the above-described canine calmegin protein and 0.5 ml of Freund's incomplete adjuvant was administered a total of 3 times in the same manner as described above. Further, concurrently with the respective administrations, 100 μg of canine interleukin 12 was administered subcutaneously. As a result, the tumor with a size of about 38 $mm^3$ at the time of administration of the therapeutic agent completely regressed 21 days after the first administration of the therapeutic agent.

(2) Immune Inducibility Assay

Blood from the canine patient in which the anti-tumor effect was obtained in the administration test in the above-described (1) was collected before administration of the therapeutic agent for a cancer(s) and 10 days and 30 days after the first administration. Peripheral blood mononuclear cells were isolated according to a conventional method, and by the ELISPOT assay for IFNγ using it, the immune inducibility of each administered recombinant protein was assayed.

In a 96-well plate manufactured by Millipore (MultiScreen-IP, MAIPS 4510), 100 μL/well of 70% ethanol was placed and the plate was left to stand for 5 minutes, followed by removal of the ethanol by aspiration. The plate was washed with sterile water and 300 μl/well of 200 mM Sodium Bicarbonate (pH8.2) was placed therein. After leaving it to stand for 5 minutes, Sodium Bicarbonate was removed by aspiration, and then the plate was washed. Subsequently, 0.5 μg/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 μL/well of a blocking solution (1% BS-5% sucrose-200 mM Sodium Bicarbonate (pH8.2)) was added to the wells, and the plate was incubated at 4° C. overnight to block the plate. After removal of the blocking solution by aspiration, 300 μL/well of 10% fetal calf serum-containing RPMI medium (manufactured by Invitrogen) was placed in the wells, and the plate was left to stand for 5 minutes, followed by removal of the medium by aspiration. Subsequently, $5 \times 10^5$ cells/well of the canine peripheral blood mononuclear cells suspended in 10% fetal calf serum-containing RPMI medium were placed in the plate, and 10 μL/well of the canine calmegin or human calmegin protein used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 μL of rabbit anti-dog polyclonal antibody 1000-fold diluted with the above-described blocking solution was placed, and the resulting mixture was incubated at 4° C. overnight. After washing the wells 3 times with the above-described washing solution, 100 μL of HRP-labeled anti-rabbit antibody 1000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and image processing of the wells was carried out, followed by counting the number of spot-forming cells (SFC) using KS ELISPOT compact system (Carl Zeiss, Inc., Germany).

As a result, in either canine patient to which canine calmegin or human calmegin was administered, peripheral blood mononuclear cells sampled before the administration showed no spots. On the other hand, in the canine patient to which canine calmegin was administered, peripheral blood mononuclear cells sampled 10 days and 30 days after the administration showed 15 and 45 spots, respectively. In the canine patient to which human calmegin was administered, peripheral blood mononuclear cells sampled 10 days and 30 days after the administration showed 12 and 39 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in (1) was exerted by immunoreactions in which these immunocytes are mainly involved.

Example C-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was $1.3 \times 10^6$ pfu/ml.

(2) Screening of cDNA Library with Serum

Using the dog testis-derived cDNA phage library prepared as described above, immunoscreening was carried out. More particularly, host *E. coli* cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking it at 4° C. overnight to suppress non-specific reactions. This filter was allowed to react with 500-fold diluted canine patient serum at room temperature for 2 to 3 hours.

As the above-described canine patient serum, serum collected from canine patients suffering from breast cancer was used. The serum was stored at −80° C. and pretreated immediately before use. The method of the pretreatment of the serum was as follows. That is, host *E. coli* cells (XL1-Blue MRF') were infected with λ ZAP Express phage to which no foreign gene was inserted, and then cultured on NZY plate medium at 37° C. overnight. Subsequently, the buffer of 0.2 M $NaHCO_3$, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+l HRP conjugated: manufactured by BETHYL Laboratories) 5,000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 µl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 µl of a solution prepared to contain a host *E. coli* (XL1-Blue MRF') such that the absorbance OD$_{600}$ should be 1.0 was mixed with 100 µl of a purified phage solution and further with 1 µl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 µl of a solution prepared to contain a phagemid host *E. coli* (SOLR) such that the absorbance OD$_{600}$ should be 1.0 was mixed with 10 µl of a purified phage solution, and the reaction was allowed to proceed at 37° C. for 15 minutes. Thereafter, 50 µl of the reaction mixture was plated on ampicillin (final concentration: 50 µg/ml)-containing LB agar medium, and cultured at 37° C. overnight. A single colony of transformed SOLR was recovered and cultured in ampicillin (final concentration: 50 µg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:25 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene has 99% homology (which was calculated only in the overlapping region) to the CEP gene described in SEQ ID NO:27 in terms of base sequence and amino acid sequence, so that the gene was judged as the CEP gene. The human homologous factor of the canine CEP was human CEP (homology to the CEP gene described in SEQ ID NO:25: base sequence, 87%; amino acid sequence, 84%). The base sequence of human CEP is shown in SEQ ID NO:29, and the amino acid sequence thereof is shown in SEQ ID NO:30.

(4) Analysis of Expression in Each Tissue

Figure 5:
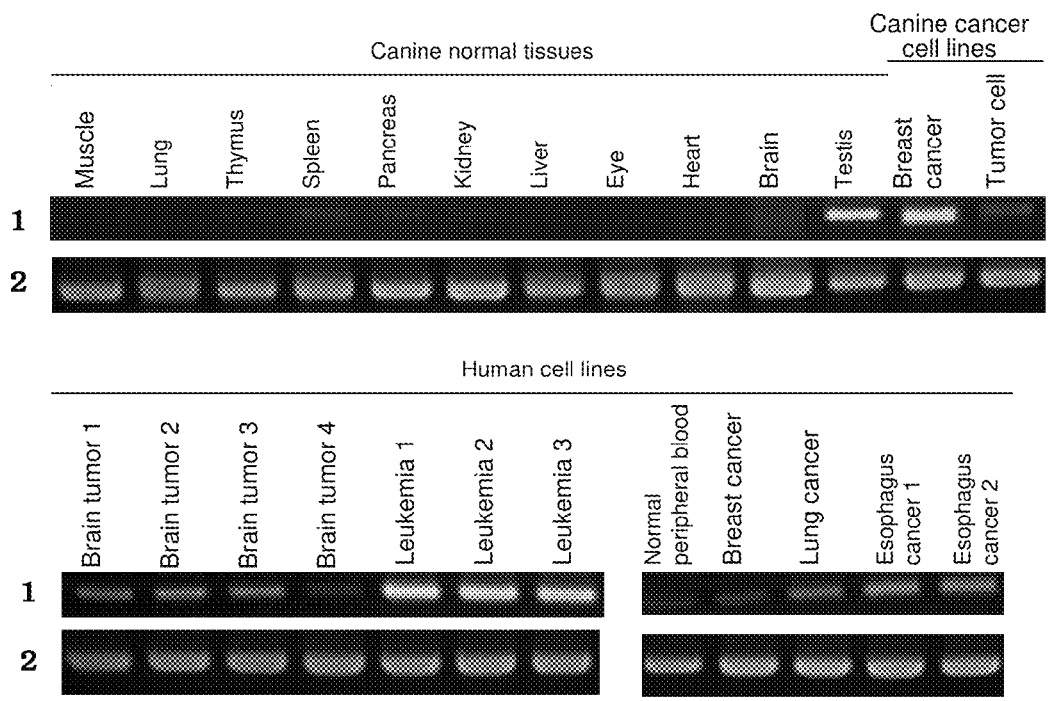
FIG. 5 shows the expression pattern of the gene encoding the CEP protein in normal tissues and tumor cell lines. Reference numeral 1: the expression pattern of the gene encoding the CEP protein; Reference numeral 2: the expression pattern of the GAPDH gene.

The expression of the gene, which was obtained by the above-described method, in normal tissues and various cell lines of dog and human were investigated by the RT-PCR (Reverse Transcription-PCR) method. The reverse transcription reaction was carried out as follows. total RNA was extracted from 50 to 100 mg of each tissue or 5 to 10×10$^6$ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:31 and 32) specific to the obtained gene. That is, respective reagents and the attached buffer were mixed such that the mixture should contain 0.25 µl of the sample prepared by the reverse transcription reaction, 2 µM each of the above primers, 0.2 mM each of dNTP and 0.65 U of ExTaq polymerase (manufactured by Takara Shuzo Co., Ltd.) in a total volume of 25 µl and the reaction was carried out with 30 cycles of 94° C. for 30 seconds, 55° C. for 30 seconds and 72° C. for 30 seconds using Thermal Cycler (manufactured by BIO RAD). The above-described gene-specific primers were those which amplify the regions of the 4582nd to 5124th bases of the base sequences of SEQ ID NOs:25 and 27 (canine CEP gene) and the 4610th to 5152nd bases of the base sequence of SEQ ID NO:29 (human CEP gene), and can be used for investigation of the expression of both the canine CEP gene and the human CEP gene. As a control for comparison, primers (described in SEQ ID NOs:9 and 10) specific to GAPDH were used simultaneously. As a result, as shown in FIG. 5, strong expression of the canine CEP gene was observed in testis among the normal dog tissues, and on the other hand, strong expression was observed in the canine breast cancer cell line. Expression of the human CEP gene was confirmed, as is the case with the canine CEP gene, only in testis among the human normal tissues, but the expression was detected in brain tumor, leukemia and esophagus cancer cells among human cancer cell lines, and especially, strong expression was observed in the leukemia cell line. Thus, the human CEP gene was also confirmed to be specifically expressed in testis and cancer cells.

In FIG. 5, reference numeral 1 in the ordinate indicates the expression pattern of the CEP gene, and reference numeral 2 indicates the expression pattern of the GAPDH gene as a control for comparison.

Example C-2

Preparation of Canine and Human CEPs (1) Preparation of Recombinant Protein

Based on the gene of SEQ ID NO:25 obtained in Example C-1, a recombinant protein was prepared by the following method. Respective reagents and the attached buffer were mixed such that the mixture should contain 1 µl of the vector that was prepared from the phagemid solution obtained in Example C-1 and was subjected to the sequence analysis, 0.4 µM each of two kinds of primers having BamHI and SalI restriction sites (described in SEQ ID NOs:33 and 34), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 5 seconds and 72° C. for 7 minutes using Thermal Cycler (manufactured by BIO RAD). The above-described two kinds of primers were those which amplify the region encoding the entire amino acid sequence of SEQ ID NO:26. After the PCR, the amplified DNA was subjected to electrophoresis using 1% agarose gel, and a DNA fragment of about 7.0 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and SalI and purified using QIAquick Gel Extraction Kit, followed by inserting the gene sequence of interest into an expression vector for *E. coli*, pET30a (manufactured by Novagen) that had been treated with BamHI and SalI. Usage of this vector enables production of a His-tag fusion recombinant protein. *E. coli* for expression, BL21 (DE3), was transformed with this plasmid, and expression of the protein of interest was induced in *E. coli* with 1 mM IPTG. In the same manner, based on the gene of SEQ ID NO:27, using the canine testis cDNA as a template and two kinds of primers having BamHI and SalI restriction sites (SEQ ID NOs:33 and 35), a recombinant protein of the registered canine CEP gene was prepared. The above-described two kinds of primers were those which amplify the region of about 7.8 kbp encoding the entire amino acid sequence of SEQ ID NO:28.

Further, based on the gene of SEQ ID NO:29, a recombinant protein of the human homologous gene was prepared by the following method. Respective reagents and the attached buffer were mixed such that the mixture should contain 1 µl of the cDNA prepared in Example C-1 whose expression could be confirmed by the RT-PCR method in various tissues/cells, 0.4 µM each of two kinds of primers having BamHI and SalI restriction sites (described in SEQ ID NOs:36 and 37), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 5 seconds and 72° C. for 7 minutes using Thermal Cycler (manufactured by BIO RAD). The above-described two kinds of primers were those which amplify the region encoding the entire amino acid sequence of SEQ ID NO:30. After the PCR, the amplified DNA was subjected to electrophoresis using 1% agarose gel, and a DNA fragment of about 7.0 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes BamHI and SalI and purified using QIAquick Gel Extraction Kit, followed by inserting the gene sequence of interest into an expression vector for *E. coli*, pET30a (manufactured by Novagen) that had been treated with BamHI and SalI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Protein

The above-obtained recombinant *E. coli* cells that expressed SEQ ID NO:25, SEQ ID NO:27, and SEQ ID NO:29, respectively, were cultured in 30 µg/ml kanamycin-containing LB medium at 37° C. until the absorbance at 600 nm reached about 0.7, and then isopropyl-β-D-1-thiogalactopyranoside was added thereto such that its final concentration should be 1 mM, followed by culturing them at 30° C. for 20 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The cells were suspended in phosphate-buffered saline and subjected to sonication on ice. The sonicated solution of *E. coli* was centrifuged at 7000 rpm for 20 minutes to obtain the supernatant as the soluble fraction and the precipitate as the insoluble fraction. The insoluble fraction was suspended in 4% Triton X-100 solution and the resulting suspension was centrifuged at 7000 rpm for 20 minutes. This operation was repeated twice and an operation of removal of proteases was carried out. The residue was suspended in 8 M urea-containing 10 mM Tris-HCl, 100 mM phosphate buffer (hereinafter referred to as 8 M urea solution) and a protease inhibitor cocktail solution, and the resulting suspension was left to stand at 4° C. for 20 hours to denature proteins.

Figure 6:
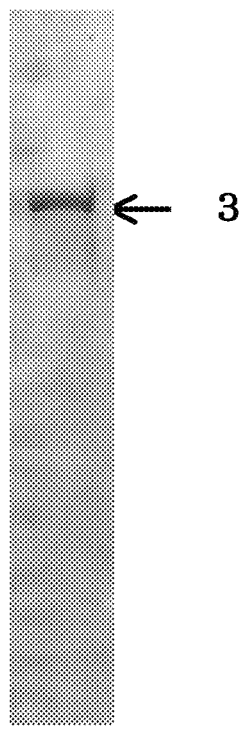
FIG. 6 shows the detection by Coomassie staining of the canine CEP of SEQ ID NO:26, which is an example of the polypeptide used in the present invention, produced in E. coli and purified in Example C. Reference numeral 3: the band for the canine CEP protein.

Thereafter, the suspension was centrifuged at 7,000 rpm for 20 minutes, and the obtained soluble fraction was placed in a nickel chelate column prepared by a conventional method (carrier: Chelating Sepharose (trademark) Fast Flow (GE Health Care); column volume: 5 mL; equilibration buffer: 8M urea solution), followed by leaving it to stand at 4° C. overnight. The supernatant was recovered by centrifugation of this column carrier at 1,500 rpm for 5 minutes, and the column carrier was suspended in phosphate-buffered saline, followed by refilling the column with the resulting suspension. The fraction that was not adsorbed to the column was washed away with 5 column volumes of 8 M urea solution, 10 column volumes of 0.5 M sodium chloride-containing 0.1 M acetate buffer (pH 5.0) and 10 mM imidazole-containing 20 mM phosphate buffer (pH 8.0), and elution was immediately carried out with a five-step density gradient of 100 mM-500 mM imidazole to obtain a purified fraction, which was used as the material for administration tests thereafter. The proteins of interest in respective eluted fractions were confirmed by Coomassie staining carried out according to a conventional method. Among these, the recombinant canine CEP described in SEQ ID NO:26 is shown in FIG. 6.

To 1 ml of a reaction buffer (20 mM Tris-HCl, 50 mM NaCl, 2 mM $CaCl_2$; pH 7.4), 200 µl of the purified preparation obtained by the above-described method was aliquoted, and 2 µl of enterokinase (manufactured by Novagen) was then added thereto, followed by leaving it to stand at room temperature overnight to cleave His tag. The resulting product was purified using Enterokinase Cleavage Capture Kit (manufactured by Novagen) in accordance with the protocol attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 µm (manufactured by PALL) and used in the following experiments.

Example C-3

Test of Administration of Recombinant Protein to Cancer-Bearing Dogs (1) Antitumor Assay The anti-tumor effect of the two kinds of recombinant proteins which were purified as described above was assessed in two individuals of cancer-bearing dogs having epidermal tumor (2 individuals having perianal adenoma).

An equal amount of Freund's incomplete adjuvant (manufactured by Wako Pure Chemicals) was mixed with 100 μg (0.5 ml) each of the recombinant canine CEP described in SEQ ID NO:26 and human CEP purified as described above to prepare therapeutic agents for a cancer(s). Each of these agents was administered to a regional lymph node in the vicinity of the tumor a total of 3 times, by carrying out the subsequent administrations 3 days and 7 days after the first administration. As a result, the tumors with a size of about 87 mm$^3$ and 69 mm$^3$ at the time of administration of the therapeutic agents, respectively, were reduced to 69 mm$^3$ and 56 mm$^3$, respectively, 10 days after the first administration; 24 mm$^3$ and 31 mm$^3$, respectively, 20 days after the first administration; and to 10 mm$^3$ and 8 mm$^3$, respectively, 30 days after the first administration of the therapeutic agent.

Further, to a canine patient suffering from mammary adenocarcinoma, a mixture of 100 μg (0.5 ml) of the canine CEP protein described in SEQ ID NO:26 with 0.5 ml of Freund's incomplete adjuvant was administered a total of 3 times in the same manner as described above. Further, concurrently with the respective administrations, 10 MU of "Intercat" which is a recombinant feline interferon was administered subcutaneously. As a result, the tumor with a size of about 126 mm$^3$ at the time of administration of the therapeutic agent completely regressed 26 days after the first administration of the therapeutic agent. Similarly, in the case where the canine CEP described in SEQ ID NO:28 was used, an anti-tumor effect was also observed in a cancer-bearing dog.

Further, to a canine patient of mastocytoma, a mixture of 100 μg (0.5 ml) of the canine CEP protein described in SEQ ID NO:26 with 0.5 ml of Freund's incomplete adjuvant was administered a total of 3 times in the same manner as described above. Further, concurrently with the respective administrations, 100 μg of canine interleukin-12 was subcutaneously administered. As a result, the tumor with a size of about 83 mm$^3$ at the time of administration of the therapeutic agent completely regressed 18 days after the first administration of the therapeutic agent.

(2) Immune Inducibility Assay

Blood from the canine patient suffering from perianal adenoma in which the anti-tumor effect was obtained in the administration test in the above-described (1) was collected before administration of the therapeutic agent for a cancer(s) and 10 days and 30 days after the first administration. Peripheral blood mononuclear cells were isolated according to a conventional method, and by the ELISPOT assay for IFNγ using it, the immune inducibility of each administered protein was assayed.

In a 96-well plate manufactured by Millipore (Multi-Screen-IP, MATS 4510), 100 μL/well of 70% ethanol was placed and the plate was left to stand for 5 minutes, followed by removal of the ethanol by aspiration. The plate was washed with sterile water and 300 μl/well of 200 mM Sodium Bicarbonate (pH8.2) was placed therein. After leaving it to stand for 5 minutes, Sodium Bicarbonate was removed by aspiration, and then the plate was washed. Subsequently, 0.5 μl/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 μL/well of a blocking solution (1% BS-5% sucrose-200 mM Sodium Bicarbonate (pH8.2)) was added to the wells, and the plate was incubated at 4° C. overnight to block the plate. After removal of the blocking solution by aspiration, 300 μL/well of 10% fetal calf serum-containing RPMI medium (manufactured by Invitrogen) was placed in the wells, and the plate was left to stand for 5 minutes, followed by removal of the medium by aspiration. Subsequently, 5×10$^5$ cells/well of the canine peripheral blood mononuclear cells suspended in 10% fetal calf serum-containing RPMI medium were placed in the plate, and 10 μL/well of the canine CEP described in SEQ ID NO:26 or the human CEP used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 μL of rabbit anti-canine polyclonal antibody 1000-fold diluted with the above-described blocking solution was placed, and the plate was incubated at 4° C. overnight. After washing the wells 3 times with the above-described washing solution, 100 μL of HRP-labeled anti-rabbit antibody 1000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and image processing of the wells was carried out, followed by counting the number of spot-forming cells (SFC) using KS ELISPOT compact system (Carl Zeiss, Inc., Germany).

As a result, in either canine patient to which the canine CEP described in SEQ ID NO: 26 or the human CEP was administered, peripheral blood mononuclear cells sampled before the administration showed no spots. On the other hand, in the canine patient to which the canine CEP was administered, peripheral blood mononuclear cells sampled 10 days and 30 days after the administration showed 23 and 52 spots, respectively. In the canine patient to which the human CEP was administered, peripheral blood mononuclear cells sampled 10 days and 30 days after the administration showed 19 and 49 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in (1) was exerted by immunoreactions in which these immunocytes are mainly involved.

Example D-1

Acquisition of Novel Cancer Antigen Protein by SEREX Method (1) Preparation of cDNA Library Total RNA was prepared from testis tissue of a healthy dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a dog testis cDNA phage library was synthesized. Preparation of the cDNA phage library was carried out using cDNA Synthesis Kit, ZAP-cDNA Synthesis Kit, and ZAP-cDNA Gigapack III Gold Cloning Kit (manufactured by STRATAGENE) in accordance with the protocols attached to the kits. The size of the prepared cDNA phage library was 1.3×10⁶ pfu/ml.

(2) Screening of cDNA Library with Serum

Using the dog testis-derived cDNA phage library prepared as described above, immuno screening was carried out. More particularly, host *E. coli* cells (XL1-Blue MRF') were infected with the library such that 2,340 clones should appear on an NZY agarose plate having the size of Φ90×15 mm, and cultured at 42° C. for 3 to 4 hours to allow the phage to form plaques. The plate was covered with nitrocellulose membrane (Hybond C Extra: manufactured by GE Healthcare Bio-Science) impregnated with IPTG (isopropyl-β-D-thiogalactoside) at 37° C. for 4 hours to induce and express proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking at 4° C. overnight to suppress non-specific reactions. This filter was allowed to react with 500-fold diluted canine patient serum at room temperature for 2 to 3 hours.

As the above-described canine patient serum, serum collected from canine patients suffering from breast cancer was used. The serum was stored at −80° C. and pretreated immediately before use. The method of the pretreatment of the serum was as follows. That is, host *E. coli* cells (XL1-Blue MRF') were infected with λ ZAP Express phage to which no foreign gene was inserted, and then cultured on NZY plate medium at 37° C. overnight. Subsequently, the buffer of 0.2 M NaHCO₃, pH 8.3 containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patients was allowed to flow through and react with this protein-immobilized column to remove antibodies adsorbed on *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+I HRP conjugated: manufactured by BETHYL Laboratories) 5,000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having the size of Φ90×15 mm, and dissolved in 500 μl of SM buffer (100 mM NaCl, 10 mM MgClSO₄, 50 mM Tris-HCl, 0.01% gelatin; pH 7.5). The screening was repeated as a second and third screening in the same manner as described above until a single coloring reaction-positive colony was obtained, thereby isolating one positive clone after screening of 30,940 phage clones reactive with IgG in the serum.

(3) Homology Search of Isolated Antigen Gene

To subject the single positive clone isolated by the above-described method to a base sequence analysis, an operation of conversion of the phage vector to a plasmid vector was carried out. More particularly, 200 μl of a solution prepared to contain a host *E. coli* (XL1-Blue MRF') such that the absorbance OD$_{600}$ should be 1.0 was mixed with 100 μl of a purified phage solution and further with 1 μl of ExAssist helper phage (manufactured by STRATAGENE), and the reaction was allowed to proceed at 37° C. for 15 minutes. To the reaction mixture, 3 ml of LB medium was added, and the mixture was cultured at 37° C. for 2.5 to 3 hours, followed by immediate incubation in a water bath at 70° C. for 20 minutes. The mixture was then centrifuged at 4° C. at 1000×g for 15 minutes, and the supernatant was recovered as a phagemid solution. Subsequently, 200 μl of a solution prepared to contain a phagemid host *E. coli* (SOLR) such that the absorbance OD$_{600}$ should be 1.0 was mixed with 10 μl of a purified phage solution, and the reaction was allowed to proceed at 37° C. for 15 minutes. Thereafter, 50 μl of the reaction mixture was plated on ampicillin (final concentration: 50 μg/ml)-containing LB agar medium, and cultured at 37° C. overnight. A single colony of transformed SOLR was recovered and cultured in ampicillin (final concentration: 50 μg/ml)-containing LB medium at 37° C., followed by purification of plasmid DNA having an insert of interest using QIAGEN plasmid Miniprep Kit (manufactured by Qiagen).

The purified plasmid was subjected to an analysis of the entire sequence of the insert by the primer walking method using the T3 primer described in SEQ ID NO:5 and the T7 primer described in SEQ ID NO:6. By this sequence analysis, the gene sequence described in SEQ ID NO:38 was obtained. Using the base sequence and the amino acid sequence of this gene, homology search against known genes was carried out using a homology search program BLAST (http://www.ncbi.nlm.nih.gov/BLAST/). As a result, it was revealed that the obtained gene is the TRIP11 gene. The human homologous factor of canine TRIP11 was human TRIP11 (homology: base sequence, 88%; amino acid sequence, 86%). The base sequence of human TRIP11 is shown in SEQ ID NO:40, and the amino acid sequence thereof is shown in SEQ ID NO:41.

(4) Analysis of Expression in Each Tissue

Figure 7:
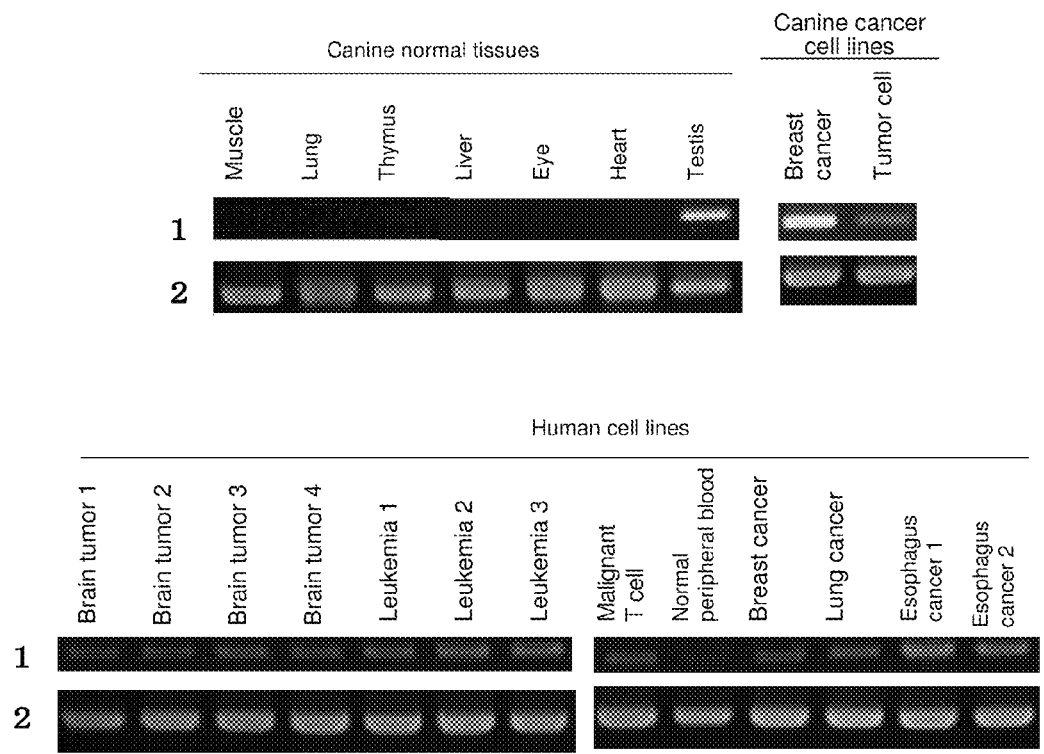
FIG. 7 shows the expression pattern of the gene encoding the TRIP11 protein in normal tissues and tumor cell lines. Reference numeral 1: the expression pattern of the gene encoding the TRIP11 protein; Reference numeral 2: the expression pattern of the GAPDH gene.

The expression of the gene, which was obtained by the above-described method, in normal tissues and various cell lines of dog and human were investigated by the RT-PCR (Reverse Transcription-PCR) method. The reverse transcription reaction was carried out as follows. That is, total RNA was extracted from 50 to 100 mg of each tissue or 5 to 10×10⁶ cells of each cell line using TRIZOL reagent (manufactured by Invitrogen) in accordance with the protocol attached to the kit. Using this total RNA, cDNA was synthesized by Superscript First-Strand Synthesis System for RT-PCR (manufactured by Invitrogen) in accordance with the protocol attached to the kit. As the cDNAs from human normal tissues (brain, hippocampus, testis, colon and placenta), Gene Pool cDNA (manufactured by Invitrogen), QUICK-Clone cDNA (manufactured by CLONTECH) and Large-Insert cDNA Library (manufactured by CLONTECH) were used. The PCR reactions were carried out as follows using primers (described in SEQ ID NOs:42 and 43) specific to the obtained gene. That is, respective reagents and the attached buffer were mixed such that the mixture should contain 0.25 μl of the sample prepared by the reverse transcription reaction, 2 μM each of the above primers, 0.2 mM each of dNTP and 0.65 U of ExTaq polymerase (manufactured by Takara Shuzo Co., Ltd.) in a total volume of 25 μl, and the reaction was carried out with 30 cycles of 94° C. for 30 seconds, 55° C. for seconds and 72° C. for 1.5 minutes using Thermal Cycler (manufactured by BIO RAD). The above-described gene-specific primers were those which amplify the regions of the 1519th to 2957th bases of the base sequence of SEQ ID NO:38 (canine TRIP11 gene) and the 1872nd to 3310th bases of the base sequence of SEQ ID NO:40 (human TRIP11 gene), and can be used for investigation of the expression of both the canine TRIP11 gene and the human TRIP11 gene. As a control for comparison, primers (described in SEQ ID NOs:9 and 10) specific to GAPDH were used simultaneously. As a result, as shown in FIG. 7, strong expression of the canine TRIP11 gene was observed in testis among the normal dog tissues, and on the other hand, strong expression was observed in the canine breast cancer cell line. Expression of the human gene was confirmed, as is the case with the canine TRIP11 gene, only in testis among the human normal tissues, but the expression was detected in many types of cancer cell lines such as brain tumor, leukemia, breast cancer, lung cancer and esophagus cancer cell lines among human cancer cell lines. Thus, the human TRIP11 gene was also confirmed to be specifically expressed in testis and cancer cells.

In FIG. 7, reference numeral 1 in the ordinate indicates the expression pattern of the TRIP11 gene, and reference numeral 2 indicates the expression pattern of the GAPDH gene as a control for comparison.

Example D-2

Preparation of Canine and Human TRIP11 Proteins (1) Preparation of Recombinant Protein Based on the gene of SEQ ID NO:38 obtained in Example D-1, a recombinant protein was prepared by the following method. NO:Respective reagents and the attached buffer were mixed such that the mixture should contain 1 µl of the vector which was prepared from the phagemid solution obtained in Example D-1 and was subjected to the sequence analysis, 0.4 µM each of two kinds of primers having SalI and XhoI restriction sites (described in SEQ ID NOs:44 and 45), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 5 seconds and 72° C. for 6 minutes using Thermal Cycler (manufactured by BIO RAD). The above-described two kinds of primers were those which amplify the region encoding the entire amino acid sequence of SEQ ID NO:39. After the PCR, the amplified DNA was subjected to electrophoresis using 1% agarose gel, and a DNA fragment of about 6.0 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes SalI and XhoI and purified using QIAquick Gel Extraction Kit, followed by inserting the gene sequence of interest into an expression vector for *E. coli*, pET30b (manufactured by Novagen) that had been treated with SalI and XhoI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

Further, based on the gene of SEQ ID NO:40, a recombinant protein of the human homologous gene was prepared by the following method. Respective reagents and the attached buffer were mixed such that the mixture should contain 1 µl of the cDNA prepared in Example D-1 whose expression could be confirmed by the RT-PCR method in various tissues/cells, 0.4 µM each of two kinds of primers having NdeI and KpnI restriction sites (described in SEQ ID NOs:46 and 47), 0.2 mM dNTP and 1.25 U of PrimeSTAR HS polymerase (manufactured by Takara Shuzo Co., Ltd.) in a total volume of 50 µl, and PCR was carried out with 30 cycles of 98° C. for 10 seconds, 55° C. for 5 seconds and 72° C. for 6 minutes using Thermal Cycler (manufactured by BIO RAD). The above-described two kinds of primers were those which amplify the region encoding the entire amino acid sequence of SEQ ID NO:41. After the PCR, the amplified DNA was subjected to electrophoresis using 1% agarose gel, and a DNA fragment of about 6.0 kbp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and plasmids were recovered thereafter, followed by confirming, by sequencing, that the amplified gene fragment matches the sequence of interest. The plasmid that matched the sequence of interest was treated with restriction enzymes NdeI and KpnI and purified using QIAquick Gel Extraction Kit, followed by inserting the gene sequence of interest into an expression vector for *E. coli*, pET30b (manufactured by Novagen) that had been treated with NdeI and KpnI. Usage of this vector enables production of a His-tag fusion recombinant protein. *E. coli* for expression, BL21 (DE3), was transformed with this plasmid, and expression of the protein of interest was induced in *E. coli* with 1 mM IPTG.

(2) Purification of Recombinant Proteins

The above-obtained recombinant *E. coli* cells that expressed SEQ ID NO:38 and SEQ ID NO:40, respectively, were cultured in 30 µg/ml kanamycin-containing LB medium at 37° C. until the absorbance at 600 nm reached about 0.7, and then isopropyl-β-D-1-thiogalactopyranoside was added thereto such that its final concentration should be 1 mM, followed by culturing them at 30° C. for 20 hours. Subsequently, the cells were collected by centrifugation at 4,800 rpm for 10 minutes. The pellet of the cells was suspended in phosphate-buffered saline and further subjected to centrifugation at 4,800 rpm for 10 minutes to wash the cells.

The obtained pellet of *E. coli* cells was suspended in phosphate-buffered saline and subjected to sonication on ice. The sonicated solution of *E. coli* was centrifuged at 7,000 rpm for 15 minutes to obtain the supernatant as the soluble fraction and the precipitate as the insoluble fraction.

The insoluble fraction was suspended in 4% Triton X-100 solution and the resulting suspension was centrifuged at 7,000 rpm for 10 minutes. This operation was repeated twice and an operation of removal of proteases was carried out. Thereafter, the residue was suspended in phosphate-buffered saline and an operation of removal of the surfactant was carried out.

Figure 8:
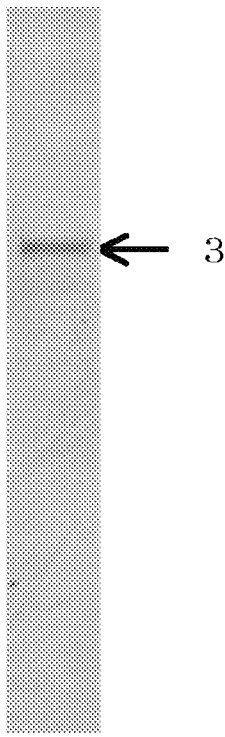
FIG. 8 shows the detection by Coomassie staining of the canine TRIP11 protein, which is one of the polypeptides used in the present invention, produced in E. coli and purified in Example D. Reference numeral 3: the band for the canine TRIP11 protein.

The residue was suspended in 6M guanidine hydrochloride-containing 20 mM phosphate buffer (pH 8.0), and the resulting suspension was left to stand at 4° C. for 20 hours to denature proteins. Thereafter, the suspension was centrifuged at 7,000 rpm for 20 minutes, and the obtained soluble fraction was placed in a nickel chelate column prepared by a conventional method (carrier: Chelating Sepharose (trademark) Fast Flow (GE Health Care); column volume: 5 mL; equilibration buffer: 6M guanidine hydrochloride-containing 20 mM phosphate buffer (pH 8.0)). The fraction that was not adsorbed to the column was washed away with 10 column volumes of 6 M sodium chloride-containing 20 mM phosphate buffer (pH 8.0) and 10 mM imidazole-containing 20 mM phosphate buffer (pH 8.0), and elution was immediately carried out with a four-step density gradient of 50 mM-500 mM imidazole to obtain a purified fraction, which was used as the material for administration tests thereafter. The proteins of interest in the eluted fractions were confirmed by Coomassie staining carried out according to a conventional method. Among these, the canine TRIP11 protein is shown in FIG. 8.

To 1 ml of a reaction buffer (20 mM Tris-HCl, 50 mM NaCl, 2 mM $CaCl_2$; pH 7.4), 200 µl of the purified preparation obtained by the above-described method was aliquoted, and 2 µl of enterokinase (manufactured by Novagen) was then added thereto, followed by leaving it to stand at room temperature overnight to cleave His tag. The resulting product was purified using Enterokinase Cleavage Capture Kit (manufactured by Novagen) in accordance with the protocol attached to the kit. Subsequently, the buffer contained in 1.2 ml of the purified preparation obtained by the above-described method was replaced with physiological phosphate buffer (manufactured by Nissui Pharmaceutical) by ultrafiltration using NANOSEP 10K OMEGA (manufactured by PALL), and the resulting solution was filtered aseptically using HT Tuffryn Acrodisc 0.22 µm (manufactured by PALL) and used in the following experiments.

Example D-3

Test of Administration of Recombinant Protein to Cancer-Bearing Dogs (1) Antitumor Assay The anti-tumor effect of the two kinds of recombinant proteins which were purified as described above was assessed in two individuals of cancer-bearing dogs having epidermal tumor (2 individuals having mammary gland tumor).

Therapeutic agents for a cancer(s) were prepared by mixing 0.5 ml of Freund's incomplete adjuvant (manufactured by Wako Pure Chemicals) with 100 µg (0.5 ml) of the recombinant canine TRIP11 and human TRIP11 proteins, respectively, purified as described above. Each of these agents was administered to a regional lymph node in the vicinity of the tumor a total of 3 times, by carrying out the subsequent administrations 3 days and 7 days after the first administration. As a result, the tumors with a size of about 75 $mm^3$ and 102 $mm^3$, respectively, at the time of administration of the therapeutic agents were reduced to 63 $mm^3$ and 85 $mm^3$, respectively, 10 days after the first administration; 35 $mm^3$ and 42 $mm^3$, respectively, 20 days after the first administration; and to 15 $mm^3$ and 19 $mm^3$, respectively, 30 days after the first administration of the therapeutic agent for a cancer(s).

Further, to a canine patient suffering from mastocytoma, a mixture of 100 µg (0.5 ml) of the canine TRP11 protein with 0.5 ml of Freund's incomplete adjuvant was administered a total of 3 times in the same manner as described above. Concurrently with the respective administrations, 100 µg of canine interleukin-12 was subcutaneously administered. As a result, the tumor with a size of about 165 $mm^3$ at the time of administration of the therapeutic agent completely regressed 23 days after the first administration of the therapeutic agent.

(2) Immune Inducibility Assay

Blood from the canine patient suffering from mammary gland tumor in which the anti-tumor effect was obtained in the administration test in the above-described (1) was collected. Peripheral blood mononuclear cells were isolated according to a conventional method, and by the ELISPOT assay for IFNγ using it, the immune inducibility of each administered protein was assayed.

In a 96-well plate manufactured by Millipore (Multi-Screen-IP, MAIPS 4510), 100 µL/well of 70% ethanol was placed and the plate was left to stand for 5 minutes, followed by removal of the ethanol by aspiration. The plate was washed with sterile water and 300 µl/well of 200 mM Sodium Bicarbonate (pH8.2) was placed therein. After leaving it to stand for 5 minutes, Sodium Bicarbonate was removed by aspiration, and then the plate was washed. Subsequently, 0.5 µg/well of anti-canine interferon γ monoclonal antibody (manufactured by R&D, clone 142529, MAB781) mixed with 200 mM Sodium Bicarbonate was placed in wells, and the plate was incubated at 37° C. overnight to immobilize the primary antibody. After removal of the primary antibody by aspiration, 300 µL/well of a blocking solution (1% BS-5% sucrose-200 mM Sodium Bicarbonate (pH8.2)) was added to the wells, and the plate was incubated at 4° C. overnight to block the plate. After removal of the blocking solution by aspiration, 300 µL/well of 10% fetal calf serum-containing RPMI medium (manufactured by Invitrogen) was placed in the wells and the plate was left to stand for 5 minutes, followed by removal of the medium by aspiration. Subsequently, $5 \times 10^5$ cells/well of the canine peripheral blood mononuclear cells suspended in 10% fetal calf serum-containing RPMI medium were placed in the plate, and 10 µL/well of the canine TRIP11 or the human TRIP11 protein used in each administration was added thereto, followed by culturing the cells under the conditions of 37° C. and 5% $CO_2$ for 24 hours, to allow immunocytes that might exist in the peripheral blood mononuclear cells to produce interferon γ. After the culture, the medium was removed, and the wells were washed 6 times with a washing solution (0.1% Tween20-200 mM Sodium Bicarbonate (pH8.2)). In each well, 100 µL of rabbit anti-dog polyclonal antibody 1000-fold diluted with the above-described blocking solution was placed, and the plate was incubated at 4° C. overnight. After washing the wells 3 times with the above-described washing solution, 100 µL of HRP-labeled anti-rabbit antibody 1,000-fold diluted with the above-described blocking solution was placed in each well, and the reaction was allowed to proceed at 37° C. for 2 hours. After washing the wells 3 times with the above-described washing solution, the resultant was colored with Konica Immunostain (manufactured by Konica), and the wells were washed with water to stop the reaction. Thereafter, the membrane was dried, and image processing of the wells was carried out, followed by counting the number of spot-forming cells (SFC) using KS ELISPOT compact system (Carl Zeiss, Inc., Germany).

As a result, in either canine patient to which the canine TRIP11 protein or the human TRIP11 protein was administered, peripheral blood mononuclear cells sampled before the administration showed no spots. On the other hand, in the canine patient to which the canine TRIP11 was administered, peripheral blood mononuclear cells sampled 10 days and 30 days after the administration showed 26 and 65 spots, respectively. In the canine patient to which the human TRIP11 was administered, peripheral blood mononuclear cells sampled 10 days and 30 days after the administration showed 31 and 72 spots, respectively.

From the above results, it is confirmed that immunocytes which specifically react with the administered recombinant protein and produce interferon γ were induced in all of the canine patients to which the recombinant protein was administered, and it is thought that the anti-tumor effect described in the above-described (1) was exerted by immunoreactions in which these immunocytes are mainly involved.

The invention claimed is:

1. A method for exerting an anti-tumor effect, said method comprising administering to a cancer-bearing individual an effective amount of polypeptide (a) or (b) below, said polypeptide having an immunity-inducing activity, or administering to a cancer-bearing individual an effective amount of a recombinant vector, wherein said recombinant vector comprises a polynucleotide encoding said polypeptide and is capable of expressing said polypeptide in vivo:
   (a) a polypeptide comprising the amino acid sequence shown in SEQ ID NO:16, or SEQ ID NO:18;
   (b) a polypeptide having a homology of not less than 95% to SEQ ID NO:16 or SEQ ID NO:18 which has immunity inducing activity,
   and wherein said cancer is calmegin-expressing cancer.

2. The method according to claim 1, wherein said polypeptide (b) has a homology of not less than 98%.

3. The method according to claim 1, wherein said polypeptide having an immunity-inducing activity has the amino acid sequence shown in SEQ ID NO: 16, or SEQ ID NO:18.

4. The method according to any one of claim 1, 2, or 3, wherein an effective amount of said polypeptide is administered.

5. The method according to claim 1, wherein said individual is a human, a dog or a cat.

6. The method according to claim 1, wherein the polypeptide having an immunity-inducing activity has the amino acid sequence shown in SEQ ID NO:16.

7. The method according to claim 1, wherein the polypeptide having an immunity-inducing activity has the amino acid sequence shown in SEQ ID NO:18.

8. The method according to claim 1, wherein immunocytes that exert an antitumor effect are induced in said cancer-bearing individual.

9. A method for exerting an anti-tumor effect, said method comprising administering to a cancer-bearing individual an effective amount of polypeptide (a) or (b) below, said polypeptide having an immunity-inducing activity, or administering to an individual an effective amount of a recombinant vector, wherein said recombinant vector comprises a polynucleotide encoding said polypeptide and is capable of expressing said polypeptide in vivo:
   (a) a polypeptide comprising the amino acid sequence shown in SEQ ID NO:16;
   (b) a polypeptide having a homology of not less than 95% to SEQ ID NO:16 which has immunity inducing activity.

10. The method according to claim 1, further comprising administering an immunoenhancer.

11. The method according to claim 10, wherein said immunoenhancer is at least one selected from the group consisting of: Freund's incomplete adjuvant; Montanide; poly I:C and derivatives thereof; CpG oligonucleotides; interleukin-12; interleukin-18; interferon-α; interferon-β; interferon-ω; interferon-γ; and Flt3 ligand.

* * * * *

SEQUENCE LISTING

<160> NUMBER OF SEQ ID NOS: 47

<210> SEQ ID NO 1
<211> LENGTH: 1508
<212> TYPE: DNA
<213> ORGANISM: Canis familiaris
<220> FEATURE:
<221> NAME/KEY: CDS
<222> LOCATION: (17)..(937)

<400> SEQUENCE: 1

| | | |
|---|---|---|
| gcggcccggg cgggac atg gcg gcg ctc tac gcc tgc acc aag tgc cac cag | 52 |
| Met Ala Ala Leu Tyr Ala Cys Thr Lys Cys His Gln | |
| 1 5 10 | |
| cgc ttc ccc ttc gag gcg ctg tct cag ggg cag cag ctg tgc aag gaa | 100 |
| Arg Phe Pro Phe Glu Ala Leu Ser Gln Gly Gln Gln Leu Cys Lys Glu | |
| 15 20 25 | |
| tgt cgg att gca cac cct gtt gtg aag tgc acc tac tgt aga act gag | 148 |
| Cys Arg Ile Ala His Pro Val Val Lys Cys Thr Tyr Cys Arg Thr Glu | |
| 30 35 40 | |
| tac cag caa gag agt aaa acc aat aca ata tgc aaa aaa tgt gct cag | 196 |
| Tyr Gln Gln Glu Ser Lys Thr Asn Thr Ile Cys Lys Lys Cys Ala Gln | |
| 45 50 55 60 | |
| aat gtg cag tta tat gga acg ccc aaa cct tgt cag tac tgc aac ata | 244 |
| Asn Val Gln Leu Tyr Gly Thr Pro Lys Pro Cys Gln Tyr Cys Asn Ile | |
| 65 70 75 | |
| att gca gca ttt att ggc aac aaa tgc cag cga tgc acg aat tca gag | 292 |
| Ile Ala Ala Phe Ile Gly Asn Lys Cys Gln Arg Cys Thr Asn Ser Glu | |
| 80 85 90 | |
| aag aag tat gga cca cca tat tca tgt gaa cag tgt aaa caa cag tgt | 340 |
| Lys Lys Tyr Gly Pro Pro Tyr Ser Cys Glu Gln Cys Lys Gln Gln Cys | |
| 95 100 105 | |
| gca ttt gac agg aaa gat gat aga aag aag gta gat ggg aaa ttg ctg | 388 |
| Ala Phe Asp Arg Lys Asp Asp Arg Lys Lys Val Asp Gly Lys Leu Leu | |
| 110 115 120 | |
| tgt tgg ctg tgc aca ctt tca tac aaa cgg gtc ctt caa aag acc aaa | 436 |
| Cys Trp Leu Cys Thr Leu Ser Tyr Lys Arg Val Leu Gln Lys Thr Lys | |
| 125 130 135 140 | |
| gag cag agg aaa cat ctg agc agc tct tcc cgt gcc agc cac cag gag | 484 |
| Glu Gln Arg Lys His Leu Ser Ser Ser Ser Arg Ala Ser His Gln Glu | |
| 145 150 155 | |
| aag gaa cag tat cga ctg agt ggt ggc agc cat tat aac agc cag aaa | 532 |
| Lys Glu Gln Tyr Arg Leu Ser Gly Gly Ser His Tyr Asn Ser Gln Lys | |
| 160 165 170 | |
| aca ctt tct acg tct tca att caa aat gaa atc cca aag aaa aaa tcc | 580 |
| Thr Leu Ser Thr Ser Ser Ile Gln Asn Glu Ile Pro Lys Lys Lys Ser | |
| 175 180 185 | |
| aag ttt gag tca atc aca act aat gga gac agc ttt tcc cca gac ctg | 628 |
| Lys Phe Glu Ser Ile Thr Thr Asn Gly Asp Ser Phe Ser Pro Asp Leu | |
| 190 195 200 | |
| gct ctg gac tca cca ggc act gac cac ttt gtc atc att gcc cag ctg | 676 |
| Ala Leu Asp Ser Pro Gly Thr Asp His Phe Val Ile Ile Ala Gln Leu | |
| 205 210 215 220 | |
| aag gaa gaa gtg gcc act ttg aag aag atg ctg cat caa aag gat caa | 724 |
| Lys Glu Glu Val Ala Thr Leu Lys Lys Met Leu His Gln Lys Asp Gln | |
| 225 230 235 | |
| atg att tta gag aaa gag aag aag atc aca gag ttg aag gct gat ttt | 772 |
| Met Ile Leu Glu Lys Glu Lys Lys Ile Thr Glu Leu Lys Ala Asp Phe | |
| 240 245 250 | |

```
caa tac caa gaa tct cag atg aga gcc aaa atg aac cag atg gag aaa    820
Gln Tyr Gln Glu Ser Gln Met Arg Ala Lys Met Asn Gln Met Glu Lys
            255                 260                 265 act cac aaa gaa gtc aca gag caa ttg cag gcc aaa aac cga gaa ctc    868
Thr His Lys Glu Val Thr Glu Gln Leu Gln Ala Lys Asn Arg Glu Leu
        270                 275                 280 ctg aag cag gca gct gcc ttg tcc aag agc aag aag tca gag aag tca    916
Leu Lys Gln Ala Ala Ala Leu Ser Lys Ser Lys Lys Ser Glu Lys Ser
285                 290                 295                 300 gga gct ata act tct cca tga gagaccataa ggaggcttcc agccacagca        967
Gly Ala Ile Thr Ser Pro
                305 aaggggtttc ctgggttagg gttggtggcc tggctgttat ctgggaattg cccacgctcc   1027 cgggaagggc ctgtcccagt cggctctgcc ctaccgccgc agcgtcccca cctggctgaa   1087 gctgacgtcc gacgacgtga aggagcagat ctacaaactg ccaagaagg gtctgactcc    1147 ctcgcagatc ggtgtgatcc tgagagactc ccatggtgtt gcacaagtac gttttgtgac   1207 aggcaataaa atcttgagaa ttcttaagtc caagggactt gcacctgatc tccctgagga   1267 tctgtaccat ttgattaaga aagctgttgc tgttcgaaag catcttgaga ggaacagaaa   1327 ggataaggat gccaaattcc gactgattct gattgagagc cgtattcacc gattggctcg   1387 atattataag accaaaagag ttctccctcc caattggaaa tacgagtcat ccacagcctc   1447 tgccctggtc gcataaattt ggctatgtac tcaagcaata aaatcattgt ctactagaaa   1507 a                                                                  1508

<210> SEQ ID NO 2
<211> LENGTH: 306
<212> TYPE: PRT
<213> ORGANISM: Canis familiaris

<400> SEQUENCE: 2

Met Ala Ala Leu Tyr Ala Cys Thr Lys Cys His Gln Arg Phe Pro Phe
1               5                   10                  15

Glu Ala Leu Ser Gln Gly Gln Gln Leu Cys Lys Glu Cys Arg Ile Ala
            20                  25                  30

His Pro Val Val Lys Cys Thr Tyr Cys Arg Thr Glu Tyr Gln Gln Glu
        35                  40                  45

Ser Lys Thr Asn Thr Ile Cys Lys Lys Cys Ala Gln Asn Val Gln Leu
    50                  55                  60

Tyr Gly Thr Pro Lys Pro Cys Gln Tyr Cys Asn Ile Ile Ala Ala Phe
65                  70                  75                  80

Ile Gly Asn Lys Cys Gln Arg Cys Thr Asn Ser Glu Lys Lys Tyr Gly
                85                  90                  95

Pro Pro Tyr Ser Cys Glu Gln Cys Lys Gln Cys Ala Phe Asp Arg
            100                 105                 110

Lys Asp Asp Arg Lys Lys Val Asp Gly Lys Leu Leu Cys Trp Leu Cys
        115                 120                 125

Thr Leu Ser Tyr Lys Arg Val Leu Gln Lys Thr Lys Glu Gln Arg Lys
    130                 135                 140

His Leu Ser Ser Ser Arg Ala Ser His Gln Glu Lys Glu Gln Tyr
145                 150                 155                 160

Arg Leu Ser Gly Gly Ser His Tyr Asn Ser Gln Lys Thr Leu Ser Thr
                165                 170                 175

Ser Ser Ile Gln Asn Glu Ile Pro Lys Lys Lys Ser Lys Phe Glu Ser
```

```
                   180                 185                 190
Ile Thr Thr Asn Gly Asp Ser Phe Ser Pro Asp Leu Ala Leu Asp Ser
            195                 200                 205
Pro Gly Thr Asp His Phe Val Ile Ile Ala Gln Leu Lys Glu Glu Val
        210                 215                 220
Ala Thr Leu Lys Lys Met Leu His Gln Lys Asp Gln Met Ile Leu Glu
225                 230                 235                 240
Lys Glu Lys Ile Thr Glu Leu Lys Ala Asp Phe Gln Tyr Gln Glu
                245                 250                 255
Ser Gln Met Arg Ala Lys Met Asn Gln Met Glu Lys Thr His Lys Glu
            260                 265                 270
Val Thr Glu Gln Leu Gln Ala Lys Asn Arg Glu Leu Leu Lys Gln Ala
        275                 280                 285
Ala Ala Leu Ser Lys Ser Lys Lys Ser Glu Lys Ser Gly Ala Ile Thr
        290                 295                 300
Ser Pro
305

<210> SEQ ID NO 3
<211> LENGTH: 2161
<212> TYPE: DNA
<213> ORGANISM: Homo sapiens
<220> FEATURE:
<221> NAME/KEY: CDS
<222> LOCATION: (103)..(1026)

<400> SEQUENCE: 3
gccgcagcca gcagcctgca gccgccgccg ggttgtgcct cagactgtca gataaatcgg      60
cgggccgggc cggcgggtcg gtgagcgcgg cccgggccgg ac atg gcg gcg ctc       114
                                             Met Ala Ala Leu
                                               1 tac gcc tgc acc aag tgc cac cag cgc ttc ccc ttc gag gcg ctg tct     162
Tyr Ala Cys Thr Lys Cys His Gln Arg Phe Pro Phe Glu Ala Leu Ser
  5                  10                  15                  20 cag ggg cag cag ctg tgc aag gaa tgt cgg att gca cac cct gtt gtg     210
Gln Gly Gln Gln Leu Cys Lys Glu Cys Arg Ile Ala His Pro Val Val
                 25                  30                  35 aag tgc acc tac tgc agg act gag tac cag cag gag agt aaa acc aat     258
Lys Cys Thr Tyr Cys Arg Thr Glu Tyr Gln Gln Glu Ser Lys Thr Asn
             40                  45                  50 aca ata tgc aag aaa tgt gct cag aac gtg cag ttg tat gga acg ccc     306
Thr Ile Cys Lys Lys Cys Ala Gln Asn Val Gln Leu Tyr Gly Thr Pro
         55                  60                  65 aaa cct tgt cag tat tgc aac ata att gca gca ttt att ggg aat aaa     354
Lys Pro Cys Gln Tyr Cys Asn Ile Ile Ala Ala Phe Ile Gly Asn Lys
     70                  75                  80 tgc cag cgc tgc aca aat tca gaa aag aag tat gga cca ccc tat tct     402
Cys Gln Arg Cys Thr Asn Ser Glu Lys Lys Tyr Gly Pro Pro Tyr Ser
 85                  90                  95                 100 tgt gaa cag tgc aag cag cag tgt gca ttt gac agg aaa gat gat aga     450
Cys Glu Gln Cys Lys Gln Gln Cys Ala Phe Asp Arg Lys Asp Asp Arg
                105                 110                 115 aag aag gta gat ggg aaa ttg ctg tgc tgg ctg tgc aca ctt tca tac     498
Lys Lys Val Asp Gly Lys Leu Leu Cys Trp Leu Cys Thr Leu Ser Tyr
            120                 125                 130 aaa cgg gtc ctt cag aag acc aaa gag cag agg aaa cac ctg agt agc     546
Lys Arg Val Leu Gln Lys Thr Lys Glu Gln Arg Lys His Leu Ser Ser
        135                 140                 145
```

| | | |
|---|---|---|
| tct tct cgt gct ggc cac cag gag aag gag cag tat agt cgc ctg agt<br>Ser Ser Arg Ala Gly His Gln Glu Lys Glu Gln Tyr Ser Arg Leu Ser<br>150                              155                            160 | 594 |
| ggt ggt ggc cat tat aac agc cag aaa aca ctt tct aca tct tca att<br>Gly Gly Gly His Tyr Asn Ser Gln Lys Thr Leu Ser Thr Ser Ser Ile<br>165                              170                      175                      180 | 642 |
| caa aat gaa atc cca aag aaa aag tcc aag ttt gag tca atc aca act<br>Gln Asn Glu Ile Pro Lys Lys Lys Ser Lys Phe Glu Ser Ile Thr Thr<br>                          185                      190                      195 | 690 |
| aat gga gac agc ttc tcc cca gac ctg gct ctg gac tca cca ggc act<br>Asn Gly Asp Ser Phe Ser Pro Asp Leu Ala Leu Asp Ser Pro Gly Thr<br>                  200                      205                      210 | 738 |
| gac cac ttt gtc atc att gcc caa ctg aag gaa gaa gtg gct acc ctg<br>Asp His Phe Val Ile Ile Ala Gln Leu Lys Glu Glu Val Ala Thr Leu<br>215                              220                      225 | 786 |
| aag aag atg ttg cat caa aag gat caa atg att tta gag aaa gag aag<br>Lys Lys Met Leu His Gln Lys Asp Gln Met Ile Leu Glu Lys Glu Lys<br>230                              235                      240 | 834 |
| aag att aca gag ttg aag gct gat ttt cag tac cag gaa tcg cag atg<br>Lys Ile Thr Glu Leu Lys Ala Asp Phe Gln Tyr Gln Glu Ser Gln Met<br>245                            250                      255                      260 | 882 |
| aga gcc aaa atg aac cag atg gag aaa acc cac aaa gaa gtc aca gaa<br>Arg Ala Lys Met Asn Gln Met Glu Lys Thr His Lys Glu Val Thr Glu<br>                          265                      270                      275 | 930 |
| caa ctg cag gcc aaa aac cga gag ctc ctg aag cag gca gct gct ttg<br>Gln Leu Gln Ala Lys Asn Arg Glu Leu Leu Lys Gln Ala Ala Ala Leu<br>                  280                      285                      290 | 978 |
| tcc aag agc aag aag tca gag aag tca gga gct ata acc tct cca tga<br>Ser Lys Ser Lys Lys Ser Glu Lys Ser Gly Ala Ile Thr Ser Pro<br>                        295                      300                      305 | 1026 |
| cagacctcaa ggaggctccc tagcaacagc aaatggagtt gtccagggtt agggttggag | 1086 |
| acctggctgt tctgtgggaa ttgcaagctt tcttaagaaa tctctatttt attacagtta | 1146 |
| tccttctttg tgcgattgca gtgggctgaa tggaaacacc tggtttgtgc tgtgttagac | 1206 |
| tgcatgcttg agtgtttggg atttcaagct cgctctcttt ctctcactat taggactttt | 1266 |
| cttttttctc ttcctcttct ctctattttg gttctattct ttttttttct tttttctttt | 1326 |
| tttttttttt tttttttttg tggtggtcac tgctcagtgt aatgtgcaga atgatttgtt | 1386 |
| ttttgttttt tttttttttt tttggtcctt cattgcatcc tgccatccc atgagcaaac | 1446 |
| agtttggcat taattatata tcactgccac cctctgaact ttgaaaactg ccatcttcag | 1506 |
| acttggtata atggaagagg ctttctctct ccaataaacc ttttgcttca gggtatactc | 1566 |
| ttcggttttt ttccagatgt attatgtatg aactttgtac tatgtatagc cagagtttta | 1626 |
| tttatttttt aaaaaagaaa cttttctctt ataaaggaat aatggtggtc tagctagttc | 1686 |
| ttgtaaaagt gatgcctctt gaaaaaaaac agtcctattc actagctttt agtaaaagaa | 1746 |
| tcagatcttt tctttcttgt taccttggag tcttaaaaac tgattgctaa ggtgaaacaa | 1806 |
| ttcaatgcat aagtatggag ctaagtgcct tttggaggat ttcttggaag agcatttatg | 1866 |
| gagatactta agggaggtag caaagatttg aaccgtctgt cttttttaagt aagggcagaa | 1926 |
| agcaaggttg tccaggttgt actggacact tctctcccca cccctttcct gattgtttta | 1986 |
| tgtgattgat tttaaattct cacactgcca cttctttaaa aaataaaatc ctttatttgc | 2046 |
| ttaaaaaaaa aaaaaaaaaa aaaaaaaaaa aaaaaaaaaa aaaaaaaaaa aaaaaaaaaa | 2106 |
| aaaaaaaaaa aaaaaaaaaa aaaaaaaaaa aaaaaaaaaa aaaaaaaaaa aaaaa | 2161 |

```
<210> SEQ ID NO 4
<211> LENGTH: 307
<212> TYPE: PRT
<213> ORGANISM: Homo sapiens

<400> SEQUENCE: 4
```

Met Ala Ala Leu Tyr Ala Cys Thr Lys Cys His Gln Arg Phe Pro Phe
1               5                   10                  15

Glu Ala Leu Ser Gln Gly Gln Gln Leu Cys Lys Glu Cys Arg Ile Ala
            20                  25                  30

His Pro Val Val Lys Cys Thr Tyr Cys Arg Thr Glu Tyr Gln Gln Glu
        35                  40                  45

Ser Lys Thr Asn Thr Ile Cys Lys Lys Cys Ala Gln Asn Val Gln Leu
    50                  55                  60

Tyr Gly Thr Pro Lys Pro Cys Gln Tyr Cys Asn Ile Ile Ala Ala Phe
65                  70                  75                  80

Ile Gly Asn Lys Cys Gln Arg Cys Thr Asn Ser Glu Lys Lys Tyr Gly
                85                  90                  95

Pro Pro Tyr Ser Cys Glu Gln Cys Lys Gln Gln Cys Ala Phe Asp Arg
            100                 105                 110

Lys Asp Asp Arg Lys Lys Val Asp Gly Lys Leu Leu Cys Trp Leu Cys
        115                 120                 125

Thr Leu Ser Tyr Lys Arg Val Leu Gln Lys Thr Lys Glu Gln Arg Lys
130                 135                 140

His Leu Ser Ser Ser Arg Ala Gly His Gln Glu Lys Glu Gln Tyr
145                 150                 155                 160

Ser Arg Leu Ser Gly Gly His Tyr Asn Ser Gln Lys Thr Leu Ser
                165                 170                 175

Thr Ser Ser Ile Gln Asn Glu Ile Pro Lys Lys Lys Ser Lys Phe Glu
            180                 185                 190

Ser Ile Thr Thr Asn Gly Asp Ser Phe Ser Pro Asp Leu Ala Leu Asp
        195                 200                 205

Ser Pro Gly Thr Asp His Phe Val Ile Ile Ala Gln Leu Lys Glu Glu
    210                 215                 220

Val Ala Thr Leu Lys Lys Met Leu His Gln Lys Asp Gln Met Ile Leu
225                 230                 235                 240

Glu Lys Glu Lys Lys Ile Thr Glu Leu Lys Ala Asp Phe Gln Tyr Gln
                245                 250                 255

Glu Ser Gln Met Arg Ala Lys Met Asn Gln Met Glu Lys Thr His Lys
            260                 265                 270

Glu Val Thr Glu Gln Leu Gln Ala Lys Asn Arg Glu Leu Leu Lys Gln
        275                 280                 285

Ala Ala Ala Leu Ser Lys Ser Lys Lys Ser Glu Lys Ser Gly Ala Ile
    290                 295                 300

Thr Ser Pro
305

```
<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
aattaaccct cactaaaggg                                             20
```

```
<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
taatacgact cactatagg                                                  19

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
agctgtgcaa ggaatgtc                                                   18

<210> SEQ ID NO 8
<211> LENGTH: 18
<212> TYPE: DNA
<213> ORGANISM: Artificial Sequence
<220> FEATURE:
<223> OTHER INFORMATION: Synthetic primer

<400> SEQUENCE: 8
ccattagttg tgattgac                                                   18

<210> SEQ ID NO 9
<211> LENGTH: 18
<212> TYPE: DNA
<213> ORGANISM: Artificial Sequence
<220> FEATURE:
<223> OTHER INFORMATION: Synthetic GAPDH primer

<400> SEQUENCE: 9
gggctgcttt taactctg                                                   18

<210> SEQ ID NO 10
<211> LENGTH: 18
<212> TYPE: DNA
<213> ORGANISM: Artificial Sequence
<220> FEATURE:
<223> OTHER INFORMATION: Synthetic GAPDH primer

<400> SEQUENCE: 10
ccaggaaatg agcttgac                                                   18

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
atcatatggc ggcgctctac gc                                              22

<210> SEQ ID NO 12
<211> LENGTH: 25
<212> TYPE: DNA
<213> ORGANISM: Artificial Sequence
<220> FEATURE:
<223> OTHER INFORMATION: Synthetic primer
```

-continued

<400> SEQUENCE: 12
cgctcgagtg gagaagttat agctc    25

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
gatatcatgg cggcgctcta cgc    23

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
gaattctcat ggagaggtta tagc    24

<210> SEQ ID NO 15
<211> LENGTH: 2326
<212> TYPE: DNA
<213> ORGANISM: Canis familiaris
<220> FEATURE:
<221> NAME/KEY: CDS
<222> LOCATION: (62)..(1894)

<400> SEQUENCE: 15

```
cagcgcctcg  acatcggag  ctgccgctgc  cgaacacggg  cccgcaacac  aggtaatcag      60 t atg cat ttc caa agc ttt tgg cta tgt ctg gga ctt ctg ttc atc tca         109
  Met His Phe Gln Ser Phe Trp Leu Cys Leu Gly Leu Leu Phe Ile Ser
   1               5                  10                  15 gtt aat gca gaa ttt atg gat gat gat gtt gag atg gaa gat ttt gat           157
Val Asn Ala Glu Phe Met Asp Asp Asp Val Glu Met Glu Asp Phe Asp
             20                  25                  30 gaa aat tca gaa gag att gat gtt aat gaa ggt gaa ctc ccc tca gag           205
Glu Asn Ser Glu Glu Ile Asp Val Asn Glu Gly Glu Leu Pro Ser Glu
         35                  40                  45 att aat tat aag aca cct cag cct atg gga gaa gta tat ttt aca gaa           253
Ile Asn Tyr Lys Thr Pro Gln Pro Met Gly Glu Val Tyr Phe Thr Glu
     50                  55                  60 act ttt gat agt gga agg ttg gct ggg tgg gtc tta tca aaa gca aag           301
Thr Phe Asp Ser Gly Arg Leu Ala Gly Trp Val Leu Ser Lys Ala Lys
 65                  70                  75                  80 aaa gat gat aca gat gca gag att tcc ata tat gat gga aga tgg gaa           349
Lys Asp Asp Thr Asp Ala Glu Ile Ser Ile Tyr Asp Gly Arg Trp Glu
                 85                  90                  95 ata gaa gaa ttg aaa gaa aac cga gtg cct ggt gac aga ggg ctg gta           397
Ile Glu Glu Leu Lys Glu Asn Arg Val Pro Gly Asp Arg Gly Leu Val
            100                 105                 110 ctg aaa tct aga gca aag cat cat gca ata gct gct gta tta gca aaa           445
Leu Lys Ser Arg Ala Lys His His Ala Ile Ala Ala Val Leu Ala Lys
        115                 120                 125 ccc ttc att ttt gct gac aaa ccc ttg atc gtt caa tat gaa gta aat           493
Pro Phe Ile Phe Ala Asp Lys Pro Leu Ile Val Gln Tyr Glu Val Asn
    130                 135                 140 ttt caa gat ggt att gat tgt gga ggt gca tac att aaa ctc cta gca           541
```

```
Phe Gln Asp Gly Ile Asp Cys Gly Gly Ala Tyr Ile Lys Leu Leu Ala
145                 150                 155                 160 gac act gat ggt ttg aat ctg gaa aac ttt tat gat aaa aca tcc tat      589
Asp Thr Asp Gly Leu Asn Leu Glu Asn Phe Tyr Asp Lys Thr Ser Tyr
                165                 170                 175 acc att atg ttt gga cca gat aaa tgt gga gaa gat tat aaa ctt cat      637
Thr Ile Met Phe Gly Pro Asp Lys Cys Gly Glu Asp Tyr Lys Leu His
            180                 185                 190 ttc atc ttc aga cac aaa cat cct aaa act gga gtt ttt gaa gag aaa      685
Phe Ile Phe Arg His Lys His Pro Lys Thr Gly Val Phe Glu Glu Lys
        195                 200                 205 cat gcc aaa cct cca gat gta gac ctt aaa aag ttc ttt aca gac agg      733
His Ala Lys Pro Pro Asp Val Asp Leu Lys Lys Phe Phe Thr Asp Arg
    210                 215                 220 aag act cat ctt tat acc ctt gtg atg aat cca gat gac aca ttt gaa      781
Lys Thr His Leu Tyr Thr Leu Val Met Asn Pro Asp Asp Thr Phe Glu
225                 230                 235                 240 gta cta att gat caa gta gtt gta aac caa gga agc ctc cta gaa gat      829
Val Leu Ile Asp Gln Val Val Val Asn Gln Gly Ser Leu Leu Glu Asp
                245                 250                 255 gtg gtt cct cct atc aat cct ccc aaa gaa att gaa gac ccc agt gat      877
Val Val Pro Pro Ile Asn Pro Pro Lys Glu Ile Glu Asp Pro Ser Asp
            260                 265                 270 aaa aag cct gat gaa tgg gat gaa aga gca aaa atc cct gat cct tct      925
Lys Lys Pro Asp Glu Trp Asp Glu Arg Ala Lys Ile Pro Asp Pro Ser
        275                 280                 285 gct gtc aaa cca gaa gac tgg gat gaa agt gaa cct gcc caa ata gaa      973
Ala Val Lys Pro Glu Asp Trp Asp Glu Ser Glu Pro Ala Gln Ile Glu
    290                 295                 300 gat tta agt gtt gtt aaa cct gat ggc tgg ctt gat gat gaa cca aaa     1021
Asp Leu Ser Val Val Lys Pro Asp Gly Trp Leu Asp Asp Glu Pro Lys
305                 310                 315                 320 ttt att cca gat cca aat gct gaa aaa cct gat gac tgg aat gaa gac     1069
Phe Ile Pro Asp Pro Asn Ala Glu Lys Pro Asp Asp Trp Asn Glu Asp
                325                 330                 335 atg gat gga gaa tgg gag gca cct cgt att tct aat cca gca tgt cga     1117
Met Asp Gly Glu Trp Glu Ala Pro Arg Ile Ser Asn Pro Ala Cys Arg
            340                 345                 350 att ggg tgt ggt gag tgg tca cct ccc atg ata gat aat ccc aaa tac     1165
Ile Gly Cys Gly Glu Trp Ser Pro Pro Met Ile Asp Asn Pro Lys Tyr
        355                 360                 365 aaa gga gta tgg aga cct cca atg ata gat aat cct aac tac cag gga     1213
Lys Gly Val Trp Arg Pro Pro Met Ile Asp Asn Pro Asn Tyr Gln Gly
    370                 375                 380 atc tgg agt cct cga aaa atc ccg aat cca gat tat ttt gaa gat gat     1261
Ile Trp Ser Pro Arg Lys Ile Pro Asn Pro Asp Tyr Phe Glu Asp Asp
385                 390                 395                 400 cat cca ttt ctt ctg act tct ttc cgt gct ctt ggt tta gag ctt tgg     1309
His Pro Phe Leu Leu Thr Ser Phe Arg Ala Leu Gly Leu Glu Leu Trp
                405                 410                 415 tct atg acc tct aat att tac ttt gat aat ttt att atc tgc tcg gaa     1357
Ser Met Thr Ser Asn Ile Tyr Phe Asp Asn Phe Ile Ile Cys Ser Glu
            420                 425                 430 aag gaa aca gca gat cgc tgg gct gca gat ggg tgg gga gtg aag ata     1405
Lys Glu Thr Ala Asp Arg Trp Ala Ala Asp Gly Trp Gly Val Lys Ile
        435                 440                 445 ctg gta gca aat gct aac gag cct ggt ata ttt aaa cag tta atg gca     1453
Leu Val Ala Asn Ala Asn Glu Pro Gly Ile Phe Lys Gln Leu Met Ala
    450                 455                 460
```

```
gct gct gaa gag cgc cca tgg ctt tgg ctc att tat ttt gtg aca gca    1501
Ala Ala Glu Glu Arg Pro Trp Leu Trp Leu Ile Tyr Phe Val Thr Ala
465                 470                 475                 480 ggg ctt cca ata gca tta att gct tca ttt tgt tgg cca aga aaa gtc    1549
Gly Leu Pro Ile Ala Leu Ile Ala Ser Phe Cys Trp Pro Arg Lys Val
                485                 490                 495 aag aaa aaa tat gaa gat tca gag tat aaa aag act gac ata tgc aag    1597
Lys Lys Lys Tyr Glu Asp Ser Glu Tyr Lys Lys Thr Asp Ile Cys Lys
            500                 505                 510 cca caa aca aag gga gca cta gag caa gaa gtg aag gaa aag aaa gct    1645
Pro Gln Thr Lys Gly Ala Leu Glu Gln Glu Val Lys Glu Lys Lys Ala
        515                 520                 525 gcc ctg gag aaa cca gta gac ttg gaa gaa gaa aaa aag caa agt gat    1693
Ala Leu Glu Lys Pro Val Asp Leu Glu Glu Glu Lys Lys Gln Ser Asp
    530                 535                 540 ggt gaa act gtt gaa aaa gaa gag gaa gct gaa cct gag gaa aag agt    1741
Gly Glu Thr Val Glu Lys Glu Glu Glu Ala Glu Pro Glu Glu Lys Ser
545                 550                 555                 560 gaa gaa gaa att gaa atc ata gaa gga caa gaa gaa ggt aat aaa tca    1789
Glu Glu Glu Ile Glu Ile Ile Glu Gly Gln Glu Glu Gly Asn Lys Ser
                565                 570                 575 aat aag tct gga tca gag gat gag atg aag gaa gcg gat gag agc aca    1837
Asn Lys Ser Gly Ser Glu Asp Glu Met Lys Glu Ala Asp Glu Ser Thr
            580                 585                 590 gga tct gga gat ggg cca gtg aag tca gtg cgc aaa aga aga gta cga    1885
Gly Ser Gly Asp Gly Pro Val Lys Ser Val Arg Lys Arg Arg Val Arg
        595                 600                 605 aag gaa taa actatattca agtatttta attcctgagc gagatatttg             1934
Lys Glu
    610 gcattctaaa atcagtgtgc cagagctgaa cttgagtcag tctgcacatg tttctaatat    1994 ctagcaatgt tattctttca gacacttatt ttagtctttc ttttcaggaa aaaaaaaact    2054 ttcaagttac ctggtctttg gatttagagt aaaaaagagg ggcatgttac gtatcagatt    2114 taagagacta ataccattag aagttaccaa gttttaatag ttggagaaag ttttggtttg    2174 tacagagaaa aataatatgc agcagctttg ctgctgttgg aaaatcagtt attggaattt    2234 cccccttaaac agctatacaa caatattact ggtagttcta taataaaaat gagagtgtgt    2294 tctgttgtac agagctaact gcaaaaaaaa aa                                  2326

<210> SEQ ID NO 16
<211> LENGTH: 610
<212> TYPE: PRT
<213> ORGANISM: Canis familiaris

<400> SEQUENCE: 16

Met His Phe Gln Ser Phe Trp Leu Cys Leu Gly Leu Leu Phe Ile Ser
1               5                   10                  15

Val Asn Ala Glu Phe Met Asp Asp Val Glu Met Glu Asp Phe Asp
            20                  25                  30

Glu Asn Ser Glu Glu Ile Asp Val Asn Glu Gly Glu Leu Pro Ser Glu
        35                  40                  45

Ile Asn Tyr Lys Thr Pro Gln Pro Met Gly Glu Val Tyr Phe Thr Glu
    50                  55                  60

Thr Phe Asp Ser Gly Arg Leu Ala Gly Trp Val Leu Ser Lys Ala Lys
65                  70                  75                  80

Lys Asp Asp Thr Asp Ala Glu Ile Ser Ile Tyr Asp Gly Arg Trp Glu
                85                  90                  95
```

```
Ile Glu Glu Leu Lys Glu Asn Arg Val Pro Gly Asp Arg Gly Leu Val
            100                 105                 110

Leu Lys Ser Arg Ala Lys His His Ala Ile Ala Ala Val Leu Ala Lys
            115                 120                 125

Pro Phe Ile Phe Ala Asp Lys Pro Leu Ile Val Gln Tyr Glu Val Asn
            130                 135                 140

Phe Gln Asp Gly Ile Asp Cys Gly Gly Ala Tyr Ile Lys Leu Leu Ala
145                 150                 155                 160

Asp Thr Asp Gly Leu Asn Leu Glu Asn Phe Tyr Asp Lys Thr Ser Tyr
                    165                 170                 175

Thr Ile Met Phe Gly Pro Asp Lys Cys Gly Glu Asp Tyr Lys Leu His
            180                 185                 190

Phe Ile Phe Arg His Lys His Pro Lys Thr Gly Val Phe Glu Glu Lys
            195                 200                 205

His Ala Lys Pro Pro Asp Val Asp Leu Lys Lys Phe Phe Thr Asp Arg
            210                 215                 220

Lys Thr His Leu Tyr Thr Leu Val Met Asn Pro Asp Asp Thr Phe Glu
225                 230                 235                 240

Val Leu Ile Asp Gln Val Val Val Asn Gln Gly Ser Leu Leu Glu Asp
                    245                 250                 255

Val Val Pro Pro Ile Asn Pro Pro Lys Glu Ile Glu Asp Pro Ser Asp
            260                 265                 270

Lys Lys Pro Asp Glu Trp Asp Glu Arg Ala Lys Ile Pro Asp Pro Ser
            275                 280                 285

Ala Val Lys Pro Glu Asp Trp Asp Glu Ser Glu Pro Ala Gln Ile Glu
            290                 295                 300

Asp Leu Ser Val Val Lys Pro Asp Gly Trp Leu Asp Asp Glu Pro Lys
305                 310                 315                 320

Phe Ile Pro Asp Pro Asn Ala Glu Lys Pro Asp Asp Trp Asn Glu Asp
                    325                 330                 335

Met Asp Gly Glu Trp Glu Ala Pro Arg Ile Ser Asn Pro Ala Cys Arg
            340                 345                 350

Ile Gly Cys Gly Glu Trp Ser Pro Pro Met Ile Asp Asn Pro Lys Tyr
            355                 360                 365

Lys Gly Val Trp Arg Pro Pro Met Ile Asp Asn Pro Asn Tyr Gln Gly
            370                 375                 380

Ile Trp Ser Pro Arg Lys Ile Pro Asn Pro Asp Tyr Phe Glu Asp Asp
385                 390                 395                 400

His Pro Phe Leu Leu Thr Ser Phe Arg Ala Leu Gly Leu Glu Leu Trp
                    405                 410                 415

Ser Met Thr Ser Asn Ile Tyr Phe Asp Asn Phe Ile Ile Cys Ser Glu
            420                 425                 430

Lys Glu Thr Ala Asp Arg Trp Ala Ala Asp Gly Trp Gly Val Lys Ile
            435                 440                 445

Leu Val Ala Asn Ala Asn Glu Pro Gly Ile Phe Lys Gln Leu Met Ala
            450                 455                 460

Ala Ala Glu Glu Arg Pro Trp Leu Trp Leu Ile Tyr Phe Val Thr Ala
465                 470                 475                 480

Gly Leu Pro Ile Ala Leu Ile Ala Ser Phe Cys Trp Pro Arg Lys Val
                    485                 490                 495

Lys Lys Lys Tyr Glu Asp Ser Glu Tyr Lys Lys Thr Asp Ile Cys Lys
            500                 505                 510
```

```
Pro Gln Thr Lys Gly Ala Leu Glu Gln Glu Val Lys Glu Lys Lys Ala
            515                 520                 525
Ala Leu Glu Lys Pro Val Asp Leu Glu Glu Lys Lys Gln Ser Asp
    530                 535                 540
Gly Glu Thr Val Glu Lys Glu Glu Ala Glu Pro Glu Glu Lys Ser
545                 550                 555                 560
Glu Glu Glu Ile Glu Ile Ile Glu Gly Gln Glu Gly Asn Lys Ser
                565                 570                 575
Asn Lys Ser Gly Ser Glu Asp Glu Met Lys Glu Ala Asp Glu Ser Thr
            580                 585                 590
Gly Ser Gly Asp Gly Pro Val Lys Ser Val Arg Lys Arg Val Arg
    595                 600                 605
Lys Glu
    610

<210> SEQ ID NO 17
<211> LENGTH: 2710
<212> TYPE: DNA
<213> ORGANISM: Homo sapiens
<220> FEATURE:
<221> NAME/KEY: CDS
<222> LOCATION: (102)..(1934)

<400> SEQUENCE: 17
cgccggcggg actggtctga agagacgcgg ggacaaagtg gcaacgactt ggacatctga       60
gctgtcactg ccgaaaacag gccgcaagag agataatcaa t atg cat ttc caa gcc    116
                                              Met His Phe Gln Ala
                                                1               5 ttt tgg cta tgt ttg ggt ctt ctg ttc atc tca att aat gca gaa ttt      164
Phe Trp Leu Cys Leu Gly Leu Leu Phe Ile Ser Ile Asn Ala Glu Phe
            10                  15                  20 atg gat gat gat gtt gag acg gaa gac ttt gaa gaa aat tca gaa gaa      212
Met Asp Asp Asp Val Glu Thr Glu Asp Phe Glu Glu Asn Ser Glu Glu
        25                  30                  35 att gat gtt aat gaa agt gaa ctt tcc tca gag att aaa tat aag aca      260
Ile Asp Val Asn Glu Ser Glu Leu Ser Ser Glu Ile Lys Tyr Lys Thr
    40                  45                  50 cct caa cct ata gga gaa gta tat ttt gca gaa act ttt gat agt gga      308
Pro Gln Pro Ile Gly Glu Val Tyr Phe Ala Glu Thr Phe Asp Ser Gly
55                  60                  65 agg ttg gct gga tgg gtc tta tca aaa gca aag aaa gat gac atg gat      356
Arg Leu Ala Gly Trp Val Leu Ser Lys Ala Lys Lys Asp Asp Met Asp
70                  75                  80                  85 gag gaa att tca ata tac gat gga aga tgg gaa att gaa gag ttg aaa      404
Glu Glu Ile Ser Ile Tyr Asp Gly Arg Trp Glu Ile Glu Glu Leu Lys
                90                  95                 100 gaa aac cag gta cct ggt gac aga gga ctg gta tta aaa tct aga gca      452
Glu Asn Gln Val Pro Gly Asp Arg Gly Leu Val Leu Lys Ser Arg Ala
            105                 110                 115 aag cat cat gca ata tct gct gta tta gca aaa cca ttc att ttt gct      500
Lys His His Ala Ile Ser Ala Val Leu Ala Lys Pro Phe Ile Phe Ala
        120                 125                 130 gat aaa ccc ttg ata gtt caa tat gaa gta aat ttt caa gat ggt att      548
Asp Lys Pro Leu Ile Val Gln Tyr Glu Val Asn Phe Gln Asp Gly Ile
    135                 140                 145 gat tgt gga ggt gca tac att aaa ctc cta gca gac act gat gat ttg      596
Asp Cys Gly Gly Ala Tyr Ile Lys Leu Leu Ala Asp Thr Asp Asp Leu
150                 155                 160                 165 att ctg gaa aac ttt tat gat aaa aca tcc tat atc att atg ttt gga      644
```

```
                                                                -continued

Ile Leu Glu Asn Phe Tyr Asp Lys Thr Ser Tyr Ile Ile Met Phe Gly
            170                 175                 180 cca gat aaa tgt gga gaa gat tat aaa ctt cat ttt atc ttc aga cat       692
Pro Asp Lys Cys Gly Glu Asp Tyr Lys Leu His Phe Ile Phe Arg His
                185                 190                 195 aaa cat ccc aaa act gga gtt ttc gaa gag aaa cat gcc aaa cct cca       740
Lys His Pro Lys Thr Gly Val Phe Glu Glu Lys His Ala Lys Pro Pro
        200                 205                 210 gat gta gac ctt aaa aag ttc ttt aca gac agg aag act cat ctt tat       788
Asp Val Asp Leu Lys Lys Phe Phe Thr Asp Arg Lys Thr His Leu Tyr
    215                 220                 225 acc ctt gtg atg aat cca gat gac aca ttt gag gtg tta gtt gat caa       836
Thr Leu Val Met Asn Pro Asp Asp Thr Phe Glu Val Leu Val Asp Gln
230                 235                 240                 245 aca gtt gta aac aaa gga agc ctc cta gag gat gtg gtt cct cct atc       884
Thr Val Val Asn Lys Gly Ser Leu Leu Glu Asp Val Val Pro Pro Ile
                250                 255                 260 aaa cct ccc aaa gaa att gaa gat ccc aat gat aaa aaa cct gag gaa       932
Lys Pro Pro Lys Glu Ile Glu Asp Pro Asn Asp Lys Lys Pro Glu Glu
        265                 270                 275 tgg gat gaa aga gca aaa att cct gat cct tct gcc gtc aaa cca gaa       980
Trp Asp Glu Arg Ala Lys Ile Pro Asp Pro Ser Ala Val Lys Pro Glu
    280                 285                 290 gac tgg gat gaa agt gaa cct gcc caa ata gaa gat tca agt gtt gtt      1028
Asp Trp Asp Glu Ser Glu Pro Ala Gln Ile Glu Asp Ser Ser Val Val
295                 300                 305 aaa cct gct ggc tgg ctt gat gat gaa cca aaa ttt atc cct gat cct      1076
Lys Pro Ala Gly Trp Leu Asp Asp Glu Pro Lys Phe Ile Pro Asp Pro
310                 315                 320                 325 aat gct gaa aaa cct gat gac tgg aat gaa gac acg gat gga gaa tgg      1124
Asn Ala Glu Lys Pro Asp Asp Trp Asn Glu Asp Thr Asp Gly Glu Trp
                330                 335                 340 gag gca cct cag att ctt aat cca gca tgt cgg att ggg tgt ggt gag      1172
Glu Ala Pro Gln Ile Leu Asn Pro Ala Cys Arg Ile Gly Cys Gly Glu
        345                 350                 355 tgg aaa cct ccc atg ata gat aac cca aaa tac aaa gga gta tgg aga      1220
Trp Lys Pro Pro Met Ile Asp Asn Pro Lys Tyr Lys Gly Val Trp Arg
    360                 365                 370 cct cca ctg gtc gat aat cct aac tat cag gga atc tgg agt cct cga      1268
Pro Pro Leu Val Asp Asn Pro Asn Tyr Gln Gly Ile Trp Ser Pro Arg
375                 380                 385 aaa att cct aat cca gat tat ttc gaa gat gat cat cca ttt ctt ctg      1316
Lys Ile Pro Asn Pro Asp Tyr Phe Glu Asp Asp His Pro Phe Leu Leu
390                 395                 400                 405 act tct ttc agt gct ctt ggt tta gag ctt tgg tct atg acc tct gat      1364
Thr Ser Phe Ser Ala Leu Gly Leu Glu Leu Trp Ser Met Thr Ser Asp
                410                 415                 420 atc tac ttt gat aat ttt att atc tgt tcg gaa aag gaa gta gca gat      1412
Ile Tyr Phe Asp Asn Phe Ile Ile Cys Ser Glu Lys Glu Val Ala Asp
        425                 430                 435 cac tgg gct gca gat ggt tgg aga tgg aaa ata atg ata gca aat gct      1460
His Trp Ala Ala Asp Gly Trp Arg Trp Lys Ile Met Ile Ala Asn Ala
    440                 445                 450 aat aag cct ggt gta tta aaa cag tta atg gca gct gct gaa ggg cac      1508
Asn Lys Pro Gly Val Leu Lys Gln Leu Met Ala Ala Ala Glu Gly His
455                 460                 465 cca tgg ctt tgg ttg att tat ctt gtg aca gca gga gtg cca ata gca      1556
Pro Trp Leu Trp Leu Ile Tyr Leu Val Thr Ala Gly Val Pro Ile Ala
                470                 475                 480                 485
```

-continued

```
tta att act tca ttt tgt tgg cca aga aaa gta aag aaa aaa cat aaa      1604
Leu Ile Thr Ser Phe Cys Trp Pro Arg Lys Val Lys Lys Lys His Lys
            490                 495                 500 gat aca gag tat aaa aaa acc gac ata tgt ata cca caa aca aaa gga      1652
Asp Thr Glu Tyr Lys Lys Thr Asp Ile Cys Ile Pro Gln Thr Lys Gly
        505                 510                 515 gta cta gag caa gaa gaa aag gaa gag aaa gca gcc ctg gaa aaa cca      1700
Val Leu Glu Gln Glu Glu Lys Glu Glu Lys Ala Ala Leu Glu Lys Pro
    520                 525                 530 atg gac ctg gaa gag gaa aaa aag caa aat gat ggt gaa atg ctt gaa      1748
Met Asp Leu Glu Glu Glu Lys Lys Gln Asn Asp Gly Glu Met Leu Glu
535                 540                 545 aaa gaa gag gaa agt gaa cct gag gaa aag gaa agt gaa gaa gaa att gaa  1796
Lys Glu Glu Glu Ser Glu Pro Glu Glu Lys Glu Ser Glu Glu Glu Ile Glu
550                 555                 560                 565 atc ata gaa ggg caa gaa gaa agt aat caa tca aat aag tct ggg tca      1844
Ile Ile Glu Gly Gln Glu Glu Ser Asn Gln Ser Asn Lys Ser Gly Ser
            570                 575                 580 gag gat gag atg aaa gaa gca gat gag agc aca gga tct gga gat ggg      1892
Glu Asp Glu Met Lys Glu Ala Asp Glu Ser Thr Gly Ser Gly Asp Gly
        585                 590                 595 ccg ata aag tca gta cgc aaa aga aga gta cga aag gac taa              1934
Pro Ile Lys Ser Val Arg Lys Arg Arg Val Arg Lys Asp
    600                 605                 610 actagattga atattttta attcccgaga ggatgtttgg cattgtaaaa atcagcatgc     1994
cagacctgaa ctttaatcag tctgcacatc ctgtttctaa tatctagcaa cattatattc   2054
tttcagacat ttatttagt ccttcatttc cgaggaaaaa gaagcaactt tgaagttacc    2114
tcatctttga atttagaata aaagtggcac attacatatc ggatctaaga gattaatacc   2174
attagaagtt acacagtttt agttgtttgg agatagtttt ggtttgtaca gaacaaaata   2234
atatgtagca gcttcattgc tattggaaaa atcagttatt ggaatttcca cttaaatggc   2294
tatacaacaa tataactggt agttctataa taaaaatgag catatgttct gttgtgaaga   2354
gctaaatgca ataaagtttc tgtatggttg tttgattcta tcaacaattg aaagtgttgt   2414
atatgaccca catttaccta gtttgtgtca aattatagtt acagtgagtt gtttgcttaa   2474
attatagatt cctttaagga catgccttgt tcataaaatc actggattat attgcagcat   2534
attttacatt tgaatacaag gataatgggt tttatcaaaa caaatgatg tacagatttt    2594
ttttcaagtt tttatagttg ctttatgcca gagtggttta ccccattcac aaaatttctt   2654
atgcatacat tgctattgaa aataaaattt aaatatttt tcatcctgaa aaaaa         2710
```

<210> SEQ ID NO 18
<211> LENGTH: 610
<212> TYPE: PRT
<213> ORGANISM: Homo sapiens

<400> SEQUENCE: 18

```
Met His Phe Gln Ala Phe Trp Leu Cys Leu Gly Leu Leu Phe Ile Ser
1               5                   10                  15

Ile Asn Ala Glu Phe Met Asp Asp Val Glu Thr Glu Asp Phe Glu
            20                  25                  30

Glu Asn Ser Glu Glu Ile Asp Val Asn Glu Ser Glu Leu Ser Ser Glu
        35                  40                  45

Ile Lys Tyr Lys Thr Pro Gln Pro Ile Gly Glu Val Tyr Phe Ala Glu
    50                  55                  60

Thr Phe Asp Ser Gly Arg Leu Ala Gly Trp Val Leu Ser Lys Ala Lys
```

```
                65                  70                  75                  80
Lys Asp Asp Met Asp Glu Glu Ile Ser Ile Tyr Asp Gly Arg Trp Glu
                        85                  90                  95

Ile Glu Glu Leu Lys Glu Asn Gln Val Pro Gly Asp Arg Gly Leu Val
                100                 105                 110

Leu Lys Ser Arg Ala Lys His His Ala Ile Ser Ala Val Leu Ala Lys
                115                 120                 125

Pro Phe Ile Phe Ala Asp Lys Pro Leu Ile Val Gln Tyr Glu Val Asn
            130                 135                 140

Phe Gln Asp Gly Ile Asp Cys Gly Gly Ala Tyr Ile Lys Leu Leu Ala
145                 150                 155                 160

Asp Thr Asp Asp Leu Ile Leu Glu Asn Phe Tyr Asp Lys Thr Ser Tyr
                    165                 170                 175

Ile Ile Met Phe Gly Pro Asp Lys Cys Gly Glu Asp Tyr Lys Leu His
                180                 185                 190

Phe Ile Phe Arg His Lys His Pro Lys Thr Gly Val Phe Glu Glu Lys
                195                 200                 205

His Ala Lys Pro Pro Asp Val Asp Leu Lys Lys Phe Phe Thr Asp Arg
        210                 215                 220

Lys Thr His Leu Tyr Thr Leu Val Met Asn Pro Asp Asp Thr Phe Glu
225                 230                 235                 240

Val Leu Val Asp Gln Thr Val Val Asn Lys Gly Ser Leu Leu Glu Asp
                    245                 250                 255

Val Val Pro Pro Ile Lys Pro Pro Lys Glu Ile Glu Asp Pro Asn Asp
                260                 265                 270

Lys Lys Pro Glu Glu Trp Asp Glu Arg Ala Lys Ile Pro Asp Pro Ser
        275                 280                 285

Ala Val Lys Pro Glu Asp Trp Asp Glu Ser Glu Pro Ala Gln Ile Glu
        290                 295                 300

Asp Ser Ser Val Val Lys Pro Ala Gly Trp Leu Asp Asp Glu Pro Lys
305                 310                 315                 320

Phe Ile Pro Asp Pro Asn Ala Glu Lys Pro Asp Asp Trp Asn Glu Asp
                    325                 330                 335

Thr Asp Gly Glu Trp Glu Ala Pro Gln Ile Leu Asn Pro Ala Cys Arg
                340                 345                 350

Ile Gly Cys Gly Glu Trp Lys Pro Pro Met Ile Asp Asn Pro Lys Tyr
            355                 360                 365

Lys Gly Val Trp Arg Pro Pro Leu Val Asp Asn Pro Asn Tyr Gln Gly
        370                 375                 380

Ile Trp Ser Pro Arg Lys Ile Pro Asn Pro Asp Tyr Phe Glu Asp Asp
385                 390                 395                 400

His Pro Phe Leu Leu Thr Ser Phe Ser Ala Leu Gly Leu Glu Leu Trp
                    405                 410                 415

Ser Met Thr Ser Asp Ile Tyr Phe Asp Asn Phe Ile Ile Cys Ser Glu
                420                 425                 430

Lys Glu Val Ala Asp His Trp Ala Ala Asp Gly Trp Arg Trp Lys Ile
            435                 440                 445

Met Ile Ala Asn Ala Asn Lys Pro Gly Val Leu Lys Gln Leu Met Ala
        450                 455                 460

Ala Ala Glu Gly His Pro Trp Leu Trp Leu Ile Tyr Leu Val Thr Ala
465                 470                 475                 480

Gly Val Pro Ile Ala Leu Ile Thr Ser Phe Cys Trp Pro Arg Lys Val
                    485                 490                 495
```

```
Lys Lys Lys His Lys Asp Thr Glu Tyr Lys Lys Thr Asp Ile Cys Ile
            500                 505                 510

Pro Gln Thr Lys Gly Val Leu Glu Gln Glu Glu Lys Glu Glu Lys Ala
            515                 520                 525

Ala Leu Glu Lys Pro Met Asp Leu Glu Glu Lys Lys Gln Asn Asp
530                 535                 540

Gly Glu Met Leu Glu Lys Glu Glu Ser Glu Pro Glu Glu Lys Ser
545                 550                 555                 560

Glu Glu Glu Ile Glu Ile Ile Glu Gly Gln Glu Ser Asn Gln Ser
                565                 570                 575

Asn Lys Ser Gly Ser Glu Asp Glu Met Lys Glu Ala Asp Glu Ser Thr
            580                 585                 590

Gly Ser Gly Asp Gly Pro Ile Lys Ser Val Arg Lys Arg Val Arg
            595                 600                 605

Lys Asp
    610

<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19
gtgatgaatc cagatgac                                                    18

<210> SEQ ID NO 20
<211> LENGTH: 18
<212> TYPE: DNA
<213> ORGANISM: Artificial Sequence
<220> FEATURE:
<223> OTHER INFORMATION: Synthetic primer

<400> SEQUENCE: 20
ggtcatagac caaagctc                                                    18

<210> SEQ ID NO 21
<211> LENGTH: 23
<212> TYPE: DNA
<213> ORGANISM: Artificial Sequence
<220> FEATURE:
<223> OTHER INFORMATION: Synthetic primer

<400> SEQUENCE: 21
aaggatccat gcatttccaa agc                                              23

<210> SEQ ID NO 22
<211> LENGTH: 25
<212> TYPE: DNA
<213> ORGANISM: Artificial Sequence
<220> FEATURE:
<223> OTHER INFORMATION: Synthetic primer

<400> SEQUENCE: 22
ccgaattctt attcctttcg tactc                                            25

<210> SEQ ID NO 23
<211> LENGTH: 26
<212> TYPE: DNA
<213> ORGANISM: Artificial Sequence
<220> FEATURE:
```

```
<223> OTHER INFORMATION: Synthetic primer

<400> SEQUENCE: 23
gaattcatgc atttccaagc cttttg                                          26

<210> SEQ ID NO 24
<211> LENGTH: 23
<212> TYPE: DNA
<213> ORGANISM: Artificial Sequence
<220> FEATURE:
<223> OTHER INFORMATION: Synthetic primer

<400> SEQUENCE: 24
ctcgagttag tcctttcgta ctc                                             23

<210> SEQ ID NO 25
<211> LENGTH: 7353
<212> TYPE: DNA
<213> ORGANISM: Canis familiaris
<220> FEATURE:
<221> NAME/KEY: CDS
<222> LOCATION: (1)..(7020)

<400> SEQUENCE: 25
```

| | | | | | | | | | | | | | | | | |
|---|---|---|---|---|---|---|---|---|---|---|---|---|---|---|---|---|
| atg | aag | aaa | ggt | tct | cag | caa | aag | ttt | ttg | aaa | gca | aag | atg | cca | cca | 48 |
| Met | Lys | Lys | Gly | Ser | Gln | Gln | Lys | Phe | Leu | Lys | Ala | Lys | Met | Pro | Pro | |
| 1 | | | | 5 | | | | | 10 | | | | | 15 | | |
| tca | tct | cac | tct | cct | agt | cca | cca | tcc | ctt | acg | tcc | aat | atg | aga | tct | 96 |
| Ser | Ser | His | Ser | Pro | Ser | Pro | Pro | Ser | Leu | Thr | Ser | Asn | Met | Arg | Ser | |
| | | | 20 | | | | | 25 | | | | | 30 | | | |
| agg | tca | ctt | tcg | cct | cta | agt | gga | tct | gag | act | ctg | cct | ttt | cat | ttt | 144 |
| Arg | Ser | Leu | Ser | Pro | Leu | Ser | Gly | Ser | Glu | Thr | Leu | Pro | Phe | His | Phe | |
| | | | 35 | | | | | 40 | | | | | 45 | | | |
| gga | gga | ccg | tgg | cat | gag | caa | gtt | gag | att | aca | gat | gaa | agc | aca | gtg | 192 |
| Gly | Gly | Pro | Trp | His | Glu | Gln | Val | Glu | Ile | Thr | Asp | Glu | Ser | Thr | Val | |
| | | | 50 | | | | | 55 | | | | | 60 | | | |
| gtt | tta | gac | tac | caa | gac | cat | aaa | gaa | gct | gat | tca | cat | gca | gga | gtc | 240 |
| Val | Leu | Asp | Tyr | Gln | Asp | His | Lys | Glu | Ala | Asp | Ser | His | Ala | Gly | Val | |
| 65 | | | | | 70 | | | | | 75 | | | | | 80 | |
| cga | tat | att | aca | gag | gcc | ctt | gtt | aga | aaa | ctt | act | aaa | cag | gac | aat | 288 |
| Arg | Tyr | Ile | Thr | Glu | Ala | Leu | Val | Arg | Lys | Leu | Thr | Lys | Gln | Asp | Asn | |
| | | | | 85 | | | | | 90 | | | | | 95 | | |
| ttg | gcc | ttg | gta | aaa | tct | ctg | aac | ctt | tca | ctt | gct | aaa | ggt | ggt | ggc | 336 |
| Leu | Ala | Leu | Val | Lys | Ser | Leu | Asn | Leu | Ser | Leu | Ala | Lys | Gly | Gly | Gly | |
| | | | 100 | | | | | 105 | | | | | 110 | | | |
| aag | aaa | ttc | agg | tgt | atc | gaa | aat | ttg | gaa | aaa | tgt | gtt | aaa | ctt | gaa | 384 |
| Lys | Lys | Phe | Arg | Cys | Ile | Glu | Asn | Leu | Glu | Lys | Cys | Val | Lys | Leu | Glu | |
| | | 115 | | | | | 120 | | | | | 125 | | | | |
| gta | ctg | aat | ctc | agc | tat | aat | cta | ata | gga | aag | att | gag | aaa | gtg | gac | 432 |
| Val | Leu | Asn | Leu | Ser | Tyr | Asn | Leu | Ile | Gly | Lys | Ile | Glu | Lys | Val | Asp | |
| | 130 | | | | | 135 | | | | | 140 | | | | | |
| aaa | ctg | tta | aaa | tta | cgt | gaa | ctc | aac | tta | tcg | tat | aac | aaa | atc | cgc | 480 |
| Lys | Leu | Leu | Lys | Leu | Arg | Glu | Leu | Asn | Leu | Ser | Tyr | Asn | Lys | Ile | Arg | |
| 145 | | | | | 150 | | | | | 155 | | | | | 160 | |
| aaa | att | gaa | ggc | ata | gaa | aat | tta | tat | aat | ctg | caa | aag | ctg | aac | ctt | 528 |
| Lys | Ile | Glu | Gly | Ile | Glu | Asn | Leu | Tyr | Asn | Leu | Gln | Lys | Leu | Asn | Leu | |
| | | | | 165 | | | | | 170 | | | | | 175 | | |
| gca | gga | aat | gaa | atc | gaa | cat | atc | cca | gta | tgg | tta | ggg | aag | aag | tta | 576 |
| Ala | Gly | Asn | Glu | Ile | Glu | His | Ile | Pro | Val | Trp | Leu | Gly | Lys | Lys | Leu | |
| | | | 180 | | | | | 185 | | | | | 190 | | | |
| aaa | tct | ttg | cga | atc | ctg | aat | ctg | aaa | ggc | aac | aag | ata | tca | tcg | ctc | 624 |
| Lys | Ser | Leu | Arg | Ile | Leu | Asn | Leu | Lys | Gly | Asn | Lys | Ile | Ser | Ser | Leu | |

-continued

| | | | |
|---|---|---|---|
| 195 | | 200 | 205 | caa gat gta agc aag ttg aaa cca ctt caa gat ttg act tct ctg atc     672
Gln Asp Val Ser Lys Leu Lys Pro Leu Gln Asp Leu Thr Ser Leu Ile
210                            215                          220 cta ctt gaa aat cca gtt gcg acc ctt cct cat tat atc cag ttt acc     720
Leu Leu Glu Asn Pro Val Ala Thr Leu Pro His Tyr Ile Gln Phe Thr
225                          230                        235                    240 att ttt cac ctt cgc tca ttg gaa agt ttg gaa ggt cag cca gta act     768
Ile Phe His Leu Arg Ser Leu Glu Ser Leu Glu Gly Gln Pro Val Thr
                          245                        250                        255 agt cag gac aga caa gaa gct ttt gcg aga ttc agt tta gat gag gta     816
Ser Gln Asp Arg Gln Glu Ala Phe Ala Arg Phe Ser Leu Asp Glu Val
        260                        265                        270 gaa aga ctg gaa aga gac ctg gag aag aag aca atg gaa act gaa gag     864
Glu Arg Leu Glu Arg Asp Leu Glu Lys Lys Thr Met Glu Thr Glu Glu
                275                        280                        285 ctt agg agt gag cag aca agg ttc ctt gag gaa att aaa agt cag gat     912
Leu Arg Ser Glu Gln Thr Arg Phe Leu Glu Glu Ile Lys Ser Gln Asp
290                            295                          300 aaa ttg aac aaa tca ctg aaa gag gag gcc aga cta caa aaa cag agc     960
Lys Leu Asn Lys Ser Leu Lys Glu Glu Ala Arg Leu Gln Lys Gln Ser
305                            310                        315                    320 tat gag gag ctg gag agt aac cta aac acc aaa aat gaa ttg cta aaa     1008
Tyr Glu Glu Leu Glu Ser Asn Leu Asn Thr Lys Asn Glu Leu Leu Lys
                          325                        330                        335 cag aag acc atg gaa cta atg cga gca tgt cag aaa cag tat gag atg     1056
Gln Lys Thr Met Glu Leu Met Arg Ala Cys Gln Lys Gln Tyr Glu Met
        340                        345                        350 gaa cag gag ttg gcc ttt tat aaa att gat gcc aaa ttt gaa cca cta     1104
Glu Gln Glu Leu Ala Phe Tyr Lys Ile Asp Ala Lys Phe Glu Pro Leu
                355                        360                        365 aat tat tac cca tca gag tat gtc gaa att gat aaa acc cca gat gaa     1152
Asn Tyr Tyr Pro Ser Glu Tyr Val Glu Ile Asp Lys Thr Pro Asp Glu
370                            375                        380 agc cct tac att ggc aaa tcc aga tac aag aga aat atg ttc act aca     1200
Ser Pro Tyr Ile Gly Lys Ser Arg Tyr Lys Arg Asn Met Phe Thr Thr
385                            390                        395                    400 gag agt tat att att gca aat gcc cag aca gta aag atc aag aag atg     1248
Glu Ser Tyr Ile Ile Ala Asn Ala Gln Thr Val Lys Ile Lys Lys Met
                          405                        410                        415 gag cta gat gaa ggg gaa caa ctc aga aat gag cac gtg aac ttg gga     1296
Glu Leu Asp Glu Gly Glu Gln Leu Arg Asn Glu His Val Asn Leu Gly
        420                        425                        430 gca tcg cca aca gac ata caa ctg gaa gac aaa gaa aaa aaa ata agt     1344
Ala Ser Pro Thr Asp Ile Gln Leu Glu Asp Lys Glu Lys Lys Ile Ser
                435                        440                        445 gca gca caa act cga cta tca gaa cta cat gat gaa ata gaa aag gca     1392
Ala Ala Gln Thr Arg Leu Ser Glu Leu His Asp Glu Ile Glu Lys Ala
        450                        455                        460 gaa caa caa att tta aga gcc act gaa gaa ttt aaa caa ctg gaa gaa     1440
Glu Gln Gln Ile Leu Arg Ala Thr Glu Glu Phe Lys Gln Leu Glu Glu
465                            470                        475                    480 gct ata caa ctt aaa aaa att tca gaa gcg gag aaa gac ctt ctt ttc     1488
Ala Ile Gln Leu Lys Lys Ile Ser Glu Ala Glu Lys Asp Leu Leu Phe
                          485                        490                        495 aag cag ttg agt ggt agg ata cag ctt ctc aat aaa tta cgc caa gaa     1536
Lys Gln Leu Ser Gly Arg Ile Gln Leu Leu Asn Lys Leu Arg Gln Glu
                500                        505                        510 gct gtg gat cta gaa aca cag atg gaa aag caa agg caa gaa att ggt     1584

-continued

```
                    Ala Val Asp Leu Glu Thr Gln Met Glu Lys Gln Arg Gln Ile Gly
                        515                 520                 525 gaa aag cag aat gag atc aag gac ctg gaa ata gtc aca gat agc ctg          1632
Glu Lys Gln Asn Glu Ile Lys Asp Leu Glu Ile Val Thr Asp Ser Leu
530                 535                 540 gat tcc aga gac cca aaa cat tgc cat atg aag gct cag aaa aga ggt          1680
Asp Ser Arg Asp Pro Lys His Cys His Met Lys Ala Gln Lys Arg Gly
545                 550                 555                 560 aaa gaa caa caa ctt gac att atg aac aag cag tac aaa cag ctt gaa          1728
Lys Glu Gln Gln Leu Asp Ile Met Asn Lys Gln Tyr Lys Gln Leu Glu
                    565                 570                 575 agc cgt ttg gat gag ata ctt tct aga att gcc aaa gaa act gaa gag          1776
Ser Arg Leu Asp Glu Ile Leu Ser Arg Ile Ala Lys Glu Thr Glu Glu
                580                 585                 590 att aag gac ctt gaa gaa cag ctt act gaa gga caa ata gcc gca aac          1824
Ile Lys Asp Leu Glu Glu Gln Leu Thr Glu Gly Gln Ile Ala Ala Asn
            595                 600                 605 gaa gcc ctg aag aag gac tta gaa agt gtc atc agt ggg ttg caa gaa          1872
Glu Ala Leu Lys Lys Asp Leu Glu Ser Val Ile Ser Gly Leu Gln Glu
610                 615                 620 tac ctg gag act gtc aaa ggt cag gcc cgt cag gcc cag aat gag tgc          1920
Tyr Leu Glu Thr Val Lys Gly Gln Ala Arg Gln Ala Gln Asn Glu Cys
625                 630                 635                 640 aga aag cta cag gat gag aag gag aca ttg ctg cag aga ttg agt gag          1968
Arg Lys Leu Gln Asp Glu Lys Glu Thr Leu Leu Gln Arg Leu Ser Glu
                    645                 650                 655 gtc gag cag gag agg gac caa ctg gaa ata gtg gcc ata gat gca gaa          2016
Val Glu Gln Glu Arg Asp Gln Leu Glu Ile Val Ala Ile Asp Ala Glu
                660                 665                 670 aat atg agg aag gag ctc gca gaa ctg gag aat gcc ctc cag gag cag          2064
Asn Met Arg Lys Glu Leu Ala Glu Leu Glu Asn Ala Leu Gln Glu Gln
            675                 680                 685 cat gag gtg aat ata tct ctg cag cag acc cag gga gat ctc agt gcc          2112
His Glu Val Asn Ile Ser Leu Gln Gln Thr Gln Gly Asp Leu Ser Ala
        690                 695                 700 tat gag gct gag cta gag gct cag ctg aaa ata cgg gat gct gaa gcc          2160
Tyr Glu Ala Glu Leu Glu Ala Gln Leu Lys Ile Arg Asp Ala Glu Ala
705                 710                 715                 720 aac cag ctc aag gag gag ttg gaa aaa ctt aga agg ttg agc cag tta          2208
Asn Gln Leu Lys Glu Glu Leu Glu Lys Leu Arg Arg Leu Ser Gln Leu
                    725                 730                 735 gaa caa tcg gcc ctt caa gca gag ctt gag aag gaa aag caa gcc ttc          2256
Glu Gln Ser Ala Leu Gln Ala Glu Leu Glu Lys Glu Lys Gln Ala Phe
                740                 745                 750 aag act gct gtc aaa aaa gcc cag ctc tca gaa gga aag gac caa gaa          2304
Lys Thr Ala Val Lys Lys Ala Gln Leu Ser Glu Gly Lys Asp Gln Glu
            755                 760                 765 aat agt gag ctc cgc aca caa ctc caa cag ctg cag gat gac aat gac          2352
Asn Ser Glu Leu Arg Thr Gln Leu Gln Gln Leu Gln Asp Asp Asn Asp
        770                 775                 780 cta ttg aaa cag caa ctt aaa gat ttc cag agt cac ctt aac cat gtg          2400
Leu Leu Lys Gln Gln Leu Lys Asp Phe Gln Ser His Leu Asn His Val
785                 790                 795                 800 gtt gat ggt ttg att cgt cca gaa gaa gtg gca gct tgt gtg gat gag          2448
Val Asp Gly Leu Ile Arg Pro Glu Glu Val Ala Ala Cys Val Asp Glu
                    805                 810                 815 cta agg aaa aaa ctg aag tca gga gct ggg gaa atg aga atc cat act          2496
Leu Arg Lys Lys Leu Lys Ser Gly Ala Gly Glu Met Arg Ile His Thr
                820                 825                 830
```

```
cct tca gat gtc tta ggg aaa agt ctt gct gac ttg cag aag caa ttc      2544
Pro Ser Asp Val Leu Gly Lys Ser Leu Ala Asp Leu Gln Lys Gln Phe
        835                 840                 845 agt gag atc ctg gca cgc tcc cag tgg gaa aga cag gaa gca caa gtg      2592
Ser Glu Ile Leu Ala Arg Ser Gln Trp Glu Arg Gln Glu Ala Gln Val
850                 855                 860 aga gag aga aaa ctc cag gag gaa atg gct ctg caa caa gag aaa ctg      2640
Arg Glu Arg Lys Leu Gln Glu Glu Met Ala Leu Gln Gln Glu Lys Leu
865                 870                 875                 880 gcg agc gga caa gag gag ttc agg cac gcc tgc gag agg gcc ctg gaa      2688
Ala Ser Gly Gln Glu Glu Phe Arg His Ala Cys Glu Arg Ala Leu Glu
                885                 890                 895 gcc cga att agt ttt gat aag agg cag cac gaa gca aga atc cag cag      2736
Ala Arg Ile Ser Phe Asp Lys Arg Gln His Glu Ala Arg Ile Gln Gln
            900                 905                 910 ttg gag aat gaa att cac tat ttg caa gaa aat cta aaa agt atg gag      2784
Leu Glu Asn Glu Ile His Tyr Leu Gln Glu Asn Leu Lys Ser Met Glu
        915                 920                 925 gaa atc caa ggt ctc aca gac ctc caa ctt cag gaa gct gat gaa gag      2832
Glu Ile Gln Gly Leu Thr Asp Leu Gln Leu Gln Glu Ala Asp Glu Glu
930                 935                 940 aag gag aga att ctg gcc caa ctc cgg gag tta gag aaa aag aag aaa      2880
Lys Glu Arg Ile Leu Ala Gln Leu Arg Glu Leu Glu Lys Lys Lys Lys
945                 950                 955                 960 ctt gag gat gcc aag tct cag gag cag ttt ctt gga tta gat aga gaa      2928
Leu Glu Asp Ala Lys Ser Gln Glu Gln Phe Leu Gly Leu Asp Arg Glu
                965                 970                 975 ttg aag aag cta aag aaa gct gtg gct gcc tct gat aag ctg gcc aca      2976
Leu Lys Lys Leu Lys Lys Ala Val Ala Ala Ser Asp Lys Leu Ala Thr
            980                 985                 990 gct gag ctc acc att gcc aaa gac cag ctc aag tcc ctt cat gga act      3024
Ala Glu Leu Thr Ile Ala Lys Asp Gln Leu Lys Ser Leu His Gly Thr
        995                 1000                1005 gtg atg aaa att aac cag gag cga gca gag gag ctg cag gag acg         3069
Val Met Lys Ile Asn Gln Glu Arg Ala Glu Glu Leu Gln Glu Thr
    1010                1015                1020 gag agg ttc agc aga aag gca gca caa gca gct agg gat ctg atc         3114
Glu Arg Phe Ser Arg Lys Ala Ala Gln Ala Ala Arg Asp Leu Ile
    1025                1030                1035 cga gca gaa gcg gag att gaa ctc ctg cag aag ctt ctc aga gat         3159
Arg Ala Glu Ala Glu Ile Glu Leu Leu Gln Lys Leu Leu Arg Asp
    1040                1045                1050 aaa gag gag cag ttt cga aat gag att gag aaa gta gat gtc ggc         3204
Lys Glu Glu Gln Phe Arg Asn Glu Ile Glu Lys Val Asp Val Gly
    1055                1060                1065 tct gga gga gca aag tca cag atg ctg gag atg gag aaa cta aat         3249
Ser Gly Gly Ala Lys Ser Gln Met Leu Glu Met Glu Lys Leu Asn
    1070                1075                1080 gag aca atg gag agg caa aga aca gag att gct agg ctg agg aat         3294
Glu Thr Met Glu Arg Gln Arg Thr Glu Ile Ala Arg Leu Arg Asn
    1085                1090                1095 tta cta gac ctc acc ggg gct gat aac aaa gga aac ttt gaa aat         3339
Leu Leu Asp Leu Thr Gly Ala Asp Asn Lys Gly Asn Phe Glu Asn
    1100                1105                1110 gtt ttg gaa gaa att gct gaa ctt cga cgt gaa gtt tct cat cag         3384
Val Leu Glu Glu Ile Ala Glu Leu Arg Arg Glu Val Ser His Gln
    1115                1120                1125 aat gat tac atc agc agc atg aca gat cct ttc aaa aga cga ggc         3429
Asn Asp Tyr Ile Ser Ser Met Thr Asp Pro Phe Lys Arg Arg Gly
    1130                1135                1140
```

-continued

| | | | | | | | | | | | | | | |
|---|---|---|---|---|---|---|---|---|---|---|---|---|---|---|
| tat | tgg | tac | ttt | atg | cca | cca | cca | tca | tca | tca | aaa | gtt | tcc | agc | 3474 |
| Tyr | Trp | Tyr | Phe | Met | Pro | Pro | Pro | Ser | Ser | Ser | Lys | Val | Ser | Ser | |
| | 1145 | | | | 1150 | | | | | 1155 | | | | | |
| cac | agt | tcc | cag | gcc | acc | aag | gac | tct | ggt | gtt | ggc | cta | aag | tac | 3519 |
| His | Ser | Ser | Gln | Ala | Thr | Lys | Asp | Ser | Gly | Val | Gly | Leu | Lys | Tyr | |
| | 1160 | | | | 1165 | | | | | 1170 | | | | | |
| aca | gcc | tcc | act | ccg | gtt | aga | aaa | cca | cat | cgt | gga | cgg | cag | gat | 3564 |
| Thr | Ala | Ser | Thr | Pro | Val | Arg | Lys | Pro | His | Arg | Gly | Arg | Gln | Asp | |
| | 1175 | | | | 1180 | | | | | 1185 | | | | | |
| gga | aag | gag | aac | agt | ggg | cct | cca | cct | gcc | tca | gga | tac | tgg | gtg | 3609 |
| Gly | Lys | Glu | Asn | Ser | Gly | Pro | Pro | Pro | Ala | Ser | Gly | Tyr | Trp | Val | |
| | 1190 | | | | 1195 | | | | | 1200 | | | | | |
| tat | tct | cct | atc | agg | agt | ggg | tta | cat | aaa | tcg | ttc | tca | aat | aga | 3654 |
| Tyr | Ser | Pro | Ile | Arg | Ser | Gly | Leu | His | Lys | Ser | Phe | Ser | Asn | Arg | |
| | 1205 | | | | 1210 | | | | | 1215 | | | | | |
| gac | gca | gac | agt | gga | gga | gat | agc | cag | gaa | gag | agc | gag | cta | gat | 3699 |
| Asp | Ala | Asp | Ser | Gly | Gly | Asp | Ser | Gln | Glu | Glu | Ser | Glu | Leu | Asp | |
| | 1220 | | | | 1225 | | | | | 1230 | | | | | |
| gac | caa | gaa | gac | cac | cca | ttt | gta | cct | cct | cct | gga | tac | atg | atg | 3744 |
| Asp | Gln | Glu | Asp | His | Pro | Phe | Val | Pro | Pro | Pro | Gly | Tyr | Met | Met | |
| | 1235 | | | | 1240 | | | | | 1245 | | | | | |
| tac | act | gtg | ttt | cct | gat | ggt | tct | cct | gta | ccc | cag | ggc | atg | gcc | 3789 |
| Tyr | Thr | Val | Phe | Pro | Asp | Gly | Ser | Pro | Val | Pro | Gln | Gly | Met | Ala | |
| | 1250 | | | | 1255 | | | | | 1260 | | | | | |
| ctg | tat | gca | ccc | cct | cct | ccc | ttg | ccc | aac | aat | agc | cag | cct | ctt | 3834 |
| Leu | Tyr | Ala | Pro | Pro | Pro | Pro | Leu | Pro | Asn | Asn | Ser | Gln | Pro | Leu | |
| | 1265 | | | | 1270 | | | | | 1275 | | | | | |
| gac | ctt | ggc | act | gtt | gtt | tat | ggc | cca | cct | cct | gtt | ggg | gct | ccc | 3879 |
| Asp | Leu | Gly | Thr | Val | Val | Tyr | Gly | Pro | Pro | Pro | Val | Gly | Ala | Pro | |
| | 1280 | | | | 1285 | | | | | 1290 | | | | | |
| atc | gtg | tat | ggg | cct | cca | cct | ccc | aac | ttc | tcc | gta | ccc | ctc | atc | 3924 |
| Ile | Val | Tyr | Gly | Pro | Pro | Pro | Pro | Asn | Phe | Ser | Val | Pro | Leu | Ile | |
| | 1295 | | | | 1300 | | | | | 1305 | | | | | |
| ccc | gtg | ggt | gtg | ctg | cac | tgc | aat | gtc | cca | gaa | cac | cat | aac | ttg | 3969 |
| Pro | Val | Gly | Val | Leu | His | Cys | Asn | Val | Pro | Glu | His | His | Asn | Leu | |
| | 1310 | | | | 1315 | | | | | 1320 | | | | | |
| gag | aat | gaa | gtt | tct | aga | tta | gaa | gac | ata | atg | cag | cat | tta | aaa | 4014 |
| Glu | Asn | Glu | Val | Ser | Arg | Leu | Glu | Asp | Ile | Met | Gln | His | Leu | Lys | |
| | 1325 | | | | 1330 | | | | | 1335 | | | | | |
| tct | ggg | aaa | cgg | gaa | cag | tgc | atg | aaa | aca | ccc | aag | ctg | cag | tcg | 4059 |
| Ser | Gly | Lys | Arg | Glu | Gln | Cys | Met | Lys | Thr | Pro | Lys | Leu | Gln | Ser | |
| | 1340 | | | | 1345 | | | | | 1350 | | | | | |
| gag | aaa | gaa | ctc | gca | gag | ctg | cag | cat | aac | att | gat | ggt | ctt | ttg | 4104 |
| Glu | Lys | Glu | Leu | Ala | Glu | Leu | Gln | His | Asn | Ile | Asp | Gly | Leu | Leu | |
| | 1355 | | | | 1360 | | | | | 1365 | | | | | |
| caa | gag | aag | aaa | gac | tta | gag | cat | gaa | gta | gaa | gaa | tta | cat | aga | 4149 |
| Gln | Glu | Lys | Lys | Asp | Leu | Glu | His | Glu | Val | Glu | Glu | Leu | His | Arg | |
| | 1370 | | | | 1375 | | | | | 1380 | | | | | |
| acc | atc | caa | aaa | cat | caa | cag | cga | aaa | gat | ttc | att | gat | gga | aac | 4194 |
| Thr | Ile | Gln | Lys | His | Gln | Gln | Arg | Lys | Asp | Phe | Ile | Asp | Gly | Asn | |
| | 1385 | | | | 1390 | | | | | 1395 | | | | | |
| gtt | gag | agt | ctt | gtg | aat | gat | cta | gaa | ata | gag | aag | tca | ctc | aaa | 4239 |
| Val | Glu | Ser | Leu | Val | Asn | Asp | Leu | Glu | Ile | Glu | Lys | Ser | Leu | Lys | |
| | 1400 | | | | 1405 | | | | | 1410 | | | | | |
| cac | cat | gaa | gat | att | gtt | gat | gaa | att | gaa | tgt | att | gag | agg | acc | 4284 |
| His | His | Glu | Asp | Ile | Val | Asp | Glu | Ile | Glu | Cys | Ile | Glu | Arg | Thr | |
| | 1415 | | | | 1420 | | | | | 1425 | | | | | |
| ctt | ctg | aag | cgc | cgt | gca | gag | ctc | agg | gaa | gcc | gac | cgg | ctg | ctg | 4329 |
| Leu | Leu | Lys | Arg | Arg | Ala | Glu | Leu | Arg | Glu | Ala | Asp | Arg | Leu | Leu | |

```
                1430              1435              1440 acg gag gct gaa agt gaa ctt tca tgc acg aaa gag aaa aca aaa        4374
Thr Glu Ala Glu Ser Glu Leu Ser Cys Thr Lys Glu Lys Thr Lys
    1445              1450              1455 cat gct gtt gag aag ttc act gat gcc aag aga aat tta ttg caa        4419
His Ala Val Glu Lys Phe Thr Asp Ala Lys Arg Asn Leu Leu Gln
    1460              1465              1470 act gag aaa gat gct gag gag tta gaa agg aga gcc cag gaa act        4464
Thr Glu Lys Asp Ala Glu Glu Leu Glu Arg Arg Ala Gln Glu Thr
    1475              1480              1485 gcc att aac ctc gtc aaa gcc gac cag cag ctg aga ttg ctc cag        4509
Ala Ile Asn Leu Val Lys Ala Asp Gln Gln Leu Arg Leu Leu Gln
    1490              1495              1500 gct gac acg aag gat ttg gag cag cac aaa atg gag caa gag gaa        4554
Ala Asp Thr Lys Asp Leu Glu Gln His Lys Met Glu Gln Glu Glu
    1505              1510              1515 atc ttg aaa gaa ata aac aaa gtt gtt gca gca aaa gac tca gac        4599
Ile Leu Lys Glu Ile Asn Lys Val Val Ala Ala Lys Asp Ser Asp
    1520              1525              1530 ttc cag agc cta aac aag aag aag gaa gta ctg aca gga gag ctg        4644
Phe Gln Ser Leu Asn Lys Lys Lys Glu Val Leu Thr Gly Glu Leu
    1535              1540              1545 cag aaa ctc cag aag gac att gag act gca cgg cac aat gag gat        4689
Gln Lys Leu Gln Lys Asp Ile Glu Thr Ala Arg His Asn Glu Asp
    1550              1555              1560 cag cac ctg cag gtc ctt aaa gag tcg gag acc ctc ctg cag gcc        4734
Gln His Leu Gln Val Leu Lys Glu Ser Glu Thr Leu Leu Gln Ala
    1565              1570              1575 aag aaa gct gag ctg gaa aat ctg aaa agc cag gtg tca gga cag        4779
Lys Lys Ala Glu Leu Glu Asn Leu Lys Ser Gln Val Ser Gly Gln
    1580              1585              1590 cag cag gag atg gcc gtc ttg gac agg gag tta gga cac aag aag        4824
Gln Gln Glu Met Ala Val Leu Asp Arg Glu Leu Gly His Lys Lys
    1595              1600              1605 gaa gag ctg cat ctc ctc cag gaa agc atg gtc cag gcc aaa gct        4869
Glu Glu Leu His Leu Leu Gln Glu Ser Met Val Gln Ala Lys Ala
    1610              1615              1620 gac ctc cag gaa gca ctg aga cta gga gaa agc gaa gta act gag        4914
Asp Leu Gln Glu Ala Leu Arg Leu Gly Glu Ser Glu Val Thr Glu
    1625              1630              1635 aag tgc aat cac att agg gaa gta aaa tct ctt ctg gaa gaa ctc        4959
Lys Cys Asn His Ile Arg Glu Val Lys Ser Leu Leu Glu Glu Leu
    1640              1645              1650 agt ttt cag aaa gga gaa ctg aat gtc cag atc agt gaa aaa aaa        5004
Ser Phe Gln Lys Gly Glu Leu Asn Val Gln Ile Ser Glu Lys Lys
    1655              1660              1665 act caa ctt gca ctc ata aag cag gaa att gaa aaa gag gaa gac        5049
Thr Gln Leu Ala Leu Ile Lys Gln Glu Ile Glu Lys Glu Glu Asp
    1670              1675              1680 aat ctt cag gta gtt tta ggg caa atg tct aaa cat aaa act gaa        5094
Asn Leu Gln Val Val Leu Gly Gln Met Ser Lys His Lys Thr Glu
    1685              1690              1695 cta aag aat att ctg gac atg ttg caa ctt gaa aat aat gag ctg        5139
Leu Lys Asn Ile Leu Asp Met Leu Gln Leu Glu Asn Asn Glu Leu
    1700              1705              1710 caa ggt ttg aag ctc caa cat gac caa aag atg tct gaa tta gag        5184
Gln Gly Leu Lys Leu Gln His Asp Gln Lys Met Ser Glu Leu Glu
    1715              1720              1725 aag act cgg gtt gaa gtg ctg gag gag aaa ctg gag tta gag agt        5229
```

```
Lys Thr Arg Val Glu Val Leu Glu Glu Lys Leu Glu Leu Glu Ser
    1730                1735                1740 ctg cag cag gca gcc ctg cga cag aga ggg gag ata gag tgg cag         5274
Leu Gln Gln Ala Ala Leu Arg Gln Arg Gly Glu Ile Glu Trp Gln
1745                1750                1755 aag cag ctc ctc cag agg aac aca cag gaa gta gag cgg atg act         5319
Lys Gln Leu Leu Gln Arg Asn Thr Gln Glu Val Glu Arg Met Thr
1760                1765                1770 gct gag acc cga gca tta cag tcg tgt gtt gag tct ttg tgc aaa         5364
Ala Glu Thr Arg Ala Leu Gln Ser Cys Val Glu Ser Leu Cys Lys
1775                1780                1785 gaa aag caa gat ctc gaa gaa aaa cag gac agc tgg gaa aag aag         5409
Glu Lys Gln Asp Leu Glu Glu Lys Gln Asp Ser Trp Glu Lys Lys
1790                1795                1800 ttg gca cag acc aaa cgg gtt cta gca gct gca gaa gag gac agc         5454
Leu Ala Gln Thr Lys Arg Val Leu Ala Ala Ala Glu Glu Asp Ser
1805                1810                1815 gag atg gag cgg gca cgc tta gaa aag ttg gaa ctg gac gcc agg         5499
Glu Met Glu Arg Ala Arg Leu Glu Lys Leu Glu Leu Asp Ala Arg
1820                1825                1830 aag ctg cag cag gag ttg gac caa cga aac agg gag aag ctc tcc         5544
Lys Leu Gln Gln Glu Leu Asp Gln Arg Asn Arg Glu Lys Leu Ser
1835                1840                1845 ctg cat caa gac ctg gca gtg gtg cag cag cag cta caa gaa aaa         5589
Leu His Gln Asp Leu Ala Val Val Gln Gln Gln Leu Gln Glu Lys
1850                1855                1860 cag gaa gca gta aac tca tta cag aag gaa cta act gat gtc cag         5634
Gln Glu Ala Val Asn Ser Leu Gln Lys Glu Leu Thr Asp Val Gln
1865                1870                1875 gag cat ttg gac cta gca gaa cag gag gtg ctc tgc acc acc aag         5679
Glu His Leu Asp Leu Ala Glu Gln Glu Val Leu Cys Thr Thr Lys
1880                1885                1890 cgc aag gac gca ctg ctc agc gaa cag acc agg ctc gag aag gac         5724
Arg Lys Asp Ala Leu Leu Ser Glu Gln Thr Arg Leu Glu Lys Asp
1895                1900                1905 gtg ggt gaa tgg acg aag aag ttt gaa gac tgc cag aaa gaa ggg         5769
Val Gly Glu Trp Thr Lys Lys Phe Glu Asp Cys Gln Lys Glu Gly
1910                1915                1920 gag aca aag cag caa cag ctt caa ggg ctt cag aag gag att gaa         5814
Glu Thr Lys Gln Gln Gln Leu Gln Gly Leu Gln Lys Glu Ile Glu
1925                1930                1935 gga aac gag gcg aag cta gcc caa caa gaa atg atg ttt cag aga         5859
Gly Asn Glu Ala Lys Leu Ala Gln Gln Glu Met Met Phe Gln Arg
1940                1945                1950 ctc cag aaa gag cga gaa tgt gaa gaa aaa aag tta gaa gct agt         5904
Leu Gln Lys Glu Arg Glu Cys Glu Glu Lys Lys Leu Glu Ala Ser
1955                1960                1965 aaa gtg act ctg aag gag cag cag caa cag ctg gaa aag gaa ttg         5949
Lys Val Thr Leu Lys Glu Gln Gln Gln Gln Leu Glu Lys Glu Leu
1970                1975                1980 atg gag cag aaa ggc aag ctg gac cag gtg ctc gct aag ctc ttg         5994
Met Glu Gln Lys Gly Lys Leu Asp Gln Val Leu Ala Lys Leu Leu
1985                1990                1995 gtg gct gag gag cgt gtc agg acc ttg cag gag gag gga agg tgg         6039
Val Ala Glu Glu Arg Val Arg Thr Leu Gln Glu Glu Gly Arg Trp
2000                2005                2010 agc gag acc ctg gag aag acg ctc tcc cag acc aag cga cag ctt         6084
Ser Glu Thr Leu Glu Lys Thr Leu Ser Gln Thr Lys Arg Gln Leu
2015                2020                2025
```

| | | | | | | | | | | |
|---|---|---|---|---|---|---|---|---|---|---|
| tca | gaa | cgg | gag | cag | cag | tta | ctg | gcc | aag | tca | gac | gag | ctg | ctg | 6129 |
| Ser | Glu | Arg | Glu | Gln | Gln | Leu | Leu | Ala | Lys | Ser | Asp | Glu | Leu | Leu | |
| 2030 | | | | 2035 | | | | | 2040 | | | | | | |

| gcc | ctg | cag | aag | gag | acg | gac | tcc | atg | agg | gcg | gac | ttc | agc | ctc | 6174 |
| Ala | Leu | Gln | Lys | Glu | Thr | Asp | Ser | Met | Arg | Ala | Asp | Phe | Ser | Leu | |
| 2045 | | | | 2050 | | | | | 2055 | | | | | | |

| ttg | cgc | aac | cag | ttc | ctg | aca | gaa | aga | aag | aaa | gcc | gag | aag | cag | 6219 |
| Leu | Arg | Asn | Gln | Phe | Leu | Thr | Glu | Arg | Lys | Lys | Ala | Glu | Lys | Gln | |
| 2060 | | | | 2065 | | | | | 2070 | | | | | | |

| gtg | gcc | agc | ctg | aag | gaa | gcc | ctt | aag | atc | cag | cgg | agc | caa | ctg | 6264 |
| Val | Ala | Ser | Leu | Lys | Glu | Ala | Leu | Lys | Ile | Gln | Arg | Ser | Gln | Leu | |
| 2075 | | | | 2080 | | | | | 2085 | | | | | | |

| gag | aag | aac | ctt | ctg | gag | caa | aag | cag | gag | aac | agc | tgc | atg | cag | 6309 |
| Glu | Lys | Asn | Leu | Leu | Glu | Gln | Lys | Gln | Glu | Asn | Ser | Cys | Met | Gln | |
| 2090 | | | | 2095 | | | | | 2100 | | | | | | |

| agg | gag | atg | gca | acc | atc | gaa | cag | gtg | gcc | cag | gac | aac | cac | gag | 6354 |
| Arg | Glu | Met | Ala | Thr | Ile | Glu | Gln | Val | Ala | Gln | Asp | Asn | His | Glu | |
| 2105 | | | | 2110 | | | | | 2115 | | | | | | |

| cgg | gcc | cgg | cgc | cta | atg | agg | gag | ctc | aac | cag | atg | cag | cgc | gag | 6399 |
| Arg | Ala | Arg | Arg | Leu | Met | Arg | Glu | Leu | Asn | Gln | Met | Gln | Arg | Glu | |
| 2120 | | | | 2125 | | | | | 2130 | | | | | | |

| tac | gtg | gag | ctc | agg | aaa | cag | atg | aca | aac | caa | aag | gat | ttg | gaa | 6444 |
| Tyr | Val | Glu | Leu | Arg | Lys | Gln | Met | Thr | Asn | Gln | Lys | Asp | Leu | Glu | |
| 2135 | | | | 2140 | | | | | 2145 | | | | | | |

| aga | aga | cag | atg | gaa | atc | agt | gat | gcg | atg | caa | gca | ctt | aaa | tgt | 6489 |
| Arg | Arg | Gln | Met | Glu | Ile | Ser | Asp | Ala | Met | Gln | Ala | Leu | Lys | Cys | |
| 2150 | | | | 2155 | | | | | 2160 | | | | | | |

| gag | gtg | aaa | gat | gaa | atc | cga | acc | agc | ctg | aag | aat | ctc | aac | cag | 6534 |
| Glu | Val | Lys | Asp | Glu | Ile | Arg | Thr | Ser | Leu | Lys | Asn | Leu | Asn | Gln | |
| 2165 | | | | 2170 | | | | | 2175 | | | | | | |

| ttt | ctt | cca | gaa | ctg | cca | gcg | gac | ctg | gag | gcc | ctt | ctg | gaa | agg | 6579 |
| Phe | Leu | Pro | Glu | Leu | Pro | Ala | Asp | Leu | Glu | Ala | Leu | Leu | Glu | Arg | |
| 2180 | | | | 2185 | | | | | 2190 | | | | | | |

| aat | gag | aac | ctt | gga | gga | ggc | ttg | gag | agc | ttg | aaa | gag | aat | ttc | 6624 |
| Asn | Glu | Asn | Leu | Gly | Gly | Gly | Leu | Glu | Ser | Leu | Lys | Glu | Asn | Phe | |
| 2195 | | | | 2200 | | | | | 2205 | | | | | | |

| ccg | ttt | acc | gtg | agc | gac | aga | cca | tca | tct | tgc | gaa | gag | aaa | ctg | 6669 |
| Pro | Phe | Thr | Val | Ser | Asp | Arg | Pro | Ser | Ser | Cys | Glu | Glu | Lys | Leu | |
| 2210 | | | | 2215 | | | | | 2220 | | | | | | |

| aat | ttt | ggc | cag | gct | cac | gtg | gcg | gat | gaa | cag | tgg | cgg | gga | gag | 6714 |
| Asn | Phe | Gly | Gln | Ala | His | Val | Ala | Asp | Glu | Gln | Trp | Arg | Gly | Glu | |
| 2225 | | | | 2230 | | | | | 2235 | | | | | | |

| gca | ctc | cgg | gag | aag | ctg | cgc | cac | cgc | gag | gac | cgg | ctc | aag | gcc | 6759 |
| Ala | Leu | Arg | Glu | Lys | Leu | Arg | His | Arg | Glu | Asp | Arg | Leu | Lys | Ala | |
| 2240 | | | | 2245 | | | | | 2250 | | | | | | |

| cag | ctg | cgc | cgc | tgc | atg | tcc | aag | cag | gcc | gag | gtg | ctg | agc | gag | 6804 |
| Gln | Leu | Arg | Arg | Cys | Met | Ser | Lys | Gln | Ala | Glu | Val | Leu | Ser | Glu | |
| 2255 | | | | 2260 | | | | | 2265 | | | | | | |

| ggc | cgg | cgg | cgc | acg | gag | ggg | acc | ctg | cac | agc | ctg | cgg | cgg | cag | 6849 |
| Gly | Arg | Arg | Arg | Thr | Glu | Gly | Thr | Leu | His | Ser | Leu | Arg | Arg | Gln | |
| 2270 | | | | 2275 | | | | | 2280 | | | | | | |

| gtg | gac | gcc | ctg | ggc | gag | ctg | gtc | acc | agc | act | tcc | ggg | gac | tcc | 6894 |
| Val | Asp | Ala | Leu | Gly | Glu | Leu | Val | Thr | Ser | Thr | Ser | Gly | Asp | Ser | |
| 2285 | | | | 2290 | | | | | 2295 | | | | | | |

| gcg | tcc | acc | cgc | agt | ctg | tcg | cgc | acc | gag | ggc | tcg | ctc | gcc | gag | 6939 |
| Ala | Ser | Thr | Arg | Ser | Leu | Ser | Arg | Thr | Glu | Gly | Ser | Leu | Ala | Glu | |
| 2300 | | | | 2305 | | | | | 2310 | | | | | | |

| gac | gaa | ccg | ccg | ggg | ccc | agc | cag | agc | tcc | cgg | cgg | ctc | ccc | cga | 6984 |
| Asp | Glu | Pro | Pro | Gly | Pro | Ser | Gln | Ser | Ser | Arg | Arg | Leu | Pro | Arg | |
| 2315 | | | | 2320 | | | | | 2325 | | | | | | |

```
gcc ccg  tcg  ccg cgg ctg gac  gcg cac cga ccc tga ggacccggag    7030
Gly Pro  Ser  Pro Arg Leu Asp  Ala His Arg Pro
    2330               2335 gacccggagg cccggcgtcc cctcggaacg cttcctccgc gtccgcggac accaggctca  7090
cgggaaggcg cgtccatgcg ggaagagccg cgagcgaaac ccggatgccc gggctggtct  7150
ctgggccttg gaaacgtgtt gccgtaaaag cagcgcccgc ggctgcggac ttgaagcccc  7210
gaactggtaa actcggcggc tgccgggcga actgtactca ggactttttt cacgacacc   7270 gtcagatttt attttggaa  atctattttc atatgaaaat aaagataaa  agcgcctgaa  7330 aaaaaaaaaa aaaaaaaact agt                                         7353
```

<210> SEQ ID NO 26
<211> LENGTH: 2339
<212> TYPE: PRT
<213> ORGANISM: Canis familiaris

<400> SEQUENCE: 26

```
Met Lys Lys Gly Ser Gln Gln Lys Phe Leu Lys Ala Lys Met Pro Pro
1               5                   10                  15

Ser Ser His Ser Pro Ser Pro Pro Ser Leu Thr Ser Asn Met Arg Ser
            20                  25                  30

Arg Ser Leu Ser Pro Leu Ser Gly Ser Glu Thr Leu Pro Phe His Phe
        35                  40                  45

Gly Gly Pro Trp His Glu Gln Val Glu Ile Thr Asp Glu Ser Thr Val
    50                  55                  60

Val Leu Asp Tyr Gln Asp His Lys Glu Ala Asp Ser His Ala Gly Val
65                  70                  75                  80

Arg Tyr Ile Thr Glu Ala Leu Val Arg Lys Leu Thr Lys Gln Asp Asn
                85                  90                  95

Leu Ala Leu Val Lys Ser Leu Asn Leu Ser Leu Ala Lys Gly Gly Gly
            100                 105                 110

Lys Lys Phe Arg Cys Ile Glu Asn Leu Glu Lys Cys Val Lys Leu Glu
        115                 120                 125

Val Leu Asn Leu Ser Tyr Asn Leu Ile Gly Lys Ile Glu Lys Val Asp
    130                 135                 140

Lys Leu Leu Lys Leu Arg Glu Leu Asn Leu Ser Tyr Asn Lys Ile Arg
145                 150                 155                 160

Lys Ile Glu Gly Ile Glu Asn Leu Tyr Asn Leu Gln Lys Leu Asn Leu
                165                 170                 175

Ala Gly Asn Glu Ile Glu His Ile Pro Val Trp Leu Gly Lys Lys Leu
            180                 185                 190

Lys Ser Leu Arg Ile Leu Asn Leu Lys Gly Asn Lys Ile Ser Ser Leu
        195                 200                 205

Gln Asp Val Ser Lys Leu Lys Pro Leu Gln Asp Leu Thr Ser Leu Ile
    210                 215                 220

Leu Leu Glu Asn Pro Val Ala Thr Leu Pro His Tyr Ile Gln Phe Thr
225                 230                 235                 240

Ile Phe His Leu Arg Ser Leu Glu Ser Leu Glu Gly Gln Pro Val Thr
                245                 250                 255

Ser Gln Asp Arg Gln Glu Ala Phe Ala Arg Phe Ser Leu Asp Glu Val
            260                 265                 270

Glu Arg Leu Glu Arg Asp Leu Glu Lys Lys Thr Met Glu Thr Glu Glu
        275                 280                 285
```

-continued

```
Leu Arg Ser Glu Gln Thr Arg Phe Leu Glu Glu Ile Lys Ser Gln Asp
    290                 295                 300
Lys Leu Asn Lys Ser Leu Lys Glu Glu Ala Arg Leu Gln Lys Gln Ser
305                 310                 315                 320
Tyr Glu Glu Leu Glu Ser Asn Leu Asn Thr Lys Asn Glu Leu Leu Lys
                325                 330                 335
Gln Lys Thr Met Glu Leu Met Arg Ala Cys Gln Lys Gln Tyr Glu Met
            340                 345                 350
Glu Gln Glu Leu Ala Phe Tyr Lys Ile Asp Ala Lys Phe Glu Pro Leu
        355                 360                 365
Asn Tyr Tyr Pro Ser Glu Tyr Val Glu Ile Asp Lys Thr Pro Asp Glu
370                 375                 380
Ser Pro Tyr Ile Gly Lys Ser Arg Tyr Lys Arg Asn Met Phe Thr Thr
385                 390                 395                 400
Glu Ser Tyr Ile Ile Ala Asn Ala Gln Thr Val Lys Ile Lys Lys Met
                405                 410                 415
Glu Leu Asp Glu Gly Gln Leu Arg Asn Glu His Val Asn Leu Gly
            420                 425                 430
Ala Ser Pro Thr Asp Ile Gln Leu Glu Asp Lys Glu Lys Lys Ile Ser
        435                 440                 445
Ala Ala Gln Thr Arg Leu Ser Glu Leu His Asp Glu Ile Glu Lys Ala
450                 455                 460
Glu Gln Gln Ile Leu Arg Ala Thr Glu Glu Phe Lys Gln Leu Glu Glu
465                 470                 475                 480
Ala Ile Gln Leu Lys Lys Ile Ser Glu Ala Glu Lys Asp Leu Leu Phe
                485                 490                 495
Lys Gln Leu Ser Gly Arg Ile Gln Leu Leu Asn Lys Leu Arg Gln Glu
            500                 505                 510
Ala Val Asp Leu Glu Thr Gln Met Glu Lys Gln Arg Gln Glu Ile Gly
        515                 520                 525
Glu Lys Gln Asn Glu Ile Lys Asp Leu Glu Ile Val Thr Asp Ser Leu
530                 535                 540
Asp Ser Arg Asp Pro Lys His Cys His Met Lys Ala Gln Lys Arg Gly
545                 550                 555                 560
Lys Glu Gln Gln Leu Asp Ile Met Asn Lys Gln Tyr Lys Gln Leu Glu
                565                 570                 575
Ser Arg Leu Asp Glu Ile Leu Ser Arg Ile Ala Lys Glu Thr Glu Glu
            580                 585                 590
Ile Lys Asp Leu Glu Glu Gln Leu Thr Glu Gly Gln Ile Ala Ala Asn
        595                 600                 605
Glu Ala Leu Lys Lys Asp Leu Glu Ser Val Ile Ser Gly Leu Gln Glu
610                 615                 620
Tyr Leu Glu Thr Val Lys Gly Gln Ala Arg Gln Ala Gln Asn Glu Cys
625                 630                 635                 640
Arg Lys Leu Gln Asp Glu Lys Glu Thr Leu Leu Gln Arg Leu Ser Glu
                645                 650                 655
Val Glu Gln Glu Arg Asp Gln Leu Glu Ile Val Ala Ile Asp Ala Glu
            660                 665                 670
Asn Met Arg Lys Glu Leu Ala Glu Leu Glu Asn Ala Leu Gln Glu Gln
        675                 680                 685
His Glu Val Asn Ile Ser Leu Gln Gln Thr Gln Gly Asp Leu Ser Ala
690                 695                 700
Tyr Glu Ala Glu Leu Glu Ala Gln Leu Lys Ile Arg Asp Ala Glu Ala
```

-continued

```
            705                 710                 715                 720
Asn Gln Leu Lys Glu Glu Leu Glu Lys Leu Arg Arg Leu Ser Gln Leu
                    725                 730                 735
Glu Gln Ser Ala Leu Gln Ala Glu Leu Glu Lys Glu Lys Gln Ala Phe
                740                 745                 750
Lys Thr Ala Val Lys Ala Gln Leu Ser Gly Lys Asp Gln Glu
            755                 760                 765
Asn Ser Glu Leu Arg Thr Gln Leu Gln Gln Leu Gln Asp Asp Asn Asp
        770                 775                 780
Leu Leu Lys Gln Gln Leu Lys Asp Phe Gln Ser His Leu Asn His Val
785                 790                 795                 800
Val Asp Gly Leu Ile Arg Pro Glu Glu Val Ala Ala Cys Val Asp Glu
                805                 810                 815
Leu Arg Lys Lys Leu Lys Ser Gly Ala Gly Glu Met Arg Ile His Thr
            820                 825                 830
Pro Ser Asp Val Leu Gly Lys Ser Leu Ala Asp Leu Gln Lys Gln Phe
            835                 840                 845
Ser Glu Ile Leu Ala Arg Ser Gln Trp Glu Arg Gln Glu Ala Gln Val
850                 855                 860
Arg Glu Arg Lys Leu Gln Glu Glu Met Ala Leu Gln Gln Glu Lys Leu
865                 870                 875                 880
Ala Ser Gly Gln Glu Glu Phe Arg His Ala Cys Glu Arg Ala Leu Glu
                885                 890                 895
Ala Arg Ile Ser Phe Asp Lys Arg Gln His Glu Ala Arg Ile Gln Gln
            900                 905                 910
Leu Glu Asn Glu Ile His Tyr Leu Gln Glu Asn Leu Lys Ser Met Glu
            915                 920                 925
Glu Ile Gln Gly Leu Thr Asp Leu Gln Leu Gln Glu Ala Asp Glu Glu
            930                 935                 940
Lys Glu Arg Ile Leu Ala Gln Leu Arg Glu Leu Glu Lys Lys Lys Lys
945                 950                 955                 960
Leu Glu Asp Ala Lys Ser Gln Glu Gln Phe Leu Gly Leu Asp Arg Glu
                965                 970                 975
Leu Lys Lys Leu Lys Lys Ala Val Ala Ala Ser Asp Lys Leu Ala Thr
            980                 985                 990
Ala Glu Leu Thr Ile Ala Lys Asp  Gln Leu Lys Ser Leu  His Gly Thr
                995                 1000                1005
Val Met  Lys Ile Asn Gln Glu  Arg Ala Glu Glu Leu  Gln Glu Thr
    1010                1015                1020
Glu Arg  Phe Ser Arg Lys Ala  Ala Gln Ala Ala Arg  Asp Leu Ile
    1025                1030                1035
Arg Ala  Glu Ala Glu Ile Glu  Leu Leu Gln Lys Leu  Leu Arg Asp
    1040                1045                1050
Lys Glu  Glu Gln Phe Arg Asn  Glu Ile Glu Lys Val  Asp Val Gly
    1055                1060                1065
Ser Gly  Gly Ala Lys Ser Gln  Met Leu Glu Met Glu  Lys Leu Asn
    1070                1075                1080
Glu Thr  Met Glu Arg Gln Arg  Thr Glu Ile Ala Arg  Leu Arg Asn
    1085                1090                1095
Leu Leu  Asp Leu Thr Gly Ala  Asp Asn Lys Gly Asn  Phe Glu Asn
    1100                1105                1110
Val Leu  Glu Glu Ile Ala Glu  Leu Arg Arg Glu Val  Ser His Gln
    1115                1120                1125
```

-continued

```
Asn Asp Tyr Ile Ser Ser Met Thr Asp Pro Phe Lys Arg Arg Gly
        1130                1135                1140

Tyr Trp Tyr Phe Met Pro Pro Ser Ser Lys Val Ser Ser
        1145                1150                1155

His Ser Ser Gln Ala Thr Lys Asp Ser Gly Val Gly Leu Lys Tyr
        1160                1165                1170

Thr Ala Ser Thr Pro Val Arg Lys Pro His Arg Gly Arg Gln Asp
        1175                1180                1185

Gly Lys Glu Asn Ser Gly Pro Pro Ala Ser Gly Tyr Trp Val
        1190                1195                1200

Tyr Ser Pro Ile Arg Ser Gly Leu His Lys Ser Phe Ser Asn Arg
        1205                1210                1215

Asp Ala Asp Ser Gly Gly Asp Ser Gln Glu Glu Ser Glu Leu Asp
        1220                1225                1230

Asp Gln Glu Asp His Pro Phe Val Pro Pro Gly Tyr Met Met
        1235                1240                1245

Tyr Thr Val Phe Pro Asp Gly Ser Pro Val Pro Gln Gly Met Ala
        1250                1255                1260

Leu Tyr Ala Pro Pro Pro Leu Pro Asn Asn Ser Gln Pro Leu
        1265                1270                1275

Asp Leu Gly Thr Val Val Tyr Gly Pro Pro Val Gly Ala Pro
        1280                1285                1290

Ile Val Tyr Gly Pro Pro Pro Asn Phe Ser Val Pro Leu Ile
        1295                1300                1305

Pro Val Gly Val Leu His Cys Asn Val Pro Glu His His Asn Leu
        1310                1315                1320

Glu Asn Glu Val Ser Arg Leu Glu Asp Ile Met Gln His Leu Lys
        1325                1330                1335

Ser Gly Lys Arg Glu Gln Cys Met Lys Thr Pro Lys Leu Gln Ser
        1340                1345                1350

Glu Lys Glu Leu Ala Glu Leu Gln His Asn Ile Asp Gly Leu Leu
        1355                1360                1365

Gln Glu Lys Lys Asp Leu Glu His Glu Val Glu Glu Leu His Arg
        1370                1375                1380

Thr Ile Gln Lys His Gln Gln Arg Lys Asp Phe Ile Asp Gly Asn
        1385                1390                1395

Val Glu Ser Leu Val Asn Asp Leu Glu Ile Glu Lys Ser Leu Lys
        1400                1405                1410

His His Glu Asp Ile Val Asp Glu Ile Glu Cys Ile Glu Arg Thr
        1415                1420                1425

Leu Leu Lys Arg Arg Ala Glu Leu Arg Glu Ala Asp Arg Leu Leu
        1430                1435                1440

Thr Glu Ala Glu Ser Glu Leu Ser Cys Thr Lys Glu Lys Thr Lys
        1445                1450                1455

His Ala Val Glu Lys Phe Thr Asp Ala Lys Arg Asn Leu Leu Gln
        1460                1465                1470

Thr Glu Lys Asp Ala Glu Glu Leu Glu Arg Arg Ala Gln Glu Thr
        1475                1480                1485

Ala Ile Asn Leu Val Lys Ala Asp Gln Gln Leu Arg Leu Leu Gln
        1490                1495                1500

Ala Asp Thr Lys Asp Leu Glu Gln His Lys Met Glu Gln Glu Glu
        1505                1510                1515
```

```
Ile Leu Lys Glu Ile Asn Lys Val Val Ala Ala Lys Asp Ser Asp
1520                1525                1530

Phe Gln Ser Leu Asn Lys Lys Glu Val Leu Thr Gly Glu Leu
1535                1540                1545

Gln Lys Leu Gln Lys Asp Ile Glu Thr Ala Arg His Asn Glu Asp
1550                1555                1560

Gln His Leu Gln Val Leu Lys Glu Ser Glu Thr Leu Leu Gln Ala
1565                1570                1575

Lys Lys Ala Glu Leu Glu Asn Leu Lys Ser Gln Val Ser Gly Gln
1580                1585                1590

Gln Gln Glu Met Ala Val Leu Asp Arg Glu Leu Gly His Lys Lys
1595                1600                1605

Glu Glu Leu His Leu Leu Gln Glu Ser Met Val Gln Ala Lys Ala
1610                1615                1620

Asp Leu Gln Glu Ala Leu Arg Leu Gly Glu Ser Glu Val Thr Glu
1625                1630                1635

Lys Cys Asn His Ile Arg Glu Val Lys Ser Leu Leu Glu Glu Leu
1640                1645                1650

Ser Phe Gln Lys Gly Glu Leu Asn Val Gln Ile Ser Glu Lys Lys
1655                1660                1665

Thr Gln Leu Ala Leu Ile Lys Gln Glu Ile Glu Lys Glu Glu Asp
1670                1675                1680

Asn Leu Gln Val Val Leu Gly Gln Met Ser Lys His Lys Thr Glu
1685                1690                1695

Leu Lys Asn Ile Leu Asp Met Leu Gln Leu Glu Asn Asn Glu Leu
1700                1705                1710

Gln Gly Leu Lys Leu Gln His Asp Gln Lys Met Ser Glu Leu Glu
1715                1720                1725

Lys Thr Arg Val Glu Val Leu Glu Glu Lys Leu Glu Leu Glu Ser
1730                1735                1740

Leu Gln Gln Ala Ala Leu Arg Gln Arg Gly Glu Ile Glu Trp Gln
1745                1750                1755

Lys Gln Leu Leu Gln Arg Asn Thr Gln Glu Val Glu Arg Met Thr
1760                1765                1770

Ala Glu Thr Arg Ala Leu Gln Ser Cys Val Glu Ser Leu Cys Lys
1775                1780                1785

Glu Lys Gln Asp Leu Glu Glu Lys Gln Asp Ser Trp Glu Lys Lys
1790                1795                1800

Leu Ala Gln Thr Lys Arg Val Leu Ala Ala Ala Glu Glu Asp Ser
1805                1810                1815

Glu Met Glu Arg Ala Arg Leu Glu Lys Leu Glu Leu Asp Ala Arg
1820                1825                1830

Lys Leu Gln Gln Glu Leu Asp Gln Arg Asn Arg Glu Lys Leu Ser
1835                1840                1845

Leu His Gln Asp Leu Ala Val Val Gln Gln Gln Leu Gln Glu Lys
1850                1855                1860

Gln Glu Ala Val Asn Ser Leu Gln Lys Glu Leu Thr Asp Val Gln
1865                1870                1875

Glu His Leu Asp Leu Ala Glu Gln Glu Val Leu Cys Thr Thr Lys
1880                1885                1890

Arg Lys Asp Ala Leu Leu Ser Glu Gln Thr Arg Leu Glu Lys Asp
1895                1900                1905

Val Gly Glu Trp Thr Lys Lys Phe Glu Asp Cys Gln Lys Glu Gly
```

```
         1910                1915                1920
Glu Thr Lys Gln Gln Gln Leu Gln Gly Leu Gln Lys Glu Ile Glu
         1925                1930                1935
Gly Asn Glu Ala Lys Leu Ala Gln Gln Glu Met Met Phe Gln Arg
         1940                1945                1950
Leu Gln Lys Glu Arg Glu Cys Glu Glu Lys Lys Leu Glu Ala Ser
         1955                1960                1965
Lys Val Thr Leu Lys Glu Gln Gln Gln Gln Leu Glu Lys Glu Leu
         1970                1975                1980
Met Glu Gln Lys Gly Lys Leu Asp Gln Val Leu Ala Lys Leu Leu
         1985                1990                1995
Val Ala Glu Glu Arg Val Arg Thr Leu Gln Glu Glu Gly Arg Trp
         2000                2005                2010
Ser Glu Thr Leu Glu Lys Thr Leu Ser Gln Thr Lys Arg Gln Leu
         2015                2020                2025
Ser Glu Arg Glu Gln Gln Leu Leu Ala Lys Ser Asp Glu Leu Leu
         2030                2035                2040
Ala Leu Gln Lys Glu Thr Asp Ser Met Arg Ala Asp Phe Ser Leu
         2045                2050                2055
Leu Arg Asn Gln Phe Leu Thr Glu Arg Lys Lys Ala Glu Lys Gln
         2060                2065                2070
Val Ala Ser Leu Lys Glu Ala Leu Lys Ile Gln Arg Ser Gln Leu
         2075                2080                2085
Glu Lys Asn Leu Leu Glu Gln Lys Gln Glu Asn Ser Cys Met Gln
         2090                2095                2100
Arg Glu Met Ala Thr Ile Glu Gln Val Ala Gln Asp Asn His Glu
         2105                2110                2115
Arg Ala Arg Arg Leu Met Arg Glu Leu Asn Gln Met Gln Arg Glu
         2120                2125                2130
Tyr Val Glu Leu Arg Lys Gln Met Thr Asn Gln Lys Asp Leu Glu
         2135                2140                2145
Arg Arg Gln Met Glu Ile Ser Asp Ala Met Gln Ala Leu Lys Cys
         2150                2155                2160
Glu Val Lys Asp Glu Ile Arg Thr Ser Leu Lys Asn Leu Asn Gln
         2165                2170                2175
Phe Leu Pro Glu Leu Pro Ala Asp Leu Glu Ala Leu Leu Glu Arg
         2180                2185                2190
Asn Glu Asn Leu Gly Gly Gly Leu Glu Ser Leu Lys Glu Asn Phe
         2195                2200                2205
Pro Phe Thr Val Ser Asp Arg Pro Ser Ser Cys Glu Glu Lys Leu
         2210                2215                2220
Asn Phe Gly Gln Ala His Val Ala Asp Glu Gln Trp Arg Gly Glu
         2225                2230                2235
Ala Leu Arg Glu Lys Leu Arg His Arg Glu Asp Arg Leu Lys Ala
         2240                2245                2250
Gln Leu Arg Arg Cys Met Ser Lys Gln Ala Glu Val Leu Ser Glu
         2255                2260                2265
Gly Arg Arg Arg Thr Glu Gly Thr Leu His Ser Leu Arg Arg Gln
         2270                2275                2280
Val Asp Ala Leu Gly Glu Leu Val Thr Ser Thr Ser Gly Asp Ser
         2285                2290                2295
Ala Ser Thr Arg Ser Leu Ser Arg Thr Glu Gly Ser Leu Ala Glu
         2300                2305                2310
```

```
Asp Glu Pro Pro Gly Pro Ser  Gln Ser Ser Arg Arg  Leu Pro Arg
    2315            2320                2325

Gly Pro  Ser Pro Arg Leu Asp  Ala His Arg Pro
    2330                2335

<210> SEQ ID NO 27
<211> LENGTH: 7770
<212> TYPE: DNA
<213> ORGANISM: Canis familiaris
<220> FEATURE:
<221> NAME/KEY: CDS
<222> LOCATION: (1)..(7770)

<400> SEQUENCE: 27 atg aag aaa ggt tct cag caa aag ttt ttg aaa gca aag atg cca cca     48
Met Lys Lys Gly Ser Gln Gln Lys Phe Leu Lys Ala Lys Met Pro Pro
1               5                   10                  15 tca tct cac tct cct agt cca cca tcc ctt acg tcc aat atg aga tct     96
Ser Ser His Ser Pro Ser Pro Pro Ser Leu Thr Ser Asn Met Arg Ser
            20                  25                  30 agg tca ctt tcg cct cta agt gga tct gag act ctg cct ttt cat ttt    144
Arg Ser Leu Ser Pro Leu Ser Gly Ser Glu Thr Leu Pro Phe His Phe
        35                  40                  45 gga gga ccg tgg cat gag caa gtt gag att aca gat gaa agc aca gtg    192
Gly Gly Pro Trp His Glu Gln Val Glu Ile Thr Asp Glu Ser Thr Val
    50                  55                  60 gtt tta gac tac caa gac cat aaa gaa gct gat tca cat gca gga gtc    240
Val Leu Asp Tyr Gln Asp His Lys Glu Ala Asp Ser His Ala Gly Val
65                  70                  75                  80 cga tat att aca gag gcc ctt gtt aga aaa ctt act aaa cag gac aat    288
Arg Tyr Ile Thr Glu Ala Leu Val Arg Lys Leu Thr Lys Gln Asp Asn
                85                  90                  95 ttg gcc ttg gta aaa tct ctg aac ctt tca ctt gct aaa ggt ggt ggc    336
Leu Ala Leu Val Lys Ser Leu Asn Leu Ser Leu Ala Lys Gly Gly Gly
            100                 105                 110 aag aaa ttc agg tgt atc gaa aat ttg gaa aaa tgt gtt aaa ctt gaa    384
Lys Lys Phe Arg Cys Ile Glu Asn Leu Glu Lys Cys Val Lys Leu Glu
        115                 120                 125 gta ctg aat ctc agc tat aat cta ata gga aag att gag aaa gtg gac    432
Val Leu Asn Leu Ser Tyr Asn Leu Ile Gly Lys Ile Glu Lys Val Asp
    130                 135                 140 aaa ctg tta aaa tta cgt gaa ctc aac tta tcg tat aac aaa atc cgc    480
Lys Leu Leu Lys Leu Arg Glu Leu Asn Leu Ser Tyr Asn Lys Ile Arg
145                 150                 155                 160 aaa att gaa ggc ata gaa aat tta tat aat ctg caa aag ctg aac ctt    528
Lys Ile Glu Gly Ile Glu Asn Leu Tyr Asn Leu Gln Lys Leu Asn Leu
                165                 170                 175 gca gga aat gaa atc gaa cat atc cca gta tgg tta ggg aag aag tta    576
Ala Gly Asn Glu Ile Glu His Ile Pro Val Trp Leu Gly Lys Lys Leu
            180                 185                 190 aaa tct ttg cga atc ctg aat ctg aaa ggc aac aag ata tca tcg ctc    624
Lys Ser Leu Arg Ile Leu Asn Leu Lys Gly Asn Lys Ile Ser Ser Leu
        195                 200                 205 caa gat gta agc aag ttg aaa cca ctt caa gat ttg act tct ctg atc    672
Gln Asp Val Ser Lys Leu Lys Pro Leu Gln Asp Leu Thr Ser Leu Ile
    210                 215                 220 cta ctt gaa aat cca gtt gcg acc ctt cct cat tat atc cag ttt acc    720
Leu Leu Glu Asn Pro Val Ala Thr Leu Pro His Tyr Ile Gln Phe Thr
225                 230                 235                 240 att ttt cac ctt cgc tca ttg gaa agt ttg gaa ggt cag cca gta act    768
```

|   |   |
|---|---|
| Ile Phe His Leu Arg Ser Leu Glu Ser Leu Glu Gly Gln Pro Val Thr<br>                      245                      250                   255 |   |
| agt cag gac aga caa gaa gct ttt gcg aga ttc agt tta gat gag gta<br>Ser Gln Asp Arg Gln Glu Ala Phe Ala Arg Phe Ser Leu Asp Glu Val<br>            260                      265                      270 | 816 |
| gaa aga ctg gaa aga gac ctg gag aag aag aca atg gaa act gaa gag<br>Glu Arg Leu Glu Arg Asp Leu Glu Lys Lys Thr Met Glu Thr Glu Glu<br>    275                      280                      285 | 864 |
| ctt agg agt gag cag aca agg ttc ctt gag gaa att aaa agt cag gat<br>Leu Arg Ser Glu Gln Thr Arg Phe Leu Glu Glu Ile Lys Ser Gln Asp<br>         290                      295                    300 | 912 |
| aaa ttg aac aaa tca ctg aaa gag gag gcc aga cta caa aaa cag agc<br>Lys Leu Asn Lys Ser Leu Lys Glu Glu Ala Arg Leu Gln Lys Gln Ser<br>305                      310                      315                    320 | 960 |
| tat gag gag ctg gag agt aac cta aac acc aaa aat gaa ttg cta aaa<br>Tyr Glu Glu Leu Glu Ser Asn Leu Asn Thr Lys Asn Glu Leu Leu Lys<br>                      325                      330                    335 | 1008 |
| cag aag acc atg gaa cta atg cga gca tgt cag aaa cag tat gag atg<br>Gln Lys Thr Met Glu Leu Met Arg Ala Cys Gln Lys Gln Tyr Glu Met<br>            340                      345                      350 | 1056 |
| gaa cag gag ttg gcc ttt tat aaa att gat gcc aaa ttt gaa cca cta<br>Glu Gln Glu Leu Ala Phe Tyr Lys Ile Asp Ala Lys Phe Glu Pro Leu<br>         355                      360                    365 | 1104 |
| aat tat tac cca tca gag tat gtc gaa att gat aaa acc cca gat gaa<br>Asn Tyr Tyr Pro Ser Glu Tyr Val Glu Ile Asp Lys Thr Pro Asp Glu<br>370                      375                      380 | 1152 |
| agc cct tac att ggc aaa tcc aga tac aag aga aat atg ttc act aca<br>Ser Pro Tyr Ile Gly Lys Ser Arg Tyr Lys Arg Asn Met Phe Thr Thr<br>385                      390                      395                    400 | 1200 |
| gag agt tat att att gca aat gcc cag aca gta aag atc aag aag atg<br>Glu Ser Tyr Ile Ile Ala Asn Ala Gln Thr Val Lys Ile Lys Lys Met<br>                      405                      410                    415 | 1248 |
| gag cta gat gaa ggg gaa caa ctc aga aat gag cac gtg aac ttg gga<br>Glu Leu Asp Glu Gly Glu Gln Leu Arg Asn Glu His Val Asn Leu Gly<br>            420                      425                    430 | 1296 |
| gca tcg cca aca gac ata caa ctg gaa gac aaa gaa aaa aaa ata agt<br>Ala Ser Pro Thr Asp Ile Gln Leu Glu Asp Lys Glu Lys Lys Ile Ser<br>                435                      440                    445 | 1344 |
| gca gca caa act cga cta tca gaa cta cat gat gaa ata gaa aag gca<br>Ala Ala Gln Thr Arg Leu Ser Glu Leu His Asp Glu Ile Glu Lys Ala<br>450                      455                      460 | 1392 |
| gaa caa caa att tta aga gcc act gaa gaa ttt aaa caa ctg gaa gaa<br>Glu Gln Gln Ile Leu Arg Ala Thr Glu Glu Phe Lys Gln Leu Glu Glu<br>465                      470                      475                    480 | 1440 |
| gct ata caa ctt aaa aaa att tca gaa gcg gag aaa gac ctt ctt ttc<br>Ala Ile Gln Leu Lys Lys Ile Ser Glu Ala Glu Lys Asp Leu Leu Phe<br>                485                      490                    495 | 1488 |
| aag cag ttg agt ggt agg ata cag ctt ctc aat aaa tta cgc caa gaa<br>Lys Gln Leu Ser Gly Arg Ile Gln Leu Leu Asn Lys Leu Arg Gln Glu<br>            500                      505                    510 | 1536 |
| gct gtg gat cta gaa aca cag atg gaa aag caa agg caa gaa att ggt<br>Ala Val Asp Leu Glu Thr Gln Met Glu Lys Gln Arg Gln Glu Ile Gly<br>         515                      520                    525 | 1584 |
| gaa aag cag aat gag atc aag gac ctg gaa ata gtc aca gat agc ctg<br>Glu Lys Gln Asn Glu Ile Lys Asp Leu Glu Ile Val Thr Asp Ser Leu<br>            530                      535                    540 | 1632 |
| gat tcc aga gac cca aaa cat tgc cat atg aag gct cag aaa aga ggt<br>Asp Ser Arg Asp Pro Lys His Cys His Met Lys Ala Gln Lys Arg Gly<br>545                      550                      555                    560 | 1680 |

```
aaa gaa caa caa ctt gac att atg aac aag cag tac aaa cag ctt gaa    1728
Lys Glu Gln Gln Leu Asp Ile Met Asn Lys Gln Tyr Lys Gln Leu Glu
                565                 570                 575 agc cgt ttg gat gag ata ctt tct aga att gcc aaa gaa act gaa gag    1776
Ser Arg Leu Asp Glu Ile Leu Ser Arg Ile Ala Lys Glu Thr Glu Glu
            580                 585                 590 att aag gac ctt gaa gaa cag ctt act gaa gga caa ata gcc gca aac    1824
Ile Lys Asp Leu Glu Glu Gln Leu Thr Glu Gly Gln Ile Ala Ala Asn
        595                 600                 605 gaa gcc ctg aag aag gac tta gaa agt gtc atc agt ggg ttg caa gaa    1872
Glu Ala Leu Lys Lys Asp Leu Glu Ser Val Ile Ser Gly Leu Gln Glu
    610                 615                 620 tac ctg gag act gtc aaa ggt cag gcc cgt cag gcc cag aat gag tgc    1920
Tyr Leu Glu Thr Val Lys Gly Gln Ala Arg Gln Ala Gln Asn Glu Cys
625                 630                 635                 640 aga aag cta cag gat gag aag gag aca ttg ctg cag aga ttg agt gag    1968
Arg Lys Leu Gln Asp Glu Lys Glu Thr Leu Leu Gln Arg Leu Ser Glu
                645                 650                 655 gtc gag cag gag agg gac caa ctg gaa ata gtg gcc ata gat gca gaa    2016
Val Glu Gln Glu Arg Asp Gln Leu Glu Ile Val Ala Ile Asp Ala Glu
            660                 665                 670 aat atg agg aag gag ctc gca gaa ctg gag aat gcc ctc cag gag cag    2064
Asn Met Arg Lys Glu Leu Ala Glu Leu Glu Asn Ala Leu Gln Glu Gln
        675                 680                 685 cat gag gtg aat ata tct ctg cag cag acc cag gga gat ctc agt gcc    2112
His Glu Val Asn Ile Ser Leu Gln Gln Thr Gln Gly Asp Leu Ser Ala
    690                 695                 700 tat gag gct gag cta gag gct cag ctg aaa ata cgg gat gct gaa gcc    2160
Tyr Glu Ala Glu Leu Glu Ala Gln Leu Lys Ile Arg Asp Ala Glu Ala
705                 710                 715                 720 aac cag ctc aag gag gag ttg gaa aaa ctt aga agg ttg agc cag tta    2208
Asn Gln Leu Lys Glu Glu Leu Glu Lys Leu Arg Arg Leu Ser Gln Leu
                725                 730                 735 gaa caa tcg gcc ctt caa gca gag ctt gag aag gaa aag caa gcc ttc    2256
Glu Gln Ser Ala Leu Gln Ala Glu Leu Glu Lys Glu Lys Gln Ala Phe
            740                 745                 750 aag act gct gtc aaa aaa gcc cag ctc tca gaa gga aag gac caa gaa    2304
Lys Thr Ala Val Lys Lys Ala Gln Leu Ser Glu Gly Lys Asp Gln Glu
        755                 760                 765 aat agt gag ctc cgc aca caa ctc caa cag ctg cag gat gac aat gac    2352
Asn Ser Glu Leu Arg Thr Gln Leu Gln Gln Leu Gln Asp Asp Asn Asp
    770                 775                 780 cta ttg aaa cag caa ctt aaa gat ttc cag agt cac ctt aac cat gtg    2400
Leu Leu Lys Gln Gln Leu Lys Asp Phe Gln Ser His Leu Asn His Val
785                 790                 795                 800 gtt gat ggt ttg att cgt cca gaa gaa gtg gca gct tgt gtg gat gag    2448
Val Asp Gly Leu Ile Arg Pro Glu Glu Val Ala Ala Cys Val Asp Glu
                805                 810                 815 cta agg aaa aaa ctg aag tca gga gct ggg gaa atg aga atc cat act    2496
Leu Arg Lys Lys Leu Lys Ser Gly Ala Gly Glu Met Arg Ile His Thr
            820                 825                 830 cct tca gat gtc tta ggg aaa agt ctt gct gac ttg cag aag caa ttc    2544
Pro Ser Asp Val Leu Gly Lys Ser Leu Ala Asp Leu Gln Lys Gln Phe
        835                 840                 845 agt gag atc ctg gca cgc tcc cag tgg gaa aga cag gaa gca caa gtg    2592
Ser Glu Ile Leu Ala Arg Ser Gln Trp Glu Arg Gln Glu Ala Gln Val
    850                 855                 860 aga gag aga aaa ctc cag gag gaa atg gct ctg caa caa gag aaa ctg    2640
Arg Glu Arg Lys Leu Gln Glu Glu Met Ala Leu Gln Gln Glu Lys Leu
865                 870                 875                 880
```

```
gcg agc gga caa gag gag ttc agg cac gcc tgc gag agg gcc ctg gaa    2688
Ala Ser Gly Gln Glu Glu Phe Arg His Ala Cys Glu Arg Ala Leu Glu
                885                 890                 895 gcc cga att agt ttt gat aag agg cag cac gaa gca aga atc cag cag    2736
Ala Arg Ile Ser Phe Asp Lys Arg Gln His Glu Ala Arg Ile Gln Gln
            900                 905                 910 ttg gag aat gaa att cac tat ttg caa gaa aat cta aaa agt atg gag    2784
Leu Glu Asn Glu Ile His Tyr Leu Gln Glu Asn Leu Lys Ser Met Glu
        915                 920                 925 gaa atc caa ggt ctc aca gac ctc caa ctt cag gaa gct gat gaa gag    2832
Glu Ile Gln Gly Leu Thr Asp Leu Gln Leu Gln Glu Ala Asp Glu Glu
    930                 935                 940 aag gag aga att ctg gcc caa ctc cgg gag tta gag aaa aag aag aaa    2880
Lys Glu Arg Ile Leu Ala Gln Leu Arg Glu Leu Glu Lys Lys Lys Lys
945                 950                 955                 960 ctt gag gat gcc aag tct cag gag cag ttt ctt gga tta gat aga gaa    2928
Leu Glu Asp Ala Lys Ser Gln Glu Gln Phe Leu Gly Leu Asp Arg Glu
                965                 970                 975 ttg aag aag cta aag aaa gct gtg gct gcc tct gat aag ctg gcc aca    2976
Leu Lys Lys Leu Lys Lys Ala Val Ala Ala Ser Asp Lys Leu Ala Thr
            980                 985                 990 gct gag ctc acc att gcc aaa gac cag ctc aag tcc ctt cat gga act    3024
Ala Glu Leu Thr Ile Ala Lys Asp Gln Leu Lys Ser Leu His Gly Thr
        995                 1000                1005 gtg atg aaa att aac cag gag cga gca gag gag ctg cag gag acg       3069
Val Met Lys Ile Asn Gln Glu Arg Ala Glu Glu Leu Gln Glu Thr
    1010                1015                1020 gag agg ttc agc aga aag gca gca caa gca gct agg gat ctg atc       3114
Glu Arg Phe Ser Arg Lys Ala Ala Gln Ala Ala Arg Asp Leu Ile
    1025                1030                1035 cga gca gaa gcg gag att gaa ctc ctg cag aag ctt ctc aga gat       3159
Arg Ala Glu Ala Glu Ile Glu Leu Leu Gln Lys Leu Leu Arg Asp
    1040                1045                1050 aaa gag gag cag ttt cga aat gag att gag aaa gta gat gtc ggc       3204
Lys Glu Glu Gln Phe Arg Asn Glu Ile Glu Lys Val Asp Val Gly
    1055                1060                1065 tct gga gga gca aag tca cag atg ctg gag atg gag aaa cta aat       3249
Ser Gly Gly Ala Lys Ser Gln Met Leu Glu Met Glu Lys Leu Asn
    1070                1075                1080 gag aca atg gag agg caa aga aca gag att gct agg ctg agg aat       3294
Glu Thr Met Glu Arg Gln Arg Thr Glu Ile Ala Arg Leu Arg Asn
    1085                1090                1095 tta cta gac ctc acc ggg gct gat aac aaa gga aac ttt gaa aat       3339
Leu Leu Asp Leu Thr Gly Ala Asp Asn Lys Gly Asn Phe Glu Asn
    1100                1105                1110 gtt ttg gaa gaa att gct gaa ctt cga cgt gaa gtt tct cat cag       3384
Val Leu Glu Glu Ile Ala Glu Leu Arg Arg Glu Val Ser His Gln
    1115                1120                1125 aat gat tac atc agc agc atg aca gat cct ttc aaa aga cga ggc       3429
Asn Asp Tyr Ile Ser Ser Met Thr Asp Pro Phe Lys Arg Arg Gly
    1130                1135                1140 tat tgg tac ttt atg cca cca cca tca tca tca aaa gtt tcc agc       3474
Tyr Trp Tyr Phe Met Pro Pro Pro Ser Ser Ser Lys Val Ser Ser
    1145                1150                1155 cac agt tcc cag gcc acc aag gac tct ggt gtt ggc cta aag tac       3519
His Ser Ser Gln Ala Thr Lys Asp Ser Gly Val Gly Leu Lys Tyr
    1160                1165                1170 aca gcc tcc act ccg gtt aga aaa cca cat cgt gga cgg cag gat       3564
Thr Ala Ser Thr Pro Val Arg Lys Pro His Arg Gly Arg Gln Asp
```

```
                              -continued 1175               1180                1185
gga aag gag aac agt ggg cct cca cct gcc tca gga tac tgg gtg    3609
Gly Lys Glu Asn Ser Gly Pro Pro Pro Ala Ser Gly Tyr Trp Val
        1190               1195                1200 tat tct cct atc agg agt ggg tta cat aaa tcg ttc tca aat aga    3654
Tyr Ser Pro Ile Arg Ser Gly Leu His Lys Ser Phe Ser Asn Arg
        1205               1210                1215 gac gca gac agt gga gga gat agc cag gaa gag agc gag cta gat    3699
Asp Ala Asp Ser Gly Gly Asp Ser Gln Glu Glu Ser Glu Leu Asp
        1220               1225                1230 gac caa gaa gac cac cca ttt gta cct cct cct gga tac atg atg    3744
Asp Gln Glu Asp His Pro Phe Val Pro Pro Pro Gly Tyr Met Met
        1235               1240                1245 tac act gtg ttt cct gat ggt tct cct gta ccc cag ggc atg gcc    3789
Tyr Thr Val Phe Pro Asp Gly Ser Pro Val Pro Gln Gly Met Ala
        1250               1255                1260 ctg tat gca ccc cct cct ccc ttg ccc aac aat agc cag cct ctt    3834
Leu Tyr Ala Pro Pro Pro Pro Leu Pro Asn Asn Ser Gln Pro Leu
        1265               1270                1275 gac ctt ggc act gtt gtt tat ggc cca cct cct gtt ggg gct ccc    3879
Asp Leu Gly Thr Val Val Tyr Gly Pro Pro Pro Val Gly Ala Pro
        1280               1285                1290 atc gtg tat ggg cct cca cct ccc aac ttc tcc gta ccc ctc atc    3924
Ile Val Tyr Gly Pro Pro Pro Pro Asn Phe Ser Val Pro Leu Ile
        1295               1300                1305 ccc gtg ggt gtg ctg cac tgc aat gtc cca gaa cac cat aac ttg    3969
Pro Val Gly Val Leu His Cys Asn Val Pro Glu His His Asn Leu
        1310               1315                1320 gag aat gaa gtt tct aga tta gaa gac ata atg cag cat tta aaa    4014
Glu Asn Glu Val Ser Arg Leu Glu Asp Ile Met Gln His Leu Lys
        1325               1330                1335 tct ggg aaa cgg gaa cag tgc atg aaa aca ccc aag ctg cag tcg    4059
Ser Gly Lys Arg Glu Gln Cys Met Lys Thr Pro Lys Leu Gln Ser
        1340               1345                1350 gag aaa gaa ctc gca gag ctg cag cat aac att gat ggt ctt ttg    4104
Glu Lys Glu Leu Ala Glu Leu Gln His Asn Ile Asp Gly Leu Leu
        1355               1360                1365 caa gag aag aaa gac tta gag cat gaa gta gaa gaa tta cat aga    4149
Gln Glu Lys Lys Asp Leu Glu His Glu Val Glu Glu Leu His Arg
        1370               1375                1380 acc atc caa aaa cat caa cag cga aaa gat ttc att gat gga aac    4194
Thr Ile Gln Lys His Gln Gln Arg Lys Asp Phe Ile Asp Gly Asn
        1385               1390                1395 gtt gag agt ctt gtg aat gat cta gaa ata gag aag tca ctc aaa    4239
Val Glu Ser Leu Val Asn Asp Leu Glu Ile Glu Lys Ser Leu Lys
        1400               1405                1410 cac cat gaa gat att gtt gat gaa att gaa tgt att gag agg acc    4284
His His Glu Asp Ile Val Asp Glu Ile Glu Cys Ile Glu Arg Thr
        1415               1420                1425 ctt ctg aag cgc cgt gca gag ctc agg gaa gcc gac cgg ctg ctg    4329
Leu Leu Lys Arg Arg Ala Glu Leu Arg Glu Ala Asp Arg Leu Leu
        1430               1435                1440 acg gag gct gaa agt gaa ctt tca tgc acg aaa gag aaa aca aaa    4374
Thr Glu Ala Glu Ser Glu Leu Ser Cys Thr Lys Glu Lys Thr Lys
        1445               1450                1455 cat gct gtt gag aag ttc act gat gcc aag aga aat tta ttg caa    4419
His Ala Val Glu Lys Phe Thr Asp Ala Lys Arg Asn Leu Leu Gln
        1460               1465                1470 act gag aaa gat gct gag gag tta gaa agg aga gcc cag gaa act    4464
```

```
Thr Glu Lys Asp Ala Glu Glu Leu Glu Arg Arg Ala Gln Glu Thr
    1475            1480                1485 gcc att aac ctc gtc aaa gcc gac cag cag ctg aga ttg ctc cag      4509
Ala Ile Asn Leu Val Lys Ala Asp Gln Gln Leu Arg Leu Leu Gln
    1490            1495                1500 gct gac acg aag gat ttg gag cag cac aaa atg gag caa gag gaa      4554
Ala Asp Thr Lys Asp Leu Glu Gln His Lys Met Glu Gln Glu Glu
    1505            1510                1515 atc ttg aaa gaa ata aac aaa gtt gtt gca gca aaa gac tca gac      4599
Ile Leu Lys Glu Ile Asn Lys Val Val Ala Ala Lys Asp Ser Asp
    1520            1525                1530 ttc cag agc cta aac aag aag aag gaa gta ctg aca gga gag ctg      4644
Phe Gln Ser Leu Asn Lys Lys Lys Glu Val Leu Thr Gly Glu Leu
    1535            1540                1545 cag aaa ctc cag aag gac att gag act gca cgg cac aat gag gat      4689
Gln Lys Leu Gln Lys Asp Ile Glu Thr Ala Arg His Asn Glu Asp
    1550            1555                1560 cag cac ctg cag gtc ctt aaa gag tcg gag acc ctc ctg cag gcc      4734
Gln His Leu Gln Val Leu Lys Glu Ser Glu Thr Leu Leu Gln Ala
    1565            1570                1575 aag aaa gct gag ctg gaa aat ctg aaa agc cag gtg tca gga cag      4779
Lys Lys Ala Glu Leu Glu Asn Leu Lys Ser Gln Val Ser Gly Gln
    1580            1585                1590 cag cag gag atg gcc gtc ttg gac agg gag tta gga cac aag aag      4824
Gln Gln Glu Met Ala Val Leu Asp Arg Glu Leu Gly His Lys Lys
    1595            1600                1605 gaa gag ctg cat ctc ctc cag gaa agc atg gtc cag gcc aaa gct      4869
Glu Glu Leu His Leu Leu Gln Glu Ser Met Val Gln Ala Lys Ala
    1610            1615                1620 gac ctc cag gaa gca ctg aga cta gga gaa agt gaa gta act gag      4914
Asp Leu Gln Glu Ala Leu Arg Leu Gly Glu Ser Glu Val Thr Glu
    1625            1630                1635 aag tgc aat cac att agg gaa gta aaa tct ctt ctg gaa gaa ctc      4959
Lys Cys Asn His Ile Arg Glu Val Lys Ser Leu Leu Glu Glu Leu
    1640            1645                1650 agt ttt cag aaa gga gaa ctg aat gtc cag atc agt gaa aaa aaa      5004
Ser Phe Gln Lys Gly Glu Leu Asn Val Gln Ile Ser Glu Lys Lys
    1655            1660                1665 act caa ctt gca ctc ata aag cag gaa att gaa aaa gag gaa gac      5049
Thr Gln Leu Ala Leu Ile Lys Gln Glu Ile Glu Lys Glu Glu Asp
    1670            1675                1680 aat ctt cag gta gtt tta ggg caa atg tct aaa cat aaa act gaa      5094
Asn Leu Gln Val Val Leu Gly Gln Met Ser Lys His Lys Thr Glu
    1685            1690                1695 cta aag aat att ctg gac atg ttg caa ctt gaa aat aat gag ctg      5139
Leu Lys Asn Ile Leu Asp Met Leu Gln Leu Glu Asn Asn Glu Leu
    1700            1705                1710 caa ggt ttg aag ctc caa cat gac caa aag atg tct gaa tta gag      5184
Gln Gly Leu Lys Leu Gln His Asp Gln Lys Met Ser Glu Leu Glu
    1715            1720                1725 aag act cgg gtt gaa gtg ctg gag gag aaa ctg gag tta gag agt      5229
Lys Thr Arg Val Glu Val Leu Glu Glu Lys Leu Glu Leu Glu Ser
    1730            1735                1740 ctg cag cag gca gcc ctg cga cag aga ggg gag ata gag tgg cag      5274
Leu Gln Gln Ala Ala Leu Arg Gln Arg Gly Glu Ile Glu Trp Gln
    1745            1750                1755 aag cag ctc ctc cag agg aac aca cag gaa gta gag cgg atg act      5319
Lys Gln Leu Leu Gln Arg Asn Thr Gln Glu Val Glu Arg Met Thr
    1760            1765                1770
```

| | | | | | | | | | | | | | | |
|---|---|---|---|---|---|---|---|---|---|---|---|---|---|---|
| gct | gag | acc | cga | gca | tta | cag | tca | tgt | gtt | gag | tct | ttg | tgc | aaa | 5364 |
| Ala | Glu | Thr | Arg | Ala | Leu | Gln | Ser | Cys | Val | Glu | Ser | Leu | Cys | Lys | |
| 1775 | | | | 1780 | | | | | 1785 | | | | | | |

| | | | | | | | | | | | | | | | |
|---|---|---|---|---|---|---|---|---|---|---|---|---|---|---|---|
| gaa | aag | caa | gat | ctc | gaa | gaa | aaa | cag | gac | agc | tgg | gaa | aag | aag | 5409 |
| Glu | Lys | Gln | Asp | Leu | Glu | Glu | Lys | Gln | Asp | Ser | Trp | Glu | Lys | Lys | |
| 1790 | | | | 1795 | | | | | 1800 | | | | | | |

| | | | | | | | | | | | | | | | |
|---|---|---|---|---|---|---|---|---|---|---|---|---|---|---|---|
| ttg | gca | cag | acc | aaa | cgg | gtt | cta | gca | gct | gca | gaa | gag | gac | agc | 5454 |
| Leu | Ala | Gln | Thr | Lys | Arg | Val | Leu | Ala | Ala | Ala | Glu | Glu | Asp | Ser | |
| 1805 | | | | 1810 | | | | | 1815 | | | | | | |

| | | | | | | | | | | | | | | | |
|---|---|---|---|---|---|---|---|---|---|---|---|---|---|---|---|
| gag | atg | gag | cgg | gca | cgc | tta | gaa | aag | ttg | gaa | ctg | gac | gcc | agg | 5499 |
| Glu | Met | Glu | Arg | Ala | Arg | Leu | Glu | Lys | Leu | Glu | Leu | Asp | Ala | Arg | |
| 1820 | | | | 1825 | | | | | 1830 | | | | | | |

| | | | | | | | | | | | | | | | |
|---|---|---|---|---|---|---|---|---|---|---|---|---|---|---|---|
| aag | ctg | cag | cag | gag | ttg | gac | caa | cga | aac | agg | gag | aag | ctc | tcc | 5544 |
| Lys | Leu | Gln | Gln | Glu | Leu | Asp | Gln | Arg | Asn | Arg | Glu | Lys | Leu | Ser | |
| 1835 | | | | 1840 | | | | | 1845 | | | | | | |

| | | | | | | | | | | | | | | | |
|---|---|---|---|---|---|---|---|---|---|---|---|---|---|---|---|
| ctg | cat | caa | gac | ctg | gca | gtg | gtg | cag | cag | cag | cta | caa | gaa | aaa | 5589 |
| Leu | His | Gln | Asp | Leu | Ala | Val | Val | Gln | Gln | Gln | Leu | Gln | Glu | Lys | |
| 1850 | | | | 1855 | | | | | 1860 | | | | | | |

| | | | | | | | | | | | | | | | |
|---|---|---|---|---|---|---|---|---|---|---|---|---|---|---|---|
| cag | gaa | gca | gta | aac | tca | tta | cag | aag | gaa | cta | gct | gat | gtc | cag | 5634 |
| Gln | Glu | Ala | Val | Asn | Ser | Leu | Gln | Lys | Glu | Leu | Ala | Asp | Val | Gln | |
| 1865 | | | | 1870 | | | | | 1875 | | | | | | |

| | | | | | | | | | | | | | | | |
|---|---|---|---|---|---|---|---|---|---|---|---|---|---|---|---|
| gag | cat | ttg | gac | cta | gca | gaa | cag | gag | gtg | ctc | tgc | acc | acc | aag | 5679 |
| Glu | His | Leu | Asp | Leu | Ala | Glu | Gln | Glu | Val | Leu | Cys | Thr | Thr | Lys | |
| 1880 | | | | 1885 | | | | | 1890 | | | | | | |

| | | | | | | | | | | | | | | | |
|---|---|---|---|---|---|---|---|---|---|---|---|---|---|---|---|
| cgc | aag | gac | gca | ctg | ctc | agc | gaa | cag | acc | agg | ctc | gag | aag | gac | 5724 |
| Arg | Lys | Asp | Ala | Leu | Leu | Ser | Glu | Gln | Thr | Arg | Leu | Glu | Lys | Asp | |
| 1895 | | | | 1900 | | | | | 1905 | | | | | | |

| | | | | | | | | | | | | | | | |
|---|---|---|---|---|---|---|---|---|---|---|---|---|---|---|---|
| gtg | ggt | gaa | tgg | acg | aag | aag | ttt | gaa | gac | tgc | cag | aaa | gaa | ggg | 5769 |
| Val | Gly | Glu | Trp | Thr | Lys | Lys | Phe | Glu | Asp | Cys | Gln | Lys | Glu | Gly | |
| 1910 | | | | 1915 | | | | | 1920 | | | | | | |

| | | | | | | | | | | | | | | | |
|---|---|---|---|---|---|---|---|---|---|---|---|---|---|---|---|
| gag | aca | aag | cag | caa | cag | ctt | caa | ggg | ctt | cag | aag | gag | att | gaa | 5814 |
| Glu | Thr | Lys | Gln | Gln | Gln | Leu | Gln | Gly | Leu | Gln | Lys | Glu | Ile | Glu | |
| 1925 | | | | 1930 | | | | | 1935 | | | | | | |

| | | | | | | | | | | | | | | | |
|---|---|---|---|---|---|---|---|---|---|---|---|---|---|---|---|
| gga | aac | gag | gcg | aag | cta | gcc | caa | caa | gaa | atg | atg | ttt | cag | aga | 5859 |
| Gly | Asn | Glu | Ala | Lys | Leu | Ala | Gln | Gln | Glu | Met | Met | Phe | Gln | Arg | |
| 1940 | | | | 1945 | | | | | 1950 | | | | | | |

| | | | | | | | | | | | | | | | |
|---|---|---|---|---|---|---|---|---|---|---|---|---|---|---|---|
| ctc | cag | aaa | gag | cga | gaa | tgt | gaa | gaa | aaa | aag | tta | gaa | gct | agt | 5904 |
| Leu | Gln | Lys | Glu | Arg | Glu | Cys | Glu | Glu | Lys | Lys | Leu | Glu | Ala | Ser | |
| 1955 | | | | 1960 | | | | | 1965 | | | | | | |

| | | | | | | | | | | | | | | | |
|---|---|---|---|---|---|---|---|---|---|---|---|---|---|---|---|
| aaa | gtg | act | ctg | aag | gag | cag | cag | caa | cag | ctg | gaa | aag | gaa | ttg | 5949 |
| Lys | Val | Thr | Leu | Lys | Glu | Gln | Gln | Gln | Gln | Leu | Glu | Lys | Glu | Leu | |
| 1970 | | | | 1975 | | | | | 1980 | | | | | | |

| | | | | | | | | | | | | | | | |
|---|---|---|---|---|---|---|---|---|---|---|---|---|---|---|---|
| atg | gag | cag | aaa | ggc | aag | ctg | gac | cag | gtg | ctc | gct | aag | ctc | ttg | 5994 |
| Met | Glu | Gln | Lys | Gly | Lys | Leu | Asp | Gln | Val | Leu | Ala | Lys | Leu | Leu | |
| 1985 | | | | 1990 | | | | | 1995 | | | | | | |

| | | | | | | | | | | | | | | | |
|---|---|---|---|---|---|---|---|---|---|---|---|---|---|---|---|
| gtg | gct | gag | gag | cgt | gtc | agg | acc | ttg | cag | gag | gag | gga | agg | tgg | 6039 |
| Val | Ala | Glu | Glu | Arg | Val | Arg | Thr | Leu | Gln | Glu | Glu | Gly | Arg | Trp | |
| 2000 | | | | 2005 | | | | | 2010 | | | | | | |

| | | | | | | | | | | | | | | | |
|---|---|---|---|---|---|---|---|---|---|---|---|---|---|---|---|
| agc | gag | acc | ctg | gag | aag | acg | ctc | tcc | cag | acc | aag | cga | cag | ctt | 6084 |
| Ser | Glu | Thr | Leu | Glu | Lys | Thr | Leu | Ser | Gln | Thr | Lys | Arg | Gln | Leu | |
| 2015 | | | | 2020 | | | | | 2025 | | | | | | |

| | | | | | | | | | | | | | | | |
|---|---|---|---|---|---|---|---|---|---|---|---|---|---|---|---|
| tca | gaa | cgg | gag | cag | cag | tta | ctg | gcc | aag | tca | gac | gag | ctg | ctg | 6129 |
| Ser | Glu | Arg | Glu | Gln | Gln | Leu | Leu | Ala | Lys | Ser | Asp | Glu | Leu | Leu | |
| 2030 | | | | 2035 | | | | | 2040 | | | | | | |

| | | | | | | | | | | | | | | | |
|---|---|---|---|---|---|---|---|---|---|---|---|---|---|---|---|
| gcc | ctg | cag | aag | gag | acg | gac | tcc | atg | agg | gcg | gac | ttc | agc | ctc | 6174 |
| Ala | Leu | Gln | Lys | Glu | Thr | Asp | Ser | Met | Arg | Ala | Asp | Phe | Ser | Leu | |
| 2045 | | | | 2050 | | | | | 2055 | | | | | | |

| | | | | | | | | | | | | | | | |
|---|---|---|---|---|---|---|---|---|---|---|---|---|---|---|---|
| ttg | cgc | aac | cag | ttc | ctg | aca | gaa | aga | aag | aaa | gcc | gag | aag | cag | 6219 |
| Leu | Arg | Asn | Gln | Phe | Leu | Thr | Glu | Arg | Lys | Lys | Ala | Glu | Lys | Gln | |
| 2060 | | | | 2065 | | | | | 2070 | | | | | | |

```
gtg gcc agc ctg aag gaa gcc ctt aag atc cag cgg agc caa ctg      6264
Val Ala Ser Leu Lys Glu Ala Leu Lys Ile Gln Arg Ser Gln Leu
    2075             2080                2085 gag aag aac ctt ctg gag caa aag cag gag aac agc tgc atg cag      6309
Glu Lys Asn Leu Leu Glu Gln Lys Gln Glu Asn Ser Cys Met Gln
2090             2095                2100 agg gag atg gca acc atc gaa cag gtg gcc cag gac aac cac gag      6354
Arg Glu Met Ala Thr Ile Glu Gln Val Ala Gln Asp Asn His Glu
    2105             2110                2115 cgg gcc cgg cgc ctg atg agg gag ctc aac cag atg cag cgc gag      6399
Arg Ala Arg Arg Leu Met Arg Glu Leu Asn Gln Met Gln Arg Glu
2120             2125                2130 tac gtg gag ctc agg aaa cag atg aca aac caa aag gat ttg gaa      6444
Tyr Val Glu Leu Arg Lys Gln Met Thr Asn Gln Lys Asp Leu Glu
    2135             2140                2145 aga aga cag atg gaa atc agt gat gcg atg caa gca ctt aaa tgt      6489
Arg Arg Gln Met Glu Ile Ser Asp Ala Met Gln Ala Leu Lys Cys
2150             2155                2160 gag gtg aaa gat gaa atc cga acc agc ctg aag aat ctc aac cag      6534
Glu Val Lys Asp Glu Ile Arg Thr Ser Leu Lys Asn Leu Asn Gln
    2165             2170                2175 ttt ctt cca gag ctg cca gcg gac ctg gag gcc ctt ctg gaa agg      6579
Phe Leu Pro Glu Leu Pro Ala Asp Leu Glu Ala Leu Leu Glu Arg
2180             2185                2190 aat gag aac ctt gga gga ggc ttg gag agc ttg aaa gag aat ttc      6624
Asn Glu Asn Leu Gly Gly Gly Leu Glu Ser Leu Lys Glu Asn Phe
    2195             2200                2205 ccg ttt acc gtg agc gac aga cca tca tct tgc gaa gag aaa ctg      6669
Pro Phe Thr Val Ser Asp Arg Pro Ser Ser Cys Glu Glu Lys Leu
2210             2215                2220 aat ttt ggc cag gct cac gtg gcg gat gaa cag tgg cgg gga gag      6714
Asn Phe Gly Gln Ala His Val Ala Asp Glu Gln Trp Arg Gly Glu
    2225             2230                2235 gca ctc cgg gag aag ctg cgc cac cgc gag gac cgg ctc aag gcc      6759
Ala Leu Arg Glu Lys Leu Arg His Arg Glu Asp Arg Leu Lys Ala
2240             2245                2250 cag ctg cgc cgc tgc atg tcc aag cag gcc gag gtg ctg agc gag      6804
Gln Leu Arg Arg Cys Met Ser Lys Gln Ala Glu Val Leu Ser Glu
    2255             2260                2265 ggc cgg cgg cgc acg gag ggg acc ctg cac agc ctg cgg cgg cag      6849
Gly Arg Arg Arg Thr Glu Gly Thr Leu His Ser Leu Arg Arg Gln
2270             2275                2280 gtg gac gcc ctg ggc gag ctg gtc acc agc act tcc ggg gac tcc      6894
Val Asp Ala Leu Gly Glu Leu Val Thr Ser Thr Ser Gly Asp Ser
    2285             2290                2295 gcg tcc acc cgc agt ctg tcg cgc acc gag ggc tcg ctc gcc gag      6939
Ala Ser Thr Arg Ser Leu Ser Arg Thr Glu Gly Ser Leu Ala Glu
2300             2305                2310 gac gaa ccg ccg ggg ccc agc cag gag ctg cac gtg ctg ggg tcg      6984
Asp Glu Pro Pro Gly Pro Ser Gln Glu Leu His Val Leu Gly Ser
    2315             2320                2325 ggc ggc agc gac cga ggt gga gga cgg ggc ggg gcc agg aag ggc      7029
Gly Gly Ser Asp Arg Gly Gly Gly Arg Gly Gly Gly Arg Lys Gly
2330             2335                2340 ctt tcc cga cgc cgc cgc tgg aac cac gga gaa gcg cgc ctc ggc      7074
Leu Ser Arg Arg Arg Arg Trp Asn His Gly Glu Ala Arg Leu Gly
    2345             2350                2355 ccg cgg agg ccc cca cgg gag ggg gca ggg cgg ggc gcg gcc ttc      7119
Pro Arg Arg Pro Pro Arg Glu Gly Ala Gly Arg Gly Ala Ala Phe
2360             2365                2370
```

```
cga gcc ttg gtc tcc tgc tcc cgc cct gca gag ctc ccg gcg gct      7164
Arg Ala Leu Val Ser Cys Ser Arg Pro Ala Glu Leu Pro Ala Ala
    2375                2380                2385 ccc ccg agg ccc gtc gcc gcg gct gga cgc gca ccg acc ctg agg      7209
Pro Pro Arg Pro Val Ala Ala Ala Gly Arg Ala Pro Thr Leu Arg
2390                2395                2400 acc cgg agg acc cgg agg ccc ggc gtc ccc tcg gaa cgc ttc ctc      7254
Thr Arg Arg Thr Arg Arg Pro Gly Val Pro Ser Glu Arg Phe Leu
    2405                2410                2415 cgc gtc cgc gga cac cag gct cac ggg aag gcg cgt cca tgc ggg      7299
Arg Val Arg Gly His Gln Ala His Gly Lys Ala Arg Pro Cys Gly
2420                2425                2430 aag agc cgc gag cgg aac ccg gat gcc cgg gct ggt ctc tgg gcc      7344
Lys Ser Arg Glu Arg Asn Pro Asp Ala Arg Ala Gly Leu Trp Ala
    2435                2440                2445 ttg gaa acg tgt tgc cgt aaa agc agc gcc cgc ggc tgc gga ctt      7389
Leu Glu Thr Cys Cys Arg Lys Ser Ser Ala Arg Gly Cys Gly Leu
2450                2455                2460 gaa gcc ccg aac tgc cgc cgt gcc cgg tgc gga gcg agc gtg cgg      7434
Glu Ala Pro Asn Cys Arg Arg Ala Arg Cys Gly Ala Ser Val Arg
    2465                2470                2475 tac cct ctc gtg cct cgg ggc cgg act gga cga ggg gcc gtg acc      7479
Tyr Pro Leu Val Pro Arg Gly Arg Thr Gly Arg Gly Ala Val Thr
2480                2485                2490 ccg tgg ggc cgc ctg cag tcc cga ggg acg cgg acc acc ccc cgg      7524
Pro Trp Gly Arg Leu Gln Ser Arg Gly Thr Arg Thr Thr Pro Arg
    2495                2500                2505 ccg gtg cga cgg gag cat ccc cag cac cag gaa agg ccc cca ggg      7569
Pro Val Arg Arg Glu His Pro Gln His Gln Glu Arg Pro Pro Gly
2510                2515                2520 cgc gtt acc gcg gcc cac act gag acc gcc cct ccc cgc cgg gtg      7614
Arg Val Thr Ala Ala His Thr Glu Thr Ala Pro Pro Arg Arg Val
    2525                2530                2535 ttc cac gcg cga gta gca gtc ggg gag gtc agc ctc ggg ccc ggc      7659
Phe His Ala Arg Val Ala Val Gly Glu Val Ser Leu Gly Pro Gly
2540                2545                2550 cgc ggt ctc gag cga aca cgg ggc ggg ggc ggg ggg gcg ggg gcg      7704
Arg Gly Leu Glu Arg Thr Arg Gly Gly Gly Gly Gly Ala Gly Ala
    2555                2560                2565 gga ctc ctc gca gag gcc gcg gcc acg gcc cgg tgc gca gac ccc      7749
Gly Leu Leu Ala Glu Ala Ala Ala Thr Ala Arg Cys Ala Asp Pro
2570                2575                2580 tcc aca gac ccc tcc gca tag                                      7770
Ser Thr Asp Pro Ser Ala
    2585
```

<210> SEQ ID NO 28
<211> LENGTH: 2589
<212> TYPE: PRT
<213> ORGANISM: Canis familiaris

<400> SEQUENCE: 28

```
Met Lys Lys Gly Ser Gln Gln Lys Phe Leu Lys Ala Lys Met Pro Pro
1               5                   10                  15

Ser Ser His Ser Pro Ser Pro Pro Ser Leu Thr Ser Asn Met Arg Ser
            20                  25                  30

Arg Ser Leu Ser Pro Leu Ser Gly Ser Glu Thr Leu Pro Phe His Phe
        35                  40                  45
```

-continued

```
Gly Gly Pro Trp His Glu Gln Val Glu Ile Thr Asp Glu Ser Thr Val
    50              55                  60
Val Leu Asp Tyr Gln Asp His Lys Glu Ala Asp Ser His Ala Gly Val
65              70                  75                  80
Arg Tyr Ile Thr Glu Ala Leu Val Arg Lys Leu Thr Lys Gln Asp Asn
                85                  90                  95
Leu Ala Leu Val Lys Ser Leu Asn Leu Ser Leu Ala Lys Gly Gly Gly
            100                 105                 110
Lys Lys Phe Arg Cys Ile Glu Asn Leu Glu Lys Cys Val Lys Leu Glu
            115                 120                 125
Val Leu Asn Leu Ser Tyr Asn Leu Ile Gly Lys Ile Glu Lys Val Asp
130                 135                 140
Lys Leu Lys Leu Arg Glu Leu Asn Leu Ser Tyr Asn Lys Ile Arg
145                 150                 155                 160
Lys Ile Glu Gly Ile Glu Asn Leu Tyr Asn Leu Gln Lys Leu Asn Leu
                165                 170                 175
Ala Gly Asn Glu Ile Glu His Ile Pro Val Trp Leu Gly Lys Lys Leu
            180                 185                 190
Lys Ser Leu Arg Ile Leu Asn Leu Lys Gly Asn Lys Ile Ser Ser Leu
        195                 200                 205
Gln Asp Val Ser Lys Leu Lys Pro Leu Gln Asp Leu Thr Ser Leu Ile
    210                 215                 220
Leu Leu Glu Asn Pro Val Ala Thr Leu Pro His Tyr Ile Gln Phe Thr
225                 230                 235                 240
Ile Phe His Leu Arg Ser Leu Glu Ser Leu Glu Gly Gln Pro Val Thr
                245                 250                 255
Ser Gln Asp Arg Gln Glu Ala Phe Ala Arg Phe Ser Leu Asp Glu Val
            260                 265                 270
Glu Arg Leu Glu Arg Asp Leu Glu Lys Lys Thr Met Glu Thr Glu Glu
        275                 280                 285
Leu Arg Ser Glu Gln Thr Arg Phe Leu Glu Glu Ile Lys Ser Gln Asp
    290                 295                 300
Lys Leu Asn Lys Ser Leu Lys Glu Glu Ala Arg Leu Gln Lys Gln Ser
305                 310                 315                 320
Tyr Glu Glu Leu Glu Ser Asn Leu Asn Thr Lys Asn Glu Leu Leu Lys
                325                 330                 335
Gln Lys Thr Met Glu Leu Met Arg Ala Cys Gln Lys Gln Tyr Glu Met
            340                 345                 350
Glu Gln Glu Leu Ala Phe Tyr Lys Ile Asp Ala Lys Phe Glu Pro Leu
        355                 360                 365
Asn Tyr Tyr Pro Ser Glu Tyr Val Glu Ile Asp Lys Thr Pro Asp Glu
    370                 375                 380
Ser Pro Tyr Ile Gly Lys Ser Arg Tyr Lys Arg Asn Met Phe Thr Thr
385                 390                 395                 400
Glu Ser Tyr Ile Ile Ala Asn Ala Gln Thr Val Lys Ile Lys Lys Met
                405                 410                 415
Glu Leu Asp Glu Gly Glu Gln Leu Arg Asn Glu His Val Asn Leu Gly
            420                 425                 430
Ala Ser Pro Thr Asp Ile Gln Leu Glu Asp Lys Glu Lys Lys Ile Ser
        435                 440                 445
Ala Ala Gln Thr Arg Leu Ser Glu Leu His Asp Glu Ile Glu Lys Ala
450                 455                 460
Glu Gln Gln Ile Leu Arg Ala Thr Glu Glu Phe Lys Gln Leu Glu Glu
```

-continued

```
            465                 470                 475                 480
        Ala Ile Gln Leu Lys Lys Ile Ser Glu Ala Glu Lys Asp Leu Leu Phe
                            485                 490                 495
        Lys Gln Leu Ser Gly Arg Ile Gln Leu Leu Asn Lys Leu Arg Gln Glu
                        500                 505                 510
        Ala Val Asp Leu Glu Thr Gln Met Glu Lys Gln Arg Gln Glu Ile Gly
                        515                 520                 525
        Glu Lys Gln Asn Glu Ile Lys Asp Leu Glu Ile Val Thr Asp Ser Leu
                        530                 535                 540
        Asp Ser Arg Asp Pro Lys His Cys His Met Lys Ala Gln Lys Arg Gly
        545                 550                 555                 560
        Lys Glu Gln Gln Leu Asp Ile Met Asn Lys Gln Tyr Lys Gln Leu Glu
                            565                 570                 575
        Ser Arg Leu Asp Glu Ile Leu Ser Arg Ile Ala Lys Glu Thr Glu Glu
                        580                 585                 590
        Ile Lys Asp Leu Glu Glu Gln Leu Thr Glu Gly Gln Ile Ala Ala Asn
                        595                 600                 605
        Glu Ala Leu Lys Lys Asp Leu Glu Ser Val Ile Ser Gly Leu Gln Glu
                        610                 615                 620
        Tyr Leu Glu Thr Val Lys Gly Gln Ala Arg Gln Ala Gln Asn Glu Cys
        625                 630                 635                 640
        Arg Lys Leu Gln Asp Glu Lys Glu Thr Leu Leu Gln Arg Leu Ser Glu
                            645                 650                 655
        Val Glu Gln Glu Arg Asp Gln Leu Glu Ile Val Ala Ile Asp Ala Glu
                        660                 665                 670
        Asn Met Arg Lys Glu Leu Ala Glu Leu Glu Asn Ala Leu Gln Glu Gln
                        675                 680                 685
        His Glu Val Asn Ile Ser Leu Gln Gln Thr Gln Gly Asp Leu Ser Ala
                        690                 695                 700
        Tyr Glu Ala Glu Leu Glu Ala Gln Leu Lys Ile Arg Asp Ala Glu Ala
        705                 710                 715                 720
        Asn Gln Leu Lys Glu Glu Leu Glu Lys Leu Arg Arg Leu Ser Gln Leu
                            725                 730                 735
        Glu Gln Ser Ala Leu Gln Ala Glu Leu Glu Lys Glu Lys Gln Ala Phe
                        740                 745                 750
        Lys Thr Ala Val Lys Lys Ala Gln Leu Ser Glu Gly Lys Asp Gln Glu
                        755                 760                 765
        Asn Ser Glu Leu Arg Thr Gln Leu Gln Gln Leu Gln Asp Asp Asn Asp
                        770                 775                 780
        Leu Leu Lys Gln Gln Leu Lys Asp Phe Gln Ser His Leu Asn His Val
        785                 790                 795                 800
        Val Asp Gly Leu Ile Arg Pro Glu Glu Val Ala Ala Cys Val Asp Glu
                            805                 810                 815
        Leu Arg Lys Lys Leu Lys Ser Gly Ala Gly Glu Met Arg Ile His Thr
                        820                 825                 830
        Pro Ser Asp Val Leu Gly Lys Ser Leu Ala Asp Leu Gln Lys Gln Phe
                        835                 840                 845
        Ser Glu Ile Leu Ala Arg Ser Gln Trp Glu Arg Gln Glu Ala Gln Val
                        850                 855                 860
        Arg Glu Arg Lys Leu Gln Glu Glu Met Ala Leu Gln Gln Glu Lys Leu
        865                 870                 875                 880
        Ala Ser Gly Gln Glu Glu Phe Arg His Ala Cys Glu Arg Ala Leu Glu
                            885                 890                 895
```

```
Ala Arg Ile Ser Phe Asp Lys Arg Gln His Glu Ala Arg Ile Gln Gln
            900                 905                 910

Leu Glu Asn Glu Ile His Tyr Leu Gln Glu Asn Leu Lys Ser Met Glu
            915                 920                 925

Glu Ile Gln Gly Leu Thr Asp Leu Gln Leu Gln Glu Ala Asp Glu Glu
            930                 935                 940

Lys Glu Arg Ile Leu Ala Gln Leu Arg Glu Leu Glu Lys Lys Lys Lys
945                 950                 955                 960

Leu Glu Asp Ala Lys Ser Gln Glu Gln Phe Leu Gly Leu Asp Arg Glu
                965                 970                 975

Leu Lys Lys Leu Lys Lys Ala Val Ala Ala Ser Asp Lys Leu Ala Thr
            980                 985                 990

Ala Glu Leu Thr Ile Ala Lys Asp Gln Leu Lys Ser Leu His Gly Thr
            995                 1000                1005

Val Met Lys Ile Asn Gln Glu Arg Ala Glu Glu Leu Gln Glu Thr
       1010                 1015                1020

Glu Arg Phe Ser Arg Lys Ala Ala Gln Ala Ala Arg Asp Leu Ile
       1025                 1030                1035

Arg Ala Glu Ala Glu Ile Glu Leu Leu Gln Lys Leu Leu Arg Asp
       1040                 1045                1050

Lys Glu Glu Gln Phe Arg Asn Glu Ile Glu Lys Val Asp Val Gly
       1055                 1060                1065

Ser Gly Gly Ala Lys Ser Gln Met Leu Glu Met Glu Lys Leu Asn
       1070                 1075                1080

Glu Thr Met Glu Arg Gln Arg Thr Glu Ile Ala Arg Leu Arg Asn
       1085                 1090                1095

Leu Leu Asp Leu Thr Gly Ala Asp Asn Lys Gly Asn Phe Glu Asn
       1100                 1105                1110

Val Leu Glu Glu Ile Ala Glu Leu Arg Arg Glu Val Ser His Gln
       1115                 1120                1125

Asn Asp Tyr Ile Ser Ser Met Thr Asp Pro Phe Lys Arg Arg Gly
       1130                 1135                1140

Tyr Trp Tyr Phe Met Pro Pro Ser Ser Lys Val Ser Ser
       1145                 1150                1155

His Ser Ser Gln Ala Thr Lys Asp Ser Gly Val Gly Leu Lys Tyr
       1160                 1165                1170

Thr Ala Ser Thr Pro Val Arg Lys Pro His Arg Gly Arg Gln Asp
       1175                 1180                1185

Gly Lys Glu Asn Ser Gly Pro Pro Ala Ser Gly Tyr Trp Val
       1190                 1195                1200

Tyr Ser Pro Ile Arg Ser Gly Leu His Lys Ser Phe Ser Asn Arg
       1205                 1210                1215

Asp Ala Asp Ser Gly Gly Asp Ser Gln Glu Glu Ser Glu Leu Asp
       1220                 1225                1230

Asp Gln Glu Asp His Pro Phe Val Pro Pro Pro Gly Tyr Met Met
       1235                 1240                1245

Tyr Thr Val Phe Pro Asp Gly Ser Pro Val Pro Gln Gly Met Ala
       1250                 1255                1260

Leu Tyr Ala Pro Pro Pro Pro Leu Pro Asn Asn Ser Gln Pro Leu
       1265                 1270                1275

Asp Leu Gly Thr Val Val Tyr Gly Pro Pro Val Gly Ala Pro
       1280                 1285                1290
```

```
Ile Val Tyr Gly Pro Pro Pro Asn Phe Ser Val Pro Leu Ile
1295             1300             1305

Pro Val Gly Val Leu His Cys Asn Val Pro Glu His His Asn Leu
1310             1315             1320

Glu Asn Glu Val Ser Arg Leu Glu Asp Ile Met Gln His Leu Lys
1325             1330             1335

Ser Gly Lys Arg Glu Gln Cys Met Lys Thr Pro Lys Leu Gln Ser
1340             1345             1350

Glu Lys Glu Leu Ala Glu Leu Gln His Asn Ile Asp Gly Leu Leu
1355             1360             1365

Gln Glu Lys Lys Asp Leu Glu His Glu Val Glu Leu His Arg
1370             1375             1380

Thr Ile Gln Lys His Gln Gln Arg Lys Asp Phe Ile Asp Gly Asn
1385             1390             1395

Val Glu Ser Leu Val Asn Asp Leu Glu Ile Glu Lys Ser Leu Lys
1400             1405             1410

His His Glu Asp Ile Val Asp Glu Ile Glu Cys Ile Glu Arg Thr
1415             1420             1425

Leu Leu Lys Arg Arg Ala Glu Leu Arg Glu Ala Asp Arg Leu Leu
1430             1435             1440

Thr Glu Ala Glu Ser Glu Leu Ser Cys Thr Lys Glu Lys Thr Lys
1445             1450             1455

His Ala Val Glu Lys Phe Thr Asp Ala Lys Arg Asn Leu Leu Gln
1460             1465             1470

Thr Glu Lys Asp Ala Glu Glu Leu Glu Arg Arg Ala Gln Glu Thr
1475             1480             1485

Ala Ile Asn Leu Val Lys Ala Asp Gln Gln Leu Arg Leu Leu Gln
1490             1495             1500

Ala Asp Thr Lys Asp Leu Glu Gln His Lys Met Glu Gln Glu Glu
1505             1510             1515

Ile Leu Lys Glu Ile Asn Lys Val Val Ala Ala Lys Asp Ser Asp
1520             1525             1530

Phe Gln Ser Leu Asn Lys Lys Glu Val Leu Thr Gly Glu Leu
1535             1540             1545

Gln Lys Leu Gln Lys Asp Ile Glu Thr Ala Arg His Asn Glu Asp
1550             1555             1560

Gln His Leu Gln Val Leu Lys Glu Ser Glu Thr Leu Leu Gln Ala
1565             1570             1575

Lys Lys Ala Glu Leu Glu Asn Leu Lys Ser Gln Val Ser Gly Gln
1580             1585             1590

Gln Gln Glu Met Ala Val Leu Asp Arg Glu Leu Gly His Lys Lys
1595             1600             1605

Glu Glu Leu His Leu Leu Gln Glu Ser Met Val Gln Ala Lys Ala
1610             1615             1620

Asp Leu Gln Glu Ala Leu Arg Leu Gly Glu Ser Glu Val Thr Glu
1625             1630             1635

Lys Cys Asn His Ile Arg Glu Val Lys Ser Leu Leu Glu Glu Leu
1640             1645             1650

Ser Phe Gln Lys Gly Glu Leu Asn Val Gln Ile Ser Glu Lys Lys
1655             1660             1665

Thr Gln Leu Ala Leu Ile Lys Gln Glu Ile Glu Lys Glu Glu Asp
1670             1675             1680

Asn Leu Gln Val Val Leu Gly Gln Met Ser Lys His Lys Thr Glu
```

```
                    1685                1690                1695

Leu Lys Asn Ile Leu Asp Met Leu Gln Leu Glu Asn Asn Glu Leu
    1700                1705                1710

Gln Gly Leu Lys Leu Gln His Asp Gln Lys Met Ser Glu Leu Glu
    1715                1720                1725

Lys Thr Arg Val Glu Val Leu Glu Glu Lys Leu Glu Leu Glu Ser
    1730                1735                1740

Leu Gln Gln Ala Ala Leu Arg Gln Arg Gly Glu Ile Glu Trp Gln
    1745                1750                1755

Lys Gln Leu Leu Gln Arg Asn Thr Gln Glu Val Glu Arg Met Thr
    1760                1765                1770

Ala Glu Thr Arg Ala Leu Gln Ser Cys Val Glu Ser Leu Cys Lys
    1775                1780                1785

Glu Lys Gln Asp Leu Glu Glu Lys Gln Asp Ser Trp Glu Lys Lys
    1790                1795                1800

Leu Ala Gln Thr Lys Arg Val Leu Ala Ala Glu Glu Asp Ser
    1805                1810                1815

Glu Met Glu Arg Ala Arg Leu Glu Lys Leu Glu Leu Asp Ala Arg
    1820                1825                1830

Lys Leu Gln Gln Glu Leu Asp Gln Arg Asn Arg Glu Lys Leu Ser
    1835                1840                1845

Leu His Gln Asp Leu Ala Val Val Gln Gln Gln Leu Gln Glu Lys
    1850                1855                1860

Gln Glu Ala Val Asn Ser Leu Gln Lys Glu Leu Ala Asp Val Gln
    1865                1870                1875

Glu His Leu Asp Leu Ala Glu Gln Glu Val Leu Cys Thr Thr Lys
    1880                1885                1890

Arg Lys Asp Ala Leu Leu Ser Glu Gln Thr Arg Leu Glu Lys Asp
    1895                1900                1905

Val Gly Glu Trp Thr Lys Lys Phe Glu Asp Cys Gln Lys Glu Gly
    1910                1915                1920

Glu Thr Lys Gln Gln Gln Leu Gln Gly Leu Gln Lys Glu Ile Glu
    1925                1930                1935

Gly Asn Glu Ala Lys Leu Ala Gln Gln Glu Met Met Phe Gln Arg
    1940                1945                1950

Leu Gln Lys Glu Arg Glu Cys Glu Glu Lys Lys Leu Glu Ala Ser
    1955                1960                1965

Lys Val Thr Leu Lys Glu Gln Gln Gln Leu Glu Lys Glu Leu
    1970                1975                1980

Met Glu Gln Lys Gly Lys Leu Asp Gln Val Leu Ala Lys Leu Leu
    1985                1990                1995

Val Ala Glu Glu Arg Val Arg Thr Leu Gln Glu Glu Gly Arg Trp
    2000                2005                2010

Ser Glu Thr Leu Glu Lys Thr Leu Ser Gln Thr Lys Arg Gln Leu
    2015                2020                2025

Ser Glu Arg Glu Gln Gln Leu Leu Ala Lys Ser Asp Glu Leu Leu
    2030                2035                2040

Ala Leu Gln Lys Glu Thr Asp Ser Met Arg Ala Asp Phe Ser Leu
    2045                2050                2055

Leu Arg Asn Gln Phe Leu Thr Glu Arg Lys Lys Ala Glu Lys Gln
    2060                2065                2070

Val Ala Ser Leu Lys Glu Ala Leu Lys Ile Gln Arg Ser Gln Leu
    2075                2080                2085
```

-continued

```
Glu Lys Asn Leu Leu Glu Gln Lys Gln Glu Asn Ser Cys Met Gln
    2090                2095                2100

Arg Glu Met Ala Thr Ile Glu Gln Val Ala Gln Asp Asn His Glu
    2105                2110                2115

Arg Ala Arg Arg Leu Met Arg Glu Leu Asn Gln Met Gln Arg Glu
    2120                2125                2130

Tyr Val Glu Leu Arg Lys Gln Met Thr Asn Gln Lys Asp Leu Glu
    2135                2140                2145

Arg Arg Gln Met Glu Ile Ser Asp Ala Met Gln Ala Leu Lys Cys
    2150                2155                2160

Glu Val Lys Asp Glu Ile Arg Thr Ser Leu Lys Asn Leu Asn Gln
    2165                2170                2175

Phe Leu Pro Glu Leu Pro Ala Asp Leu Glu Ala Leu Leu Glu Arg
    2180                2185                2190

Asn Glu Asn Leu Gly Gly Gly Leu Glu Ser Leu Lys Glu Asn Phe
    2195                2200                2205

Pro Phe Thr Val Ser Asp Arg Pro Ser Ser Cys Glu Glu Lys Leu
    2210                2215                2220

Asn Phe Gly Gln Ala His Val Ala Asp Glu Gln Trp Arg Gly Glu
    2225                2230                2235

Ala Leu Arg Glu Lys Leu Arg His Arg Glu Asp Arg Leu Lys Ala
    2240                2245                2250

Gln Leu Arg Arg Cys Met Ser Lys Gln Ala Glu Val Leu Ser Glu
    2255                2260                2265

Gly Arg Arg Arg Thr Glu Gly Thr Leu His Ser Leu Arg Arg Gln
    2270                2275                2280

Val Asp Ala Leu Gly Glu Leu Val Thr Ser Thr Ser Gly Asp Ser
    2285                2290                2295

Ala Ser Thr Arg Ser Leu Ser Arg Thr Glu Gly Ser Leu Ala Glu
    2300                2305                2310

Asp Glu Pro Pro Gly Pro Ser Gln Glu Leu His Val Leu Gly Ser
    2315                2320                2325

Gly Gly Ser Asp Arg Gly Gly Gly Arg Gly Gly Gly Arg Lys Gly
    2330                2335                2340

Leu Ser Arg Arg Arg Arg Trp Asn His Gly Glu Ala Arg Leu Gly
    2345                2350                2355

Pro Arg Arg Pro Pro Arg Glu Gly Ala Gly Arg Gly Ala Ala Phe
    2360                2365                2370

Arg Ala Leu Val Ser Cys Ser Arg Pro Ala Glu Leu Pro Ala Ala
    2375                2380                2385

Pro Pro Arg Pro Val Ala Ala Ala Gly Arg Ala Pro Thr Leu Arg
    2390                2395                2400

Thr Arg Arg Thr Arg Arg Pro Gly Val Pro Ser Glu Arg Phe Leu
    2405                2410                2415

Arg Val Arg Gly His Gln Ala His Gly Lys Ala Arg Pro Cys Gly
    2420                2425                2430

Lys Ser Arg Glu Arg Asn Pro Asp Ala Arg Ala Gly Leu Trp Ala
    2435                2440                2445

Leu Glu Thr Cys Cys Arg Lys Ser Ser Ala Arg Gly Cys Gly Leu
    2450                2455                2460

Glu Ala Pro Asn Cys Arg Arg Ala Arg Cys Gly Ala Ser Val Arg
    2465                2470                2475
```

```
Tyr Pro Leu Val Pro Arg Gly Arg Thr Gly Arg Gly Ala Val Thr
    2480            2485            2490

Pro Trp Gly Arg Leu Gln Ser Arg Gly Thr Arg Thr Thr Pro Arg
2495            2500            2505

Pro Val Arg Arg Glu His Pro Gln His Gln Glu Arg Pro Pro Gly
    2510            2515            2520

Arg Val Thr Ala Ala His Thr Glu Thr Ala Pro Pro Arg Arg Val
2525            2530            2535

Phe His Ala Arg Val Ala Val Gly Glu Val Ser Leu Gly Pro Gly
    2540            2545            2550

Arg Gly Leu Glu Arg Thr Arg Gly Gly Gly Gly Ala Gly Ala
2555            2560            2565

Gly Leu Leu Ala Glu Ala Ala Thr Ala Arg Cys Ala Asp Pro
    2570            2575            2580

Ser Thr Asp Pro Ser Ala
2585

<210> SEQ ID NO 29
<211> LENGTH: 7431
<212> TYPE: DNA
<213> ORGANISM: Homo sapiens
<220> FEATURE:
<221> NAME/KEY: CDS
<222> LOCATION: (32)..(7009)

<400> SEQUENCE: 29
gttttgatga cacctggct ttattcttgc a atg aag aaa ggt tct caa caa        52
                                  Met Lys Lys Gly Ser Gln Gln
                                   1               5 aaa ata ttc tcc aaa gca aag ata cca tca tca tct cac tct cct atc     100
Lys Ile Phe Ser Lys Ala Lys Ile Pro Ser Ser Ser His Ser Pro Ile
         10                  15                  20 cca tca tct atg tcc aat atg aga tct agg tca ctt tca cct ttg att    148
Pro Ser Ser Met Ser Asn Met Arg Ser Arg Ser Leu Ser Pro Leu Ile
 25                  30                  35 gga tca gag act cta cct ttt cat tct gga gga cag tgg tgt gag caa    196
Gly Ser Glu Thr Leu Pro Phe His Ser Gly Gly Gln Trp Cys Glu Gln
40                  45                  50                  55 gtt gag att gca gat gaa aac aat atg ctt ttg gac tat caa gac cat    244
Val Glu Ile Ala Asp Glu Asn Asn Met Leu Leu Asp Tyr Gln Asp His
                 60                  65                  70 aaa gga gct gat tca cat gca gga gtt aga tat att aca gag gcc ctc    292
Lys Gly Ala Asp Ser His Ala Gly Val Arg Tyr Ile Thr Glu Ala Leu
             75                  80                  85 att aaa aaa ctt act aaa cag gat aat ttg gct ttg ata aaa tct ctg    340
Ile Lys Lys Leu Thr Lys Gln Asp Asn Leu Ala Leu Ile Lys Ser Leu
         90                  95                 100 aac ctt tca ctt tct aaa gac ggt ggc aag aaa ttt aag tat att gag    388
Asn Leu Ser Leu Ser Lys Asp Gly Gly Lys Lys Phe Lys Tyr Ile Glu
 105                 110                 115 aat ttg gaa aaa tgt gtt aaa ctt gaa gta ctg aat ctc agc tat aat    436
Asn Leu Glu Lys Cys Val Lys Leu Glu Val Leu Asn Leu Ser Tyr Asn
120                 125                 130                 135 cta ata ggg aag att gaa aag ttg gac aag ctg tta aaa tta cgt gaa    484
Leu Ile Gly Lys Ile Glu Lys Leu Asp Lys Leu Leu Lys Leu Arg Glu
                 140                 145                 150 ctc aac tta tca tat aac aaa atc agc aaa att gaa ggc ata gaa aat    532
Leu Asn Leu Ser Tyr Asn Lys Ile Ser Lys Ile Glu Gly Ile Glu Asn
             155                 160                 165
```

```
atg tgt aat ctg caa aag ctt aac ctt gca gga aat gaa att gag cat       580
Met Cys Asn Leu Gln Lys Leu Asn Leu Ala Gly Asn Glu Ile Glu His
    170                 175                 180 att cca gta tgg tta ggg aag aag tta aaa tct ttg cga gtc ctc aat       628
Ile Pro Val Trp Leu Gly Lys Lys Leu Lys Ser Leu Arg Val Leu Asn
185                 190                 195 ttg aaa ggc aac aag ata tca tcg ctc caa gat ata agc aag ttg aaa       676
Leu Lys Gly Asn Lys Ile Ser Ser Leu Gln Asp Ile Ser Lys Leu Lys
200                 205                 210                 215 ccg ctt caa gat ttg att tct ctg atc cta gtt gaa aat cca gtt gtg       724
Pro Leu Gln Asp Leu Ile Ser Leu Ile Leu Val Glu Asn Pro Val Val
                220                 225                 230 acc ctt cct cat tac ctc cag ttt acc att ttc cac ctc cgt tca ttg       772
Thr Leu Pro His Tyr Leu Gln Phe Thr Ile Phe His Leu Arg Ser Leu
            235                 240                 245 gaa agt ttg gaa ggt cag cca gta acc act cag gat aga cag gag gct       820
Glu Ser Leu Glu Gly Gln Pro Val Thr Thr Gln Asp Arg Gln Glu Ala
250                 255                 260 ttt gag aga ttc agt tta gaa gag gta gaa aga ctg gaa aga gac cta       868
Phe Glu Arg Phe Ser Leu Glu Glu Val Glu Arg Leu Glu Arg Asp Leu
265                 270                 275 gaa aaa aag atg ata gaa act gaa gag ctt aag agc aaa caa aca agg       916
Glu Lys Lys Met Ile Glu Thr Glu Glu Leu Lys Ser Lys Gln Thr Arg
280                 285                 290                 295 ttc ctt gag gaa att aaa aat caa gat aaa ttg aat aaa tca tta aaa       964
Phe Leu Glu Glu Ile Lys Asn Gln Asp Lys Leu Asn Lys Ser Leu Lys
                300                 305                 310 gag gag gcc atg tta cag aaa cag agc tgt gag gaa ctc aag agt gac      1012
Glu Glu Ala Met Leu Gln Lys Gln Ser Cys Glu Glu Leu Lys Ser Asp
            315                 320                 325 tta aac aca aaa aat gaa ttg cta aaa cag aag acc ata gaa tta aca      1060
Leu Asn Thr Lys Asn Glu Leu Leu Lys Gln Lys Thr Ile Glu Leu Thr
330                 335                 340 cga gca tgt cag aag caa tat gag ctg gaa cag gaa ttg gcc ttt tat      1108
Arg Ala Cys Gln Lys Gln Tyr Glu Leu Glu Gln Glu Leu Ala Phe Tyr
345                 350                 355 aaa att gat gct aaa ttt gag cca cta aat tat tat cca tca gag tat      1156
Lys Ile Asp Ala Lys Phe Glu Pro Leu Asn Tyr Tyr Pro Ser Glu Tyr
360                 365                 370                 375 gct gaa att gat aaa gcc cca gat gaa agc cct tac att ggc aaa tcc      1204
Ala Glu Ile Asp Lys Ala Pro Asp Glu Ser Pro Tyr Ile Gly Lys Ser
                380                 385                 390 aga tac aag aga aat atg ttt gcc aca gag agt tat att att gac agt      1252
Arg Tyr Lys Arg Asn Met Phe Ala Thr Glu Ser Tyr Ile Ile Asp Ser
            395                 400                 405 gct cag gca gta cag atc aag aag atg gag cca gat gaa caa ctt aga      1300
Ala Gln Ala Val Gln Ile Lys Lys Met Glu Pro Asp Glu Gln Leu Arg
410                 415                 420 aat gat cac atg aac ttg aga ggc cac aca cca ctg gac acg caa ctg      1348
Asn Asp His Met Asn Leu Arg Gly His Thr Pro Leu Asp Thr Gln Leu
425                 430                 435 gaa gac aaa gaa aaa aaa ata agt gca gca caa act cga cta tca gaa      1396
Glu Asp Lys Glu Lys Lys Ile Ser Ala Ala Gln Thr Arg Leu Ser Glu
440                 445                 450                 455 ctg cat gat gaa ata gaa aag gca gaa caa caa att ttg aga gct act      1444
Leu His Asp Glu Ile Glu Lys Ala Glu Gln Gln Ile Leu Arg Ala Thr
                460                 465                 470 gaa gaa ttt aaa caa ctg gaa gaa gct ata caa cta aaa aag att tca      1492
Glu Glu Phe Lys Gln Leu Glu Glu Ala Ile Gln Leu Lys Lys Ile Ser
            475                 480                 485
```

```
gaa gca ggg aaa gac ctt ctt tac aag cag ttg agt ggt aga cta caa      1540
Glu Ala Gly Lys Asp Leu Leu Tyr Lys Gln Leu Ser Gly Arg Leu Gln
        490                 495                 500 ctt gta aat aaa tta cgc cag gaa gct ctg gat cta gaa ctg cag atg      1588
Leu Val Asn Lys Leu Arg Gln Glu Ala Leu Asp Leu Glu Leu Gln Met
505                 510                 515 gaa aag caa aag cag gaa att gcc gga aag cag aag gag att aag gac      1636
Glu Lys Gln Lys Gln Glu Ile Ala Gly Lys Gln Lys Glu Ile Lys Asp
520                 525                 530                 535 ctg caa ata gcc ata gat agc ctg gat tcc aaa gac cca aaa cat tcc      1684
Leu Gln Ile Ala Ile Asp Ser Leu Asp Ser Lys Asp Pro Lys His Ser
                540                 545                 550 cat atg aag gct caa aag agc ggt aaa gaa caa cag ctt gac att atg      1732
His Met Lys Ala Gln Lys Ser Gly Lys Glu Gln Gln Leu Asp Ile Met
            555                 560                 565 aac aag cag tac caa caa ctt gaa agt cgt ttg gat gag ata ctt tct      1780
Asn Lys Gln Tyr Gln Gln Leu Glu Ser Arg Leu Asp Glu Ile Leu Ser
        570                 575                 580 aga att gct aag gaa acg gaa gag att aag gac ctt gaa gaa cag ctt      1828
Arg Ile Ala Lys Glu Thr Glu Glu Ile Lys Asp Leu Glu Glu Gln Leu
585                 590                 595 act gaa ggc cag ata gca gca aat gaa gcc ctg aag aag gat tta gaa      1876
Thr Glu Gly Gln Ile Ala Ala Asn Glu Ala Leu Lys Lys Asp Leu Glu
600                 605                 610                 615 ggt gtt atc agt ggg ttg caa gaa tac ctg ggg acc att aaa ggc cag      1924
Gly Val Ile Ser Gly Leu Gln Glu Tyr Leu Gly Thr Ile Lys Gly Gln
                620                 625                 630 gca act cag gcc cag aat gag tgc agg aag ctg cgg gat gag aaa gag      1972
Ala Thr Gln Ala Gln Asn Glu Cys Arg Lys Leu Arg Asp Glu Lys Glu
            635                 640                 645 aca ttg ttg cag aga ttg aca gaa gtc gag cag gag aga gac cag ctg      2020
Thr Leu Leu Gln Arg Leu Thr Glu Val Glu Gln Glu Arg Asp Gln Leu
        650                 655                 660 gaa ata gtt gcc atg gat gca gaa aat atg agg aag gag ctt gca gag      2068
Glu Ile Val Ala Met Asp Ala Glu Asn Met Arg Lys Glu Leu Ala Glu
665                 670                 675 cta gaa agt gcc ctc caa gag cag cat gag gtg aat gca tct ttg cag      2116
Leu Glu Ser Ala Leu Gln Glu Gln His Glu Val Asn Ala Ser Leu Gln
680                 685                 690                 695 cag acc cag gga gat ctc agt gcc tat gaa gct gag cta gag gct cgg      2164
Gln Thr Gln Gly Asp Leu Ser Ala Tyr Glu Ala Glu Leu Glu Ala Arg
                700                 705                 710 cta aac cta agg gat gct gaa gcc aac cag ctc aag gaa gag ttg gaa      2212
Leu Asn Leu Arg Asp Ala Glu Ala Asn Gln Leu Lys Glu Glu Leu Glu
            715                 720                 725 aaa gta aca aga ctt acc cag tta gaa caa tca gcc ctt caa gca gaa      2260
Lys Val Thr Arg Leu Thr Gln Leu Glu Gln Ser Ala Leu Gln Ala Glu
        730                 735                 740 ctt gag aag gaa agg caa gcc ctc aag aat gcc ctt gga aaa gcc cag      2308
Leu Glu Lys Glu Arg Gln Ala Leu Lys Asn Ala Leu Gly Lys Ala Gln
745                 750                 755 ttc tca gaa gaa aag gag caa gag aac agt gag ctc cat gca aaa ctt      2356
Phe Ser Glu Glu Lys Glu Gln Glu Asn Ser Glu Leu His Ala Lys Leu
760                 765                 770                 775 aaa cac ttg cag gat gac aat aat ctg tta aaa cag caa ctt aaa gat      2404
Lys His Leu Gln Asp Asp Asn Asn Leu Leu Lys Gln Gln Leu Lys Asp
                780                 785                 790 ttc cag aat cac ctt aac cat gtg gtt gat ggt ttg gtt cgt cca gaa      2452
Phe Gln Asn His Leu Asn His Val Val Asp Gly Leu Val Arg Pro Glu
```

-continued

| | | |
|---|---|---|
| gaa gtg gca gct cgt gtg gat gag cta aga aga aaa ctg aaa tta gga<br>Glu Val Ala Ala Arg Val Asp Glu Leu Arg Arg Lys Leu Lys Leu Gly<br>       810                   815                 820 | 2500 |
| act ggg gaa atg aac atc cat agt cct tca gat gtc tta ggg aaa agt<br>Thr Gly Glu Met Asn Ile His Ser Pro Ser Asp Val Leu Gly Lys Ser<br>825                     830                   835 | 2548 |
| ctt gct gat tta cag aaa caa ttc agt gaa att ctt gca cgc tcc aag<br>Leu Ala Asp Leu Gln Lys Gln Phe Ser Glu Ile Leu Ala Arg Ser Lys<br>840                   845                 850               855 | 2596 |
| tgg gaa aga gat gaa gca caa gtt aga gag aga aaa ctc caa gaa gaa<br>Trp Glu Arg Asp Glu Ala Gln Val Arg Glu Arg Lys Leu Gln Glu Glu<br>              860                   865               870 | 2644 |
| atg gct ctg cag caa gag aaa ctg gca act gga caa gaa gag ttc agg<br>Met Ala Leu Gln Gln Glu Lys Leu Ala Thr Gly Gln Glu Glu Phe Arg<br>              875                 880               885 | 2692 |
| cag gcc tgt gag aga gcc ctg gaa gca aga atg aat ttt gat aag agg<br>Gln Ala Cys Glu Arg Ala Leu Glu Ala Arg Met Asn Phe Asp Lys Arg<br>              890                   895               900 | 2740 |
| caa cat gaa gca aga atc cag caa atg gag aat gaa att cac tat ttg<br>Gln His Glu Ala Arg Ile Gln Gln Met Glu Asn Glu Ile His Tyr Leu<br>905                     910                   915 | 2788 |
| caa gaa aat cta aaa agt atg gag gaa atc caa ggc ctt aca gat ctc<br>Gln Glu Asn Leu Lys Ser Met Glu Glu Ile Gln Gly Leu Thr Asp Leu<br>920                     925                 930               935 | 2836 |
| caa ctt cag gaa gct gat gaa gag aag gag aga att ctg gcc caa ctc<br>Gln Leu Gln Glu Ala Asp Glu Glu Lys Glu Arg Ile Leu Ala Gln Leu<br>              940                   945               950 | 2884 |
| cga gag tta gag aaa aag aag aaa ctt gaa gat gcc aaa tct cag gag<br>Arg Glu Leu Glu Lys Lys Lys Lys Leu Glu Asp Ala Lys Ser Gln Glu<br>              955                   960               965 | 2932 |
| caa gtt ttt ggt tta gat aaa gaa ctg aag aaa cta aag aaa gcc gtg<br>Gln Val Phe Gly Leu Asp Lys Glu Leu Lys Lys Leu Lys Lys Ala Val<br>              970                   975               980 | 2980 |
| gcc acc tct gat aag cta gcc aca gct gag ctc acc att gcc aaa gac<br>Ala Thr Ser Asp Lys Leu Ala Thr Ala Glu Leu Thr Ile Ala Lys Asp<br>985                     990                   995 | 3028 |
| cag ctg aag tcc ctt cat gga act gtt atg aaa att aac cag gag<br>Gln Leu Lys Ser Leu His Gly Thr Val Met Lys Ile Asn Gln Glu<br>1000                  1005               1010 | 3073 |
| cga gca gag gag ttg cag gaa gca gag agg ttc agc aga aag gca<br>Arg Ala Glu Glu Leu Gln Glu Ala Glu Arg Phe Ser Arg Lys Ala<br>1015                  1020               1025 | 3118 |
| gca caa gca gcc aga gat ctc acc cga gca gaa gct gag atc gaa<br>Ala Gln Ala Ala Arg Asp Leu Thr Arg Ala Glu Ala Glu Ile Glu<br>1030                  1035               1040 | 3163 |
| ctc ctg cag aat ctc ctc agg cag aag ggg gag cag ttt cga ctt<br>Leu Leu Gln Asn Leu Leu Arg Gln Lys Gly Glu Gln Phe Arg Leu<br>1045                  1050               1055 | 3208 |
| gag atg gag aaa aca ggt gta ggt act gga gca aac tca cag gtc<br>Glu Met Glu Lys Thr Gly Val Gly Thr Gly Ala Asn Ser Gln Val<br>1060                  1065               1070 | 3253 |
| cta gaa att gag aaa ctg aat gag aca atg gaa cga caa agg aca<br>Leu Glu Ile Glu Lys Leu Asn Glu Thr Met Glu Arg Gln Arg Thr<br>1075                  1080               1085 | 3298 |
| gag att gca agg ctg cag aat gta cta gac ctc act gga agt gac<br>Glu Ile Ala Arg Leu Gln Asn Val Leu Asp Leu Thr Gly Ser Asp<br>1090                  1095               1100 | 3343 |
| aac aaa gga ggc ttt gaa aat gtt tta gaa gaa att gct gaa ctt | 3388 |

```
                                           -continued
Asn Lys Gly Gly Phe Glu  Asn Val Leu Glu Glu  Ile Ala Glu Leu
1105              1110                   1115 cga cgt gaa gtt tct tat  cag aat gat tac ata  agc agc atg gca       3433
Arg Arg Glu Val Ser Tyr  Gln Asn Asp Tyr Ile  Ser Ser Met Ala
1120              1125                   1130 gat cct ttc aaa aga cga  ggc tat tgg tac ttt  atg cca cca cca       3478
Asp Pro Phe Lys Arg Arg  Gly Tyr Trp Tyr Phe  Met Pro Pro Pro
1135              1140                   1145 cca tca tca aaa gtt tcc  agc cat agt tcc cag  gcc acc aag gac       3523
Pro Ser Ser Lys Val Ser  Ser His Ser Ser Gln  Ala Thr Lys Asp
1150              1155                   1160 tct ggt gtt ggc ctt aag  tac tca gcc tca act  cct gtt aga aaa       3568
Ser Gly Val Gly Leu Lys  Tyr Ser Ala Ser Thr  Pro Val Arg Lys
1165              1170                   1175 cca cgc cct ggg cag cag  gat ggg aag gaa ggc  agt caa cct ccc       3613
Pro Arg Pro Gly Gln Gln  Asp Gly Lys Glu Gly  Ser Gln Pro Pro
1180              1185                   1190 cct gcc tca gga tac tgg  gtt tat tct ccc atc  agg agt ggg tta       3658
Pro Ala Ser Gly Tyr Trp  Val Tyr Ser Pro Ile  Arg Ser Gly Leu
1195              1200                   1205 cat aaa ctg ttt cca agt  aga gat gca gac agt  gga gga gat agt       3703
His Lys Leu Phe Pro Ser  Arg Asp Ala Asp Ser  Gly Gly Asp Ser
1210              1215                   1220 cag gaa gag agt gag ctg  gat gac caa gaa gaa  ccc cca ttt gtg       3748
Gln Glu Glu Ser Glu Leu  Asp Asp Gln Glu Glu  Pro Pro Phe Val
1225              1230                   1235 cct cct cct gga tac atg  atg tat act gtg ctt  cct gat ggt tct       3793
Pro Pro Pro Gly Tyr Met  Met Tyr Thr Val Leu  Pro Asp Gly Ser
1240              1245                   1250 cct gta ccc cag ggc atg  gcc ctg tat gca cca  cct cct ccc ttg       3838
Pro Val Pro Gln Gly Met  Ala Leu Tyr Ala Pro  Pro Pro Pro Leu
1255              1260                   1265 cca aac aat agc cga cct  ctc acc cct ggc act  gtt gtt tat ggc       3883
Pro Asn Asn Ser Arg Pro  Leu Thr Pro Gly Thr  Val Val Tyr Gly
1270              1275                   1280 cca cct cct gct ggg gcc  ccc atg gtg tat ggg  cct cca ccc ccc       3928
Pro Pro Pro Ala Gly Ala  Pro Met Val Tyr Gly  Pro Pro Pro Pro
1285              1290                   1295 aac ttc tcc atc ccc ttc  atc cct atg ggt gtg  ctg cat tgc aac       3973
Asn Phe Ser Ile Pro Phe  Ile Pro Met Gly Val  Leu His Cys Asn
1300              1305                   1310 gtc cct gaa cac cat aac  tta gag aat gaa gtt  tct aga tta gaa       4018
Val Pro Glu His His Asn  Leu Glu Asn Glu Val  Ser Arg Leu Glu
1315              1320                   1325 gac ata atg cag cat tta  aaa tca aag aag cgg  gaa gaa agg tgg       4063
Asp Ile Met Gln His Leu  Lys Ser Lys Lys Arg  Glu Glu Arg Trp
1330              1335                   1340 atg aga gca tcc aag cgg  cag tcg gag aaa gaa  atg gaa gaa ctg       4108
Met Arg Ala Ser Lys Arg  Gln Ser Glu Lys Glu  Met Glu Glu Leu
1345              1350                   1355 cat cat aat att gat gat  ctt ttg caa gag aag  aaa agc tta gag       4153
His His Asn Ile Asp Asp  Leu Leu Gln Glu Lys  Lys Ser Leu Glu
1360              1365                   1370 tgt gaa gta gaa gaa tta  cat aga act gtc cag  aaa cgt caa cag       4198
Cys Glu Val Glu Glu Leu  His Arg Thr Val Gln  Lys Arg Gln Gln
1375              1380                   1385 caa aag gac ttc att gat  gga aat gtt gag agt  ctt atg act gaa       4243
Gln Lys Asp Phe Ile Asp  Gly Asn Val Glu Ser  Leu Met Thr Glu
1390              1395                   1400
```

```
cta gaa ata gaa aaa tca ctc aaa cat cat gaa  gat att gta gat         4288
Leu Glu Ile Glu Lys Ser Leu Lys His His Glu  Asp Ile Val Asp
1405                1410                1415 gaa att gag tgc att gag aag act ctt ctg aaa  cgt cgc tca gag         4333
Glu Ile Glu Cys Ile Glu Lys Thr Leu Leu Lys  Arg Arg Ser Glu
1420                1425                1430 ctc agg gaa gct gac cga ctc ctg gca gag gct  gag agt gaa ctt         4378
Leu Arg Glu Ala Asp Arg Leu Leu Ala Glu Ala  Glu Ser Glu Leu
1435                1440                1445 tca tgc act aaa gaa aag aca aaa aat gct gtt  gaa aag ttc act         4423
Ser Cys Thr Lys Glu Lys Thr Lys Asn Ala Val  Glu Lys Phe Thr
1450                1455                1460 gat gcc aag aga agt tta ttg caa act gag tca  gat gct gag gaa         4468
Asp Ala Lys Arg Ser Leu Leu Gln Thr Glu Ser  Asp Ala Glu Glu
1465                1470                1475 tta gaa agg aga gct cag gaa act gct gtt aac  ctc gtc aaa gct         4513
Leu Glu Arg Arg Ala Gln Glu Thr Ala Val Asn  Leu Val Lys Ala
1480                1485                1490 gat cag cag cta aga tcg ctc cag gct gat gca  aag gat ttg gag         4558
Asp Gln Gln Leu Arg Ser Leu Gln Ala Asp Ala  Lys Asp Leu Glu
1495                1500                1505 cag cac aaa atc aag caa gaa gaa atc ttg aaa  gaa ata aac aaa         4603
Gln His Lys Ile Lys Gln Glu Glu Ile Leu Lys  Glu Ile Asn Lys
1510                1515                1520 att gta gca gca aaa gac tca gac ttc caa tgt  tta agc aag aag         4648
Ile Val Ala Ala Lys Asp Ser Asp Phe Gln Cys  Leu Ser Lys Lys
1525                1530                1535 aag gaa aaa ctg aca gaa gag ctt cag aaa cta  cag aaa gac ata         4693
Lys Glu Lys Leu Thr Glu Glu Leu Gln Lys Leu  Gln Lys Asp Ile
1540                1545                1550 gag atg gca gaa cgc aat gag gat cac cac ctg  cag gtc ctt aaa         4738
Glu Met Ala Glu Arg Asn Glu Asp His His Leu  Gln Val Leu Lys
1555                1560                1565 gaa tct gag gtg ctt ctt cag gcc aaa aga gcc  gag ctg gaa aag         4783
Glu Ser Glu Val Leu Leu Gln Ala Lys Arg Ala  Glu Leu Glu Lys
1570                1575                1580 ctg aaa agc cag gtg aca agt cag cag cag gag  atg gct gtc ttg         4828
Leu Lys Ser Gln Val Thr Ser Gln Gln Gln Glu  Met Ala Val Leu
1585                1590                1595 gac agg cag tta ggg cat aaa aag gag gag ctg  cat cta ctc caa         4873
Asp Arg Gln Leu Gly His Lys Lys Glu Glu Leu  His Leu Leu Gln
1600                1605                1610 gga agc atg gtc cag gca aaa gct gac ctc cag  gaa gct ctg aga         4918
Gly Ser Met Val Gln Ala Lys Ala Asp Leu Gln  Glu Ala Leu Arg
1615                1620                1625 ctg gga gag act gaa gta act gag aag tgc aat  cac att agg gaa         4963
Leu Gly Glu Thr Glu Val Thr Glu Lys Cys Asn  His Ile Arg Glu
1630                1635                1640 gta aaa tct ctt ctg gaa gaa ctg agt ttt cag  aaa gga gaa cta         5008
Val Lys Ser Leu Leu Glu Glu Leu Ser Phe Gln  Lys Gly Glu Leu
1645                1650                1655 aat gtt cag att agt gaa aga aaa act caa ctt  aca ctt ata aag         5053
Asn Val Gln Ile Ser Glu Arg Lys Thr Gln Leu  Thr Leu Ile Lys
1660                1665                1670 cag gaa att gaa aaa gag gaa gaa aat ctt cag  gtt gtt tta agg         5098
Gln Glu Ile Glu Lys Glu Glu Glu Asn Leu Gln  Val Val Leu Arg
1675                1680                1685 cag atg tct aaa cat aaa acc gaa cta aag aat  att ctg gac atg         5143
Gln Met Ser Lys His Lys Thr Glu Leu Lys Asn  Ile Leu Asp Met
1690                1695                1700
```

```
ttg caa ctt gaa aac cat gag cta caa ggt ttg aag cta caa cat      5188
Leu Gln Leu Glu Asn His Glu Leu Gln Gly Leu Lys Leu Gln His
1705                1710                1715 gac caa agg gta tct gaa tta gag aag act cag gtg gca gtg cta      5233
Asp Gln Arg Val Ser Glu Leu Glu Lys Thr Gln Val Ala Val Leu
1720                1725                1730 gag gag aaa ctg gag tta gag aat ttg cag cag ata tcc cag cag      5278
Glu Glu Lys Leu Glu Leu Glu Asn Leu Gln Gln Ile Ser Gln Gln
1735                1740                1745 cag aaa ggg gaa ata gag tgg cag aag cag ctc ctt gag agg gat      5323
Gln Lys Gly Glu Ile Glu Trp Gln Lys Gln Leu Leu Glu Arg Asp
1750                1755                1760 aaa cga gaa ata gaa cga atg act gct gag tcc cga gct tta caa      5368
Lys Arg Glu Ile Glu Arg Met Thr Ala Glu Ser Arg Ala Leu Gln
1765                1770                1775 tcg tgt gtt gag tgt ttg agc aaa gaa aag gaa gat ctc caa gag      5413
Ser Cys Val Glu Cys Leu Ser Lys Glu Lys Glu Asp Leu Gln Glu
1780                1785                1790 aaa tgt gac att tgg gaa aaa aag ttg gca caa acc aaa agg gtt      5458
Lys Cys Asp Ile Trp Glu Lys Lys Leu Ala Gln Thr Lys Arg Val
1795                1800                1805 tta gca gca gca gaa gaa aat agc aaa atg gag caa tca aac tta      5503
Leu Ala Ala Ala Glu Glu Asn Ser Lys Met Glu Gln Ser Asn Leu
1810                1815                1820 gaa aag ttg gaa ttg aat gtc aga aaa ctg cag cag gaa cta gac      5548
Glu Lys Leu Glu Leu Asn Val Arg Lys Leu Gln Gln Glu Leu Asp
1825                1830                1835 caa cta aac aga gac aag ttg tca ctg cat aac gac att tca gca      5593
Gln Leu Asn Arg Asp Lys Leu Ser Leu His Asn Asp Ile Ser Ala
1840                1845                1850 atg caa cag cag ctc caa gaa aaa cga gaa gca gta aac tca ctg      5638
Met Gln Gln Gln Leu Gln Glu Lys Arg Glu Ala Val Asn Ser Leu
1855                1860                1865 cag gag gaa cta gct aat gtc caa gac cat ttg aac cta gca aaa      5683
Gln Glu Glu Leu Ala Asn Val Gln Asp His Leu Asn Leu Ala Lys
1870                1875                1880 cag gac ctg ctt cac acc acc aag cat cag gat gtg ttg ctc agt      5728
Gln Asp Leu Leu His Thr Thr Lys His Gln Asp Val Leu Leu Ser
1885                1890                1895 gag cag acc cga ctc cag aag gac atc agt gaa tgg gca aat agg      5773
Glu Gln Thr Arg Leu Gln Lys Asp Ile Ser Glu Trp Ala Asn Arg
1900                1905                1910 ttt gaa gac tgt cag aaa gaa gag gag aca aaa caa caa caa ctt      5818
Phe Glu Asp Cys Gln Lys Glu Glu Glu Thr Lys Gln Gln Gln Leu
1915                1920                1925 caa gtg ctt cag aat gag att gaa gaa aac aag ctc aaa cta gtc      5863
Gln Val Leu Gln Asn Glu Ile Glu Glu Asn Lys Leu Lys Leu Val
1930                1935                1940 caa caa gaa atg atg ttt cag aga ctc cag aaa gag aga gaa agt      5908
Gln Gln Glu Met Met Phe Gln Arg Leu Gln Lys Glu Arg Glu Ser
1945                1950                1955 gaa gaa agc aaa tta gaa acc agt aaa gtg aca ctg aag gag caa      5953
Glu Glu Ser Lys Leu Glu Thr Ser Lys Val Thr Leu Lys Glu Gln
1960                1965                1970 cag cac cag ctg gaa aag gaa tta aca gac cag aaa agc aaa ctg      5998
Gln His Gln Leu Glu Lys Glu Leu Thr Asp Gln Lys Ser Lys Leu
1975                1980                1985 gac caa gtg ctc tca aag gtg ctg gca gct gaa gag cgt gtt agg      6043
Asp Gln Val Leu Ser Lys Val Leu Ala Ala Glu Glu Arg Val Arg
```

-continued

| | | | | | | | | | | | | |
|---|---|---|---|---|---|---|---|---|---|---|---|---|
| 1990 | | | | | 1995 | | | | | 2000 | | |
| act | ctg | cag | gaa | gag | gag | agg | tgg | tgt | gag | agc | ctg | gag | aag | aca | 6088 |
| Thr | Leu | Gln | Glu | Glu | Glu | Arg | Trp | Cys | Glu | Ser | Leu | Glu | Lys | Thr | |
| 2005 | | | | | 2010 | | | | | 2015 | | | | | |

```
act ctg cag gaa gag gag agg tgg tgt gag agc ctg gag aag aca      6088
Thr Leu Gln Glu Glu Glu Arg Trp Cys Glu Ser Leu Glu Lys Thr
2005                2010                2015 ctc tcc caa act aaa cgg cag ctt tca gaa agg gag cag caa ttg      6133
Leu Ser Gln Thr Lys Arg Gln Leu Ser Glu Arg Glu Gln Gln Leu
2020                2025                2030 gtg gag aaa tca ggt gag ctg ttg gcc ctc cag aaa gag gca gat      6178
Val Glu Lys Ser Gly Glu Leu Leu Ala Leu Gln Lys Glu Ala Asp
2035                2040                2045 tct atg agg gca gac ttc agc ctt ctg cgg aac cag ttc ttg aca      6223
Ser Met Arg Ala Asp Phe Ser Leu Leu Arg Asn Gln Phe Leu Thr
2050                2055                2060 gaa aga aag aaa gct gag aag cag gtg gcc agc ctg aag gaa gca      6268
Glu Arg Lys Lys Ala Glu Lys Gln Val Ala Ser Leu Lys Glu Ala
2065                2070                2075 ctt aag atc cag cgg agc cag ctg gag aaa aac ctt ctt gag caa      6313
Leu Lys Ile Gln Arg Ser Gln Leu Glu Lys Asn Leu Leu Glu Gln
2080                2085                2090 aaa cag gag aac agc tgc ata caa aag gaa atg gca aca att gaa      6358
Lys Gln Glu Asn Ser Cys Ile Gln Lys Glu Met Ala Thr Ile Glu
2095                2100                2105 ctg gta gcc cag gac aac cat gag cgg gcc agg cgc ctg atg aag      6403
Leu Val Ala Gln Asp Asn His Glu Arg Ala Arg Arg Leu Met Lys
2110                2115                2120 gag ctc aac cag atg cag tat gag tac acg gag ctc aag aaa cag      6448
Glu Leu Asn Gln Met Gln Tyr Glu Tyr Thr Glu Leu Lys Lys Gln
2125                2130                2135 atg gca aac caa aaa gat ttg gag aga aga caa atg gaa atc agt      6493
Met Ala Asn Gln Lys Asp Leu Glu Arg Arg Gln Met Glu Ile Ser
2140                2145                2150 gat gca atg agg aca ctt aaa tct gag gtg aag gat gaa atc aga      6538
Asp Ala Met Arg Thr Leu Lys Ser Glu Val Lys Asp Glu Ile Arg
2155                2160                2165 acc agc ttg aag aat ctt aat cag ttt ctt cca gaa cta cca gca      6583
Thr Ser Leu Lys Asn Leu Asn Gln Phe Leu Pro Glu Leu Pro Ala
2170                2175                2180 gat cta gaa gct att ttg gaa aga aac gaa aac cta gaa gga gaa      6628
Asp Leu Glu Ala Ile Leu Glu Arg Asn Glu Asn Leu Glu Gly Glu
2185                2190                2195 ttg gaa agc ttg aaa gag aac ctt cca ttt acc atg aat gag gga      6673
Leu Glu Ser Leu Lys Glu Asn Leu Pro Phe Thr Met Asn Glu Gly
2200                2205                2210 cct ttt gaa gaa aaa ctg aac ttt tcc caa gtt cac ata atg gat      6718
Pro Phe Glu Glu Lys Leu Asn Phe Ser Gln Val His Ile Met Asp
2215                2220                2225 gaa cac tgg cgt gga gaa gca ctc cgg gag aaa ctg cgt cac cgg      6763
Glu His Trp Arg Gly Glu Ala Leu Arg Glu Lys Leu Arg His Arg
2230                2235                2240 gaa gac cga ctc aag gcc caa ctc cga cac tgt atg tcc aag caa      6808
Glu Asp Arg Leu Lys Ala Gln Leu Arg His Cys Met Ser Lys Gln
2245                2250                2255 gca gaa gta tta att aaa gga aag cgg cag aca gag ggc act tta      6853
Ala Glu Val Leu Ile Lys Gly Lys Arg Gln Thr Glu Gly Thr Leu
2260                2265                2270 cac agt ttg agg aga caa gta gat gct tta ggg gaa ttg gtc acc      6898
His Ser Leu Arg Arg Gln Val Asp Ala Leu Gly Glu Leu Val Thr
2275                2280                2285 agc acc tct gca gat tca gcg tca tca ccc agt ctg tct cag ctg      6943
```

```
Ser  Thr  Ser  Ala  Asp  Ser  Ala  Ser  Ser  Pro  Ser  Leu  Ser  Gln  Leu
2290                2295                2300 gag  tct  tcc  ctc  aca  gag  gac  tct  caa  ctt  gga  caa  aat  cag  gaa    6988
Glu  Ser  Ser  Leu  Thr  Glu  Asp  Ser  Gln  Leu  Gly  Gln  Asn  Gln  Glu
2305                2310                2315 aag  aat  gcc  tca  gcc  aga  tga  ggaatactgt cttgtgtaaa tatattcaag           7039
Lys  Asn  Ala  Ser  Ala  Arg
2320                2325 gaaacacct  ccactacctc  actgacttca  taattggaat  gtcacatggt  tttttaatc          7099 aagatgcagt  gaactgagat  tctgaaactc  cactgtagtt  tactttgcct  gtaccattaa        7159
tgccaatgtt  tttataaatc  acttgtacat  agtacatatg  ggaatagttg  catatgggaa        7219
tttaaaccaa  catgtggctg  agccttttt   tttttaatct  tcgtaacatg  tttaaaaaaa        7279
aacagtgatt  ttaactgcat  atttgaacct  acaaactggt  aaatcttatt  aacaaaaaga        7339
atgtacttaa  ggccctcttt  atttatagtg  tcgagttatt  tttgaatttt  gcttaaaatc        7399 tattttcat   atgaaaataa  aagataacaa  tc                                        7431

<210> SEQ ID NO 30
<211> LENGTH: 2325
<212> TYPE: PRT
<213> ORGANISM: Homo sapiens

<400> SEQUENCE: 30

Met  Lys  Lys  Gly  Ser  Gln  Gln  Lys  Ile  Phe  Ser  Lys  Ala  Lys  Ile  Pro
1                   5                   10                  15

Ser  Ser  Ser  His  Ser  Pro  Ile  Pro  Ser  Ser  Met  Ser  Asn  Met  Arg  Ser
                    20                  25                  30

Arg  Ser  Leu  Ser  Pro  Leu  Ile  Gly  Ser  Glu  Thr  Leu  Pro  Phe  His  Ser
                35                      40                  45

Gly  Gly  Gln  Trp  Cys  Glu  Gln  Val  Glu  Ile  Ala  Asp  Glu  Asn  Asn  Met
            50                      55                  60

Leu  Leu  Asp  Tyr  Gln  Asp  His  Lys  Gly  Ala  Asp  Ser  His  Ala  Gly  Val
65                  70                      75                      80

Arg  Tyr  Ile  Thr  Glu  Ala  Leu  Ile  Lys  Lys  Leu  Thr  Lys  Gln  Asp  Asn
                85                      90                      95

Leu  Ala  Leu  Ile  Lys  Ser  Leu  Asn  Leu  Ser  Leu  Ser  Lys  Asp  Gly  Gly
                100                     105                     110

Lys  Lys  Phe  Lys  Tyr  Ile  Glu  Asn  Leu  Glu  Lys  Cys  Val  Lys  Leu  Glu
            115                     120                     125

Val  Leu  Asn  Leu  Ser  Tyr  Asn  Leu  Ile  Gly  Lys  Ile  Glu  Lys  Leu  Asp
    130                     135                     140

Lys  Leu  Leu  Lys  Leu  Arg  Glu  Leu  Asn  Leu  Ser  Tyr  Asn  Lys  Ile  Ser
145                     150                     155                     160

Lys  Ile  Glu  Gly  Ile  Glu  Asn  Met  Cys  Asn  Leu  Gln  Lys  Leu  Asn  Leu
                165                     170                     175

Ala  Gly  Asn  Glu  Ile  Glu  His  Ile  Pro  Val  Trp  Leu  Gly  Lys  Lys  Leu
                180                     185                     190

Lys  Ser  Leu  Arg  Val  Leu  Asn  Leu  Lys  Gly  Asn  Lys  Ile  Ser  Ser  Leu
            195                     200                     205

Gln  Asp  Ile  Ser  Lys  Leu  Lys  Pro  Leu  Gln  Asp  Leu  Ile  Ser  Leu  Ile
    210                     215                     220

Leu  Val  Glu  Asn  Pro  Val  Val  Thr  Leu  Pro  His  Tyr  Leu  Gln  Phe  Thr
225                     230                     235                     240

Ile  Phe  His  Leu  Arg  Ser  Leu  Glu  Ser  Leu  Glu  Gly  Gln  Pro  Val  Thr
```

-continued

```
                245                 250                 255
Thr Gln Asp Arg Gln Glu Ala Phe Glu Arg Phe Ser Leu Glu Glu Val
                260                 265                 270

Glu Arg Leu Glu Arg Asp Leu Glu Lys Lys Met Ile Glu Thr Glu Glu
            275                 280                 285

Leu Lys Ser Lys Gln Thr Arg Phe Leu Glu Glu Ile Lys Asn Gln Asp
        290                 295                 300

Lys Leu Asn Lys Ser Leu Lys Glu Glu Ala Met Leu Gln Lys Gln Ser
305                 310                 315                 320

Cys Glu Glu Leu Lys Ser Asp Leu Asn Thr Lys Asn Glu Leu Leu Lys
                325                 330                 335

Gln Lys Thr Ile Glu Leu Thr Arg Ala Cys Gln Lys Gln Tyr Glu Leu
            340                 345                 350

Glu Gln Glu Leu Ala Phe Tyr Lys Ile Asp Ala Lys Phe Glu Pro Leu
        355                 360                 365

Asn Tyr Tyr Pro Ser Glu Tyr Ala Glu Ile Asp Lys Ala Pro Asp Glu
    370                 375                 380

Ser Pro Tyr Ile Gly Lys Ser Arg Tyr Lys Arg Asn Met Phe Ala Thr
385                 390                 395                 400

Glu Ser Tyr Ile Ile Asp Ser Ala Gln Ala Val Gln Ile Lys Lys Met
                405                 410                 415

Glu Pro Asp Glu Gln Leu Arg Asn Asp His Met Asn Leu Arg Gly His
            420                 425                 430

Thr Pro Leu Asp Thr Gln Leu Glu Asp Lys Glu Lys Lys Ile Ser Ala
        435                 440                 445

Ala Gln Thr Arg Leu Ser Glu Leu His Asp Glu Ile Glu Lys Ala Glu
    450                 455                 460

Gln Gln Ile Leu Arg Ala Thr Glu Glu Phe Lys Gln Leu Glu Glu Ala
465                 470                 475                 480

Ile Gln Leu Lys Lys Ile Ser Glu Ala Gly Lys Asp Leu Leu Tyr Lys
                485                 490                 495

Gln Leu Ser Gly Arg Leu Gln Leu Val Asn Lys Leu Arg Gln Glu Ala
            500                 505                 510

Leu Asp Leu Glu Leu Gln Met Glu Lys Gln Lys Gln Glu Ile Ala Gly
        515                 520                 525

Lys Gln Lys Glu Ile Lys Asp Leu Gln Ile Ala Ile Asp Ser Leu Asp
    530                 535                 540

Ser Lys Asp Pro Lys His Ser His Met Lys Ala Gln Lys Ser Gly Lys
545                 550                 555                 560

Glu Gln Gln Leu Asp Ile Met Asn Lys Gln Tyr Gln Leu Glu Ser
                565                 570                 575

Arg Leu Asp Glu Ile Leu Ser Arg Ile Ala Lys Glu Thr Glu Glu Ile
            580                 585                 590

Lys Asp Leu Glu Glu Gln Leu Thr Gly Gln Ile Ala Ala Asn Glu
        595                 600                 605

Ala Leu Lys Lys Asp Leu Glu Gly Val Ile Ser Gly Leu Gln Glu Tyr
    610                 615                 620

Leu Gly Thr Ile Lys Gly Gln Ala Thr Gln Ala Gln Asn Glu Cys Arg
625                 630                 635                 640

Lys Leu Arg Asp Glu Lys Glu Thr Leu Leu Gln Arg Leu Thr Glu Val
                645                 650                 655

Glu Gln Glu Arg Asp Gln Leu Glu Ile Val Ala Met Asp Ala Glu Asn
            660                 665                 670
```

-continued

```
Met Arg Lys Glu Leu Ala Glu Leu Glu Ser Ala Leu Gln Glu Gln His
        675                 680                 685
Glu Val Asn Ala Ser Leu Gln Gln Thr Gln Gly Asp Leu Ser Ala Tyr
        690                 695                 700
Glu Ala Glu Leu Glu Ala Arg Leu Asn Leu Arg Asp Ala Glu Ala Asn
705                 710                 715                 720
Gln Leu Lys Glu Leu Glu Lys Val Thr Arg Leu Thr Gln Leu Glu
                725                 730                 735
Gln Ser Ala Leu Gln Ala Glu Leu Glu Lys Glu Arg Gln Ala Leu Lys
            740                 745                 750
Asn Ala Leu Gly Lys Ala Gln Phe Ser Glu Lys Glu Gln Glu Asn
            755                 760                 765
Ser Glu Leu His Ala Lys Leu Lys His Leu Gln Asp Asp Asn Asn Leu
        770                 775                 780
Leu Lys Gln Gln Leu Lys Asp Phe Gln Asn His Leu Asn His Val Val
785                 790                 795                 800
Asp Gly Leu Val Arg Pro Glu Glu Val Ala Ala Arg Val Asp Glu Leu
                805                 810                 815
Arg Arg Lys Leu Lys Leu Gly Thr Gly Glu Met Asn Ile His Ser Pro
            820                 825                 830
Ser Asp Val Leu Gly Lys Ser Leu Ala Asp Leu Gln Lys Gln Phe Ser
        835                 840                 845
Glu Ile Leu Ala Arg Ser Lys Trp Glu Arg Asp Glu Ala Gln Val Arg
        850                 855                 860
Glu Arg Lys Leu Gln Glu Met Ala Leu Gln Glu Lys Leu Ala
865                 870                 875                 880
Thr Gly Gln Glu Glu Phe Arg Gln Ala Cys Glu Arg Ala Leu Glu Ala
                885                 890                 895
Arg Met Asn Phe Asp Lys Arg Gln His Glu Ala Arg Ile Gln Gln Met
            900                 905                 910
Glu Asn Glu Ile His Tyr Leu Gln Glu Asn Leu Lys Ser Met Glu Glu
            915                 920                 925
Ile Gln Gly Leu Thr Asp Leu Gln Leu Gln Glu Ala Asp Glu Glu Lys
        930                 935                 940
Glu Arg Ile Leu Ala Gln Leu Arg Glu Leu Glu Lys Lys Lys Lys Leu
945                 950                 955                 960
Glu Asp Ala Lys Ser Gln Glu Gln Val Phe Gly Leu Asp Lys Glu Leu
                965                 970                 975
Lys Lys Leu Lys Lys Ala Val Ala Thr Ser Asp Lys Leu Ala Thr Ala
            980                 985                 990
Glu Leu Thr Ile Ala Lys Asp Gln Leu Lys Ser Leu His Gly Thr Val
            995                 1000                 1005
Met Lys Ile Asn Gln Glu Arg Ala Glu Glu Leu Gln Glu Ala Glu
        1010                 1015                 1020
Arg Phe Ser Arg Lys Ala Ala Gln Ala Ala Arg Asp Leu Thr Arg
        1025                 1030                 1035
Ala Glu Ala Glu Ile Glu Leu Leu Gln Asn Leu Leu Arg Gln Lys
        1040                 1045                 1050
Gly Glu Gln Phe Arg Leu Glu Met Glu Lys Thr Gly Val Gly Thr
        1055                 1060                 1065
Gly Ala Asn Ser Gln Val Leu Glu Ile Glu Lys Leu Asn Glu Thr
        1070                 1075                 1080
```

-continued

```
Met Glu Arg Gln Arg Thr Glu Ile Ala Arg Leu Gln Asn Val Leu
    1085                1090                1095

Asp Leu Thr Gly Ser Asp Asn Lys Gly Phe Glu Asn Val Leu
    1100                1105                1110

Glu Glu Ile Ala Glu Leu Arg Arg Glu Val Ser Tyr Gln Asn Asp
    1115                1120                1125

Tyr Ile Ser Ser Met Ala Asp Pro Phe Lys Arg Arg Gly Tyr Trp
    1130                1135                1140

Tyr Phe Met Pro Pro Pro Ser Ser Lys Val Ser Ser His Ser
    1145                1150                1155

Ser Gln Ala Thr Lys Asp Ser Gly Val Gly Leu Lys Tyr Ser Ala
    1160                1165                1170

Ser Thr Pro Val Arg Lys Pro Arg Pro Gly Gln Gln Asp Gly Lys
    1175                1180                1185

Glu Gly Ser Gln Pro Pro Ala Ser Gly Tyr Trp Val Tyr Ser
    1190                1195                1200

Pro Ile Arg Ser Gly Leu His Lys Leu Phe Pro Ser Arg Asp Ala
    1205                1210                1215

Asp Ser Gly Gly Asp Ser Gln Glu Glu Ser Glu Leu Asp Asp Gln
    1220                1225                1230

Glu Glu Pro Pro Phe Val Pro Pro Gly Tyr Met Met Tyr Thr
    1235                1240                1245

Val Leu Pro Asp Gly Ser Pro Val Pro Gln Gly Met Ala Leu Tyr
    1250                1255                1260

Ala Pro Pro Pro Pro Leu Pro Asn Asn Ser Arg Pro Leu Thr Pro
    1265                1270                1275

Gly Thr Val Val Tyr Gly Pro Pro Ala Gly Ala Pro Met Val
    1280                1285                1290

Tyr Gly Pro Pro Pro Pro Asn Phe Ser Ile Pro Phe Ile Pro Met
    1295                1300                1305

Gly Val Leu His Cys Asn Val Pro Glu His His Asn Leu Glu Asn
    1310                1315                1320

Glu Val Ser Arg Leu Glu Asp Ile Met Gln His Leu Lys Ser Lys
    1325                1330                1335

Lys Arg Glu Glu Arg Trp Met Arg Ala Ser Lys Arg Gln Ser Glu
    1340                1345                1350

Lys Glu Met Glu Glu Leu His His Asn Ile Asp Asp Leu Leu Gln
    1355                1360                1365

Glu Lys Lys Ser Leu Glu Cys Glu Val Glu Glu Leu His Arg Thr
    1370                1375                1380

Val Gln Lys Arg Gln Gln Gln Lys Asp Phe Ile Asp Gly Asn Val
    1385                1390                1395

Glu Ser Leu Met Thr Glu Leu Glu Ile Glu Lys Ser Leu Lys His
    1400                1405                1410

His Glu Asp Ile Val Asp Glu Ile Glu Cys Ile Glu Lys Thr Leu
    1415                1420                1425

Leu Lys Arg Arg Ser Glu Leu Arg Glu Ala Asp Arg Leu Leu Ala
    1430                1435                1440

Glu Ala Glu Ser Glu Leu Ser Cys Thr Lys Glu Lys Thr Lys Asn
    1445                1450                1455

Ala Val Glu Lys Phe Thr Asp Ala Lys Arg Ser Leu Leu Gln Thr
    1460                1465                1470

Glu Ser Asp Ala Glu Glu Leu Glu Arg Arg Ala Gln Glu Thr Ala
```

```
                1475                1480                1485

Val Asn Leu Val Lys Ala Asp Gln Gln Leu Arg Ser Leu Gln Ala
    1490                1495                1500

Asp Ala Lys Asp Leu Glu Gln His Lys Ile Lys Gln Glu Glu Ile
    1505                1510                1515

Leu Lys Glu Ile Asn Lys Ile Val Ala Ala Lys Asp Ser Asp Phe
    1520                1525                1530

Gln Cys Leu Ser Lys Lys Lys Glu Lys Leu Thr Glu Glu Leu Gln
    1535                1540                1545

Lys Leu Gln Lys Asp Ile Glu Met Ala Glu Arg Asn Glu Asp His
    1550                1555                1560

His Leu Gln Val Leu Lys Glu Ser Glu Val Leu Leu Gln Ala Lys
    1565                1570                1575

Arg Ala Glu Leu Glu Lys Leu Lys Ser Gln Val Thr Ser Gln Gln
    1580                1585                1590

Gln Glu Met Ala Val Leu Asp Arg Gln Leu Gly His Lys Lys Glu
    1595                1600                1605

Glu Leu His Leu Leu Gln Gly Ser Met Val Gln Ala Lys Ala Asp
    1610                1615                1620

Leu Gln Glu Ala Leu Arg Leu Gly Glu Thr Glu Val Thr Glu Lys
    1625                1630                1635

Cys Asn His Ile Arg Glu Val Lys Ser Leu Leu Glu Glu Leu Ser
    1640                1645                1650

Phe Gln Lys Gly Glu Leu Asn Val Gln Ile Ser Glu Arg Lys Thr
    1655                1660                1665

Gln Leu Thr Leu Ile Lys Gln Glu Ile Glu Lys Glu Glu Glu Asn
    1670                1675                1680

Leu Gln Val Val Leu Arg Gln Met Ser Lys His Lys Thr Glu Leu
    1685                1690                1695

Lys Asn Ile Leu Asp Met Leu Gln Leu Glu Asn His Glu Leu Gln
    1700                1705                1710

Gly Leu Lys Leu Gln His Asp Gln Arg Val Ser Glu Leu Glu Lys
    1715                1720                1725

Thr Gln Val Ala Val Leu Glu Glu Lys Leu Glu Leu Glu Asn Leu
    1730                1735                1740

Gln Gln Ile Ser Gln Gln Lys Gly Glu Ile Glu Trp Gln Lys
    1745                1750                1755

Gln Leu Leu Glu Arg Asp Lys Arg Glu Ile Glu Arg Met Thr Ala
    1760                1765                1770

Glu Ser Arg Ala Leu Gln Ser Cys Val Glu Cys Leu Ser Lys Glu
    1775                1780                1785

Lys Glu Asp Leu Gln Glu Lys Cys Asp Ile Trp Glu Lys Lys Leu
    1790                1795                1800

Ala Gln Thr Lys Arg Val Leu Ala Ala Ala Glu Glu Asn Ser Lys
    1805                1810                1815

Met Glu Gln Ser Asn Leu Glu Lys Leu Glu Leu Asn Val Arg Lys
    1820                1825                1830

Leu Gln Gln Glu Leu Asp Gln Leu Asn Arg Asp Lys Leu Ser Leu
    1835                1840                1845

His Asn Asp Ile Ser Ala Met Gln Gln Gln Leu Gln Glu Lys Arg
    1850                1855                1860

Glu Ala Val Asn Ser Leu Gln Glu Glu Leu Ala Asn Val Gln Asp
    1865                1870                1875
```

```
His Leu Asn Leu Ala Lys Gln Asp Leu Leu His Thr Thr Lys His
    1880            1885            1890

Gln Asp Val Leu Leu Ser Glu Gln Thr Arg Leu Gln Lys Asp Ile
    1895            1900            1905

Ser Glu Trp Ala Asn Arg Phe Glu Asp Cys Gln Lys Glu Glu Glu
    1910            1915            1920

Thr Lys Gln Gln Gln Leu Gln Val Leu Gln Asn Glu Ile Glu Glu
    1925            1930            1935

Asn Lys Leu Lys Leu Val Gln Gln Glu Met Met Phe Gln Arg Leu
    1940            1945            1950

Gln Lys Glu Arg Glu Ser Glu Ser Lys Leu Glu Thr Ser Lys
    1955            1960            1965

Val Thr Leu Lys Glu Gln Gln His Gln Leu Glu Lys Glu Leu Thr
    1970            1975            1980

Asp Gln Lys Ser Lys Leu Asp Gln Val Leu Ser Lys Val Leu Ala
    1985            1990            1995

Ala Glu Glu Arg Val Arg Thr Leu Gln Glu Glu Glu Arg Trp Cys
    2000            2005            2010

Glu Ser Leu Glu Lys Thr Leu Ser Gln Thr Lys Arg Gln Leu Ser
    2015            2020            2025

Glu Arg Glu Gln Gln Leu Val Glu Lys Ser Gly Glu Leu Leu Ala
    2030            2035            2040

Leu Gln Lys Glu Ala Asp Ser Met Arg Ala Asp Phe Ser Leu Leu
    2045            2050            2055

Arg Asn Gln Phe Leu Thr Glu Arg Lys Lys Ala Glu Lys Gln Val
    2060            2065            2070

Ala Ser Leu Lys Glu Ala Leu Lys Ile Gln Arg Ser Gln Leu Glu
    2075            2080            2085

Lys Asn Leu Leu Glu Gln Lys Gln Glu Asn Ser Cys Ile Gln Lys
    2090            2095            2100

Glu Met Ala Thr Ile Glu Leu Val Ala Gln Asp Asn His Glu Arg
    2105            2110            2115

Ala Arg Arg Leu Met Lys Glu Leu Asn Gln Met Gln Tyr Glu Tyr
    2120            2125            2130

Thr Glu Leu Lys Lys Gln Met Ala Asn Gln Lys Asp Leu Glu Arg
    2135            2140            2145

Arg Gln Met Glu Ile Ser Asp Ala Met Arg Thr Leu Lys Ser Glu
    2150            2155            2160

Val Lys Asp Glu Ile Arg Thr Ser Leu Lys Asn Leu Asn Gln Phe
    2165            2170            2175

Leu Pro Glu Leu Pro Ala Asp Leu Glu Ala Ile Leu Glu Arg Asn
    2180            2185            2190

Glu Asn Leu Glu Gly Glu Leu Glu Ser Leu Lys Glu Asn Leu Pro
    2195            2200            2205

Phe Thr Met Asn Glu Gly Pro Phe Glu Glu Lys Leu Asn Phe Ser
    2210            2215            2220

Gln Val His Ile Met Asp Glu His Trp Arg Gly Glu Ala Leu Arg
    2225            2230            2235

Glu Lys Leu Arg His Arg Glu Asp Arg Leu Lys Ala Gln Leu Arg
    2240            2245            2250

His Cys Met Ser Lys Gln Ala Glu Val Leu Ile Lys Gly Lys Arg
    2255            2260            2265
```

```
Gln Thr Glu Gly Thr Leu His Ser Leu Arg Arg Gln Val Asp Ala
    2270                2275                2280

Leu Gly Glu Leu Val Thr Ser Thr Ser Ala Asp Ser Ala Ser Ser
    2285                2290                2295

Pro Ser Leu Ser Gln Leu Glu Ser Ser Leu Thr Glu Asp Ser Gln
    2300                2305                2310

Leu Gly Gln Asn Gln Glu Lys Asn Ala Ser Ala Arg
    2315                2320                2325

<210> SEQ ID NO 31
<211> LENGTH: 18
<212> TYPE: DNA
<213> ORGANISM: Artificial Sequence
<220> FEATURE:
<223> OTHER INFORMATION: Synthetic primer

<400> SEQUENCE: 31
gcagcaaaag actcagac                                              18

<210> SEQ ID NO 32
<211> LENGTH: 18
<212> TYPE: DNA
<213> ORGANISM: Artificial Sequence
<220> FEATURE:
<223> OTHER INFORMATION: Synthetic primer

<400> SEQUENCE: 32
aagttgcaac atgtccag                                              18

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
ggatccatga agaaaggttc tcag                                       24

<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34
gtcgactcag ggtcggtgcg cgtc                                       24

<210> SEQ ID NO 35
<211> LENGTH: 23
<212> TYPE: DNA
<213> ORGANISM: Artificial Sequence
<220> FEATURE:
<223> OTHER INFORMATION: Synthetic primer

<400> SEQUENCE: 35
gtcgacctat gcggaggggt ctg                                        23

<210> SEQ ID NO 36
<211> LENGTH: 25
<212> TYPE: DNA
<213> ORGANISM: Artificial Sequence
<220> FEATURE:
<223> OTHER INFORMATION: Synthetic primer
```

```
<400> SEQUENCE: 36
ggatccatga agaaaggttc tcaac                                        25

<210> SEQ ID NO 37
<211> LENGTH: 25
<212> TYPE: DNA
<213> ORGANISM: Artificial Sequence
<220> FEATURE:
<223> OTHER INFORMATION: Synthetic primer

<400> SEQUENCE: 37
gtcgactcat ctggctgagg cattc                                        25

<210> SEQ ID NO 38
<211> LENGTH: 6046
<212> TYPE: DNA
<213> ORGANISM: Canis familiaris
<220> FEATURE:
<221> NAME/KEY: CDS
<222> LOCATION: (1)..(5934)

<400> SEQUENCE: 38
```

| | | | | | | | | | | | | | | | | |
|---|---|---|---|---|---|---|---|---|---|---|---|---|---|---|---|---|
| atg | tcg | tcc | tgg | ctc | ggg | ggc | ctg | ggc | tcc | ggc | ctg | ggc | cag | tcg | ctg | 48 |
| Met | Ser | Ser | Trp | Leu | Gly | Gly | Leu | Gly | Ser | Gly | Leu | Gly | Gln | Ser | Leu | |
| 1 | | | | 5 | | | | | 10 | | | | | 15 | | |
| ggg | caa | gtc | gga | ggc | agc | ctg | gcc | tcc | ctc | act | ggc | cag | att | tca | aac | 96 |
| Gly | Gln | Val | Gly | Gly | Ser | Leu | Ala | Ser | Leu | Thr | Gly | Gln | Ile | Ser | Asn | |
| | | 20 | | | | | 25 | | | | | 30 | | | | |
| ttt | acg | aag | gac | atg | ctg | atg | gag | ggc | acg | gag | gag | gtg | gaa | gca | gaa | 144 |
| Phe | Thr | Lys | Asp | Met | Leu | Met | Glu | Gly | Thr | Glu | Glu | Val | Glu | Ala | Glu | |
| | 35 | | | | | 40 | | | | | 45 | | | | | |
| tta | cct | aat | tct | agg | aga | aag | gaa | gtt | gaa | gcc | att | cat | gca | atc | tta | 192 |
| Leu | Pro | Asn | Ser | Arg | Arg | Lys | Glu | Val | Glu | Ala | Ile | His | Ala | Ile | Leu | |
| 50 | | | | | 55 | | | | | 60 | | | | | | |
| aga | tca | gag | aat | gag | aga | ctc | aaa | gaa | ctt | tgt | act | gat | tta | gaa | gag | 240 |
| Arg | Ser | Glu | Asn | Glu | Arg | Leu | Lys | Glu | Leu | Cys | Thr | Asp | Leu | Glu | Glu | |
| 65 | | | | | 70 | | | | | 75 | | | | | 80 | |
| aag | cat | gaa | gca | tca | gag | ctt | caa | ata | aag | caa | caa | tct | aca | aat | tac | 288 |
| Lys | His | Glu | Ala | Ser | Glu | Leu | Gln | Ile | Lys | Gln | Gln | Ser | Thr | Asn | Tyr | |
| | | | | 85 | | | | | 90 | | | | | 95 | | |
| cga | aat | caa | cta | caa | cag | aaa | gag | gta | gaa | atc | agc | cat | ctt | aaa | gca | 336 |
| Arg | Asn | Gln | Leu | Gln | Gln | Lys | Glu | Val | Glu | Ile | Ser | His | Leu | Lys | Ala | |
| | | | 100 | | | | | 105 | | | | | 110 | | | |
| aga | cag | att | gca | ctg | cag | gat | cag | ttg | ctg | aag | ctg | cag | tca | gct | gct | 384 |
| Arg | Gln | Ile | Ala | Leu | Gln | Asp | Gln | Leu | Leu | Lys | Leu | Gln | Ser | Ala | Ala | |
| | | 115 | | | | | 120 | | | | | 125 | | | | |
| cag | tct | gca | cat | tca | gga | gct | agc | agc | gta | cca | gca | gcc | ctg | gca | tca | 432 |
| Gln | Ser | Ala | His | Ser | Gly | Ala | Ser | Ser | Val | Pro | Ala | Ala | Leu | Ala | Ser | |
| | 130 | | | | | 135 | | | | | 140 | | | | | |
| tct | ccg | ttc | agc | tat | tct | gtc | agt | cat | cat | gct | tca | gct | ttc | cat | gac | 480 |
| Ser | Pro | Phe | Ser | Tyr | Ser | Val | Ser | His | His | Ala | Ser | Ala | Phe | His | Asp | |
| 145 | | | | | 150 | | | | | 155 | | | | | 160 | |
| gat | gac | atg | gac | ttc | agt | gac | ata | att | tca | tca | caa | caa | gaa | ata | aac | 528 |
| Asp | Asp | Met | Asp | Phe | Ser | Asp | Ile | Ile | Ser | Ser | Gln | Gln | Glu | Ile | Asn | |
| | | | | 165 | | | | | 170 | | | | | 175 | | |
| aga | tta | tca | aat | gaa | gtt | tca | aga | ctt | gag | tct | gag | gtt | ggc | cat | tgg | 576 |
| Arg | Leu | Ser | Asn | Glu | Val | Ser | Arg | Leu | Glu | Ser | Glu | Val | Gly | His | Trp | |
| | | | 180 | | | | | 185 | | | | | 190 | | | |
| agg | cat | att | gct | cag | act | tct | aaa | gca | caa | gga | tca | aat | agc | tct | gat | 624 |
| Arg | His | Ile | Ala | Gln | Thr | Ser | Lys | Ala | Gln | Gly | Ser | Asn | Ser | Ser | Asp | |
| | | 195 | | | | | 200 | | | | | 205 | | | | |

| | | |
|---|---|---|
| caa agt gaa atc tgt aaa cta caa agt atc att aag gaa ctc aaa cag<br>Gln Ser Glu Ile Cys Lys Leu Gln Ser Ile Ile Lys Glu Leu Lys Gln<br>210                 215                     220 | | 672 |
| att cga agt cag gaa atc gat gac cat caa cat gaa atg tca gtg ttg<br>Ile Arg Ser Gln Glu Ile Asp Asp His Gln His Glu Met Ser Val Leu<br>225                 230                     235                     240 | | 720 |
| cag aat gca cat caa cag aag ttg aca gat ata agt cgt cgg cat cga<br>Gln Asn Ala His Gln Gln Lys Leu Thr Asp Ile Ser Arg Arg His Arg<br>                 245                     250                     255 | | 768 |
| gaa gaa tta cgt gac tat gaa gaa cga att gaa gaa ctg gaa aat ctg<br>Glu Glu Leu Arg Asp Tyr Glu Glu Arg Ile Glu Glu Leu Glu Asn Leu<br>                 260                     265                     270 | | 816 |
| tta gaa caa ggt ggc tca gga att gta ata cct gat cac tca aaa atc<br>Leu Glu Gln Gly Gly Ser Gly Ile Val Ile Pro Asp His Ser Lys Ile<br>275                 280                     285 | | 864 |
| cat gag atg caa aaa act att cag aat cta caa act gaa aaa gta gca<br>His Glu Met Gln Lys Thr Ile Gln Asn Leu Gln Thr Glu Lys Val Ala<br>                 290                     295                     300 | | 912 |
| tct ata aaa aaa att gaa gaa ctt gag gat aaa ata aaa gac ata gat<br>Ser Ile Lys Lys Ile Glu Glu Leu Glu Asp Lys Ile Lys Asp Ile Asp<br>305                 310                     315                     320 | | 960 |
| aaa aaa ttg tct tct gca gaa aat gac aga gat gtt ttg agg aag gag<br>Lys Lys Leu Ser Ser Ala Glu Asn Asp Arg Asp Val Leu Arg Lys Glu<br>                 325                     330                     335 | | 1008 |
| aaa gaa tgc cta aat gtt gaa aac aga caa ata aca gaa caa tgt gaa<br>Lys Glu Cys Leu Asn Val Glu Asn Arg Gln Ile Thr Glu Gln Cys Glu<br>                 340                     345                     350 | | 1056 |
| agc ttg aaa ctg gaa tgt aaa ttg cag cat gat gct gag aag caa ggt<br>Ser Leu Lys Leu Glu Cys Lys Leu Gln His Asp Ala Glu Lys Gln Gly<br>355                 360                     365 | | 1104 |
| gat act gtg aca gaa aaa gaa aga atc ctt cca cag agt aca tca gtg<br>Asp Thr Val Thr Glu Lys Glu Arg Ile Leu Pro Gln Ser Thr Ser Val<br>                 370                     375                     380 | | 1152 |
| gaa gag gaa gtg ctc aaa ctg cag caa gca ctg tct gat gcg gaa aat<br>Glu Glu Glu Val Leu Lys Leu Gln Gln Ala Leu Ser Asp Ala Glu Asn<br>385                 390                     395                     400 | | 1200 |
| gaa att atg aga ctg agt aat tta tac cag gat aac agt ctc act gaa<br>Glu Ile Met Arg Leu Ser Asn Leu Tyr Gln Asp Asn Ser Leu Thr Glu<br>                 405                     410                     415 | | 1248 |
| gat aat ttg aaa ctt aaa atg cat gtc gaa ttt tta gaa aaa cag aag<br>Asp Asn Leu Lys Leu Lys Met His Val Glu Phe Leu Glu Lys Gln Lys<br>                 420                     425                     430 | | 1296 |
| tcc tta ttg agt caa gaa aag gaa gag ctt caa cta tca ctt tta aag<br>Ser Leu Leu Ser Gln Glu Lys Glu Glu Leu Gln Leu Ser Leu Leu Lys<br>                 435                     440                     445 | | 1344 |
| ttg aac aat gaa tat gaa gtg att aaa agt aca gct gtg aga gac atg<br>Leu Asn Asn Glu Tyr Glu Val Ile Lys Ser Thr Ala Val Arg Asp Met<br>450                 455                     460 | | 1392 |
| gat atg gat tca aca tta tgt gat tta aga ctg acc ttg gag gca aag<br>Asp Met Asp Ser Thr Leu Cys Asp Leu Arg Leu Thr Leu Glu Ala Lys<br>465                 470                     475                     480 | | 1440 |
| gac cag gaa ctc aat cag agt ctc act gag aag gaa ata ttg gtt gct<br>Asp Gln Glu Leu Asn Gln Ser Leu Thr Glu Lys Glu Ile Leu Val Ala<br>                 485                     490                     495 | | 1488 |
| gag tta gag gaa ttg gac aga caa aac caa gaa gct aca aag cac atg<br>Glu Leu Glu Glu Leu Asp Arg Gln Asn Gln Glu Ala Thr Lys His Met<br>                 500                     505                     510 | | 1536 |
| att ctg ata aaa gat cag cta tca aaa caa caa agt gag gga gaa act<br>Ile Leu Ile Lys Asp Gln Leu Ser Lys Gln Gln Ser Glu Gly Glu Thr | | 1584 |

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 515 |     |     |     | 520 |     |     |     | 525 |     |     |     |     |     |     |      |
| atc | att | agt | aaa | ctg | aga | aaa | gat | cta | aat | gat | gaa | aac | aag | aga | gtc | 1632 |
| Ile | Ile | Ser | Lys | Leu | Arg | Lys | Asp | Leu | Asn | Asp | Glu | Asn | Lys | Arg | Val |      |
|     | 530 |     |     |     | 535 |     |     |     | 540 |     |     |     |     |     |     |      |
| cat | caa | ctt | gaa | gat | gat | aaa | aag | aat | atg | act | aaa | gaa | cta | aat | gtg | 1680 |
| His | Gln | Leu | Glu | Asp | Asp | Lys | Lys | Asn | Met | Thr | Lys | Glu | Leu | Asn | Val |      |
| 545 |     |     |     |     | 550 |     |     |     | 555 |     |     |     |     |     | 560 |      |
| cag | aaa | gag | aag | tta | gtt | caa | agt | gaa | ctc | gtc | cta | aat | ggc | ttg | cat | 1728 |
| Gln | Lys | Glu | Lys | Leu | Val | Gln | Ser | Glu | Leu | Val | Leu | Asn | Gly | Leu | His |      |
|     |     |     |     | 565 |     |     |     |     | 570 |     |     |     |     | 575 |     |      |
| tta | gcc | aag | cag | aag | ctt | gag | gag | aaa | gta | gaa | gat | tta | gtg | gat | cag | 1776 |
| Leu | Ala | Lys | Gln | Lys | Leu | Glu | Glu | Lys | Val | Glu | Asp | Leu | Val | Asp | Gln |      |
|     |     |     | 580 |     |     |     |     | 585 |     |     |     |     | 590 |     |     |      |
| cta | aat | aaa | tca | caa | aaa | agt | aat | tta | aac | atg | cag | aag | gag | aac | ttt | 1824 |
| Leu | Asn | Lys | Ser | Gln | Lys | Ser | Asn | Leu | Asn | Met | Gln | Lys | Glu | Asn | Phe |      |
|     |     | 595 |     |     |     |     | 600 |     |     |     |     | 605 |     |     |     |      |
| gga | ctt | aag | gaa | cat | att | aaa | caa | aat | gag | gaa | gag | ctt | tct | aga | gtc | 1872 |
| Gly | Leu | Lys | Glu | His | Ile | Lys | Gln | Asn | Glu | Glu | Glu | Leu | Ser | Arg | Val |      |
|     | 610 |     |     |     |     | 615 |     |     |     |     | 620 |     |     |     |     |      |
| agg | gat | gag | tta | act | cag | tct | cta | agt | cga | gac | tct | ggc | agt | gat | ttt | 1920 |
| Arg | Asp | Glu | Leu | Thr | Gln | Ser | Leu | Ser | Arg | Asp | Ser | Gly | Ser | Asp | Phe |      |
| 625 |     |     |     |     | 630 |     |     |     | 635 |     |     |     |     |     | 640 |      |
| aag | gat | gac | tta | ctt | aaa | gaa | agg | gaa | gct | gaa | gtc | aga | aac | tta | aaa | 1968 |
| Lys | Asp | Asp | Leu | Leu | Lys | Glu | Arg | Glu | Ala | Glu | Val | Arg | Asn | Leu | Lys |      |
|     |     |     |     | 645 |     |     |     |     | 650 |     |     |     |     | 655 |     |      |
| caa | aat | ctt | tca | gaa | ata | gaa | cag | ctc | aat | gac | agt | tta | aac | aaa | gtt | 2016 |
| Gln | Asn | Leu | Ser | Glu | Ile | Glu | Gln | Leu | Asn | Asp | Ser | Leu | Asn | Lys | Val |      |
|     |     |     | 660 |     |     |     |     | 665 |     |     |     |     | 670 |     |     |      |
| gcc | ttt | gat | ctc | aaa | atg | gaa | aat | gaa | aag | ttg | gtc | tta | gcg | tgt | gaa | 2064 |
| Ala | Phe | Asp | Leu | Lys | Met | Glu | Asn | Glu | Lys | Leu | Val | Leu | Ala | Cys | Glu |      |
|     |     | 675 |     |     |     |     | 680 |     |     |     |     | 685 |     |     |     |      |
| gat | ata | aga | cat | cag | ttg | gaa | gaa | tca | att | gtt | ggc | agc | aat | cag | atg | 2112 |
| Asp | Ile | Arg | His | Gln | Leu | Glu | Glu | Ser | Ile | Val | Gly | Ser | Asn | Gln | Met |      |
|     | 690 |     |     |     |     | 695 |     |     |     |     | 700 |     |     |     |     |      |
| tct | ctg | gaa | aga | aac | act | att | gtg | gag | gct | cta | aaa | atg | gaa | aaa | gga | 2160 |
| Ser | Leu | Glu | Arg | Asn | Thr | Ile | Val | Glu | Ala | Leu | Lys | Met | Glu | Lys | Gly |      |
| 705 |     |     |     |     | 710 |     |     |     | 715 |     |     |     |     |     | 720 |      |
| cag | tta | gaa | gca | gaa | ttg | agt | cga | gct | gac | caa | agg | ctg | ttg | gaa | gaa | 2208 |
| Gln | Leu | Glu | Ala | Glu | Leu | Ser | Arg | Ala | Asp | Gln | Arg | Leu | Leu | Glu | Glu |      |
|     |     |     |     | 725 |     |     |     |     | 730 |     |     |     |     | 735 |     |      |
| gcc | agt | aag | tat | gaa | cag | acg | att | caa | gag | cta | tca | aag | gca | cgt | gat | 2256 |
| Ala | Ser | Lys | Tyr | Glu | Gln | Thr | Ile | Gln | Glu | Leu | Ser | Lys | Ala | Arg | Asp |      |
|     |     |     | 740 |     |     |     |     | 745 |     |     |     |     | 750 |     |     |      |
| ttg | agg | acc | tct | gct | tta | cag | ctg | gag | cag | cag | cat | tta | atg | aaa | ctc | 2304 |
| Leu | Arg | Thr | Ser | Ala | Leu | Gln | Leu | Glu | Gln | Gln | His | Leu | Met | Lys | Leu |      |
|     |     | 755 |     |     |     |     | 760 |     |     |     |     | 765 |     |     |     |      |
| agt | caa | gag | aag | gac | ttc | gaa | ata | gca | gaa | ctt | aaa | aag | aac | att | gaa | 2352 |
| Ser | Gln | Glu | Lys | Asp | Phe | Glu | Ile | Ala | Glu | Leu | Lys | Lys | Asn | Ile | Glu |      |
|     | 770 |     |     |     |     | 775 |     |     |     |     | 780 |     |     |     |     |      |
| cag | atg | gat | act | gat | cat | aaa | gaa | act | aag | gca | att | ttg | tca | tct | att | 2400 |
| Gln | Met | Asp | Thr | Asp | His | Lys | Glu | Thr | Lys | Ala | Ile | Leu | Ser | Ser | Ile |      |
| 785 |     |     |     |     | 790 |     |     |     | 795 |     |     |     |     |     | 800 |      |
| tta | gaa | gag | cag | aag | caa | ttg | acg | caa | ctt | ata | agt | gag | aag | gaa | att | 2448 |
| Leu | Glu | Glu | Gln | Lys | Gln | Leu | Thr | Gln | Leu | Ile | Ser | Glu | Lys | Glu | Ile |      |
|     |     |     |     | 805 |     |     |     |     | 810 |     |     |     |     | 815 |     |      |
| ttt | att | gag | aaa | ctt | aaa | gaa | aga | agt | tca | gag | ctt | cag | gag | gaa | tta | 2496 |
| Phe | Ile | Glu | Lys | Leu | Lys | Glu | Arg | Ser | Ser | Glu | Leu | Gln | Glu | Glu | Leu |      |
|     |     |     | 820 |     |     |     |     | 825 |     |     |     |     | 830 |     |     |      |
| gag | aaa | tct | act | cag | gcc | tca | agg | aaa | att | gaa | att | tta | aag | caa | acc | 2544 |

```
                  Glu Lys Ser Thr Gln Ala Ser Arg Lys Ile Glu Ile Leu Lys Gln Thr
                                  835                 840                 845 att gag gag aaa gac aga agt ctt ggg tcc atg aaa gaa gaa aac aat          2592
Ile Glu Glu Lys Asp Arg Ser Leu Gly Ser Met Lys Glu Glu Asn Asn
        850                 855                 860 cat ctg aaa gaa gaa ctg gaa cgg ctc cgt gaa cag cag agt cga gcc          2640
His Leu Lys Glu Glu Leu Glu Arg Leu Arg Glu Gln Gln Ser Arg Ala
865                 870                 875                 880 gtg cct gtg gtg gag cct aaa ccc ctg gat agt gtt aca gag cta gaa          2688
Val Pro Val Val Glu Pro Lys Pro Leu Asp Ser Val Thr Glu Leu Glu
                885                 890                 895 tct gag gtg ttg cag cta aat ata gta aag agg aat ctt gag gag gaa          2736
Ser Glu Val Leu Gln Leu Asn Ile Val Lys Arg Asn Leu Glu Glu Glu
        900                 905                 910 ata aaa cgt cat cag aag att ata gaa gat caa aac cag agt aaa atg          2784
Ile Lys Arg His Gln Lys Ile Ile Glu Asp Gln Asn Gln Ser Lys Met
    915                 920                 925 cag ctg ctt cag tct cta gag gag cag aag aag gaa atg gat gaa ttt          2832
Gln Leu Leu Gln Ser Leu Glu Glu Gln Lys Lys Glu Met Asp Glu Phe
930                 935                 940 aag tgc cag cat gag caa atg aac gtc aca cac acc caa ctc ttc tta          2880
Lys Cys Gln His Glu Gln Met Asn Val Thr His Thr Gln Leu Phe Leu
945                 950                 955                 960 gag aaa gat gag gag att aag aat ttg caa aaa aca att gaa caa atc          2928
Glu Lys Asp Glu Glu Ile Lys Asn Leu Gln Lys Thr Ile Glu Gln Ile
                965                 970                 975 aaa acc caa tgg cat gaa gaa aga cag gac gtt caa atg gag aat tct          2976
Lys Thr Gln Trp His Glu Glu Arg Gln Asp Val Gln Met Glu Asn Ser
        980                 985                 990 gag ttc ttt caa gaa aca aaa gtg  cag agc ctt aat cta  gaa aat ggc        3024
Glu Phe Phe Gln Glu Thr Lys Val  Gln Ser Leu Asn Leu  Glu Asn Gly
    995                 1000                1005 agt gaa  aag cat gat tta tcg  aaa gcc gaa act gag  agg tta gta           3069
Ser Glu  Lys His Asp Leu Ser  Lys Ala Glu Thr Glu  Arg Leu Val
    1010                1015                1020 aaa gga  ata aaa gaa cga gag  ctg gag att aaa ctt  cta aat gaa           3114
Lys Gly  Ile Lys Glu Arg Glu  Leu Glu Ile Lys Leu  Leu Asn Glu
    1025                1030                1035 aag aat  ata tct tta aca aaa  caa att gat cag ctg  tcc aaa gat           3159
Lys Asn  Ile Ser Leu Thr Lys  Gln Ile Asp Gln Leu  Ser Lys Asp
    1040                1045                1050 gag gtt  ggt aaa ctc act cag  atc atc cag cag aaa  gac tta gag           3204
Glu Val  Gly Lys Leu Thr Gln  Ile Ile Gln Gln Lys  Asp Leu Glu
    1055                1060                1065 ata caa  gct ctt cat gct agg  att tct tca gct tcc  tac acc cag           3249
Ile Gln  Ala Leu His Ala Arg  Ile Ser Ser Ala Ser  Tyr Thr Gln
    1070                1075                1080 gat gtt  gtc tac ctt cag cag  cag ctg cag gcc tat  gct atg gag           3294
Asp Val  Val Tyr Leu Gln Gln  Gln Leu Gln Ala Tyr  Ala Met Glu
    1085                1090                1095 aga gaa  caa gta tta gct gtt  ttg agt gag aag acc  agg gaa aat           3339
Arg Glu  Gln Val Leu Ala Val  Leu Ser Glu Lys Thr  Arg Glu Asn
    1100                1105                1110 agc cat  ctg aaa aca gaa tac  cac aaa atg atg gat  atc gtt gct           3384
Ser His  Leu Lys Thr Glu Tyr  His Lys Met Met Asp  Ile Val Ala
    1115                1120                1125 gct aaa  gaa gca gct ctc att  aag ctg caa gat gaa  aat aaa aaa           3429
Ala Lys  Glu Ala Ala Leu Ile  Lys Leu Gln Asp Glu  Asn Lys Lys
    1130                1135                1140
```

| | | | | | | | | | | |
|---|---|---|---|---|---|---|---|---|---|---|
| ttg<br>Leu<br>1145 | tct<br>Ser | gct<br>Ala | aga<br>Arg | tcc<br>Ser | gaa<br>Glu<br>1150 | ggt<br>Gly | ggt<br>Gly | ggc<br>Gly | cag<br>Gln | gat<br>Asp<br>1155 | atg<br>Met | ttt<br>Phe | aga<br>Arg | gag<br>Glu | 3474 |
| act<br>Thr<br>1160 | gtc<br>Val | cag<br>Gln | aat<br>Asn | tta<br>Leu | tca<br>Ser<br>1165 | cgt<br>Arg | atc<br>Ile | att<br>Ile | cga<br>Arg | gaa<br>Glu<br>1170 | aaa<br>Lys | gac<br>Asp | att<br>Ile | gag<br>Glu | 3519 |
| ata<br>Ile<br>1175 | gat<br>Asp | gcg<br>Ala | tta<br>Leu | agt<br>Ser | cag<br>Gln<br>1180 | aag<br>Lys | tgc<br>Cys | cag<br>Gln | acc<br>Thr | tta<br>Leu<br>1185 | ttg<br>Leu | aca<br>Thr | gtt<br>Val | tta<br>Leu | 3564 |
| caa<br>Gln<br>1190 | aca<br>Thr | tcg<br>Ser | agc<br>Ser | act<br>Thr | ggg<br>Gly<br>1195 | aat<br>Asn | gag<br>Glu | gtt<br>Val | gga<br>Gly | ggc<br>Gly<br>1200 | gtt<br>Val | aat<br>Asn | agc<br>Ser | aat<br>Asn | 3609 |
| cag<br>Gln<br>1205 | ttt<br>Phe | gag<br>Glu | gag<br>Glu | ctt<br>Leu | cta<br>Leu<br>1210 | cag<br>Gln | gaa<br>Glu | cgc<br>Arg | gac<br>Asp | aaa<br>Lys<br>1215 | tta<br>Leu | aaa<br>Lys | caa<br>Gln | caa<br>Gln | 3654 |
| gta<br>Val<br>1220 | aag<br>Lys | aag<br>Lys | atg<br>Met | gaa<br>Glu | gag<br>Glu<br>1225 | tgg<br>Trp | aaa<br>Lys | cag<br>Gln | cag<br>Gln | gtg<br>Val<br>1230 | atg<br>Met | acc<br>Thr | aca<br>Thr | gtt<br>Val | 3699 |
| cag<br>Gln<br>1235 | aat<br>Asn | atg<br>Met | cag<br>Gln | cat<br>His | gag<br>Glu<br>1240 | tca<br>Ser | gcc<br>Ala | cag<br>Gln | ctt<br>Leu | caa<br>Gln<br>1245 | gaa<br>Glu | gaa<br>Glu | ctt<br>Leu | cat<br>His | 3744 |
| cag<br>Gln<br>1250 | ctt<br>Leu | cag<br>Gln | gca<br>Ala | caa<br>Gln | gtt<br>Val<br>1255 | ttg<br>Leu | gtt<br>Val | gac<br>Asp | agt<br>Ser | gat<br>Asp<br>1260 | aat<br>Asn | aat<br>Asn | tct<br>Ser | aaa<br>Lys | 3789 |
| tta<br>Leu<br>1265 | caa<br>Gln | gtg<br>Val | gat<br>Asp | tat<br>Tyr | act<br>Thr<br>1270 | ggc<br>Gly | ctg<br>Leu | atc<br>Ile | caa<br>Gln | agt<br>Ser<br>1275 | tat<br>Tyr | gag<br>Glu | cag<br>Gln | aat<br>Asn | 3834 |
| gaa<br>Glu<br>1280 | act<br>Thr | aaa<br>Lys | ctc<br>Leu | aaa<br>Lys | aat<br>Asn<br>1285 | ttt<br>Phe | ggg<br>Gly | cag<br>Gln | gag<br>Glu | cta<br>Leu<br>1290 | gca<br>Ala | caa<br>Gln | gtt<br>Val | cag<br>Gln | 3879 |
| cac<br>His<br>1295 | agc<br>Ser | ata<br>Ile | ggg<br>Gly | cag<br>Gln | ctg<br>Leu<br>1300 | tac<br>Tyr | agt<br>Ser | acc<br>Thr | aaa<br>Lys | gac<br>Asp<br>1305 | ctt<br>Leu | ctc<br>Leu | tta<br>Leu | gga<br>Gly | 3924 |
| aaa<br>Lys<br>1310 | ctt<br>Leu | gat<br>Asp | att<br>Ile | att<br>Ile | tct<br>Ser<br>1315 | cct<br>Pro | caa<br>Gln | ctc<br>Leu | ccc<br>Pro | tcc<br>Ser<br>1320 | gga<br>Gly | tca<br>Ser | tcg<br>Ser | cct<br>Pro | 3969 |
| cct<br>Pro<br>1325 | tcc<br>Ser | cag<br>Gln | tca<br>Ser | gca<br>Ala | gag<br>Glu<br>1330 | tct<br>Ser | ctt<br>Leu | gga<br>Gly | atg<br>Met | gat<br>Asp<br>1335 | aag<br>Lys | cgt<br>Arg | gat<br>Asp | aca<br>Thr | 4014 |
| tca<br>Ser<br>1340 | agt<br>Ser | gag<br>Glu | tct<br>Ser | tca<br>Ser | aaa<br>Lys<br>1345 | cag<br>Gln | gag<br>Glu | cta<br>Leu | gaa<br>Glu | gag<br>Glu<br>1350 | cta<br>Leu | aga<br>Arg | aag<br>Lys | tca<br>Ser | 4059 |
| ctg<br>Leu<br>1355 | cag<br>Gln | gaa<br>Glu | aaa<br>Lys | gat<br>Asp | gca<br>Ala<br>1360 | acg<br>Thr | att<br>Ile | aaa<br>Lys | aca<br>Thr | ctc<br>Leu<br>1365 | cag<br>Gln | gaa<br>Glu | aat<br>Asn | aac<br>Asn | 4104 |
| cac<br>His<br>1370 | aga<br>Arg | ttg<br>Leu | tcc<br>Ser | gat<br>Asp | tca<br>Ser<br>1375 | att<br>Ile | gct<br>Ala | gcc<br>Ala | acc<br>Thr | tca<br>Ser<br>1380 | gag<br>Glu | cta<br>Leu | gaa<br>Glu | aga<br>Arg | 4149 |
| aaa<br>Lys<br>1385 | gaa<br>Glu | cac<br>His | gaa<br>Glu | cag<br>Gln | act<br>Thr<br>1390 | gat<br>Asp | tca<br>Ser | gaa<br>Glu | att<br>Ile | aag<br>Lys<br>1395 | cag<br>Gln | cta<br>Leu | aag<br>Lys | gag<br>Glu | 4194 |
| aaa<br>Lys<br>1400 | caa<br>Gln | gat<br>Asp | gtt<br>Val | tta<br>Leu | caa<br>Gln<br>1405 | aag<br>Lys | tca<br>Ser | ctt<br>Leu | aag<br>Lys | gag<br>Glu<br>1410 | aaa<br>Lys | gac<br>Asp | ctc<br>Leu | tta<br>Leu | 4239 |
| atc<br>Ile<br>1415 | aaa<br>Lys | gcc<br>Ala | aaa<br>Lys | agt<br>Ser | gat<br>Asp<br>1420 | cag<br>Gln | tta<br>Leu | ctt<br>Leu | tct<br>Ser | tta<br>Leu<br>1425 | aat<br>Asn | gaa<br>Glu | aat<br>Asn | ttc<br>Phe | 4284 |
| acc<br>Thr<br>1430 | aac<br>Asn | aaa<br>Lys | gtg<br>Val | aat<br>Asn | gaa<br>Glu<br>1435 | aat<br>Asn | gaa<br>Glu | ctc<br>Leu | ttg<br>Leu | agg<br>Arg<br>1440 | cag<br>Gln | gca<br>Ala | gta<br>Val | acc<br>Thr | 4329 |

-continued

| | | | | | | | | | | | | |
|---|---|---|---|---|---|---|---|---|---|---|---|---|
| aac | ctg | aag | gag | cgg | gta | tta | att | tta | gaa | atg | gac | att | ggt | aaa | 4374 |
| Asn | Leu | Lys | Glu | Arg | Val | Leu | Ile | Leu | Glu | Met | Asp | Ile | Gly | Lys | |
| | 1445 | | | | 1450 | | | | | 1455 | | | | | |

| cta | aaa | gaa | gaa | aat | gaa | aaa | ata | gtt | gaa | aga | acc | agg | gaa | aag | 4419 |
| Leu | Lys | Glu | Glu | Asn | Glu | Lys | Ile | Val | Glu | Arg | Thr | Arg | Glu | Lys | |
| 1460 | | | | | 1465 | | | | | 1470 | | | | | |

| gaa | acg | gag | tat | caa | gca | tta | cag | gag | act | aat | atg | aag | ttt | tcc | 4464 |
| Glu | Thr | Glu | Tyr | Gln | Ala | Leu | Gln | Glu | Thr | Asn | Met | Lys | Phe | Ser | |
| 1475 | | | | | 1480 | | | | | 1485 | | | | | |

| atg | atg | ctt | cga | gaa | aaa | gag | ttt | gag | tgc | cat | tca | atg | aag | gaa | 4509 |
| Met | Met | Leu | Arg | Glu | Lys | Glu | Phe | Glu | Cys | His | Ser | Met | Lys | Glu | |
| | 1490 | | | | 1495 | | | | | 1500 | | | | | |

| aaa | tct | ctt | gca | ttt | gag | cag | cta | ctg | aaa | gaa | aaa | gag | cag | ggc | 4554 |
| Lys | Ser | Leu | Ala | Phe | Glu | Gln | Leu | Leu | Lys | Glu | Lys | Glu | Gln | Gly | |
| 1505 | | | | | 1510 | | | | | 1515 | | | | | |

| aag | act | ggg | gag | tta | aat | caa | ctt | tta | aat | gca | gtt | aag | tca | atg | 4599 |
| Lys | Thr | Gly | Glu | Leu | Asn | Gln | Leu | Leu | Asn | Ala | Val | Lys | Ser | Met | |
| 1520 | | | | | 1525 | | | | | 1530 | | | | | |

| cag | gag | aag | aca | gtt | aag | ttt | caa | caa | gag | aga | gac | cag | gtc | atg | 4644 |
| Gln | Glu | Lys | Thr | Val | Lys | Phe | Gln | Gln | Glu | Arg | Asp | Gln | Val | Met | |
| | 1535 | | | | 1540 | | | | | 1545 | | | | | |

| ttg | gcc | ctg | aaa | cag | aaa | caa | atg | gaa | aac | agt | gct | tta | cag | aat | 4689 |
| Leu | Ala | Leu | Lys | Gln | Lys | Gln | Met | Glu | Asn | Ser | Ala | Leu | Gln | Asn | |
| 1550 | | | | | 1555 | | | | | 1560 | | | | | |

| gag | gtt | caa | cat | tta | cgc | gac | aaa | gaa | tta | cgc | tta | aac | cag | gag | 4734 |
| Glu | Val | Gln | His | Leu | Arg | Asp | Lys | Glu | Leu | Arg | Leu | Asn | Gln | Glu | |
| 1565 | | | | | 1570 | | | | | 1575 | | | | | |

| cta | gag | aga | ttg | cgt | aac | cat | ctt | tta | gaa | tca | gag | gat | tct | tac | 4779 |
| Leu | Glu | Arg | Leu | Arg | Asn | His | Leu | Leu | Glu | Ser | Glu | Asp | Ser | Tyr | |
| | 1580 | | | | 1585 | | | | | 1590 | | | | | |

| acc | cgt | gaa | gct | ttg | gct | gca | gaa | gag | aga | gag | gcc | aaa | ctg | aga | 4824 |
| Thr | Arg | Glu | Ala | Leu | Ala | Ala | Glu | Glu | Arg | Glu | Ala | Lys | Leu | Arg | |
| 1595 | | | | | 1600 | | | | | 1605 | | | | | |

| agg | aaa | gtc | aca | gta | ttg | gag | gaa | aag | cta | gtt | tca | tct | tct | aat | 4869 |
| Arg | Lys | Val | Thr | Val | Leu | Glu | Glu | Lys | Leu | Val | Ser | Ser | Ser | Asn | |
| 1610 | | | | | 1615 | | | | | 1620 | | | | | |

| gca | atg | gaa | aat | gca | agc | cat | cag | gcc | agt | ttg | cag | gta | gag | tca | 4914 |
| Ala | Met | Glu | Asn | Ala | Ser | His | Gln | Ala | Ser | Leu | Gln | Val | Glu | Ser | |
| | 1625 | | | | 1630 | | | | | 1635 | | | | | |

| ctg | cag | gag | cag | ctg | aat | gtg | gtc | tct | aag | cag | agg | gat | gaa | acc | 4959 |
| Leu | Gln | Glu | Gln | Leu | Asn | Val | Val | Ser | Lys | Gln | Arg | Asp | Glu | Thr | |
| 1640 | | | | | 1645 | | | | | 1650 | | | | | |

| gcc | ctg | cag | ctc | tct | gtg | tct | cgg | gaa | caa | gta | aag | cag | tat | gct | 5004 |
| Ala | Leu | Gln | Leu | Ser | Val | Ser | Arg | Glu | Gln | Val | Lys | Gln | Tyr | Ala | |
| 1655 | | | | | 1660 | | | | | 1665 | | | | | |

| ctc | tca | ctc | tcc | aac | ctg | cag | atg | gta | cta | gag | cat | ttc | cag | caa | 5049 |
| Leu | Ser | Leu | Ser | Asn | Leu | Gln | Met | Val | Leu | Glu | His | Phe | Gln | Gln | |
| | 1670 | | | | 1675 | | | | | 1680 | | | | | |

| gag | gaa | aaa | gct | gtg | tat | tct | gct | gaa | cta | gaa | aag | cac | aaa | cag | 5094 |
| Glu | Glu | Lys | Ala | Val | Tyr | Ser | Ala | Glu | Leu | Glu | Lys | His | Lys | Gln | |
| 1685 | | | | | 1690 | | | | | 1695 | | | | | |

| ctt | gta | gct | gaa | tgg | aag | aaa | aag | gca | gaa | aat | ctg | gaa | gga | aaa | 5139 |
| Leu | Val | Ala | Glu | Trp | Lys | Lys | Lys | Ala | Glu | Asn | Leu | Glu | Gly | Lys | |
| 1700 | | | | | 1705 | | | | | 1710 | | | | | |

| ctg | atg | tca | tta | cag | gag | cgt | ttt | gat | gaa | gca | aat | gct | gcg | ttg | 5184 |
| Leu | Met | Ser | Leu | Gln | Glu | Arg | Phe | Asp | Glu | Ala | Asn | Ala | Ala | Leu | |
| | 1715 | | | | 1720 | | | | | 1725 | | | | | |

| gat | tca | gca | tca | aga | ctt | aca | gag | cag | tta | gat | tta | aag | gaa | gaa | 5229 |
| Asp | Ser | Ala | Ser | Arg | Leu | Thr | Glu | Gln | Leu | Asp | Leu | Lys | Glu | Glu | |

```
                          1730                1735                1740
caa att gaa gaa ctt aaa aaa caa aat gaa ctc cga caa gaa atg    5274
Gln Ile Glu Glu Leu Lys Lys Gln Asn Glu Leu Arg Gln Glu Met
        1745                1750                1755 ctg gat gat gta caa aag aaa ttg atg aac tta gta aac agc aca    5319
Leu Asp Asp Val Gln Lys Lys Leu Met Asn Leu Val Asn Ser Thr
    1760                1765                1770 gaa gga aaa gtg gac aaa gtc cta atg aga aac ctc ttc att gga    5364
Glu Gly Lys Val Asp Lys Val Leu Met Arg Asn Leu Phe Ile Gly
        1775                1780                1785 cat ttc cac aca cca aag cat cag cgc cac gag gtg tta cga tta    5409
His Phe His Thr Pro Lys His Gln Arg His Glu Val Leu Arg Leu
    1790                1795                1800 atg gga agc atc ctt ggt atc aag agg gag gaa atg gaa cag ttg    5454
Met Gly Ser Ile Leu Gly Ile Lys Arg Glu Glu Met Glu Gln Leu
        1805                1810                1815 ctt cat gaa gat cag ggt ggt gtt acc agg tgg atg act gga tgg    5499
Leu His Glu Asp Gln Gly Gly Val Thr Arg Trp Met Thr Gly Trp
    1820                1825                1830 ctt gga gga gga tca aaa agt gtc ccc aac aca cct ctg aga cca    5544
Leu Gly Gly Gly Ser Lys Ser Val Pro Asn Thr Pro Leu Arg Pro
        1835                1840                1845 aat caa caa tct gtg ctt aat agc tct ttt tca gaa ctt ttt gtt    5589
Asn Gln Gln Ser Val Leu Asn Ser Ser Phe Ser Glu Leu Phe Val
    1850                1855                1860 aaa ttt cta gaa aca gaa tct cat cca tct gtt cca cca cca aag    5634
Lys Phe Leu Glu Thr Glu Ser His Pro Ser Val Pro Pro Pro Lys
        1865                1870                1875 ctt tct gtt cat gat atg aaa cct ctg gat tca cca gga agg aga    5679
Leu Ser Val His Asp Met Lys Pro Leu Asp Ser Pro Gly Arg Arg
    1880                1885                1890 aaa gta gtc ata cat gta tca gaa agt ttt aaa gaa acc aca gag    5724
Lys Val Val Ile His Val Ser Glu Ser Phe Lys Glu Thr Thr Glu
        1895                1900                1905 tcc aga tgt gga agg aga aca gat gtg aat cca ttc ttg gct ccc    5769
Ser Arg Cys Gly Arg Arg Thr Asp Val Asn Pro Phe Leu Ala Pro
    1910                1915                1920 cgc tct gca gct gtg cct ctc att aac cca gct gga ctt gga cct    5814
Arg Ser Ala Ala Val Pro Leu Ile Asn Pro Ala Gly Leu Gly Pro
        1925                1930                1935 ggt ggg cct ggg cat ctt ctt ttg aag ccc atc tca gac gtg ttg    5859
Gly Gly Pro Gly His Leu Leu Leu Lys Pro Ile Ser Asp Val Leu
    1940                1945                1950 ccc aca ttt aca cct ttg ccg gtg tca cct gac aac agt gct gga    5904
Pro Thr Phe Thr Pro Leu Pro Val Ser Pro Asp Asn Ser Ala Gly
        1955                1960                1965 gtt gtg ttg aaa gac ctt tta aag caa tag atgattctca agccagagac   5954
Val Val Leu Lys Asp Leu Leu Lys Gln
    1970                1975 aacatatgta gcactttaaa gaaaccatga acactatgtg tatgtacttt atcacaaagt  6014
ggcctttcag aaaaagtcat gtgtttgttt gc                               6046

<210> SEQ ID NO 39
<211> LENGTH: 1977
<212> TYPE: PRT
<213> ORGANISM: Canis familiaris

<400> SEQUENCE: 39

Met Ser Ser Trp Leu Gly Gly Leu Gly Ser Gly Leu Gly Gln Ser Leu
```

-continued

```
1               5                   10                  15
Gly Gln Val Gly Gly Ser Leu Ala Ser Leu Thr Gly Gln Ile Ser Asn
            20                  25                  30
Phe Thr Lys Asp Met Leu Met Glu Gly Thr Glu Val Glu Ala Glu
            35                  40                  45
Leu Pro Asn Ser Arg Arg Lys Glu Val Glu Ala Ile His Ala Ile Leu
50                  55                  60
Arg Ser Glu Asn Glu Arg Leu Lys Glu Leu Cys Thr Asp Leu Glu Glu
65                  70                  75                  80
Lys His Glu Ala Ser Glu Leu Gln Ile Lys Gln Gln Ser Thr Asn Tyr
                85                  90                  95
Arg Asn Gln Leu Gln Gln Lys Glu Val Glu Ile Ser His Leu Lys Ala
            100                 105                 110
Arg Gln Ile Ala Leu Gln Asp Gln Leu Leu Lys Leu Gln Ser Ala Ala
            115                 120                 125
Gln Ser Ala His Ser Gly Ala Ser Ser Val Pro Ala Ala Leu Ala Ser
130                 135                 140
Ser Pro Phe Ser Tyr Ser Val Ser His His Ala Ser Ala Phe His Asp
145             150                 155                 160
Asp Asp Met Asp Phe Ser Asp Ile Ile Ser Ser Gln Gln Glu Ile Asn
            165                 170                 175
Arg Leu Ser Asn Glu Val Ser Arg Leu Glu Ser Glu Val Gly His Trp
            180                 185                 190
Arg His Ile Ala Gln Thr Ser Lys Ala Gln Gly Ser Asn Ser Ser Asp
            195                 200                 205
Gln Ser Glu Ile Cys Lys Leu Gln Ser Ile Ile Lys Glu Leu Lys Gln
210                 215                 220
Ile Arg Ser Gln Glu Ile Asp Asp His Gln His Glu Met Ser Val Leu
225                 230                 235                 240
Gln Asn Ala His Gln Gln Lys Leu Thr Asp Ile Ser Arg Arg His Arg
            245                 250                 255
Glu Glu Leu Arg Asp Tyr Glu Glu Arg Ile Glu Glu Leu Glu Asn Leu
            260                 265                 270
Leu Glu Gln Gly Gly Ser Gly Ile Val Ile Pro Asp His Ser Lys Ile
            275                 280                 285
His Glu Met Gln Lys Thr Ile Gln Asn Leu Gln Thr Glu Lys Val Ala
            290                 295                 300
Ser Ile Lys Lys Ile Glu Glu Leu Glu Asp Lys Ile Lys Asp Ile Asp
305                 310                 315                 320
Lys Lys Leu Ser Ser Ala Glu Asn Asp Arg Asp Val Leu Arg Lys Glu
                325                 330                 335
Lys Glu Cys Leu Asn Val Glu Asn Arg Gln Ile Thr Glu Gln Cys Glu
            340                 345                 350
Ser Leu Lys Leu Glu Cys Lys Leu Gln His Asp Ala Glu Lys Gln Gly
            355                 360                 365
Asp Thr Val Thr Glu Lys Glu Arg Ile Leu Pro Gln Ser Thr Ser Val
            370                 375                 380
Glu Glu Glu Val Leu Lys Leu Gln Gln Ala Leu Ser Asp Ala Glu Asn
385                 390                 395                 400
Glu Ile Met Arg Leu Ser Asn Leu Tyr Gln Asp Asn Ser Leu Thr Glu
                405                 410                 415
Asp Asn Leu Lys Leu Lys Met His Val Glu Phe Leu Glu Lys Gln Lys
            420                 425                 430
```

```
Ser Leu Leu Ser Gln Glu Lys Glu Glu Leu Gln Leu Ser Leu Leu Lys
        435                 440                 445
Leu Asn Asn Glu Tyr Glu Val Ile Lys Ser Thr Ala Val Arg Asp Met
450                 455                 460
Asp Met Asp Ser Thr Leu Cys Asp Leu Arg Leu Thr Leu Glu Ala Lys
465                 470                 475                 480
Asp Gln Glu Leu Asn Gln Ser Leu Thr Glu Lys Glu Ile Leu Val Ala
                485                 490                 495
Glu Leu Glu Glu Leu Asp Arg Gln Asn Gln Glu Ala Thr Lys His Met
            500                 505                 510
Ile Leu Ile Lys Asp Gln Leu Ser Lys Gln Gln Ser Glu Gly Glu Thr
        515                 520                 525
Ile Ile Ser Lys Leu Arg Lys Asp Leu Asn Asp Glu Asn Lys Arg Val
        530                 535                 540
His Gln Leu Glu Asp Asp Lys Lys Asn Met Thr Lys Glu Leu Asn Val
545                 550                 555                 560
Gln Lys Glu Lys Leu Val Gln Ser Glu Leu Val Leu Asn Gly Leu His
                565                 570                 575
Leu Ala Lys Gln Lys Leu Glu Glu Lys Val Glu Asp Leu Val Asp Gln
            580                 585                 590
Leu Asn Lys Ser Gln Lys Ser Asn Leu Asn Met Gln Lys Glu Asn Phe
        595                 600                 605
Gly Leu Lys Glu His Ile Lys Gln Asn Glu Glu Leu Ser Arg Val
        610                 615                 620
Arg Asp Glu Leu Thr Gln Ser Leu Ser Arg Asp Ser Gly Ser Asp Phe
625                 630                 635                 640
Lys Asp Asp Leu Leu Lys Glu Arg Glu Ala Glu Val Arg Asn Leu Lys
                645                 650                 655
Gln Asn Leu Ser Glu Ile Glu Gln Leu Asn Asp Ser Leu Asn Lys Val
            660                 665                 670
Ala Phe Asp Leu Lys Met Glu Asn Glu Lys Leu Val Leu Ala Cys Glu
        675                 680                 685
Asp Ile Arg His Gln Leu Glu Glu Ser Ile Val Gly Ser Asn Gln Met
690                 695                 700
Ser Leu Glu Arg Asn Thr Ile Val Glu Ala Leu Lys Met Glu Lys Gly
705                 710                 715                 720
Gln Leu Glu Ala Glu Leu Ser Arg Ala Asp Gln Arg Leu Leu Glu Glu
                725                 730                 735
Ala Ser Lys Tyr Glu Gln Thr Ile Gln Glu Leu Ser Lys Ala Arg Asp
            740                 745                 750
Leu Arg Thr Ser Ala Leu Gln Leu Glu Gln His Leu Met Lys Leu
        755                 760                 765
Ser Gln Glu Lys Asp Phe Glu Ile Ala Glu Leu Lys Lys Asn Ile Glu
        770                 775                 780
Gln Met Asp Thr Asp His Lys Glu Thr Lys Ala Ile Leu Ser Ser Ile
785                 790                 795                 800
Leu Glu Glu Gln Lys Gln Leu Thr Gln Leu Ile Ser Glu Lys Glu Ile
                805                 810                 815
Phe Ile Glu Lys Leu Lys Glu Arg Ser Ser Glu Leu Gln Glu Glu Leu
            820                 825                 830
Glu Lys Ser Thr Gln Ala Ser Arg Lys Ile Glu Ile Leu Lys Gln Thr
        835                 840                 845
```

-continued

Ile Glu Glu Lys Asp Arg Ser Leu Gly Ser Met Lys Glu Asn Asn
850                 855                 860

His Leu Lys Glu Glu Leu Glu Arg Leu Arg Glu Gln Gln Ser Arg Ala
865                 870                 875                 880

Val Pro Val Val Glu Pro Lys Pro Leu Asp Ser Val Thr Glu Leu Glu
            885                 890                 895

Ser Glu Val Leu Gln Leu Asn Ile Val Lys Arg Asn Leu Glu Glu Glu
        900                 905                 910

Ile Lys Arg His Gln Lys Ile Ile Glu Asp Gln Asn Gln Ser Lys Met
    915                 920                 925

Gln Leu Leu Gln Ser Leu Glu Glu Gln Lys Glu Met Asp Glu Phe
930                 935                 940

Lys Cys Gln His Glu Gln Met Asn Val Thr His Thr Gln Leu Phe Leu
945                 950                 955                 960

Glu Lys Asp Glu Glu Ile Lys Asn Leu Gln Lys Thr Ile Glu Gln Ile
            965                 970                 975

Lys Thr Gln Trp His Glu Glu Arg Gln Asp Val Gln Met Glu Asn Ser
        980                 985                 990

Glu Phe Phe Gln Glu Thr Lys Val Gln Ser Leu Asn Leu Glu Asn Gly
    995                 1000                1005

Ser Glu Lys His Asp Leu Ser Lys Ala Glu Thr Glu Arg Leu Val
1010                1015                1020

Lys Gly Ile Lys Glu Arg Glu Leu Glu Ile Lys Leu Leu Asn Glu
1025                1030                1035

Lys Asn Ile Ser Leu Thr Lys Gln Ile Asp Gln Leu Ser Lys Asp
1040                1045                1050

Glu Val Gly Lys Leu Thr Gln Ile Ile Gln Gln Lys Asp Leu Glu
1055                1060                1065

Ile Gln Ala Leu His Ala Arg Ile Ser Ser Ala Ser Tyr Thr Gln
1070                1075                1080

Asp Val Val Tyr Leu Gln Gln Gln Leu Gln Ala Tyr Ala Met Glu
1085                1090                1095

Arg Glu Gln Val Leu Ala Val Leu Ser Glu Lys Thr Arg Glu Asn
1100                1105                1110

Ser His Leu Lys Thr Glu Tyr His Lys Met Met Asp Ile Val Ala
1115                1120                1125

Ala Lys Glu Ala Ala Leu Ile Lys Leu Gln Asp Glu Asn Lys Lys
1130                1135                1140

Leu Ser Ala Arg Ser Glu Gly Gly Gly Gln Asp Met Phe Arg Glu
1145                1150                1155

Thr Val Gln Asn Leu Ser Arg Ile Ile Arg Glu Lys Asp Ile Glu
1160                1165                1170

Ile Asp Ala Leu Ser Gln Lys Cys Gln Thr Leu Leu Thr Val Leu
1175                1180                1185

Gln Thr Ser Ser Thr Gly Asn Glu Val Gly Gly Val Asn Ser Asn
1190                1195                1200

Gln Phe Glu Glu Leu Leu Gln Glu Arg Asp Lys Leu Lys Gln Gln
1205                1210                1215

Val Lys Lys Met Glu Glu Trp Lys Gln Gln Val Met Thr Thr Val
1220                1225                1230

Gln Asn Met Gln His Glu Ser Ala Gln Leu Gln Glu Glu Leu His
1235                1240                1245

Gln Leu Gln Ala Gln Val Leu Val Asp Ser Asp Asn Asn Ser Lys

-continued

```
            1250                1255                1260

Leu Gln Val Asp Tyr Thr Gly Leu Ile Gln Ser Tyr Glu Gln Asn
            1265                1270                1275

Glu Thr Lys Leu Lys Asn Phe Gly Gln Glu Leu Ala Gln Val Gln
            1280                1285                1290

His Ser Ile Gly Gln Leu Tyr Ser Thr Lys Asp Leu Leu Leu Gly
            1295                1300                1305

Lys Leu Asp Ile Ile Ser Pro Gln Leu Pro Ser Gly Ser Ser Pro
            1310                1315                1320

Pro Ser Gln Ser Ala Glu Ser Leu Gly Met Asp Lys Arg Asp Thr
            1325                1330                1335

Ser Ser Glu Ser Ser Lys Gln Glu Leu Glu Glu Leu Arg Lys Ser
            1340                1345                1350

Leu Gln Glu Lys Asp Ala Thr Ile Lys Thr Leu Gln Glu Asn Asn
            1355                1360                1365

His Arg Leu Ser Asp Ser Ile Ala Ala Thr Ser Glu Leu Glu Arg
            1370                1375                1380

Lys Glu His Glu Gln Thr Asp Ser Glu Ile Lys Gln Leu Lys Glu
            1385                1390                1395

Lys Gln Asp Val Leu Gln Lys Ser Leu Lys Glu Lys Asp Leu Leu
            1400                1405                1410

Ile Lys Ala Lys Ser Asp Gln Leu Leu Ser Leu Asn Glu Asn Phe
            1415                1420                1425

Thr Asn Lys Val Asn Glu Asn Glu Leu Leu Arg Gln Ala Val Thr
            1430                1435                1440

Asn Leu Lys Glu Arg Val Leu Ile Leu Glu Met Asp Ile Gly Lys
            1445                1450                1455

Leu Lys Glu Glu Asn Glu Lys Ile Val Glu Arg Thr Arg Glu Lys
            1460                1465                1470

Glu Thr Glu Tyr Gln Ala Leu Gln Glu Thr Asn Met Lys Phe Ser
            1475                1480                1485

Met Met Leu Arg Glu Lys Glu Phe Glu Cys His Ser Met Lys Glu
            1490                1495                1500

Lys Ser Leu Ala Phe Glu Gln Leu Leu Lys Glu Lys Glu Gln Gly
            1505                1510                1515

Lys Thr Gly Glu Leu Asn Gln Leu Leu Asn Ala Val Lys Ser Met
            1520                1525                1530

Gln Glu Lys Thr Val Lys Phe Gln Gln Glu Arg Asp Gln Val Met
            1535                1540                1545

Leu Ala Leu Lys Gln Lys Gln Met Glu Asn Ser Ala Leu Gln Asn
            1550                1555                1560

Glu Val Gln His Leu Arg Asp Lys Glu Leu Arg Leu Asn Gln Glu
            1565                1570                1575

Leu Glu Arg Leu Arg Asn His Leu Leu Glu Ser Glu Asp Ser Tyr
            1580                1585                1590

Thr Arg Glu Ala Leu Ala Ala Glu Glu Arg Glu Ala Lys Leu Arg
            1595                1600                1605

Arg Lys Val Thr Val Leu Glu Glu Lys Leu Val Ser Ser Ser Asn
            1610                1615                1620

Ala Met Glu Asn Ala Ser His Gln Ala Ser Leu Gln Val Glu Ser
            1625                1630                1635

Leu Gln Glu Gln Leu Asn Val Val Ser Lys Gln Arg Asp Glu Thr
            1640                1645                1650
```

| Ala | Leu | Gln | Leu | Ser | Val | Ser | Arg | Glu | Gln | Val | Lys | Gln | Tyr | Ala |
|---|---|---|---|---|---|---|---|---|---|---|---|---|---|---|
| 1655 | | | | 1660 | | | | | 1665 | | | | | |

Leu Ser Leu Ser Asn Leu Gln Met Val Leu Glu His Phe Gln Gln
1670              1675                  1680

Glu Glu Lys Ala Val Tyr Ser Ala Glu Leu Glu Lys His Lys Gln
1685              1690                  1695

Leu Val Ala Glu Trp Lys Lys Lys Ala Glu Asn Leu Glu Gly Lys
1700              1705                  1710

Leu Met Ser Leu Gln Glu Arg Phe Asp Glu Ala Asn Ala Ala Leu
1715              1720                  1725

Asp Ser Ala Ser Arg Leu Thr Glu Gln Leu Asp Leu Lys Glu Glu
1730              1735                  1740

Gln Ile Glu Glu Leu Lys Lys Gln Asn Glu Leu Arg Gln Glu Met
1745              1750                  1755

Leu Asp Asp Val Gln Lys Lys Leu Met Asn Leu Val Asn Ser Thr
1760              1765                  1770

Glu Gly Lys Val Asp Lys Val Leu Met Arg Asn Leu Phe Ile Gly
1775              1780                  1785

His Phe His Thr Pro Lys His Gln Arg His Glu Val Leu Arg Leu
1790              1795                  1800

Met Gly Ser Ile Leu Gly Ile Lys Arg Glu Glu Met Glu Gln Leu
1805              1810                  1815

Leu His Glu Asp Gln Gly Gly Val Thr Arg Trp Met Thr Gly Trp
1820              1825                  1830

Leu Gly Gly Gly Ser Lys Ser Val Pro Asn Thr Pro Leu Arg Pro
1835              1840                  1845

Asn Gln Gln Ser Val Leu Asn Ser Ser Phe Ser Glu Leu Phe Val
1850              1855                  1860

Lys Phe Leu Glu Thr Glu Ser His Pro Ser Val Pro Pro Pro Lys
1865              1870                  1875

Leu Ser Val His Asp Met Lys Pro Leu Asp Ser Pro Gly Arg Arg
1880              1885                  1890

Lys Val Val Ile His Val Ser Glu Ser Phe Lys Glu Thr Thr Glu
1895              1900                  1905

Ser Arg Cys Gly Arg Arg Thr Asp Val Asn Pro Phe Leu Ala Pro
1910              1915                  1920

Arg Ser Ala Ala Val Pro Leu Ile Asn Pro Ala Gly Leu Gly Pro
1925              1930                  1935

Gly Gly Pro Gly His Leu Leu Leu Lys Pro Ile Ser Asp Val Leu
1940              1945                  1950

Pro Thr Phe Thr Pro Leu Pro Val Ser Pro Asp Asn Ser Ala Gly
1955              1960                  1965

Val Val Leu Lys Asp Leu Leu Lys Gln
1970              1975

<210> SEQ ID NO 40
<211> LENGTH: 6452
<212> TYPE: DNA
<213> ORGANISM: Homo sapiens
<220> FEATURE:
<221> NAME/KEY: CDS
<222> LOCATION: (357)..(6296)

<400> SEQUENCE: 40
cgagcgagtg tcatggcggc cggcgtcgag ttggcaggag taacccacgg aactgaggaa    60

```
agtcattaga gctgagaaag aagtggccca atctggacgg tgggaattcg tgggaatgag       120
cagaaggccc tccgtagtga ctgtgtcact agaggcgggc ccctggtaaa attccaggcc       180
aggcctctgc gtttctaggc agaacctgga gtcggccttg cctgagaacc cagctttgtg       240
ttatcgtatc ctgtctcgcg aaggcaggcg ttcaaggata tttggtcgga tcgcccggcg       300
gcgctaaacg ttttcttttt tccgagcgga ccgggtcgtt ctctaaactc gccgcg atg       359
                                                                   Met
                                                                   1
```

```
tcg tcc tgg ctt ggg ggc ctc ggc tcc gga ttg ggc cag tct ctg ggt       407
Ser Ser Trp Leu Gly Gly Leu Gly Ser Gly Leu Gly Gln Ser Leu Gly
          5              10              15 caa gtc ggg ggc agc ctg gct tcc ctc act ggc cag ata tca aac ttt       455
Gln Val Gly Gly Ser Leu Ala Ser Leu Thr Gly Gln Ile Ser Asn Phe
     20              25              30 aca aag gat atg ctg atg gag ggc acg gag gaa gtg gaa gca gaa tta       503
Thr Lys Asp Met Leu Met Glu Gly Thr Glu Glu Val Glu Ala Glu Leu
 35              40              45 cct gat tct agg aca aag gaa att gaa gcc att cat gca atc ttg aga       551
Pro Asp Ser Arg Thr Lys Glu Ile Glu Ala Ile His Ala Ile Leu Arg
50              55              60              65 tca gag aat gaa agg ctt aag aaa ctt tgt act gat cta gaa gag aaa       599
Ser Glu Asn Glu Arg Leu Lys Lys Leu Cys Thr Asp Leu Glu Glu Lys
              70              75              80 cat gaa gca tca gag att caa ata aag cag caa tct aca agt tac cga       647
His Glu Ala Ser Glu Ile Gln Ile Lys Gln Gln Ser Thr Ser Tyr Arg
         85              90              95 aat caa ctt caa caa aaa gag gta gaa atc agc cat ctt aaa gcc aga       695
Asn Gln Leu Gln Gln Lys Glu Val Glu Ile Ser His Leu Lys Ala Arg
    100             105             110 cag att gca ctc cag gat cag ttg ctg aaa ctg cag tca gct gct cag       743
Gln Ile Ala Leu Gln Asp Gln Leu Leu Lys Leu Gln Ser Ala Ala Gln
115             120             125 tca gta cct tca gga gct ggt gta cca gca acc act gca tca tct tca       791
Ser Val Pro Ser Gly Ala Gly Val Pro Ala Thr Thr Ala Ser Ser Ser
130             135             140             145 ttc gct tat ggg att agt cat cat cct tca gct ttc cat gac gat gac       839
Phe Ala Tyr Gly Ile Ser His His Pro Ser Ala Phe His Asp Asp Asp
            150             155             160 atg gac ttt ggt gat ata att tca tcc caa caa gaa ata aac cga ctc       887
Met Asp Phe Gly Asp Ile Ile Ser Ser Gln Gln Glu Ile Asn Arg Leu
        165             170             175 tca aat gaa gtt tca aga ctt gag tct gaa gtt ggc cat tgg agg cat       935
Ser Asn Glu Val Ser Arg Leu Glu Ser Glu Val Gly His Trp Arg His
    180             185             190 att gct cag act tcc aaa gca caa gga aca gat aac tct gat caa agt       983
Ile Ala Gln Thr Ser Lys Ala Gln Gly Thr Asp Asn Ser Asp Gln Ser
195             200             205 gaa ata tgt aaa cta caa aat atc att aag gaa cta aaa cag aac cga      1031
Glu Ile Cys Lys Leu Gln Asn Ile Ile Lys Glu Leu Lys Gln Asn Arg
210             215             220             225 agt cag gaa att gat gac cat caa cat gaa atg tca gta ctg cag aat      1079
Ser Gln Glu Ile Asp Asp His Gln His Glu Met Ser Val Leu Gln Asn
            230             235             240 gca cac caa cag aaa ttg aca gaa ata agt cga cga cat cga gaa gaa      1127
Ala His Gln Gln Lys Leu Thr Glu Ile Ser Arg Arg His Arg Glu Glu
        245             250             255 tta agt gac tat gaa gaa cga att gaa gaa ctt gaa aat ctg tta caa      1175
Leu Ser Asp Tyr Glu Glu Arg Ile Glu Glu Leu Glu Asn Leu Leu Gln
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 260 |     |     |     |     | 265 |     |     |     |     |     | 270 |     |     |      |
| caa | ggt | ggc | tct | gga | gtt | ata | gaa | act | gat | ctc | tct | aaa | atc | tat | gag | 1223 |
| Gln | Gly | Gly | Ser | Gly | Val | Ile | Glu | Thr | Asp | Leu | Ser | Lys | Ile | Tyr | Glu |      |
|     | 275 |     |     |     | 280 |     |     |     |     | 285 |     |     |     |     |     |      |
| atg | caa | aaa | act | att | caa | gtt | cta | caa | ata | gaa | aaa | gtg | gag | tct | acc | 1271 |
| Met | Gln | Lys | Thr | Ile | Gln | Val | Leu | Gln | Ile | Glu | Lys | Val | Glu | Ser | Thr |      |
| 290 |     |     |     |     | 295 |     |     |     |     | 300 |     |     |     |     | 305 |      |
| aaa | aaa | atg | gaa | caa | ctt | gag | gat | aaa | ata | aaa | gat | ata | aat | aaa | aaa | 1319 |
| Lys | Lys | Met | Glu | Gln | Leu | Glu | Asp | Lys | Ile | Lys | Asp | Ile | Asn | Lys | Lys |      |
|     |     |     |     | 310 |     |     |     |     | 315 |     |     |     |     | 320 |     |      |
| tta | tct | tct | gca | gaa | aat | gac | aga | gat | att | ttg | agg | agg | gaa | caa | gaa | 1367 |
| Leu | Ser | Ser | Ala | Glu | Asn | Asp | Arg | Asp | Ile | Leu | Arg | Arg | Glu | Gln | Glu |      |
|     |     | 325 |     |     |     |     | 330 |     |     |     |     | 335 |     |     |     |      |
| cag | cta | aat | gtg | gaa | aag | aga | caa | ata | atg | gaa | gaa | tgt | gaa | aac | ttg | 1415 |
| Gln | Leu | Asn | Val | Glu | Lys | Arg | Gln | Ile | Met | Glu | Glu | Cys | Glu | Asn | Leu |      |
| 340 |     |     |     |     | 345 |     |     |     |     | 350 |     |     |     |     |     |      |
| aaa | ttg | gaa | tgt | agt | aaa | ttg | cag | cct | tct | gct | gtg | aag | caa | agt | gat | 1463 |
| Lys | Leu | Glu | Cys | Ser | Lys | Leu | Gln | Pro | Ser | Ala | Val | Lys | Gln | Ser | Asp |      |
|     | 355 |     |     |     |     | 360 |     |     |     |     | 365 |     |     |     |     |      |
| act | atg | aca | gaa | aag | gaa | aga | att | ctt | gcc | cag | agt | gca | tca | gtg | gaa | 1511 |
| Thr | Met | Thr | Glu | Lys | Glu | Arg | Ile | Leu | Ala | Gln | Ser | Ala | Ser | Val | Glu |      |
| 370 |     |     |     |     | 375 |     |     |     |     | 380 |     |     |     |     | 385 |      |
| gaa | gtg | ttc | aga | cta | caa | caa | gca | ctg | tct | gat | gcc | gaa | aat | gaa | ata | 1559 |
| Glu | Val | Phe | Arg | Leu | Gln | Gln | Ala | Leu | Ser | Asp | Ala | Glu | Asn | Glu | Ile |      |
|     |     |     |     | 390 |     |     |     |     | 395 |     |     |     |     | 400 |     |      |
| atg | aga | ttg | agt | agt | tta | aac | cag | gat | aac | agt | ctt | gct | gaa | gac | aat | 1607 |
| Met | Arg | Leu | Ser | Ser | Leu | Asn | Gln | Asp | Asn | Ser | Leu | Ala | Glu | Asp | Asn |      |
|     |     |     | 405 |     |     |     |     | 410 |     |     |     |     | 415 |     |     |      |
| ctg | aaa | ctt | aaa | atg | cgt | atc | gaa | gtt | tta | gaa | aaa | gag | aag | tca | tta | 1655 |
| Leu | Lys | Leu | Lys | Met | Arg | Ile | Glu | Val | Leu | Glu | Lys | Glu | Lys | Ser | Leu |      |
|     |     | 420 |     |     |     |     | 425 |     |     |     |     | 430 |     |     |     |      |
| ctg | agt | caa | gaa | aag | gaa | gaa | ctt | cag | atg | tca | ctt | tta | aaa | ttg | aac | 1703 |
| Leu | Ser | Gln | Glu | Lys | Glu | Glu | Leu | Gln | Met | Ser | Leu | Leu | Lys | Leu | Asn |      |
| 435 |     |     |     |     | 440 |     |     |     |     | 445 |     |     |     |     |     |      |
| aat | gaa | tat | gaa | gta | att | aaa | agt | aca | gct | aca | aga | gac | ata | agt | ttg | 1751 |
| Asn | Glu | Tyr | Glu | Val | Ile | Lys | Ser | Thr | Ala | Thr | Arg | Asp | Ile | Ser | Leu |      |
| 450 |     |     |     |     | 455 |     |     |     |     | 460 |     |     |     |     | 465 |      |
| gat | tca | gaa | tta | cat | gac | tta | aga | ctt | aat | ttg | gag | gca | aag | gaa | caa | 1799 |
| Asp | Ser | Glu | Leu | His | Asp | Leu | Arg | Leu | Asn | Leu | Glu | Ala | Lys | Glu | Gln |      |
|     |     |     |     | 470 |     |     |     |     | 475 |     |     |     |     | 480 |     |      |
| gaa | ctc | aat | cag | agt | att | agt | gaa | aag | gaa | aca | ctg | ata | gct | gag | ata | 1847 |
| Glu | Leu | Asn | Gln | Ser | Ile | Ser | Glu | Lys | Glu | Thr | Leu | Ile | Ala | Glu | Ile |      |
|     |     |     | 485 |     |     |     |     | 490 |     |     |     |     | 495 |     |     |      |
| gaa | gaa | ttg | gac | aga | cag | aat | caa | gaa | gct | aca | aag | cac | atg | att | ttg | 1895 |
| Glu | Glu | Leu | Asp | Arg | Gln | Asn | Gln | Glu | Ala | Thr | Lys | His | Met | Ile | Leu |      |
|     |     | 500 |     |     |     |     | 505 |     |     |     |     | 510 |     |     |     |      |
| ata | aaa | gat | cag | cta | tca | aaa | caa | caa | aat | gaa | gga | gat | agc | atc | atc | 1943 |
| Ile | Lys | Asp | Gln | Leu | Ser | Lys | Gln | Gln | Asn | Glu | Gly | Asp | Ser | Ile | Ile |      |
| 515 |     |     |     |     | 520 |     |     |     |     | 525 |     |     |     |     |     |      |
| agt | aaa | ctg | aaa | caa | gat | cta | aat | gat | gaa | aaa | aag | aga | gtt | cat | caa | 1991 |
| Ser | Lys | Leu | Lys | Gln | Asp | Leu | Asn | Asp | Glu | Lys | Lys | Arg | Val | His | Gln |      |
|     | 530 |     |     |     |     | 535 |     |     |     |     | 540 |     |     |     | 545 |      |
| ctt | gaa | gat | gat | aaa | atg | gac | att | act | aaa | gag | tta | gat | gta | cag | aaa | 2039 |
| Leu | Glu | Asp | Asp | Lys | Met | Asp | Ile | Thr | Lys | Glu | Leu | Asp | Val | Gln | Lys |      |
|     |     |     |     | 550 |     |     |     |     | 555 |     |     |     |     | 560 |     |      |
| gaa | aag | cta | att | caa | agt | gaa | gtg | gcc | cta | aat | gat | tta | cat | tta | acc | 2087 |
| Glu | Lys | Leu | Ile | Gln | Ser | Glu | Val | Ala | Leu | Asn | Asp | Leu | His | Leu | Thr |      |
|     |     |     | 565 |     |     |     |     | 570 |     |     |     |     | 575 |     |     |      |
| aag | cag | aaa | ctt | gag | gac | aaa | gta | gaa | aat | tta | gta | gat | cag | cta | aat | 2135 |

```
                Lys Gln Lys Leu Glu Asp Lys Val Glu Asn Leu Val Asp Gln Leu Asn
                            580                 585                 590 aaa tca caa gaa agt aat gta agc atc cag aag gag aat tta gaa ctt        2183
Lys Ser Gln Glu Ser Asn Val Ser Ile Gln Lys Glu Asn Leu Glu Leu
            595                 600                 605 aag gag cat att aga caa aat gag gag gag ctt tct aga ata agg aat        2231
Lys Glu His Ile Arg Gln Asn Glu Glu Glu Leu Ser Arg Ile Arg Asn
610                 615                 620                 625 gag tta atg cag tct cta aat caa gac tct aat agt aat ttt aag gat        2279
Glu Leu Met Gln Ser Leu Asn Gln Asp Ser Asn Ser Asn Phe Lys Asp
                630                 635                 640 acc tta ctt aaa gaa aga gaa gct gaa gtt aga aac tta aag caa aat        2327
Thr Leu Leu Lys Glu Arg Glu Ala Glu Val Arg Asn Leu Lys Gln Asn
            645                 650                 655 ctt tca gaa tta gaa cag ctc aat gaa aat tta aag aaa gtt gct ttt        2375
Leu Ser Glu Leu Glu Gln Leu Asn Glu Asn Leu Lys Lys Val Ala Phe
        660                 665                 670 gat gtc aaa atg gaa aat gaa aag tta gtt tta gca tgt gaa gat gtg        2423
Asp Val Lys Met Glu Asn Glu Lys Leu Val Leu Ala Cys Glu Asp Val
675                 680                 685 agg cat cag tta gaa gaa tgt ctt gct ggt aac aat cag ctt tct ctg        2471
Arg His Gln Leu Glu Glu Cys Leu Ala Gly Asn Asn Gln Leu Ser Leu
690                 695                 700                 705 gaa aaa aac act att gtg gag act cta aaa atg gaa aaa gga gag ata        2519
Glu Lys Asn Thr Ile Val Glu Thr Leu Lys Met Glu Lys Gly Glu Ile
            710                 715                 720 gag gca gaa ttg tgt tgg gct aaa aag agg ctg ttg gaa gaa gca aac        2567
Glu Ala Glu Leu Cys Trp Ala Lys Lys Arg Leu Leu Glu Glu Ala Asn
        725                 730                 735 aag tat gag aaa acc att gaa gaa ctg tca aat gca cgt aat ttg aat        2615
Lys Tyr Glu Lys Thr Ile Glu Glu Leu Ser Asn Ala Arg Asn Leu Asn
            740                 745                 750 acc tct gcc tta cag ctg gaa cat gag cat tta att aaa ctc aat caa        2663
Thr Ser Ala Leu Gln Leu Glu His Glu His Leu Ile Lys Leu Asn Gln
755                 760                 765 aag aaa gac atg gaa ata gca gaa ctc aaa aag aat att gaa caa atg        2711
Lys Lys Asp Met Glu Ile Ala Glu Leu Lys Lys Asn Ile Glu Gln Met
770                 775                 780                 785 gat act gac cat aaa gaa act aag gac gtt ttg tca tct agt tta gaa        2759
Asp Thr Asp His Lys Glu Thr Lys Asp Val Leu Ser Ser Ser Leu Glu
            790                 795                 800 gag cag aag cag ttg aca caa ctt ata aac aag aaa gaa att ttt att        2807
Glu Gln Lys Gln Leu Thr Gln Leu Ile Asn Lys Lys Glu Ile Phe Ile
        805                 810                 815 gaa aag ctt aaa gaa aga agt tca aag ctg cag gag gaa ttg gat aaa        2855
Glu Lys Leu Lys Glu Arg Ser Ser Lys Leu Gln Glu Glu Leu Asp Lys
            820                 825                 830 tat tct cag gcc tta aga aaa aat gaa att tta aga cag acc ata gag        2903
Tyr Ser Gln Ala Leu Arg Lys Asn Glu Ile Leu Arg Gln Thr Ile Glu
835                 840                 845 gaa aaa gac cga agt ctt gga tcc atg aaa gag gaa aat aat cat ctg        2951
Glu Lys Asp Arg Ser Leu Gly Ser Met Lys Glu Glu Asn Asn His Leu
850                 855                 860                 865 caa gaa gaa ttg gaa cga ctc agg gaa gag cag agt cga acc gca cct        2999
Gln Glu Glu Leu Glu Arg Leu Arg Glu Glu Gln Ser Arg Thr Ala Pro
            870                 875                 880 gtg gct gac cct aaa acc ctt gat agt gtt act gaa cta gca tct gag        3047
Val Ala Asp Pro Lys Thr Leu Asp Ser Val Thr Glu Leu Ala Ser Glu
        885                 890                 895
```

| | |
|---|---|
| gta tct caa ctg aac acg atc aag gaa cat ctt gaa gag gaa att aaa<br>Val Ser Gln Leu Asn Thr Ile Lys Glu His Leu Glu Glu Glu Ile Lys<br>900                       905                   910 | 3095 |
| cat cat caa aag ata att gaa gat caa aac cag agt aag atg caa cta<br>His His Gln Lys Ile Ile Glu Asp Gln Asn Gln Ser Lys Met Gln Leu<br>915                       920                   925 | 3143 |
| ctt cag tct tta caa gag caa aag aag gaa atg gat gag ttt aga tac<br>Leu Gln Ser Leu Gln Glu Gln Lys Lys Glu Met Asp Glu Phe Arg Tyr<br>930                       935                   940                   945 | 3191 |
| cag cat gag caa atg aac gcc aca cac acc cag ctc ttt tta gag aag<br>Gln His Glu Gln Met Asn Ala Thr His Thr Gln Leu Phe Leu Glu Lys<br>                   950                   955                   960 | 3239 |
| gat gag gaa att aag agt ttg caa aaa aca att gaa caa atc aaa acc<br>Asp Glu Glu Ile Lys Ser Leu Gln Lys Thr Ile Glu Gln Ile Lys Thr<br>965                       970                   975 | 3287 |
| cag ttg cat gaa gaa aga cag gac att caa aca gat aac tct gat att<br>Gln Leu His Glu Glu Arg Gln Asp Ile Gln Thr Asp Asn Ser Asp Ile<br>                   980                   985                   990 | 3335 |
| ttt caa gaa aca aaa gtt cag agc ctt aat ata gaa  aat gga agt gaa<br>Phe Gln Glu Thr Lys Val Gln Ser Leu Asn Ile Glu  Asn Gly Ser Glu<br>995                       1000                 1005 | 3383 |
| aag  cat gat tta tct aaa  gct gaa acg gaa aga  tta gtg aaa gga<br>Lys  His Asp Leu Ser Lys  Ala Glu Thr Glu Arg  Leu Val Lys Gly<br>1010                    1015                  1020 | 3428 |
| ata  aaa gag cga gaa ctg  gag att aaa ctt cta  aat gaa aag aat<br>Ile  Lys Glu Arg Glu Leu  Glu Ile Lys Leu Leu  Asn Glu Lys Asn<br>1025                    1030                  1035 | 3473 |
| ata  tct tta act aaa cag  att gat cag ttg tcc  aaa gat gaa gtt<br>Ile  Ser Leu Thr Lys Gln  Ile Asp Gln Leu Ser  Lys Asp Glu Val<br>1040                    1045                  1050 | 3518 |
| ggt  aaa cta act cag att  att cag cag aaa gat  ttg gag ata caa<br>Gly  Lys Leu Thr Gln Ile  Ile Gln Gln Lys Asp  Leu Glu Ile Gln<br>1055                    1060                  1065 | 3563 |
| gct  ctt cat gct aga att  tct tca act tcc cat  act caa gat gtt<br>Ala  Leu His Ala Arg Ile  Ser Ser Thr Ser His  Thr Gln Asp Val<br>1070                    1075                  1080 | 3608 |
| gtt  tac ctt caa cag caa  ctg cag gct tat gct  atg gaa aga gaa<br>Val  Tyr Leu Gln Gln Gln  Leu Gln Ala Tyr Ala  Met Glu Arg Glu<br>1085                    1090                  1095 | 3653 |
| aag  gta ttt gct gtt ttg  aat gag aag act agg  gaa aat agc cat<br>Lys  Val Phe Ala Val Leu  Asn Glu Lys Thr Arg  Glu Asn Ser His<br>1100                    1105                  1110 | 3698 |
| cta  aaa aca gaa tat cac  aaa atg atg gat att  gtt gct gcc aag<br>Leu  Lys Thr Glu Tyr His  Lys Met Met Asp Ile  Val Ala Ala Lys<br>1115                    1120                  1125 | 3743 |
| gaa  gca gct ctt atc aaa  ctg caa gat gaa aat  aaa aaa ttg tcc<br>Glu  Ala Ala Leu Ile Lys  Leu Gln Asp Glu Asn  Lys Lys Leu Ser<br>1130                    1135                  1140 | 3788 |
| act  aga ttt gaa agt agt  ggc caa gat atg ttt  aga gaa act att<br>Thr  Arg Phe Glu Ser Ser  Gly Gln Asp Met Phe  Arg Glu Thr Ile<br>1145                    1150                  1155 | 3833 |
| cag  aat tta tca cgt atc  att cga gaa aaa gac  atc gaa ata gat<br>Gln  Asn Leu Ser Arg Ile  Ile Arg Glu Lys Asp  Ile Glu Ile Asp<br>1160                    1165                  1170 | 3878 |
| gca  cta agt cag aaa tgt  cag act tta ttg gca  gtt tta caa aca<br>Ala  Leu Ser Gln Lys Cys  Gln Thr Leu Leu Ala  Val Leu Gln Thr<br>1175                    1180                  1185 | 3923 |
| tcc  agc act ggt aat gag  gct gga ggt gtt aat  agt cat caa ttt<br>Ser  Ser Thr Gly Asn Glu  Ala Gly Gly Val Asn  Ser His Gln Phe<br>1190                    1195                  1200 | 3968 |

| | | | | | | | | | | | | |
|---|---|---|---|---|---|---|---|---|---|---|---|---|
| gag | gag | ctt | cta | cag | gaa | cgt | gac | aag | tta | aaa | cag | caa | gta | aag | 4013 |
| Glu | Glu | Leu | Leu | Gln | Glu | Arg | Asp | Lys | Leu | Lys | Gln | Gln | Val | Lys | |
| 1205 | | | | 1210 | | | | | 1215 | | | | | | |

| aaa | atg | gaa | gag | tgg | aag | cag | cag | gtg | atg | acc | aca | gta | caa | aat | 4058 |
| Lys | Met | Glu | Glu | Trp | Lys | Gln | Gln | Val | Met | Thr | Thr | Val | Gln | Asn | |
| 1220 | | | | | 1225 | | | | 1230 | | | | | | |

| atg | caa | cac | gag | tca | gcc | cag | ctt | cag | gaa | gag | ctt | cac | caa | ctt | 4103 |
| Met | Gln | His | Glu | Ser | Ala | Gln | Leu | Gln | Glu | Glu | Leu | His | Gln | Leu | |
| 1235 | | | | | 1240 | | | | | 1245 | | | | | |

| caa | gca | cag | gtt | ttg | gtt | gac | agt | gat | aat | aat | tct | aaa | tta | caa | 4148 |
| Gln | Ala | Gln | Val | Leu | Val | Asp | Ser | Asp | Asn | Asn | Ser | Lys | Leu | Gln | |
| 1250 | | | | | 1255 | | | | | 1260 | | | | | |

| gtg | gac | tat | act | ggc | ctg | atc | caa | agt | tat | gag | cag | aat | gaa | acc | 4193 |
| Val | Asp | Tyr | Thr | Gly | Leu | Ile | Gln | Ser | Tyr | Glu | Gln | Asn | Glu | Thr | |
| 1265 | | | | | 1270 | | | | | 1275 | | | | | |

| aaa | ctc | aaa | aat | ttt | ggg | cag | gaa | tta | gca | caa | gtt | cag | cac | agc | 4238 |
| Lys | Leu | Lys | Asn | Phe | Gly | Gln | Glu | Leu | Ala | Gln | Val | Gln | His | Ser | |
| 1280 | | | | | 1285 | | | | | 1290 | | | | | |

| att | ggg | cag | ctt | tgc | aat | acc | aag | gat | ctt | ctt | tta | gga | aaa | ctt | 4283 |
| Ile | Gly | Gln | Leu | Cys | Asn | Thr | Lys | Asp | Leu | Leu | Leu | Gly | Lys | Leu | |
| 1295 | | | | | 1300 | | | | | 1305 | | | | | |

| gat | att | att | tca | ccc | cag | ctg | tct | tct | gca | tca | ttg | ctt | act | ccc | 4328 |
| Asp | Ile | Ile | Ser | Pro | Gln | Leu | Ser | Ser | Ala | Ser | Leu | Leu | Thr | Pro | |
| 1310 | | | | | 1315 | | | | | 1320 | | | | | |

| cag | tct | gca | gag | tgt | ctt | aga | gca | agt | aag | tct | gaa | gta | ttg | agt | 4373 |
| Gln | Ser | Ala | Glu | Cys | Leu | Arg | Ala | Ser | Lys | Ser | Glu | Val | Leu | Ser | |
| 1325 | | | | | 1330 | | | | | 1335 | | | | | |

| gaa | tct | tct | gaa | ttg | ctt | cag | caa | gag | tta | gaa | gag | cta | aga | aaa | 4418 |
| Glu | Ser | Ser | Glu | Leu | Leu | Gln | Gln | Glu | Leu | Glu | Glu | Leu | Arg | Lys | |
| 1340 | | | | | 1345 | | | | | 1350 | | | | | |

| tca | cta | cag | gaa | aaa | gat | gca | aca | att | aga | act | ctc | cag | gaa | aat | 4463 |
| Ser | Leu | Gln | Glu | Lys | Asp | Ala | Thr | Ile | Arg | Thr | Leu | Gln | Glu | Asn | |
| 1355 | | | | | 1360 | | | | | 1365 | | | | | |

| aac | cac | aga | ttg | tct | gat | tcg | att | gct | gcc | acc | tca | gag | cta | gaa | 4508 |
| Asn | His | Arg | Leu | Ser | Asp | Ser | Ile | Ala | Ala | Thr | Ser | Glu | Leu | Glu | |
| 1370 | | | | | 1375 | | | | | 1380 | | | | | |

| aga | aaa | gaa | cac | gaa | caa | acc | gat | tca | gaa | atc | aag | cag | cta | aag | 4553 |
| Arg | Lys | Glu | His | Glu | Gln | Thr | Asp | Ser | Glu | Ile | Lys | Gln | Leu | Lys | |
| 1385 | | | | | 1390 | | | | | 1395 | | | | | |

| gag | aaa | caa | gat | gtt | ttg | caa | aag | tta | ctt | aag | gaa | aaa | gac | ctc | 4598 |
| Glu | Lys | Gln | Asp | Val | Leu | Gln | Lys | Leu | Leu | Lys | Glu | Lys | Asp | Leu | |
| 1400 | | | | | 1405 | | | | | 1410 | | | | | |

| tta | atc | aaa | gcc | aaa | agt | gat | caa | cta | ctt | tct | tcc | aat | gaa | aat | 4643 |
| Leu | Ile | Lys | Ala | Lys | Ser | Asp | Gln | Leu | Leu | Ser | Ser | Asn | Glu | Asn | |
| 1415 | | | | | 1420 | | | | | 1425 | | | | | |

| ttc | act | aac | aaa | gta | aat | gaa | aac | gaa | ctt | ttg | agg | cag | gca | gta | 4688 |
| Phe | Thr | Asn | Lys | Val | Asn | Glu | Asn | Glu | Leu | Leu | Arg | Gln | Ala | Val | |
| 1430 | | | | | 1435 | | | | | 1440 | | | | | |

| aca | aac | ctg | aag | gag | aga | ata | tta | att | cta | gag | atg | gac | att | ggc | 4733 |
| Thr | Asn | Leu | Lys | Glu | Arg | Ile | Leu | Ile | Leu | Glu | Met | Asp | Ile | Gly | |
| 1445 | | | | | 1450 | | | | | 1455 | | | | | |

| aaa | cta | aaa | gga | gaa | aat | gaa | aaa | ata | gtg | gaa | aca | tac | agg | gga | 4778 |
| Lys | Leu | Lys | Gly | Glu | Asn | Glu | Lys | Ile | Val | Glu | Thr | Tyr | Arg | Gly | |
| 1460 | | | | | 1465 | | | | | 1470 | | | | | |

| aag | gaa | aca | gaa | tat | caa | gcg | tta | caa | gag | act | aac | atg | aag | ttt | 4823 |
| Lys | Glu | Thr | Glu | Tyr | Gln | Ala | Leu | Gln | Glu | Thr | Asn | Met | Lys | Phe | |
| 1475 | | | | | 1480 | | | | | 1485 | | | | | |

| tct | atg | atg | ctg | cga | gaa | aaa | gag | ttt | gag | tgc | cac | tca | atg | aag | 4868 |
| Ser | Met | Met | Leu | Arg | Glu | Lys | Glu | Phe | Glu | Cys | His | Ser | Met | Lys | |

-continued

| | | | |
|---|---|---|---|
| 1490 | 1495 | 1500 | |
| gag aag gct ctt gct ttt gaa cag cta ttg aaa gag aaa gaa cag<br>Glu Lys Ala Leu Ala Phe Glu Gln Leu Leu Lys Glu Lys Glu Gln<br>1505                           1510                        1515 | | | 4913 |
| ggc aag act gga gag tta aat cag ctt tta aat gca gtt aaa tca<br>Gly Lys Thr Gly Glu Leu Asn Gln Leu Leu Asn Ala Val Lys Ser<br>1520                           1525                        1530 | | | 4958 |
| atg cag gag aag aca gtt gtg ttt caa cag gag aga gac caa gtc<br>Met Gln Glu Lys Thr Val Val Phe Gln Gln Glu Arg Asp Gln Val<br>1535                           1540                        1545 | | | 5003 |
| atg ttg gcc ctg aaa caa aaa caa atg gaa aat act gcc cta cag<br>Met Leu Ala Leu Lys Gln Lys Gln Met Glu Asn Thr Ala Leu Gln<br>1550                           1555                        1560 | | | 5048 |
| aat gag gtt caa cgt tta cgt gac aaa gaa ttt cgt tca aac caa<br>Asn Glu Val Gln Arg Leu Arg Asp Lys Glu Phe Arg Ser Asn Gln<br>1565                           1570                        1575 | | | 5093 |
| gag cta gag aga ttg cgt aat cat ctt tta gaa tca gaa gat tct<br>Glu Leu Glu Arg Leu Arg Asn His Leu Leu Glu Ser Glu Asp Ser<br>1580                           1585                        1590 | | | 5138 |
| tat acc cgt gaa gct ttg gct gca gaa gat aga gag gct aaa cta<br>Tyr Thr Arg Glu Ala Leu Ala Ala Glu Asp Arg Glu Ala Lys Leu<br>1595                           1600                        1605 | | | 5183 |
| aga aag aaa gtc aca gta ttg gag gaa aag cta gtt tca tcc tct<br>Arg Lys Lys Val Thr Val Leu Glu Glu Lys Leu Val Ser Ser Ser<br>1610                           1615                        1620 | | | 5228 |
| aat gca atg gaa aat gca agc cat caa gcc agt gtg cag gta gag<br>Asn Ala Met Glu Asn Ala Ser His Gln Ala Ser Val Gln Val Glu<br>1625                           1630                        1635 | | | 5273 |
| tca ttg caa gaa cag ttg aat gta gtt tcc aag caa agg gat gaa<br>Ser Leu Gln Glu Gln Leu Asn Val Val Ser Lys Gln Arg Asp Glu<br>1640                           1645                        1650 | | | 5318 |
| act gcg ctg cag ctt tct gtc tct cag gaa caa gta aag cag tat<br>Thr Ala Leu Gln Leu Ser Val Ser Gln Glu Gln Val Lys Gln Tyr<br>1655                           1660                        1665 | | | 5363 |
| gct ctg tca ctg gcc aac ctg cag atg gta cta gag cat ttc caa<br>Ala Leu Ser Leu Ala Asn Leu Gln Met Val Leu Glu His Phe Gln<br>1670                           1675                        1680 | | | 5408 |
| caa gag gaa aaa gct atg tat tct gct gaa ctc gaa aag caa aaa<br>Gln Glu Glu Lys Ala Met Tyr Ser Ala Glu Leu Glu Lys Gln Lys<br>1685                           1690                        1695 | | | 5453 |
| cag ctt ata gct gaa tgg aag aaa aac gca gaa aat ctg gaa gga<br>Gln Leu Ile Ala Glu Trp Lys Lys Asn Ala Glu Asn Leu Glu Gly<br>1700                           1705                        1710 | | | 5498 |
| aaa gtg ata tca tta cag gaa tgt ttg gat gaa gca aat gct gca<br>Lys Val Ile Ser Leu Gln Glu Cys Leu Asp Glu Ala Asn Ala Ala<br>1715                           1720                        1725 | | | 5543 |
| ttg gat tca gca tca aga ctt aca gaa cag tta gat gta aaa gaa<br>Leu Asp Ser Ala Ser Arg Leu Thr Glu Gln Leu Asp Val Lys Glu<br>1730                           1735                        1740 | | | 5588 |
| gaa caa att gaa gaa ctt aaa aga caa aat gag ctc cga caa gaa<br>Glu Gln Ile Glu Glu Leu Lys Arg Gln Asn Glu Leu Arg Gln Glu<br>1745                           1750                        1755 | | | 5633 |
| atg ctg gat gat gta caa aag aaa ttg atg agc tta gca aac agc<br>Met Leu Asp Asp Val Gln Lys Lys Leu Met Ser Leu Ala Asn Ser<br>1760                           1765                        1770 | | | 5678 |
| tca gaa gga aaa gta gac aaa gtc cta atg aga aac ctc ttc att<br>Ser Glu Gly Lys Val Asp Lys Val Leu Met Arg Asn Leu Phe Ile<br>1775                           1780                        1785 | | | 5723 |
| ggt cat ttc cac aca ccg aaa aat cag cgt cat gaa gtg tta cgg | | | 5768 |

```
Gly His Phe His Thr Pro Lys Asn Gln Arg His Glu Val Leu Arg
1790            1795                1800 tta atg ggg agc atc ctg ggc gtc aga agg gag gag atg gag cag    5813
Leu Met Gly Ser Ile Leu Gly Val Arg Arg Glu Glu Met Glu Gln
1805            1810                1815 ttg ttt cat gac gat cag ggc agt gtt acc agg tgg atg act ggg    5858
Leu Phe His Asp Asp Gln Gly Ser Val Thr Arg Trp Met Thr Gly
1820            1825                1830 tgg ctt gga gga gga tca aaa agt gtt ccc aac aca cct ttg aga    5903
Trp Leu Gly Gly Gly Ser Lys Ser Val Pro Asn Thr Pro Leu Arg
1835            1840                1845 cca aat cag caa tct gtg gtt aat agt tct ttt tca gaa ctt ttt    5948
Pro Asn Gln Gln Ser Val Val Asn Ser Ser Phe Ser Glu Leu Phe
1850            1855                1860 gtt aaa ttt cta gaa aca gaa tct cat cca tcc att cca cca cca    5993
Val Lys Phe Leu Glu Thr Glu Ser His Pro Ser Ile Pro Pro Pro
1865            1870                1875 aag ctt tct gtt cat gat atg aaa cct ctg gat tca cca gga aga    6038
Lys Leu Ser Val His Asp Met Lys Pro Leu Asp Ser Pro Gly Arg
1880            1885                1890 aga aaa aga gat aca aat gca cca gaa agt ttt aaa gat aca gca    6083
Arg Lys Arg Asp Thr Asn Ala Pro Glu Ser Phe Lys Asp Thr Ala
1895            1900                1905 gaa tcc agg tct ggt aga aga aca gat gta aat ccg ttt ttg gct    6128
Glu Ser Arg Ser Gly Arg Arg Thr Asp Val Asn Pro Phe Leu Ala
1910            1915                1920 cct cgc tcg gca gct gta cct ctt att aac cca gct gga ctt gga    6173
Pro Arg Ser Ala Ala Val Pro Leu Ile Asn Pro Ala Gly Leu Gly
1925            1930                1935 cct ggt ggg ccc ggg cat ctt ctt ctg aaa ccc atc tca gat gtt    6218
Pro Gly Gly Pro Gly His Leu Leu Leu Lys Pro Ile Ser Asp Val
1940            1945                1950 ttg ccc aca ttt aca cct ttg cca gcg tta cct gac aac agt gct    6263
Leu Pro Thr Phe Thr Pro Leu Pro Ala Leu Pro Asp Asn Ser Ala
1955            1960                1965 ggg gtt gtg ctg aaa gac ctt tta aag caa tag atgattctca         6306
Gly Val Val Leu Lys Asp Leu Leu Lys Gln
1970            1975 agccagagac aatctagcac tttaaagaaa ccatgaacac tatatgtatg tactttatca    6366
caaagtggcc tttggggaga aagtcatgta tttgttcgca attatgcttt ctctgaattt    6426
aataaaaata ttcctaatgc ttttag                                          6452

<210> SEQ ID NO 41
<211> LENGTH: 1979
<212> TYPE: PRT
<213> ORGANISM: Homo sapiens

<400> SEQUENCE: 41

Met Ser Ser Trp Leu Gly Gly Leu Gly Ser Gly Leu Gly Gln Ser Leu
1               5                   10                  15

Gly Gln Val Gly Gly Ser Leu Ala Ser Leu Thr Gly Gln Ile Ser Asn
                20                  25                  30

Phe Thr Lys Asp Met Leu Met Glu Gly Thr Glu Glu Val Glu Ala Glu
            35                  40                  45

Leu Pro Asp Ser Arg Thr Lys Glu Ile Glu Ala Ile His Ala Ile Leu
        50                  55                  60

Arg Ser Glu Asn Glu Arg Leu Lys Lys Leu Cys Thr Asp Leu Glu Glu
65                  70                  75                  80
```

```
Lys His Glu Ala Ser Glu Ile Gln Ile Lys Gln Gln Ser Thr Ser Tyr
                85                  90                  95

Arg Asn Gln Leu Gln Gln Lys Glu Val Glu Ile Ser His Leu Lys Ala
            100                 105                 110

Arg Gln Ile Ala Leu Gln Asp Gln Leu Leu Lys Leu Gln Ser Ala Ala
            115                 120                 125

Gln Ser Val Pro Ser Gly Ala Gly Val Pro Ala Thr Thr Ala Ser Ser
        130                 135                 140

Ser Phe Ala Tyr Gly Ile Ser His His Pro Ser Ala Phe His Asp Asp
145                 150                 155                 160

Asp Met Asp Phe Gly Asp Ile Ile Ser Ser Gln Gln Glu Ile Asn Arg
                165                 170                 175

Leu Ser Asn Glu Val Ser Arg Leu Glu Ser Glu Val Gly His Trp Arg
            180                 185                 190

His Ile Ala Gln Thr Ser Lys Ala Gln Gly Thr Asp Asn Ser Asp Gln
            195                 200                 205

Ser Glu Ile Cys Lys Leu Gln Asn Ile Ile Lys Glu Leu Lys Gln Asn
        210                 215                 220

Arg Ser Gln Glu Ile Asp Asp His Gln His Glu Met Ser Val Leu Gln
225                 230                 235                 240

Asn Ala His Gln Gln Lys Leu Thr Glu Ile Ser Arg Arg His Arg Glu
                245                 250                 255

Glu Leu Ser Asp Tyr Glu Glu Arg Ile Glu Glu Leu Glu Asn Leu Leu
            260                 265                 270

Gln Gln Gly Gly Ser Gly Val Ile Glu Thr Asp Leu Ser Lys Ile Tyr
        275                 280                 285

Glu Met Gln Lys Thr Ile Gln Val Leu Gln Ile Glu Lys Val Glu Ser
            290                 295                 300

Thr Lys Lys Met Glu Gln Leu Glu Asp Lys Ile Lys Asp Ile Asn Lys
305                 310                 315                 320

Lys Leu Ser Ser Ala Glu Asn Asp Arg Asp Ile Leu Arg Arg Glu Gln
                325                 330                 335

Glu Gln Leu Asn Val Glu Lys Arg Gln Ile Met Glu Glu Cys Glu Asn
            340                 345                 350

Leu Lys Leu Glu Cys Ser Lys Leu Gln Pro Ser Ala Val Lys Gln Ser
        355                 360                 365

Asp Thr Met Thr Glu Lys Glu Arg Ile Leu Ala Gln Ser Ala Ser Val
    370                 375                 380

Glu Glu Val Phe Arg Leu Gln Gln Ala Leu Ser Asp Ala Glu Asn Glu
385                 390                 395                 400

Ile Met Arg Leu Ser Ser Leu Asn Gln Asp Asn Ser Leu Ala Glu Asp
                405                 410                 415

Asn Leu Lys Leu Lys Met Arg Ile Glu Val Leu Glu Lys Glu Lys Ser
            420                 425                 430

Leu Leu Ser Gln Glu Lys Glu Leu Gln Met Ser Leu Leu Lys Leu
        435                 440                 445

Asn Asn Glu Tyr Glu Val Ile Lys Ser Thr Ala Thr Arg Asp Ile Ser
450                 455                 460

Leu Asp Ser Glu Leu His Asp Leu Arg Leu Asn Leu Glu Ala Lys Glu
465                 470                 475                 480

Gln Glu Leu Asn Gln Ser Ile Ser Glu Lys Glu Thr Leu Ile Ala Glu
                485                 490                 495
```

```
Ile Glu Glu Leu Asp Arg Gln Asn Gln Ala Thr Lys His Met Ile
            500                 505                 510

Leu Ile Lys Asp Gln Leu Ser Lys Gln Gln Asn Glu Gly Asp Ser Ile
            515                 520                 525

Ile Ser Lys Leu Lys Gln Asp Leu Asn Asp Glu Lys Lys Arg Val His
        530                 535                 540

Gln Leu Glu Asp Asp Lys Met Asp Ile Thr Lys Glu Leu Asp Val Gln
545                 550                 555                 560

Lys Glu Lys Leu Ile Gln Ser Glu Val Ala Leu Asn Asp Leu His Leu
            565                 570                 575

Thr Lys Gln Lys Leu Glu Asp Lys Val Glu Asn Leu Val Asp Gln Leu
            580                 585                 590

Asn Lys Ser Gln Glu Ser Asn Val Ser Ile Gln Lys Glu Asn Leu Glu
        595                 600                 605

Leu Lys Glu His Ile Arg Gln Asn Glu Glu Leu Ser Arg Ile Arg
        610                 615                 620

Asn Glu Leu Met Gln Ser Leu Asn Gln Asp Ser Asn Ser Asn Phe Lys
625                 630                 635                 640

Asp Thr Leu Leu Lys Glu Arg Glu Ala Glu Val Arg Asn Leu Lys Gln
            645                 650                 655

Asn Leu Ser Glu Leu Glu Gln Leu Asn Glu Asn Leu Lys Lys Val Ala
            660                 665                 670

Phe Asp Val Lys Met Glu Asn Glu Lys Leu Val Leu Ala Cys Glu Asp
        675                 680                 685

Val Arg His Gln Leu Glu Glu Cys Leu Ala Gly Asn Asn Gln Leu Ser
        690                 695                 700

Leu Glu Lys Asn Thr Ile Val Glu Thr Leu Lys Met Glu Lys Gly Glu
705                 710                 715                 720

Ile Glu Ala Glu Leu Cys Trp Ala Lys Lys Arg Leu Leu Glu Glu Ala
            725                 730                 735

Asn Lys Tyr Glu Lys Thr Ile Glu Glu Leu Ser Asn Ala Arg Asn Leu
            740                 745                 750

Asn Thr Ser Ala Leu Gln Leu Glu His Glu His Leu Ile Lys Leu Asn
        755                 760                 765

Gln Lys Lys Asp Met Glu Ile Ala Glu Leu Lys Lys Asn Ile Glu Gln
        770                 775                 780

Met Asp Thr Asp His Lys Glu Thr Lys Asp Val Leu Ser Ser Ser Leu
785                 790                 795                 800

Glu Glu Gln Lys Gln Leu Thr Gln Leu Ile Asn Lys Lys Glu Ile Phe
            805                 810                 815

Ile Glu Lys Leu Lys Glu Arg Ser Ser Lys Leu Gln Glu Glu Leu Asp
            820                 825                 830

Lys Tyr Ser Gln Ala Leu Arg Lys Asn Glu Ile Leu Arg Gln Thr Ile
            835                 840                 845

Glu Glu Lys Asp Arg Ser Leu Gly Ser Met Lys Glu Glu Asn Asn His
        850                 855                 860

Leu Gln Glu Glu Leu Glu Arg Leu Arg Glu Glu Gln Ser Arg Thr Ala
865                 870                 875                 880

Pro Val Ala Asp Pro Lys Thr Leu Asp Ser Val Thr Glu Leu Ala Ser
            885                 890                 895

Glu Val Ser Gln Leu Asn Thr Ile Lys Glu His Leu Glu Glu Glu Ile
        900                 905                 910

Lys His His Gln Lys Ile Ile Glu Asp Gln Asn Gln Ser Lys Met Gln
```

-continued

```
            915                 920                 925
Leu Leu Gln Ser Leu Gln Glu Gln Lys Lys Glu Met Asp Glu Phe Arg
        930                 935                 940
Tyr Gln His Glu Gln Met Asn Ala Thr His Thr Gln Leu Phe Leu Glu
945                 950                 955                 960
Lys Asp Glu Glu Ile Lys Ser Leu Gln Lys Thr Ile Glu Gln Ile Lys
                965                 970                 975
Thr Gln Leu His Glu Glu Arg Gln Asp Ile Gln Thr Asp Asn Ser Asp
            980                 985                 990
Ile Phe Gln Glu Thr Lys Val Gln Ser Leu Asn Ile Glu Asn Gly Ser
        995                 1000                1005
Glu Lys His Asp Leu Ser Lys Ala Glu Thr Glu Arg Leu Val Lys
    1010                1015                1020
Gly Ile Lys Glu Arg Glu Leu Glu Ile Lys Leu Leu Asn Glu Lys
    1025                1030                1035
Asn Ile Ser Leu Thr Lys Gln Ile Asp Gln Leu Ser Lys Asp Glu
    1040                1045                1050
Val Gly Lys Leu Thr Gln Ile Ile Gln Gln Lys Asp Leu Glu Ile
    1055                1060                1065
Gln Ala Leu His Ala Arg Ile Ser Ser Thr Ser His Thr Gln Asp
    1070                1075                1080
Val Val Tyr Leu Gln Gln Leu Gln Ala Tyr Ala Met Glu Arg
    1085                1090                1095
Glu Lys Val Phe Ala Val Leu Asn Glu Lys Thr Arg Glu Asn Ser
    1100                1105                1110
His Leu Lys Thr Glu Tyr His Lys Met Met Asp Ile Val Ala Ala
    1115                1120                1125
Lys Glu Ala Ala Leu Ile Lys Leu Gln Asp Glu Asn Lys Lys Leu
    1130                1135                1140
Ser Thr Arg Phe Glu Ser Ser Gly Gln Asp Met Phe Arg Glu Thr
    1145                1150                1155
Ile Gln Asn Leu Ser Arg Ile Ile Arg Glu Lys Asp Ile Glu Ile
    1160                1165                1170
Asp Ala Leu Ser Gln Lys Cys Gln Thr Leu Leu Ala Val Leu Gln
    1175                1180                1185
Thr Ser Ser Thr Gly Asn Glu Ala Gly Gly Val Asn Ser His Gln
    1190                1195                1200
Phe Glu Glu Leu Leu Gln Glu Arg Asp Lys Leu Lys Gln Gln Val
    1205                1210                1215
Lys Lys Met Glu Glu Trp Lys Gln Gln Val Met Thr Thr Val Gln
    1220                1225                1230
Asn Met Gln His Glu Ser Ala Gln Leu Gln Glu Glu Leu His Gln
    1235                1240                1245
Leu Gln Ala Gln Val Leu Val Asp Ser Asp Asn Ser Lys Leu
    1250                1255                1260
Gln Val Asp Tyr Thr Gly Leu Ile Gln Ser Tyr Glu Gln Asn Glu
    1265                1270                1275
Thr Lys Leu Lys Asn Phe Gly Gln Glu Leu Ala Gln Val Gln His
    1280                1285                1290
Ser Ile Gly Gln Leu Cys Asn Thr Lys Asp Leu Leu Leu Gly Lys
    1295                1300                1305
Leu Asp Ile Ile Ser Pro Gln Leu Ser Ser Ala Ser Leu Leu Thr
    1310                1315                1320
```

```
Pro Gln Ser Ala Glu Cys Leu Arg Ala Ser Lys Ser Glu Val Leu
1325                1330                1335

Ser Glu Ser Ser Glu Leu Leu Gln Gln Glu Leu Gln Glu Leu Arg
1340                1345                1350

Lys Ser Leu Gln Glu Lys Asp Ala Thr Ile Arg Thr Leu Gln Glu
1355                1360                1365

Asn Asn His Arg Leu Ser Asp Ser Ile Ala Ala Thr Ser Glu Leu
1370                1375                1380

Glu Arg Lys Glu His Glu Gln Thr Asp Ser Glu Ile Lys Gln Leu
1385                1390                1395

Lys Glu Lys Gln Asp Val Leu Gln Lys Leu Leu Lys Glu Lys Asp
1400                1405                1410

Leu Leu Ile Lys Ala Lys Ser Asp Gln Leu Leu Ser Ser Asn Glu
1415                1420                1425

Asn Phe Thr Asn Lys Val Asn Glu Asn Glu Leu Leu Arg Gln Ala
1430                1435                1440

Val Thr Asn Leu Lys Glu Arg Ile Leu Ile Leu Glu Met Asp Ile
1445                1450                1455

Gly Lys Leu Lys Gly Glu Asn Glu Lys Ile Val Glu Thr Tyr Arg
1460                1465                1470

Gly Lys Glu Thr Glu Tyr Gln Ala Leu Gln Glu Thr Asn Met Lys
1475                1480                1485

Phe Ser Met Met Leu Arg Glu Lys Glu Phe Glu Cys His Ser Met
1490                1495                1500

Lys Glu Lys Ala Leu Ala Phe Glu Gln Leu Leu Lys Glu Lys Glu
1505                1510                1515

Gln Gly Lys Thr Gly Glu Leu Asn Gln Leu Leu Asn Ala Val Lys
1520                1525                1530

Ser Met Gln Glu Lys Thr Val Val Phe Gln Gln Glu Arg Asp Gln
1535                1540                1545

Val Met Leu Ala Leu Lys Gln Lys Gln Met Glu Asn Thr Ala Leu
1550                1555                1560

Gln Asn Glu Val Gln Arg Leu Arg Asp Lys Glu Phe Arg Ser Asn
1565                1570                1575

Gln Glu Leu Glu Arg Leu Arg Asn His Leu Leu Glu Ser Glu Asp
1580                1585                1590

Ser Tyr Thr Arg Glu Ala Leu Ala Ala Glu Asp Arg Glu Ala Lys
1595                1600                1605

Leu Arg Lys Lys Val Thr Val Leu Glu Glu Lys Leu Val Ser Ser
1610                1615                1620

Ser Asn Ala Met Glu Asn Ala Ser His Gln Ala Ser Val Gln Val
1625                1630                1635

Glu Ser Leu Gln Glu Gln Leu Asn Val Val Ser Lys Gln Arg Asp
1640                1645                1650

Glu Thr Ala Leu Gln Leu Ser Val Ser Gln Glu Gln Val Lys Gln
1655                1660                1665

Tyr Ala Leu Ser Leu Ala Asn Leu Gln Met Val Leu Glu His Phe
1670                1675                1680

Gln Gln Glu Glu Lys Ala Met Tyr Ser Ala Glu Leu Glu Lys Gln
1685                1690                1695

Lys Gln Leu Ile Ala Glu Trp Lys Lys Asn Ala Glu Asn Leu Glu
1700                1705                1710
```

```
Gly Lys Val Ile Ser Leu Gln Glu Cys Leu Asp Glu Ala Asn Ala
    1715                1720                1725
Ala Leu Asp Ser Ala Ser Arg Leu Thr Glu Gln Leu Asp Val Lys
    1730                1735                1740
Glu Glu Gln Ile Glu Glu Leu Lys Arg Gln Asn Glu Leu Arg Gln
    1745                1750                1755
Glu Met Leu Asp Asp Val Gln Lys Lys Leu Met Ser Leu Ala Asn
    1760                1765                1770
Ser Ser Glu Gly Lys Val Asp Lys Val Leu Met Arg Asn Leu Phe
    1775                1780                1785
Ile Gly His Phe His Thr Pro Lys Asn Gln Arg His Glu Val Leu
    1790                1795                1800
Arg Leu Met Gly Ser Ile Leu Gly Val Arg Arg Glu Glu Met Glu
    1805                1810                1815
Gln Leu Phe His Asp Asp Gln Gly Ser Val Thr Arg Trp Met Thr
    1820                1825                1830
Gly Trp Leu Gly Gly Ser Lys Ser Val Pro Asn Thr Pro Leu
    1835                1840                1845
Arg Pro Asn Gln Gln Ser Val Val Asn Ser Ser Phe Ser Glu Leu
    1850                1855                1860
Phe Val Lys Phe Leu Glu Thr Glu Ser His Pro Ser Ile Pro Pro
    1865                1870                1875
Pro Lys Leu Ser Val His Asp Met Lys Pro Leu Asp Ser Pro Gly
    1880                1885                1890
Arg Arg Lys Arg Asp Thr Asn Ala Pro Glu Ser Phe Lys Asp Thr
    1895                1900                1905
Ala Glu Ser Arg Ser Gly Arg Arg Thr Asp Val Asn Pro Phe Leu
    1910                1915                1920
Ala Pro Arg Ser Ala Ala Val Pro Leu Ile Asn Pro Ala Gly Leu
    1925                1930                1935
Gly Pro Gly Gly Pro Gly His Leu Leu Leu Lys Pro Ile Ser Asp
    1940                1945                1950
Val Leu Pro Thr Phe Thr Pro Leu Pro Ala Leu Pro Asp Asn Ser
    1955                1960                1965
Ala Gly Val Val Leu Lys Asp Leu Leu Lys Gln
    1970                1975

<210> SEQ ID NO 42
<211> LENGTH: 18
<212> TYPE: DNA
<213> ORGANISM: Artificial Sequence
<220> FEATURE:
<223> OTHER INFORMATION: Synthetic primer

<400> SEQUENCE: 42
gaagctacaa agcacatg                                                  18

<210> SEQ ID NO 43
<211> LENGTH: 18
<212> TYPE: DNA
<213> ORGANISM: Artificial Sequence
<220> FEATURE:
<223> OTHER INFORMATION: Synthetic primer

<400> SEQUENCE: 43
tcctgtcttt cttcatgc                                                  18
```

```
<210> SEQ ID NO 44
<211> LENGTH: 24
<212> TYPE: DNA
<213> ORGANISM: Artificial Sequence
<220> FEATURE:
<223> OTHER INFORMATION: Synthetic primer

<400> SEQUENCE: 44
gtcgacatgt cgtcctggct cggg                                              24

<210> SEQ ID NO 45
<211> LENGTH: 24
<212> TYPE: DNA
<213> ORGANISM: Artificial Sequence
<220> FEATURE:
<223> OTHER INFORMATION: Synthetic primer

<400> SEQUENCE: 45
ctcgagctat tgctttaaaa ggtc                                              24

<210> SEQ ID NO 46
<211> LENGTH: 24
<212> TYPE: DNA
<213> ORGANISM: Artificial Sequence
<220> FEATURE:
<223> OTHER INFORMATION: Synthetic primer

<400> SEQUENCE: 46
catatgtcgt cctggcttgg gggc                                              24

<210> SEQ ID NO 47
<211> LENGTH: 25
<212> TYPE: DNA
<213> ORGANISM: Artificial Sequence
<220> FEATURE:
<223> OTHER INFORMATION: Synthetic primer

<400> SEQUENCE: 47
ggtaccttgc tttaaaaggt ctttc                                             25
```